US011946040B2

(12) United States Patent
Joung et al.

(10) Patent No.: US 11,946,040 B2
(45) Date of Patent: Apr. 2, 2024

(54) ADENINE DNA BASE EDITOR VARIANTS WITH REDUCED OFF-TARGET RNA EDITING

(71) Applicant: The General Hospital Corporation, Boston, MA (US)

(72) Inventors: J. Keith Joung, Winchester, MA (US); Julian Grunewald, Charlestown, MA (US); Ronghao Zhou, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 761 days.

(21) Appl. No.: 16/781,979

(22) Filed: Feb. 4, 2020

(65) Prior Publication Data

US 2020/0308571 A1   Oct. 1, 2020

Related U.S. Application Data

(60) Provisional application No. 62/844,717, filed on May 7, 2019, provisional application No. 62/800,974, filed on Feb. 4, 2019.

(51) Int. Cl.
C12N 15/10 (2006.01)
C12N 15/113 (2010.01)

(52) U.S. Cl.
CPC ........ *C12N 15/1024* (2013.01); *C12N 15/113* (2013.01); *C12Y 305/04004* (2013.01)

(58) Field of Classification Search
CPC .............. C12N 15/1024; C12N 15/113; C12Y 305/04004
See application file for complete search history.

(56) References Cited

U.S. PATENT DOCUMENTS

| | | |
|---|---|---|
| 6,294,330 B1 | 9/2001 | Michnick et al. |
| 2007/0016974 A1 | 1/2007 | Byrum et al. |
| 2011/0104787 A1 | 5/2011 | Church et al. |
| 2015/0174169 A1 | 6/2015 | Genovese et al. |
| 2016/0177278 A1 | 6/2016 | Wolfe et al. |
| 2017/0058271 A1 | 3/2017 | Joung et al. |
| 2017/0121693 A1 | 5/2017 | Liu et al. |
| 2018/0073012 A1 | 3/2018 | Liu |
| 2018/0127780 A1 | 5/2018 | Liu et al. |
| 2018/0312828 A1 | 11/2018 | Liu et al. |
| 2019/0010481 A1 | 1/2019 | Joung et al. |
| 2019/0093128 A1 | 3/2019 | Chen et al. |
| 2019/0106687 A1 | 4/2019 | Joung et al. |
| 2020/0140842 A1 | 5/2020 | Joung et al. |
| 2020/0172885 A1 | 6/2020 | Joung et al. |
| 2020/0172895 A1 | 6/2020 | Joung et al. |
| 2021/0395730 A1 | 12/2021 | Grunewald et al. |

FOREIGN PATENT DOCUMENTS

| | | |
|---|---|---|
| CA | 2915837 A1 | 12/2014 |
| CN | 105745221 | 7/2016 |
| WO | WO 2008/027899 | 3/2008 |
| WO | WO 2010/132092 | 11/2010 |
| WO | WO 2014/152432 | 9/2014 |
| WO | WO 2016/028682 | 2/2016 |
| WO | WO 2016/103233 | 6/2016 |
| WO | WO 2016/112242 | 7/2016 |
| WO | WO 2016/141224 | 9/2016 |
| WO | WO 2016/183438 | 11/2016 |
| WO | WO 2017/011721 | 1/2017 |
| WO | WO 2017/040348 | 3/2017 |
| WO | WO 2017/189308 | 11/2017 |
| WO | WO 2018/035387 | 2/2018 |
| WO | WO 2018/165629 | 9/2018 |
| WO | WO 2018/176009 | 9/2018 |
| WO | WO 2018/218166 | 11/2018 |
| WO | WO 2018/218188 | 11/2018 |
| WO | WO 2018/218206 | 11/2018 |
| WO | WO 2019/023680 | 1/2019 |
| WO | WO 2019/042284 | 3/2019 |
| WO | WO 2020/028823 | 2/2020 |
| WO | WO 2020/077138 | 5/2020 |
| WO | WO 2021/042047 | 3/2021 |
| WO | WO 2021/042062 | 3/2021 |
| WO | WO 2021/113611 | 6/2021 |

OTHER PUBLICATIONS

Siloto R et al. Site Saturation Mutagenesis: Methods and Applications in Protein Engineering. 2012. Biocatalysis and Agricultural Biotechnology. 181-189. (Year: 2012).*
Fan et al., "Cytosine and adenine deaminase base-editors induce broad and nonspecific changes in gene expression and splicing," Communications Biology, 2021, 4:882, 12 pages.
Anzalone et al., "Search-and-replace genome editing without double-strand breaks or donor DNA," Nature, Dec. 2019, 576(7785):149-157, 30 pages.
Aynaud et al., "Human Tribbles 3 protects nuclear DNA from cytidine deamination by APOBEC3A," Journal of Biological Chemistry, Nov. 2012, 287(46):39182-39192.
Berríos et al., "Controllable genome editing with split-engineered base editors," Natural Chemical Biology, Oct. 2021, 17(12):1262-1270.
Blanc et al., "Genome-wide identification and functional analysis of Apobec-1-mediated C-to-U RNA editing in mouse small intestine and liver," Genome Biol., 2014, 15:R79, 17 pages.
Boissel et al., "MegaTALs: A Rare-cleaving Nuclease Architecture for Therapeutic Genome Engineering," Nucleic Acids Research, Feb. 2014, 42(4):2591-2601.
Bolukbasi et al., "DNA-binding-domain Fusions Enhance the Targeting Range and Precision of Cas9," Nature Methods, Dec. 2015, 12(12):1150-1156.
Bransteitter et al., "The Current Structural and Functional Understanding of APOBEC Deaminases," Cellular and Molecular Life Sciences, Oct. 2009, 66(19):3137-3147.

(Continued)

*Primary Examiner* — Paul J Holland
(74) *Attorney, Agent, or Firm* — Fish & Richardson P.C.

(57) ABSTRACT

Engineered adenine base editor (ABE) variants with reduced RNA editing activity, and methods of using the same.

19 Claims, 22 Drawing Sheets

Specification includes a Sequence Listing.

(56) References Cited

OTHER PUBLICATIONS

Bulliard et al., "Structure-Function Analyses Point to a Polynucleotide-Accommodating Groove Essential for APOBEC3A Restriction Activities," J. Virol., Feb. 2011, 85(4):1765-1776.
Byeon et al., "NMR Structure of Human Restriction Factor APOBEC3 A Reveals Substrate Binding and Enzyme Specificity," Nature Communication, May 2013, 4(1):1890, 11 pages.
Chadwick et al., "Reduced Blood Lipid Levels With In Vivo CRISPR-Cas9 Base Editing of ANGPTL3," Circulation, 2018, 137:975-977.
Chen et al., "Apolipoprotein B-48 is the product of a messenger RNA with an organ-specific in-frame stop codon," Science, 1987, 238:363-366.
Chen et al., "Structure of the DNA Deaminase Domain of the HIV-1 Restriction Factor APOBEC3G," Nature, Mar. 2008, 452(7183):116-119.
Chen et al., "Targeted activation of diverse CRIPSR-Cas systems for mammalian genome editing via proximal CRISPR targeting," Nature Communications, Apr. 2017, 8(1):1-12.
Cho et al., "Targeted genome engineering in human cells with the Cas9 RNA-guided endonuclease," Nat. Biotechnol., Mar. 2013, 31(3):230-232.
Chylinski et al., "The tracrRNA and Cas9 families of type II CRISPR-Cas immunity systems," RNA Biol., May 2013, 10(5):726-37.
Cone et al., "Inhibitor of uracil-DNA glycosylase induced by bacteriophage PBS2. Purification and preliminary characterization," Journal of Biological Chemistry, Nov. 1980, 255(21):10354-10358.
Cong et al., "Multiplex genome engineering using CRISPR/Cas systems," Science, Feb. 2013, 339(6121):819-823.
Dahlman et al., "Orthogonal Gene Knockout and Activation with a Catalytically Active Cas9 Nuclease," Nature Biotechnology, Nov. 2015, 33(11):1159-1161.
Dicarlo et al., "Genome engineering in Saccharomyces cerevisiae using CRISPR-Cas systems," Nucleic Acids Res., Mar. 2013, 41(7):4336-4343.
Doman et al., "Evaluation and minimization of Cas9-independent off-target DNA editing by cytosine base editors," Nat. Biotechnol., Feb. 2020, 38(5):620-628, 15 pages.
Ear & Michnick, "A General Life-death Selection Strategy for Dissecting Protein Functions," Nature Methods, Nov. 2009, 6(11):813-816.
EP Extended European Search Report in European Appln. No. 18806041.2, dated Dec. 10, 2020, 8 pages.
EP Extended European Search Report in European Appln. No. 18806459.6, dated Dec. 2, 2020, 9 pages.
Fagerlund et al., "The Cpf1 CRISPR-Cas protein expands genome-editing tools," Genome Biol., Dec. 2015, 16(1):251, 3 pages.
Friedland et al., "Characterization of *Staphylococcus aureus* Cas9: a Smaller Cas9 for All-in-One Adeno-Associated Virus Delivery and Paired Nickase Applications," Genome Biology, Dec. 2015, 16(1):257, 10 pages.
Fu et al., "Improving CRISPR-Cas nuclease specificity using truncated guide RNAs," Nature biotechnology, Mar. 2014, 32(3):279-284.
Fu et al., "Targeted genome editing in human cells using CRISPR/Cas nucleases and truncated guide RNAs," Methods Enzymol, Jan. 2014, 546:21-45.
Gannon et al., "Identification of ADAR1 adenosine deaminase dependency in a subset of cancer cells," Nat. Commun., Dec. 2018, 9(1):5450, 10 pages.
Gasiunas et al., "Cas9-CrRNA Ribonucleoprotein Complex Mediates Specific DNA Cleavage for Adaptive Immunity in Bacteria," Proceedings of the National Academy of Sciences, Sep. 2012, 109(39):E2579-E2586.
Gaudelli et al., "Directed evolution of adenine base editors with increased activity and therapeutic application," Nature Biotechnology, Jul. 2020, 38(7):892-900.

Gehrke et al., "High-precision CRISPR-Cas9 base editors with minimized bystander and off-target mutations," bioRxiv, Jan. 2008, 1:273938, 22 pages.
Grünewald et al., "A dual-deaminase CRISPR base editor enables concurrent adenine and cytosine editing," Nature Biotechnol., Jun. 2020, 38:861-864.
Grünewald et al., "CRISPR adenine and cytosine base editors with reduced RNA off-target activities," Nature Biotechnology, 2019, 37:1041-1048, 25 pages.
Grünewald et al., "CRISPR DNA base editors with reduced RNA off-target and self-editing activities," Nat Biotechnol., Sep. 2019, 37:1041-1048.
Harris et al., "RNA Editing Enzyme APOBEC1 and Some of Its Homologs Can Act as DNA Mutators," Molecular Cell, Nov. 2002, 10(5):1247-1253.
Henry et al., "Evolution of the Primate APOBEC3A Cytidine Deaminase Gene and Identification of Related Coding Regions," PLoS One, 2012, 7(1): E30036, 7 pages.
Hess et al., "Directed Evolution Using DCas9-targeted Somatic Hypermutation in Mammalian Cells," Nat Methods, Dec. 2016, 13(12):1036-1042.
Hess et al., "Methods and Applications of CRISPR-Mediated Base Editing in Eukaryotic Genomes," Mol. Cell., Oct. 2017, 68(1):26-43.
Hirano et al. "Crystal Structure of *Francisella novicida* Cas9," Cell, Feb. 2016, 164(5):950-961, 22 pages.
Holden et al., "Crystal structure of the anti-viral APOBEC3G catalytic domain and functional implications," Nature, Nov. 2008, 456(7218):121-124.
Holtz et al., "APOBEC3G cytosine deamination hotspots are defined by both sequence context and single-stranded DNA secondary structure," Nucleic Acids Research, Jul. 2013, 41(12):6139-6148.
Hu et al., "Evolved Cas9 variants with broad PAM compatibility and high DNA specificity," Nature, Apr. 2018, 556(7699):57-63.
Hwang et al., "Efficient genome editing in zebrafish using a CRISPR-Cas system," Nat. Biotechnol., Jan. 2013, 31(3):227-229.
Hwang et al., "Targeted mutagenesis in zebrafish using CRISPR RNA-guided nucleases," Methods Mol. Biol., 2015, 1311:317-34.
Jasin & Rothstein., "Repair of strand breaks by homologous recombination," Cold Spring Harbor Perspectives in Biology, Nov. 2013, 5(11):a012740, 18 pages.
Jiang et al., "Structures of a CRISPR-Cas9 R-loop Complex Primed for DNA Cleavage," Science, Feb. 2016, 351(6275):867-71, 8 pages.
Jiang et al., "BE-PLUS: a new base editing tool with broadened editing window and enhanced fidelity," Cell Res., Aug. 2018, 28(8):855-861, 7 pages.
Jiang et al., "RNA-guided editing of bacterial genomes using CRISPR-Cas systems," Nat. Biotechnol., Mar. 2013, 31(3):233-239.
Jiang et al., "A Cas9-Guide RNA Complex Preorganized for Target DNA Recognition," Science, Jun. 2015, 348(6242):1477-81.
Jinek et al., "A Programmable Dual-RNA-Guided DNA Endonuclease in Adaptive Bacterial Immunity," Science, Aug. 2012, 337(6096):816-821.
Jinek et al., "RNA-programmed genome editing in human cells," eLife 2, Jan. 2013, 2:e00471, 9 pages.
Jinek et al., "Structures of Cas9 endonucleases reveal RNA-mediated conformational activation," Science, Mar. 2014, 343(6176):154997, 28 pages.
Katrekar et al., "Comprehensive interrogation of the ADAR2 deaminase domain for engineering enhanced RNA editing activity and specificity," eLife, 2022, 11:e75555, 19 pages.
Kim et al. "Increasing the Genome-Targeting Scope and Precision of Base Editing with Engineered Cas9-Cytosine Deaminase Fusions," Nature Biotechnology, Apr. 2017, 35(4):371-376.
Kim et al., "Genome-wide Target Specificities of CRISPR RNA-guided Programmable Deaminases," Nature Biotechnology, May 2017, 34(5):475-480.
Kleinstiver et al., "Broadening the targeting range of *Staphylococcus aureus* CRISPR-Cas9 by modifying PAM recognition," Nat. Biotechnol., Dec. 2015, 33(12):1293-1298.
Kleinstiver et al., "Engineered CRISPR-Cas9 nucleases with altered PAM specificities," Nature, Jul. 2015, 523(7561):481-485.

(56) References Cited

OTHER PUBLICATIONS

Kleinstiver et al., "Genome-wide specificities of CRISPR-Cas Cpf1 nucleases in human cells," Nat. Biotechnol., Aug. 2016, 34(8):869-874.
Kleinstiver et al., "High-fidelity CRISPR-Cas9 nucleases with no detectable genome-wide off-target effects," Nature, Jan. 2016, 529(7587):490-495.
Kohli et al., "A Portable Hot Spot Recognition Loop Transfers Sequence Preferences from APOBEC Family Members to Activation-induced Cytidine Deaminase," Journal of Biological Chemistry, Aug. 2009, 284(34):22898-22904.
Komor et al., "CRISPR-Based Technologies for the Manipulation of Eukaryotic Genomes," Cell, 2017, 168:20-36.
Konermann et al., "Genome-scale transcriptional activation by an engineered CRISPR-Cas9 complex," Nature, Jan. 2015, 517(7536):583-588.
Kouno et al., "Crystal structure of APOBEC3 A bound to single-stranded DNA reveals structural basis for cytidine deamination and specificity," Nat Commun., 2017, 8(15024):1-8.
Kurt et al., "CRISPR C-to-G base editors for inducing targeted DNA transversions in human cells," Nat Biotechnol, Jul. 2020, 39:41-46, 18 pages.
Kuscu & Adli., "CRISPR-Cas9-AID Base Editor Is a Powerful Gain-of-function Screening Tool," Nature Methods, Dec. 2016, 13(12):983-984.
Langlois et al., "Mutational comparison of the single-domained APOBEC3C and double-domained APOBEC3F/G anti-retroviral cytidine deaminases provides insight into their DNA target site specificities," Nucleic Acids Research, Jan. 2005, 33(6):1913-1923.
Lee et al., "New Family of Deamination Repair Enzymes in Uracil-DNA Glycosylase Superfamily," J Biol Chem., Jun. 2011, 286(36):31282-31287.
Li et al., "Targeted, random mutagenesis of plant genes with dual cytosine and adenine base editors," Nature Biotechnology, Jul. 2020, 38(7): 12 pages.
Logue et al., "A DNA sequence recognition loop on APOBEC3A controls substrate specificity," PloS One, May 2014, (5):e97062, 10 pages.
Long et al., "A split cytosine deaminase architecture enables robust inducible base editing," FASEB J, Dec. 2021, 35(12):e22045.
Luscombe et al., "Amino acid-base interactions: a three-dimensional analysis of protein-DNA interactions at an atomic level," Nucleic Acids Research, Jul. 2001, 29(13):2860-2874.
Ma et al., "Single-stranded DNA cleavage by divergent CRISPR-Cas9 enzymes," Molecular Cell, Nov. 2015, 60(3):398-407.
Maeder et al., "Rapid 'Open-Source' Engineering of Customized Zinc-Finger Nucleases for Highly Efficient Gene Modification," Molecular Cell, Jul. 2008, 31(2):294-301.
Makarova et al., "An updated evolutionary classification of CRISPR-Cas systems," Nat. Rev. Microbiol, Nov. 2015, 13(11):722-736.
Mali et al., "RNA-Guided Human Genome Engineering via Cas9," Science, Feb. 2013, 339(6121):823-826.
Michnick et al., Chapter 25: Protein-Fragment Complementation Assays for Large-Scale Analysis, Functional Dissection and Dynamic Studies of Protein-Protein Interactions in Living Cells, Signal Transduction Protocols, Methods in Molecular Biology, Jul. 2011, 395-425.
Mitra et al., "Sequence and Structural Determinants of Human APOBEC3H Deaminase and Anti-HIV-1 Activities," Retrovirology, Dec. 2015, 12(1):3, 15 pages.
Mitra et al., "Structural determinants of human APOBEC3A enzymatic and nucleic acid binding properties,," Nucleic Acids Res., 2014, 42(2):1095-1110.
Mok et al., "A bacterial cytidine deaminase toxin enables CRISPR-free mitochondrial base editing," Nature, Jul. 2020, 583(7817):631-637.
Nair et al., "Biochemical and Biological Studies of Mouse APOBEC3," Journal of Virology, Apr. 2014, 88(7):3850-3860.
Nishimasu et al., "Crystal structure of Cas9 in complex with guide RNA and target DNA," Cell, Feb. 2014, 156(5):935-949.
Nishimasu et al., "Engineered CRISPR-Cas9 nuclease with expanded targeting space," Science, Sep. 2018, 361(6408):1259-1262, 8 pages.
Osborn et al., "Fanconi anemia gene editing by the CRISPR/Cas9 system," Hum. Gene. Ther., Feb. 2015, 26(2):114-126.
Park et al., "Off-target Editing by CRISPR-guided DNA base editors," Biochemistry, 2019, 58(36):3727-3734.
Pattanayak et al., "Revealing off-Target Cleavage Specificities of Zinc-Finger Nucleases by in Vitro Selection," Nature Methods, Sep. 2011, 8(9):765.
PCT International Preliminary Report on Patentability in International Appln. No. PCT/US2018/034687, dated Dec. 5, 2019, 9 pages.
PCT International Preliminary Report on Patentability in International Appln. No. PCT/US2018/034719, dated Dec. 5, 2019, 8 pages.
PCT International Preliminary Report on Patentability in International Appln. No. PCT/US2018/034742, dated Dec. 5, 2019, 8 pages.
PCT International Preliminary Report on Patentability in International Appln. No. PCT/US2019/055705, dated Apr. 22, 2021, 12 pages.
PCT International Preliminary Report on Patentability in International Appln. No. PCT/US2020/016664, dated Aug. 19, 2021, 6 pages.
PCT International Search Report and Written Opinion in International Appln. No. PCT/US2018/034687, dated Sep. 24, 2018, 13 pages.
PCT International Search Report and Written Opinion in International Appln. No. PCT/US2018/034719, dated Sep. 20, 2018, 13 pages.
PCT International Search Report and Written Opinion in International Appln. No. PCT/US2018/034742, dated Sep. 24, 2018, 13 pages.
PCT International Search Report and Written Opinion in International Appln. No. PCT/US2019/055705, dated Apr. 1, 2020, 17 pages.
PCT International Search Report and Written Opinion in International Appln. No. PCT/US2020/048777, dated Feb. 2, 2021, 12 pages.
PCT International Search Report and Written Opinion in International Appln. No. PCT/US2020/048825, dated Feb. 26, 2021, 13 pages.
Pham et al., "Structural Analysis of the Activation-induced Deoxycytidine Deaminase Required in Immunoglobulin Diversification," DNA Repair, Jul. 2016, 43:48-56.
Porto et al., "Base editing: advances and therapeutic opportunities," Nature Reviews Drug Discovery, Dec. 2020, 19(12):839-859.
Rathore et al., "The local dinucleotide preference of APOBEC3G can be altered from 5'-CC to 5'-TC by a single amino acid substitution," J. Mol. Biol., Nov. 2013, 425(22):4442-4454.
Rebhandl et al., "AID/APOBEC Deaminases and Cancer," Oncoscience 2, Apr. 2015, 2(4):320-333.
Rees et al., "Analysis and minimization of cellular RNA editing by DNA adenine base editors," Sci. Adv., May 2019, 5(5):eaax5717, 10 pages.
Rees et al., "Improving the DNA specificity and applicability of base editing through protein engineering and protein delivery," Nat Commun., Jun. 2017, 8(1):1-10.
Richter et al., "Phage-assisted evolution of an adenine base editor with improved Cas domain compatibility and activity," Nature Biotechnology, Mar. 2020, 38:883-891.
Rosenberg et al., "Transcriptome-wide sequencing reveals numerous APOBEC1 mRNA-editing targets in transcript 3' UTRs," Nat Struct Mol Biol., 2011, 18:230-236.
Sakata et al., "A single CRISPR base editor to induce simultaneous C-to-T and A-to-G mutations," bioRxiv, Aug. 2019, 17 pages.
Salter et al., "The APOBEC Protein Family: United by Structure, Divergent in Function," Trends Biochem Sci., Jul. 2016, 41(7):578-594.
Sanjana et al., "A transcription activator-like effector toolbox for genome engineering," Nature Protocols, Jan. 2012, 7(1):171-192.

(56) References Cited

OTHER PUBLICATIONS

Santos-Pereira et al., "R Loops: New Modulators of Genome Dynamics and Function," Nature Reviews Genetics, Oct. 2015, 16(10):583-597.
Schunder et al., "First indication for a functional CRISPR/Cas system in *Francisella tularensis*," Int. J. Med. Microbiol., Mar. 2013, 303(2):51-60, 29 pages.
Shandilya et al., "Crystal Structure of the APOBEC3G Catalytic Domain Reveals Potential Oligomerization Interfaces," Structure, Jan. 2010, 18(1):28-38.
Shen et al., "Generation of gene-modified mice via Cas9/RNA-mediated gene targeting," Cell Res., Apr. 2013, 23(5):720-723.
Shi et al., "Crystal Structure of the DNA Deaminase APOBEC3B Catalytic Domain," Journal of Biological Chemistry, Nov. 2015, 290(47):28120-28130.
Shi et al., "Structural Basis for Targeted DNA Cytosine Deamination and Mutagenesis by APOBEC3A and APOBEC3B," Nature Structural & Molecular Biology, Feb. 2017, 24(2):131-139.
Shimatani et al., "Targeted base editing in rice and tomato using a CRISPR-Cas9 cytidine deaminase fusion," Nat Biotechnol., 2017, 35:441-443.
Shinmura et al., "Aberrant Expression and Mutation-Inducing Activity of AID in Human Lung Cancer," Ann. Surg. Oncol., Feb. 2011, 18(7):2084-2092.
Shinohara et al., "APOBEC3B can impair genomic stability by inducing base substitutions in genomic DNA in human cells," Scientific Reports, 2012, 2:806.
Shmakov et al., "Discovery and functional characterization of diverse class 2 CRISPR-Cas systems," Mol. Cell., Nov. 2015, 60(3):385-397.
Skuse et al., "The neurofibromatosis type I messenger RNA undergoes base-modification RNA editing," Nucleic Acids Res., 1996, 24:478-485.
Slaymaker et al., "Rationally Engineered Cas9 Nucleases with Improved Specificity," Science, Jan. 2016, 351(6268):84-88.
Sowden et al., "Overexpression of APOBEC-1 results in mooring sequence-dependent promiscuous RNA editing," J Biol Chem., 1996, 271:3011-3017.
Sternberg et al., "DNA interrogation by the CRISPR RNA-guided endonuclease Cas9," Nature, Mar. 2014, 507(7490):62-67, 17 pages.
Suspène et al., "Recovery of APOBEC3-edited human immunodeficiency virus G→ A hypermutants by differential DNA denaturation PCR," Journal of General Virology, Jan. 2005, 86(1):125-129.
Tang et al., "A CRISPR-Cpf1 System for Efficient Genome Editing and Transcriptional Repression in Plants," Nature Plants, Feb. 2017, 3:17108, 5 pages.
Teng et al., "Molecular cloning of an apolipoprotein B messenger RNA editing protein," Science, 1993, 260:1816-1819.
Thuronyi et al., "Continuous evolution of base editors with expanded target compatibility and improved activity," Nat Biotechnol., 2019, 37:1070-1079.
Tsai & Joung., "Defining and improving the genome-wide specificities of CRISPR-Cas9 nucleases," Nat. Rev. Genet., May 2016, 17(5):300-312.
Tsai et al., "Dimeric CRISPR RNA-guided FokI nucleases for highly specific genome editing," Nat. Biotechnol., Jun. 2014, 2(6):569-576.
Tsai et al., "GUIDE-seq Enables Genome-wide Profiling of Off-target Cleavage by CRISPR-Cas Nucleases," Nature Biotechnology, Feb. 2015, 33(2):187-197.
Weeks et al., "Uracil-DNA glycosylase expression determines human lung cancer cell sensitivity to pemetrexed," Mol. Cancer Ther., 2013, 12(10):2248-60.
Woolf et al., "To cleave or not to cleave: therapeutic gene editing with and without programmable nucleases," Nat. Rev. Drug Discov., Mar. 2017, 16(4):296, 3 pages.
Wu et al., "Genome-wide Binding of the CRISPR Endonuclease Cas9 in Mammalian Cells," Nature Biotechnology, Jul. 2014, 32(7):670-676.
Wyvekens et al., "Dimeric CRISPR RNA-Guided FokI-dCas9 Nucleases Directed by Truncated gRNAs for Highly Specific Genome Editing," Hum. Gene. Ther., Jul. 2015, 26(7):425-431.
Xin et al., "Off-Targeting of Base Editors: BE3 but not ABE induces substantial off-target single nucleotide variants," Signal Transduct. Target. Ther., Apr. 2019, 4(9): 2 pages.
Yamada et al., "Crystal Structure of the Minimal Cas9 from *Campylobacter jejuni* Reveals the Molecular Diversity in the CRISPR-Cas9 Systems," Molecular Cell, Mar. 2017, 65(6):1109-1121.
Yamanaka et al., "A novel translational repressor mRNA is edited extensively in livers containing tumors caused by the transgene expression of the apoB mRNA-editing enzyme," Genes Dev., 1997, 11:321-333.
Yamanaka et al., "Hyperediting of multiple cytidines of apolipoprotein B mRNA by APOBEC-1 requires auxiliary protein(s) but not a mooring sequence motif," J Biol Chem., 1996, 271:11506-11510.
Yamano et al., "Crystal Structure of *Acidaminococcus* Sp. Cpf1 in Complex with CrRNA and Target DNA," May 2016, 165(4):949-962.
Yang et al., "APOBEC: from mutator to editor," J. Genet. Genomics., Sep. 2017, 20;44(9):423-437.
Yang et al., "Engineering and optimising deaminase fusions for genome editing," Nature Communications, 2016, 7:1-12.
Yeh et al., "In vivo base editing of post-mitotic sensory cells," Nat Commun., 2018, 9:2184, 10 pages.
Zafra et al., "Optimized base editors enable efficient editing in cells, organoids and mice," Nat Biotechnol., 2018, 36:888-893.
Zetsche et al., "Cpf1 is a single RNA-guided endonuclease of a class 2 CRISPR-Cas system," Cell, 2015, 163(3):759-771.
Zhang et al., "Annual Review of Biochemistry Synthetic Genomes," Annu. Rev. Biochem., Jun. 2020, 89:77-101.
Zhang et al., "Programmable base editing of zebrafish genome using a modified CRISPR-Cas9 system," Nat Commun., 2017, 8:118, 5 pages.
Zhou et al., "Off-target RNA mutation induced by DNA base editing and its elimination by mutagenesis," Nature, Jul. 2019, 571(7764):275-278, 18 pages.
Zong et al., "Precise base editing in rice, wheat and maize with a Cas9-cytidine deaminase fusion," Nat Biotechnol., 2017, 35:438-440.
Chen et al., "Hypermutation induced by APOBEC-1 overexpression can be eliminated," RNA, May 2010, 16(5):1040-1052.
Chester et al., "The apolipoprotein B mRNA editing complex performs a multifunctional cycle and suppresses nonsense-mediated decay," EMBO J. Aug. 2003, (15):3971-3982.
Clement et al., "CRISPResso2 provides accurate and rapid genome editing sequence analysis," Nat. Biotechnol., Mar. 2019, 37(3):224-226.
DePristo et al., "A framework for variation discovery and genotyping using next-generation DNA sequencing data," Nat. Genet., May 2011, 43(5):491-498.
Dobin et al., "STAR: ultrafast universal RNA-seq aligner," Bioinformatics, Jan. 2013, 29(1):15-21.
Fritz et al., "A comprehensive analysis of the effects of the deaminase AID on the transcriptome and methylome of activated B cells," Nat. Immunol., Jul. 2013, 14(7):749-755.
Gaudelli et al., "Programmable Base Editing of A•T to G•C in Genomic DNA Without DNA Cleavage," Nature, Nov. 2017, 551(7681):464-471.
Gehrke et al., "An APOBEC3A-Cas9 base editor with minimized bystander and off-target activities," Nat. Biotechnol., Oct. 2018, 36(10):977-982.
Grünewald et al., "Transcriptome-wide off-target RNA editing induced by CRISPR-guided DNA base editors," Nature, May 2019, 569(7756):433-437.
Kim et al., "Structural and kinetic characterization of *Escherichia coli* TadA, the wobble-Specific tRNA deaminase," Biochemistry, May 2006, 45(20):6407-6416.
Koblan et al., "Improving cytidine and adenine base editors by expression optimization and ancestral reconstruction, Supplementary Information," Nat. Biotechnol. 2018, 43 pages.

(56) References Cited

OTHER PUBLICATIONS

Koblan et al., "Improving cytidine and adenine base editors by expression optimization and ancestral reconstruction," Nat. Biotechnol., Oct. 2018, 36(9):843-846.

Komor et al., "Improved base excision repair inhibition and bacteriophage Mu Gam protein yields C:G-to-T:A base editors with higher efficiency and product purity," Sci. Adv., Aug. 2017, 3(8):eaao4774.

Komor et al., "Programmable editing of a target base in genomic DNA without double-stranded DNA cleavage," Nature, May 2016, 533(7603):420-424.

Laird et al., "Simplified mammalian DNA isolation procedure," Nucleic Acids Res., Aug. 1991, 19(15):4293.

MacGinnitie et al., "Mutagenesis of apobec-1, the Catalytic Subunit of the Mammalian Apolipoprotein B mRNA Editing Enzyme, Reveals Distinct Domains That Mediate Cytosine Nucleoside Deaminase, RNA Binding, and RNA Editing Activity," J. Biol. Chem., Jun. 1995, 270(24):14768-14775.

McKenna et al., "The Genome Analysis Toolkit: a MapReduce framework for analyzing next-generation DNA sequencing data," Genome Res., Sep. 2010, 20(9):1297-1303.

Navaratnam et al., "Evolutionary origins of apoB mRNA editing: Catalysis by a cytidine deaminase that has acquired a novel RNA-binding motif at its active site," Cell, Apr. 1995, 81(2):187-195.

Nishida et al., "Targeted nucleotide editing using hybrid prokaryotic and vertebrate adaptive immune systems," Science, Sep. 2016, 353(6305):aaf8729.

PCT International Search Report and Written Opinion in International Appln. No. PCT/US2020/016664, dated May 22, 2020,.

Rees & Liu, "Base editing: precision chemistry on the genome and transcriptome of living cells," Nat. Rev. Genet., Dec. 2018, 19(12):770-788.

Rohland & Reich, "Cost-effective, high-throughput DNA sequencing libraries for multiplexed target capture," Genome Res., Jan. 2012, 22:939-946.

Sharma et al., "Transient overexpression of exogenous APOBEC3A causes C-to-U RNA editing of thousands of genes," RNA Biol., May 2017, 14(5):603-610.

Teng et al., "Mutational Analysis of Apolipoprotein B mRNA Editing Enzyme (APOBEC1). Structure-Function Relationships of RNA Editing and Dimerization," J. Lipid Res., Apr. 1999, 40(4):623-635.

Wang et al., "Efficient base editing in methylated regions with a human APOBEC3A-Cas9 fusion," Nat. Biotechnol., Aug. 2018, 36(10):946-949.

Wolf et al., "tadA, an essential tRNA-specific adenosine deaminase from *Escherichia coli*," EMBO J., Jul. 2002, 21(14):841-3851.

Yamanaka et al., "Cloning and mutagenesis of the rabbit ApoB mRNA editing protein. A zinc motif is essential for catalytic activity, and noncatalytic auxiliary factor(s) of the editing complex are widely distributed," J Biol Chem., Aug. 1994, 269(34):21725-21734.

Yan and Kurgan, "DRNApred, fast sequence-based method that accurately predicts and discriminates DNA- and RNA-binding residues," Nucleic Acids Res., Jun. 2017, 45(10):e84.

Mali et al., "CAS9 transcriptional activators for target specificity screening and paired nickases for cooperative genome engineering," Nat. Biotechnol., Sep. 2013, 31(9):833-838, 8 pages.

Extended European Search Report in European Appln. No. 20752430.7, dated Oct. 7, 2022, 11 pages.

Singh et al., "Protein Engineering Approaches in the Post-Genomic Era," Curr. Protein Pept. Sci., 2017, 18:1-11.

Stier et al., "Cytosine-to-uracil deamination by SssI DNA methyltransferase," PLoS One, Oct. 2013, 8(10):e79003, 10 pages.

Ma et al., "AID-mediated in situ target mutations: a new technology for mammalian DNA base editing," Chinese Journal of Cell Biology, 2017, 39(3):255-260, 8 pages (with English abstract).

Gajula, "Designing an Elusive C•G→G•C CRISPR Base Editor," Trends Biochem Sci., Feb. 2019, 44(2):91-94.

Ma et al., "Integration and exchange of split dCas9 domains for transcriptional controls in mammalian cells," Nat. Comm., Oct. 2016, 7:13056, 7 pages.

Molla et al., "Base Editing Landscape Extends to Perform Transversion Mutation," Trends Genet., Dec. 2020, 36(12):899-901.

Shivarov et al., "Dissociation of in vitro DNA deamination activity and physiological functions of AID mutants," Proc. Natl. Acad. Sci. USA, Oct. 2008, 105(41):15866-15871.

Zhao et al., "Glycosylase base editors enable C-to-A and C-to-G base changes," Nat Biotechnol., Jan. 2021, 39(1):35-40, 11 pages.

\* cited by examiner

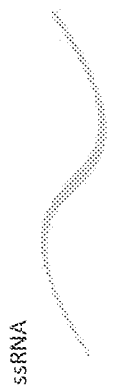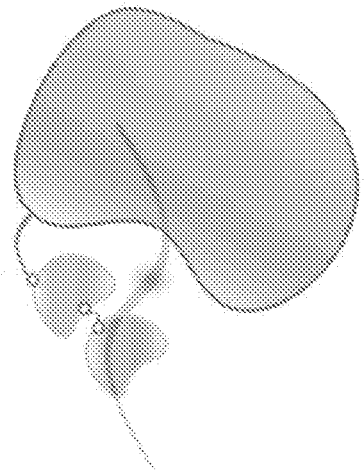
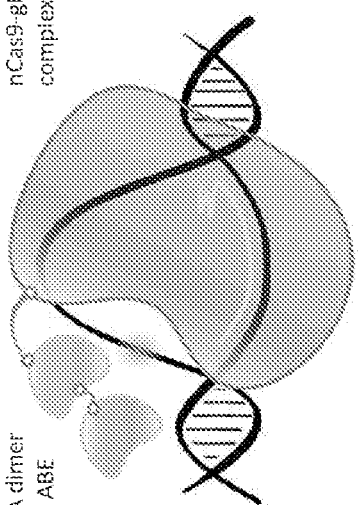
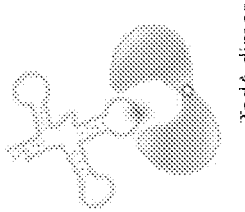

Figs. 6A-F

Supplementary Table 2: guide RNA sequences, primer sequences, and amplicon sequences All gRNAs were of the form 5'-NNNNNNNNNNNNNNNNNNNNGTTTTAGAGCTAGAAATAGCAAGTTAAAATAAGGCTAGTCCGTTATCAACTTGAAAAAGTGGCACCGAGTCGGTGCTTTTTT-3'.
BPK1520, Addgene #65777

Shown below are the protospacer regions (NNNNNNNNNNNNNNNNNNNN in for these gRNAs (all written 5' to 3'), primers to amplify genomic loci for these gRNAs, and the genomic amplicon.

| gRNA # | target gene/site | protospacer sequence | PAM | Fwd PCR1 | Rev PCR1 | Amplicon |
|---|---|---|---|---|---|---|
| Cas9 guide RNA 1 | non-targeting | GGAGACGATTAATGCGTCTCC | - | - | - | non-targeting |
| Cas9 guide RNA 2 | HEK site 2 | GAACACAAAGCATAGACTGC | GGG | ACACTCTTTCCCTACACGACGCTCTTCCGATCtCACAAG ACCTGGCTGAGCTAACTGTG | GACTGGAGTTCAGACGTGTGCTCTTCCGATCtC CAGCCCCATCTCTGTCAAACTGTG | ACAAGACCTGGCTGAGCTAACTGTGACAGCATGTGGTAATTTTCCAGCCGCTGGCCTGT AAAGGAAACTGGAACACAAAGCATAGACTGCGGGCCGGGCCAGCCTGAATAGCTGCAAAC AAGTGCAGAATATCTGATGTCATACGCACAGTTGACAGATGGGGCTGG |
| Cas9 guide RNA 3 | ABE site 14 | GGCTAAAGACCATAGACTGT | GGG | ACACTCTTTCCCTACACGACGCTCTTCCGATCtAGTGT TGGGATTACAGCCTGA | GACTGGAGTTCAGACGTGTGCTCTTCCGATCtA ACCTGAAGGCCTTTCCCAA | ACCTGAAGGCCTTTCCCAAACCATTTGGATGCTTGAAGAACTCAATAGGCATCTGAGAGA CTGGGCTAAAGACCATAGACTGTGGGAATGAAACTCACACATTGAGTGCTTGTACTTTCCTT ATGCCAAGTGTCACACAGGTTAGAGAATACTCCATCTTTGGCCGGCACGGTGGCTCAGGC TGTAATCCCAACACT |
| Cas9 guide RNA 4 | ABE site 16 | GGGAATAAATCATAGAATCC | TGG | ACACTCTTTCCCTACACGACGCTCTTCCGATCtCTCT ATCCACCTGAATGAGTTT | GACTGGAGTTCAGACGTGTGCTCTTCCGATCtC AGCAATCCACGCAACACGC | CAGCAATCCAGCAACACGCGGGAGGTGAGAGAGGATGTTTTGCTTATCCAGAAAAGGG AGTGATTGCTTCCAGGGGCCTCAGGGAATAAATCATAGAATCCTGGACAAGGTTGAAGG ACAGGATGGATTTGGGTGGGTGGAGGAGGGTGCATGGGGTCAGAATTGTAACCGAAAACT CATTCCAGGTGGATAGAGC |
| Cas9 guide RNA 5 | ABE site 19 | CACACACACTTAGAATCTG | TGG | ACACTCTTTCCCTACACGACGCTCTTCCGATCtATCTC AGCGCTTTCGTCCAC | GACTGGAGTTCAGACGTGTGCTCTTCCGATCtC TCATTTCCCCACTCCTCC | ATCTCAGCGCTTTCGTCCACCACCCCTCTACACACACAGACCACACACACACTTAGAATCT GTGGAAGTGAGACCCAGCAATCTCTGTTTGCACAAACCCTCCAGGAATTCTGATGCCCG TGAAGTTTGAGAACTACATACGTTTCTGCAGGGAGAACCTGGAACAAGGAG GGAGTGGGGAAATGAG |
| Cas9 guide RNA 6 | RNF2 site 1 | GTCATCTTAGTCATTACCTG | AGG | ACACTCTTTCCCTACACGACGCTCTTCCGATCtGTGC AGACAAACGGAACTCAACC | GACTGGAGTTCAGACGTGTGCTCTTCCGATCtG CAACATACAGAGTCAGGAATGCTTAG | CCAACATACAGAGTCAGGAATGCTTACCCAGTTAACTCATAAACTGAGTTCCATGTTGCTTAATGGTT TTTCATGTTCTAAAAATGTATCCCAGTTTACACGTCTCATATGCCCCTTGGCtCATCTTAG TCATTACCTAGGTGTCGTTGAATAGGTGCACGTGCAGGATAGGCAC GAGTTCCGTTTGTCTGCAC |
| | RNA site 1 (DNAJB1) (chr19: 14518195) | - | - | ACACTCTTTCCCTACACGACGCTCTTCCGATCtCCATGG CATGAGGGGTCTCCATCG | GACTGGAGTTCAGACGTGTGCTCTTCCGATCtG CGCTACCACCCCGGACACG | GCGCTACCACCCCGGACAAGAACAAGGAGGCCGGCGCCGAGGAGAAGTTCAAGGAGATCG CTGAGGCCTACGACGTCCAGGGACCCGCCAAGCGCGAGATCTTCGACCGCTACGGG GAGGAAGGCCTAAAGGGAGTGGCCCCATGGGGTAGCGCGGTGGTGCCAATGGTAC CTCTTCAGCTACACATTCCATTGGAGACCCCATGCCATG |
| | RNA site 2 (MT1A2) (chr11: 62594034) | - | - | ACACTCTTTCCCTACACGACGCTCTTCCGATCtATGG GAGGGTGCAGGTAGAGGG | GACTGGAGTTCAGACGTGTGCTCTTCCGATCtG GGATTCGTTCAAGCTCACAGC | GGGATTCGTTCAAGCTCACAGCAGCAGCAGCGAAGGGTCAGAAACTAAACCGCGATGCCC CCAATCCTCTGTGTTTTCTGCCCACAAAGGATACCAGGGGCCTCGGAAAGCCTCTGACCCA TCTGGAAATGCGGCGGCCCATTGCTCGCGCAGCCAACTTGCCGCTGAAGGTGAAGCCAAGCT GATTGCAGTGCGGGGCCCCTGTCCCTGTCCCACCCTCACTC |
| | RNA site 3 (PTBP2) (chr1: 98613053) | - | - | ACACTCTTTCCCTACACGACGCTCTTCCGATCtGATT TTGGTAATTCCCCATTGCCATG | GACTGGAGTTCAGACGTGTGCTCTTCCGATCtC CTGAATAGCTTCTTCCACTGTTGCC | AGATTTTGGTAATTCCCCATTGCATGGTTTTAAGAAACCTGATCCAAAAATTTTCAAAACAT TTTCCTTCTGCCACCCTTCACCTATCTAATATCCCTCCATCAGTAGCAGAGAGGATCA CGAACACTGTTCCCTAACACTGGGGACTGTGAAAGCATTAAGTTTTTTCAAAGAGATCA CAAAATGGCTCTTCTTCAGAGCAACAGTGGAAGAAGCATTCAGG |
| | RNA site 4 (SAP30BP) (chr17: 75703318) | - | - | ACACTCTTTCCCTACACGACGCTCTTCCGATCtCAGAA CCCCTGGCAGATGTTC | GACTGGAGTTCAGACGTGTGCTCTTCCGATCtT CCTCAGACCCAGCCATGGGG | CAGAACCCCTGGCAGTGTTCAAATCACTTGCAAGACAAGATCCAGAAGCTTATGAACGA AAGATAAAGAGGGAATGGAATATGAACTACATTATCCAAAGGAGAAAGAATTTCGGAACCG TAGCATCTACGAGAAGCTGATCCAGTTCTCTGTGCCATTGGACGAGGCTTGGCACCAACTACCCA AAGGATATGTTTGATCCCCATGGCTGTCTGAAGGA |
| | RNA site 5 (LCMT1) (chr16: 25164711) | - | - | ACACTCTTTCCCTACACGACGCTCTTCCGATCtATTGC CAACACTCCTGATAGCTGAATG | GACTGGAGTTCAGACGTGTGCTCTTCCGATCtG ACTTGCAGGGTCTCCACTCCCG | ATTGCCAACACTCCTGATAGCTGAATGTGTTGGTTTACATGACTCCAGAGAGTCCGCA ACCTCCTGAAGTGGGCAGCCAACAGTTTTGAGAGCATGTTCATGTCATAAACACGAACAGGT GAACATGGGTGATCGGTTTGGGCAGATCATGATTGAAAACCTGGAGAGCCAGTGTGAC CTGGCGGGAGTGGAGACCTGCAAGTC |
| | RNA site 6 (SCAP) (chr3: 47420696) | - | - | ACACTCTTTCCCTACACGACGCTCTTCCGATCtAAGT AGACAACAGCAGCCTCTTG | GACTGGAGTTCAGACGTGTGCTCTTCCGATCtG CATTGACATTCGCAGGAGAG | CTCCATCCGGGAATGTCAATGGCTAGCAGACCTGAATGGCTAGCACGGCCTGAAGCCT AGCTGCCCTCAGCCAAGCCAGTGGACAGCAGCCAAGCGACTGCTCAAAGCGGCCTGCTGTG AGCCGCTCCAGCACCACCATCACGTTGCAGCCGTTCTCCTTCCGAAACCTGCGGCTCC CCAAGAGGCTGCGTGTTGTCTACTTC | red = Illumina adpter sequence    green = Illumina adpter sequence

The gRNA1 protospacer sequence is the "BsmbI filler sequence" in gRNA entry vector BPK1520. This gRNA is not targeting a known sequence in the human genome.
We used CasOFFinder, an online tool to predict potential Cas9 off-target sites (up to 6 mismatches, excluding bulges), to check for potential binding sites of Cas9 when using gRNA1: http://www.rgenome.net/cas-offinder/
this method was described by Bae et al, Bioinformatics 2014 - PMID 24463181

| # Mismatches | Number of Found Targets |
|---|---|
| 4 | 6 |
| 5 | 88 |
| 6 | 946 |

ABE gRNAs were described by Gaudelli et al, Nature 2017

All remaining gRNAs are widely used in the field and e.g. described in Kleinstiver et al, Nature 2016 - PMID 28735016 or Komor et al, Sci Adv 2017 - PMID 28875174

| | Average DNA on-target (A>G editing efficiency) | | | | | | | | |
|---|---|---|---|---|---|---|---|---|---|
| | HEKs2_A5 | HEKs2_A7 | ABEs3_A5 | ABEs3_A4 | ABEs3_A5 | ABEs3_A7 | ABEs4_A5 | ABEs4_A6 | ABEs4_A7 |
| Control | 1% | 0% | 1% | 0% | 3% | 1% | 1% | 0% | 0% |
| ABEmax | 31% | 6% | 73% | 6% | 71% | 14% | 71% | 56% | 13% |
| miniABE | 39% | 15% | 70% | 15% | 62% | 26% | 72% | 63% | 24% |
| ABEmaxAW | 26% | 2% | 64% | 3% | 53% | 7% | 59% | 53% | 8% |
| *K20A/R21A | 33% | 6% | 64% | 6% | 41% | 10% | 58% | 42% | 11% |
| *V82G | 25% | 13% | 53% | 15% | 46% | 25% | 58% | 52% | 27% |
| Y10A | 36% | 15% | 64% | 14% | 57% | 24% | 67% | 57% | 23% |
| W11A | 26% | 5% | 50% | 3% | 25% | 10% | 50% | 37% | 13% |
| MI1A | 3% | 0% | 9% | 0% | 3% | 1% | 5% | 1% | 1% |
| T17A | 37% | 18% | 73% | 15% | 65% | 28% | 68% | 58% | 23% |
| R23W | 38% | 7% | 69% | 8% | 46% | 14% | 67% | 55% | 13% |
| H57A | 1% | 0% | 1% | 0% | 3% | 1% | 1% | 0% | 0% |
| A58G | 18% | 5% | 54% | 4% | 29% | 10% | 54% | 42% | 14% |
| E59A | 1% | 0% | 1% | 0% | 3% | 1% | 1% | 0% | 0% |
| Q71A | 32% | 14% | 68% | 14% | 59% | 26% | 69% | 59% | 23% |
| N72A | 29% | 9% | 65% | 11% | 53% | 23% | 62% | 51% | 18% |
| R74A | 17% | 0% | 51% | 0% | 5% | 0% | 22% | 3% | 1% |
| D77A | 31% | 17% | 67% | 15% | 64% | 35% | 70% | 64% | 28% |
| M89A | 2% | 0% | 4% | 0% | 3% | 0% | 2% | 1% | 0% |
| V106W | 28% | 5% | 61% | 6% | 49% | 12% | 54% | 55% | 16% |
| R107A | 32% | 8% | 64% | 6% | 44% | 20% | 60% | 51% | 18% |
| A109W | 33% | 4% | 66% | 6% | 61% | 9% | 63% | 50% | 20% |
| K110A | 23% | 1% | 64% | 1% | 28% | 3% | 29% | 27% | 9% |
| H122A | 19% | 5% | 62% | 5% | 36% | 10% | 58% | 46% | 14% |
| Y123A | 23% | 5% | 47% | 2% | 26% | 6% | 43% | 32% | 11% |
| H128A/R129A | 29% | 7% | 55% | 2% | 31% | 8% | 48% | 43% | 15% |
| A138W | 28% | 12% | 65% | 11% | 44% | 13% | 56% | 47% | 16% |
| D139A/E140A | 24% | 11% | 47% | 6% | 44% | 14% | 49% | 41% | 18% |
| A142W | 29% | 4% | 65% | 6% | 47% | 9% | 57% | 53% | 16% |
| L14SA | 17% | 1% | 48% | 0% | 10% | 0% | 6% | 4% | 1% |
| C146A | 20% | 14% | 50% | 14% | 55% | 35% | 50% | 46% | 27% |
| F148A | 24% | 4% | 62% | 1% | 18% | 3% | 30% | 26% | 6% |
| R150A | 22% | 2% | 64% | 2% | 27% | 4% | 44% | 20% | 6% |
| R153A | 23% | 7% | 65% | 6% | 34% | 15% | 54% | 45% | 14% |
| F156A | 19% | 1% | 59% | 3% | 43% | 5% | 43% | 41% | 15% |
| N157A | 19% | 10% | 44% | 11% | 41% | 22% | 47% | 41% | 19% |

FIG. 16A

| Average RNA off-target (A>G editing efficiency) | | | | | | | |
|---|---|---|---|---|---|---|---|
|  | RNAs1 | RNAs1.1 | RNAs2 | RNAs3 | RNAs4 | RNAs5 | RNAs6 |
| Control | 0.3% | 0.1% | 0.1% | 0.1% | 0.1% | 0.1% | 0.1% |
| ABEmax | 90.2% | 3.3% | 61.0% | 58.5% | 50.3% | 61.9% | 60.0% |
| miniABE | 12.4% | 5.0% | 6.0% | 0.8% | 1.9% | 5.1% | 1.6% |
| ABEmaxAW | 13.8% | 0.5% | 16.7% | 4.1% | 2.9% | 20.1% | 7.9% |
| *K20A/R21A | 2.3% | 0.8% | 1.4% | 0.0% | 0.3% | 2.0% | 0.5% |
| *V82G | 0.5% | 0.1% | 0.7% | 0.0% | 0.1% | 0.7% | 0.3% |
| Y10A | 6.0% | 2.5% | 4.0% | 0.4% | 0.8% | 4.1% | 0.9% |
| W11A | 0.1% | 0.1% | 0.1% | 0.0% | 0.0% | 0.2% | 0.1% |
| MI1A | 0.1% | 0.0% | 0.0% | 0.0% | 0.0% | 0.1% | 0.0% |
| T17A | 11.5% | 4.4% | 4.9% | 0.8% | 1.3% | 4.7% | 1.6% |
| R23W | 12.9% | 4.6% | 5.6% | 0.2% | 1.0% | 6.1% | 1.3% |
| H57A | 0.1% | 0.1% | 0.1% | 0.1% | 0.1% | 0.1% | 0.1% |
| A58G | 2.2% | 0.9% | 1.6% | 0.3% | 0.2% | 2.0% | 0.5% |
| E59A | 0.3% | 0.1% | 0.2% | 0.1% | 0.1% | 0.4% | 0.1% |
| Q71A | 7.0% | 2.9% | 3.2% | 0.3% | 0.8% | 3.3% | 0.9% |
| N72A | 4.1% | 1.9% | 3.8% | 0.1% | 0.5% | 2.3% | 0.6% |
| R74A | 0.4% | 0.2% | 0.2% | 0.2% | 0.0% | 0.2% | 0.1% |
| D77A | 9.2% | 4.6% | 4.6% | 0.6% | 1.2% | 4.7% | 1.2% |
| M89A | 0.1% | 0.1% | 0.0% | 0.0% | 0.0% | 0.1% | 0.0% |
| V106W | 3.7% | 2.7% | 2.3% | 0.1% | 0.3% | 1.6% | 0.5% |
| R107A | 3.9% | 1.5% | 2.1% | 0.3% | 0.5% | 2.9% | 0.5% |
| A109W | 11.6% | 2.9% | 3.2% | 0.3% | 1.0% | 6.9% | 0.8% |
| K110A | 1.8% | 0.9% | 0.7% | 0.1% | 0.2% | 0.8% | 0.3% |
| H122A | 7.4% | 2.6% | 2.9% | 0.1% | 0.5% | 3.6% | 0.9% |
| Y123A | 7.3% | 2.2% | 3.1% | 0.2% | 0.8% | 4.2% | 0.9% |
| H128A/R129A | 1.9% | 0.8% | 1.3% | 0.1% | 0.2% | 1.2% | 0.5% |
| A138W | 5.1% | 1.8% | 2.6% | 0.2% | 0.6% | 2.7% | 0.7% |
| D139A/E140A | 0.2% | 0.1% | 0.4% | 0.1% | 0.1% | 0.7% | 0.2% |
| A142W | 4.8% | 2.8% | 2.3% | 0.2% | 0.3% | 1.3% | 0.6% |
| L145A | 1.2% | 0.5% | 0.6% | 0.1% | 0.1% | 0.8% | 0.1% |
| C146A | 14.8% | 8.1% | 6.7% | 0.8% | 2.6% | 4.7% | 2.1% |
| F148A | 5.6% | 2.8% | 2.5% | 0.2% | 0.7% | 2.5% | 0.7% |
| R150A | 3.5% | 1.2% | 1.5% | 0.1% | 0.2% | 3.0% | 0.3% |
| R153A | 7.9% | 4.1% | 4.1% | 0.2% | 0.7% | 2.7% | 0.9% |
| F156A | 14.2% | 2.1% | 4.7% | 0.7% | 0.6% | 9.8% | 1.4% |
| N157A | 12.1% | 5.5% | 4.8% | 0.5% | 1.6% | 4.7% | 1.3% |

FIG. 16B

```
                            SEQUENCE LISTING

<160> NUMBER OF SEQ ID NOS: 106

<210> SEQ ID NO 1
<211> LENGTH: 167
<212> TYPE: PRT
<213> ORGANISM: Escherichia coli

<400> SEQUENCE: 1

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
                20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp
                165

<210> SEQ ID NO 2
<211> LENGTH: 156
<212> TYPE: PRT
<213> ORGANISM: Staphylococcus aureus

<400> SEQUENCE: 2

Met Thr Asn Asp Ile Tyr Phe Met Thr Leu Ala Ile Glu Glu Ala Lys
1               5                   10                  15

Lys Ala Ala Gln Leu Gly Glu Val Pro Ile Gly Ala Ile Ile Thr Lys
                20                  25                  30

Asp Asp Glu Val Ile Ala Arg Ala His Asn Leu Arg Glu Thr Leu Gln
            35                  40                  45

Gln Pro Thr Ala His Ala Glu His Ile Ala Ile Glu Arg Ala Ala Lys
    50                  55                  60

Val Leu Gly Ser Trp Arg Leu Glu Gly Cys Thr Leu Tyr Val Thr Leu
65                  70                  75                  80

Glu Pro Cys Val Met Cys Ala Gly Thr Ile Val Met Ser Arg Ile Pro
                85                  90                  95

Arg Val Val Tyr Gly Ala Asp Asp Pro Lys Gly Gly Cys Ser Gly Ser
            100                 105                 110
```

```
Leu Met Asn Leu Leu Gln Gln Ser Asn Phe Asn His Arg Ala Ile Val
            115                 120                 125

Asp Lys Gly Val Leu Lys Glu Ala Cys Ser Thr Leu Leu Thr Thr Phe
        130                 135                 140

Phe Lys Asn Leu Arg Ala Asn Lys Lys Ser Thr Asn
145                 150                 155

<210> SEQ ID NO 3
<211> LENGTH: 171
<212> TYPE: PRT
<213> ORGANISM: Streptococcus pyogenes

<400> SEQUENCE: 3

Met Pro Tyr Ser Leu Glu Glu Gln Thr Tyr Phe Met Gln Glu Ala Leu
1               5                   10                  15

Lys Glu Ala Glu Lys Ser Leu Gln Lys Ala Glu Ile Pro Ile Gly Cys
            20                  25                  30

Val Ile Val Lys Asp Gly Glu Ile Ile Gly Arg Gly His Asn Ala Arg
        35                  40                  45

Glu Glu Ser Asn Gln Ala Ile Met His Ala Glu Met Ala Ile Asn
    50                  55                  60

Glu Ala Asn Ala His Glu Gly Asn Trp Arg Leu Leu Asp Thr Thr Leu
65                  70                  75                  80

Phe Val Thr Ile Glu Pro Cys Val Met Cys Ser Gly Ala Ile Gly Leu
                85                  90                  95

Ala Arg Ile Pro His Val Ile Tyr Gly Ala Ser Asn Gln Lys Phe Gly
                100                 105                 110

Gly Ala Asp Ser Leu Tyr Gln Ile Leu Thr Asp Glu Arg Leu Asn His
            115                 120                 125

Arg Val Gln Val Glu Arg Gly Leu Leu Ala Ala Asp Cys Ala Asn Ile
        130                 135                 140

Met Gln Thr Phe Phe Arg Gln Gly Arg Glu Arg Lys Lys Ile Ala Lys
145                 150                 155                 160

His Leu Ile Lys Glu Gln Ser Asp Pro Phe Asp
                165                 170

<210> SEQ ID NO 4
<211> LENGTH: 172
<212> TYPE: PRT
<213> ORGANISM: Salmonella typhi

<400> SEQUENCE: 4

Met Ser Asp Val Glu Leu Asp His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn His Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Leu Gln Asn Tyr Arg Leu Leu Asp Thr Thr Leu
65                  70                  75                  80

Tyr Val Thr Leu Glu Pro Cys Val Met Cys Ala Gly Ala Met Val His
                85                  90                  95

Ser Arg Ile Gly Arg Val Val Phe Gly Ala Arg Asp Ala Lys Thr Gly
                100                 105                 110
```

-continued

Ala Ala Gly Ser Leu Ile Asp Val Leu His His Pro Gly Met Asn His
            115                 120                 125

Arg Val Glu Ile Ile Glu Gly Val Leu Arg Asp Glu Cys Ala Thr Leu
    130                 135                 140

Leu Ser Asp Phe Phe Arg Met Arg Arg Gln Glu Ile Lys Ala Leu Lys
145                 150                 155                 160

Lys Ala Asp Arg Ala Glu Gly Ala Gly Pro Ala Val
                165                 170

<210> SEQ ID NO 5
<211> LENGTH: 151
<212> TYPE: PRT
<213> ORGANISM: Aquifex aeolicus

<400> SEQUENCE: 5

Met Gly Lys Glu Tyr Phe Leu Lys Val Ala Leu Arg Glu Ala Lys Arg
1               5                   10                  15

Ala Phe Glu Lys Gly Glu Val Pro Val Gly Ala Ile Ile Val Lys Glu
            20                  25                  30

Gly Glu Ile Ile Ser Lys Ala His Asn Ser Val Glu Glu Leu Lys Asp
        35                  40                  45

Pro Thr Ala His Ala Glu Met Leu Ala Ile Lys Glu Ala Cys Arg Arg
    50                  55                  60

Leu Asn Thr Lys Tyr Leu Glu Gly Cys Glu Leu Tyr Val Thr Leu Glu
65                  70                  75                  80

Pro Cys Ile Met Cys Ser Tyr Ala Leu Val Leu Ser Arg Ile Glu Lys
                85                  90                  95

Val Ile Phe Ser Ala Leu Asp Lys Lys His Gly Gly Val Val Ser Val
            100                 105                 110

Phe Asn Ile Leu Asp Glu Pro Thr Leu Asn His Arg Val Lys Trp Glu
        115                 120                 125

Tyr Tyr Pro Leu Glu Gly Ala Ser Glu Leu Leu Ser Glu Phe Phe Lys
    130                 135                 140

Lys Leu Arg Asn Asn Ile Ile
145                 150

<210> SEQ ID NO 6
<211> LENGTH: 389
<212> TYPE: PRT
<213> ORGANISM: Schizosaccharomyces pombe

<400> SEQUENCE: 6

Met Ala Gly Asp Ser Val Lys Ser Ala Ile Ile Gly Ile Ala Gly Gly
1               5                   10                  15

Pro Phe Ser Gly Lys Thr Gln Leu Cys Glu Gln Leu Leu Glu Arg Leu
            20                  25                  30

Lys Ser Ser Ala Pro Ser Thr Phe Ser Lys Leu Ile His Leu Thr Ser
        35                  40                  45

Phe Leu Tyr Pro Asn Ser Val Asp Arg Tyr Ala Leu Ser Ser Tyr Asp
    50                  55                  60

Ile Glu Ala Phe Lys Lys Val Leu Ser Leu Ile Ser Gln Gly Ala Glu
65                  70                  75                  80

Lys Ile Cys Leu Pro Asp Gly Ser Cys Ile Lys Leu Pro Val Asp Gln
                85                  90                  95

Asn Arg Ile Leu Ile Glu Gly Tyr Tyr Leu Leu Leu Pro Glu Leu
            100                 105                 110

-continued

```
Leu Pro Tyr Tyr Thr Ser Lys Ile Phe Val Tyr Glu Asp Ala Asp Thr
            115                 120                 125

Arg Leu Glu Arg Cys Val Leu Gln Arg Val Lys Ala Glu Lys Gly Asp
130                 135                 140

Leu Thr Lys Val Leu Asn Asp Phe Val Thr Leu Ser Lys Pro Ala Tyr
145                 150                 155                 160

Asp Ser Ser Ile His Pro Thr Arg Glu Asn Ala Asp Ile Ile Leu Pro
                165                 170                 175

Gln Lys Glu Asn Ile Asp Thr Ala Leu Leu Phe Val Ser Gln His Leu
            180                 185                 190

Gln Asp Ile Leu Ala Glu Met Asn Lys Thr Ser Ser Asn Thr Val
        195                 200                 205

Lys Tyr Asp Thr Gln His Glu Thr Tyr Met Lys Leu Ala His Glu Ile
    210                 215                 220

Leu Asn Leu Gly Pro Tyr Phe Val Ile Gln Pro Arg Ser Pro Gly Ser
225                 230                 235                 240

Cys Val Phe Val Tyr Lys Gly Glu Val Ile Gly Arg Gly Phe Asn Glu
                245                 250                 255

Thr Asn Cys Ser Leu Ser Gly Ile Arg His Ala Glu Leu Ile Ala Ile
            260                 265                 270

Glu Lys Ile Leu Glu His Tyr Pro Ala Ser Val Phe Lys Glu Thr Thr
    275                 280                 285

Leu Tyr Val Thr Val Glu Pro Cys Leu Met Cys Ala Ala Ala Leu Lys
290                 295                 300

Gln Leu His Ile Lys Ala Val Tyr Phe Gly Cys Gly Asn Asp Arg Phe
305                 310                 315                 320

Gly Gly Cys Gly Ser Val Phe Ser Ile Asn Lys Asp Gln Ser Ile Asp
                325                 330                 335

Pro Ser Tyr Pro Val Tyr Pro Gly Leu Phe Tyr Ser Glu Ala Val Met
            340                 345                 350

Leu Met Arg Glu Phe Tyr Val Gln Glu Asn Val Lys Ala Pro Val Pro
        355                 360                 365

Gln Ser Lys Lys Gln Arg Val Leu Lys Arg Glu Val Lys Ser Leu Asp
370                 375                 380

Leu Ser Arg Phe Lys
385

<210> SEQ ID NO 7
<211> LENGTH: 400
<212> TYPE: PRT
<213> ORGANISM: Saccharomyces cerevisiae

<400> SEQUENCE: 7

Met Val Ser Cys Gln Gly Thr Arg Pro Cys Ile Val Asn Leu Leu Thr
1               5                   10                  15

Met Pro Ser Glu Asp Lys Leu Gly Glu Glu Ile Ser Thr Arg Val Ile
            20                  25                  30

Asn Glu Tyr Ser Lys Leu Lys Ser Ala Cys Arg Pro Ile Ile Arg Pro
        35                  40                  45

Ser Gly Ile Arg Glu Trp Thr Ile Leu Ala Gly Val Ala Ala Ile Asn
    50                  55                  60

Arg Asp Gly Gly Ala Asn Lys Ile Glu Ile Leu Ser Ile Ala Thr Gly
65                  70                  75                  80

Val Lys Ala Leu Pro Asp Ser Glu Leu Gln Arg Ser Glu Gly Lys Ile
                85                  90                  95
```

Leu His Asp Cys His Ala Glu Ile Leu Ala Leu Arg Gly Ala Asn Thr
            100                 105                 110

Val Leu Leu Asn Arg Ile Gln Asn Tyr Asn Pro Ser Ser Gly Asp Lys
        115                 120                 125

Phe Ile Gln His Asn Asp Glu Ile Pro Ala Arg Phe Asn Leu Lys Glu
130                 135                 140

Asn Trp Glu Leu Ala Leu Tyr Ile Ser Arg Leu Pro Cys Gly Asp Ala
145                 150                 155                 160

Ser Met Ser Phe Leu Asn Asp Asn Cys Lys Asn Asp Phe Ile Lys
                165                 170                 175

Ile Glu Asp Ser Asp Glu Phe Gln Tyr Val Asp Arg Ser Val Lys Thr
            180                 185                 190

Ile Leu Arg Gly Arg Leu Asn Phe Asn Arg Arg Asn Val Val Arg Thr
        195                 200                 205

Lys Pro Gly Arg Tyr Asp Ser Asn Ile Thr Leu Ser Lys Ser Cys Ser
210                 215                 220

Asp Lys Leu Leu Met Lys Gln Arg Ser Ser Val Leu Asn Cys Leu Asn
225                 230                 235                 240

Tyr Glu Leu Phe Glu Lys Pro Val Phe Leu Lys Tyr Ile Val Ile Pro
            245                 250                 255

Asn Leu Glu Asp Glu Thr Lys His His Leu Glu Gln Ser Phe His Thr
        260                 265                 270

Arg Leu Pro Asn Leu Asp Asn Glu Ile Lys Phe Leu Asn Cys Leu Lys
    275                 280                 285

Pro Phe Tyr Asp Asp Lys Leu Asp Glu Asp Val Pro Gly Leu Met
290                 295                 300

Cys Ser Val Lys Leu Phe Met Asp Asp Phe Ser Thr Glu Glu Ala Ile
305                 310                 315                 320

Leu Asn Gly Val Arg Asn Gly Phe Tyr Thr Lys Ser Ser Lys Pro Leu
            325                 330                 335

Arg Lys His Cys Gln Ser Gln Val Ser Arg Phe Ala Gln Trp Glu Leu
        340                 345                 350

Phe Lys Lys Ile Arg Pro Glu Tyr Glu Gly Ile Ser Tyr Leu Glu Phe
    355                 360                 365

Lys Ser Arg Gln Lys Lys Arg Ser Gln Leu Ile Ile Ala Ile Lys Asn
370                 375                 380

Ile Leu Ser Pro Asp Gly Trp Ile Pro Thr Thr Asp Asp Val Lys
385                 390                 395                 400

<210> SEQ ID NO 8
<211> LENGTH: 250
<212> TYPE: PRT
<213> ORGANISM: Saccharomyces cerevisiae

<400> SEQUENCE: 8

Met Gln His Ile Lys His Met Arg Thr Ala Val Arg Leu Ala Arg Tyr
1               5                   10                  15

Ala Leu Asp His Asp Glu Thr Pro Val Ala Cys Ile Phe Val His Thr
            20                  25                  30

Pro Thr Gly Gln Val Met Ala Tyr Gly Met Asn Asp Thr Asn Lys Ser
        35                  40                  45

Leu Thr Gly Val Ala His Ala Glu Phe Met Gly Ile Asp Gln Ile Lys
    50                  55                  60

Ala Met Leu Gly Ser Arg Gly Val Val Asp Val Phe Lys Asp Ile Thr

```
                65                  70                  75                  80
        Leu Tyr Val Thr Val Glu Pro Cys Ile Met Cys Ala Ser Ala Leu Lys
                            85                  90                  95

Gln Leu Asp Ile Gly Lys Val Val Phe Gly Cys Gly Asn Glu Arg Phe
                            100                 105                 110

Gly Gly Asn Gly Thr Val Leu Ser Val Asn His Asp Thr Cys Thr Leu
                            115                 120                 125

Val Pro Lys Asn Asn Ser Ala Ala Gly Tyr Glu Ser Ile Pro Gly Ile
                130                 135                 140

Leu Arg Lys Glu Ala Ile Met Leu Leu Arg Tyr Phe Tyr Val Arg Gln
        145                 150                 155                 160

Asn Glu Arg Ala Pro Lys Pro Arg Ser Lys Ser Asp Arg Val Leu Asp
                            165                 170                 175

Lys Asn Thr Phe Pro Pro Met Glu Trp Ser Lys Tyr Leu Asn Glu Glu
                            180                 185                 190

Ala Phe Ile Glu Thr Phe Gly Asp Asp Tyr Arg Thr Cys Phe Ala Asn
                            195                 200                 205

Lys Val Asp Leu Ser Ser Asn Ser Val Asp Trp Asp Leu Ile Asp Ser
                210                 215                 220

His Gln Asp Asn Ile Ile Gln Glu Leu Glu Glu Gln Cys Lys Met Phe
        225                 230                 235                 240

Lys Phe Asn Val His Lys Lys Ser Lys Val
                            245                 250

<210> SEQ ID NO 9
<211> LENGTH: 182
<212> TYPE: PRT
<213> ORGANISM: Arabidopsis thaliana

<400> SEQUENCE: 9

Met Glu Glu Asp His Cys Glu Asp Ser His Asn Tyr Met Gly Phe Ala
        1               5                   10                  15

Leu His Gln Ala Lys Leu Ala Leu Glu Ala Leu Glu Val Pro Val Gly
                            20                  25                  30

Cys Val Phe Leu Glu Asp Gly Lys Val Ile Ala Ser Gly Arg Asn Arg
                            35                  40                  45

Thr Asn Glu Thr Arg Asn Ala Thr Arg His Ala Glu Met Glu Ala Ile
                            50                  55                  60

Asp Gln Leu Val Gly Gln Trp Gln Lys Asp Gly Leu Ser Pro Ser Gln
        65                  70                  75                  80

Val Ala Glu Lys Phe Ser Lys Cys Val Leu Tyr Val Thr Cys Glu Pro
                            85                  90                  95

Cys Ile Met Cys Ala Ser Ala Leu Ser Phe Leu Gly Ile Lys Glu Val
                            100                 105                 110

Tyr Tyr Gly Cys Pro Asn Asp Lys Phe Gly Gly Cys Gly Ser Ile Leu
                            115                 120                 125

Ser Leu His Leu Gly Ser Glu Glu Ala Gln Arg Gly Lys Gly Tyr Lys
                130                 135                 140

Cys Arg Gly Gly Ile Met Ala Glu Glu Ala Val Ser Leu Phe Lys Cys
        145                 150                 155                 160

Phe Tyr Glu Gln Gly Asn Pro Asn Ala Pro Lys Pro His Arg Pro Val
                            165                 170                 175

Val Gln Arg Glu Arg Thr
                            180
```

<210> SEQ ID NO 10
<211> LENGTH: 175
<212> TYPE: PRT
<213> ORGANISM: Xenopus laevis

<400> SEQUENCE: 10

```
Met Glu Pro Leu Gln Ile Thr Glu Glu Ile Gln Asn Trp Met His Lys
1               5                   10                  15

Ala Phe Gln Met Ala Gln Asp Ala Leu Asn Asn Gly Glu Val Pro Val
            20                  25                  30

Gly Cys Leu Met Val Tyr Gly Asn Gln Val Val Gly Lys Gly Arg Asn
        35                  40                  45

Glu Val Asn Glu Thr Lys Asn Ala Thr Gln His Ala Glu Met Val Ala
    50                  55                  60

Ile Asp Gln Val Leu Asp Trp Cys Glu Met Asn Ser Lys Lys Ser Thr
65                  70                  75                  80

Asp Val Phe Glu Asn Ile Val Leu Tyr Val Thr Val Glu Pro Cys Ile
                85                  90                  95

Met Cys Ala Gly Ala Leu Arg Leu Leu Lys Ile Pro Leu Val Val Tyr
            100                 105                 110

Gly Cys Arg Asn Glu Arg Phe Gly Gly Cys Gly Ser Val Leu Asn Val
        115                 120                 125

Ser Gly Asp Asp Ile Pro Asp Thr Gly Thr Lys Phe Lys Cys Ile Gly
    130                 135                 140

Gly Tyr Gln Ala Glu Lys Ala Ile Glu Leu Leu Lys Thr Phe Tyr Lys
145                 150                 155                 160

Gln Glu Asn Pro Asn Ala Pro Lys Ser Lys Val Arg Lys Lys Glu
                165                 170                 175
```

<210> SEQ ID NO 11
<211> LENGTH: 170
<212> TYPE: PRT
<213> ORGANISM: Xenopus tropicalis

<400> SEQUENCE: 11

```
Met Thr Glu Glu Ile Gln Asn Trp Met His Lys Ala Phe Gln Met Ala
1               5                   10                  15

Gln Asp Ala Leu Asn Asn Gly Glu Val Pro Val Gly Cys Leu Met Val
            20                  25                  30

Tyr Asp Asn Gln Val Val Gly Lys Gly Arg Asn Glu Val Asn Glu Thr
        35                  40                  45

Lys Asn Ala Thr Arg His Ala Glu Met Val Ala Ile Asp Gln Val Leu
    50                  55                  60

Asp Trp Cys Glu Lys Asn Ser Lys Lys Ser Arg Asp Val Phe Glu Asn
65                  70                  75                  80

Ile Val Leu Tyr Val Thr Val Glu Pro Cys Ile Met Cys Ala Gly Ala
                85                  90                  95

Leu Arg Leu Leu Lys Ile Pro Leu Val Val Tyr Gly Cys Arg Asn Glu
            100                 105                 110

Arg Phe Gly Gly Cys Gly Ser Val Leu Asn Val Ala Gly Asp Asn Ile
        115                 120                 125

Pro Asp Thr Gly Thr Glu Phe Lys Tyr Ile Gly Gly Tyr Gln Ala Glu
    130                 135                 140

Lys Ala Val Glu Leu Leu Lys Thr Phe Tyr Lys Gln Glu Asn Pro Asn
145                 150                 155                 160
```

```
Ala Pro Arg Ser Lys Val Arg Lys Glu
            165             170

<210> SEQ ID NO 12
<211> LENGTH: 214
<212> TYPE: PRT
<213> ORGANISM: Danio rerio

<400> SEQUENCE: 12

Met Gln Glu Val Gly Val Asp Pro Glu Lys Asn Asp Phe Leu Gln Pro
1               5                   10                  15

Ser Asp Ser Glu Val Gln Thr Trp Met Ala Lys Ala Phe Asp Met Ala
            20                  25                  30

Val Glu Ala Leu Glu Asn Gly Glu Val Pro Val Gly Cys Leu Met Val
        35                  40                  45

Tyr Asn Asn Glu Ile Ile Gly Lys Gly Arg Asn Glu Val Asn Glu Thr
    50                  55                  60

Lys Asn Ala Thr Arg His Ala Glu Met Val Ala Leu Asp Gln Val Leu
65                  70                  75                  80

Asp Trp Cys Arg Leu Arg Glu Lys Asp Cys Lys Glu Val Cys Glu Gln
                85                  90                  95

Thr Val Leu Tyr Val Thr Val Glu Pro Cys Ile Met Cys Ala Ala Ala
            100                 105                 110

Leu Arg Leu Leu Arg Ile Pro Phe Val Val Tyr Gly Cys Lys Asn Glu
        115                 120                 125

Arg Phe Gly Gly Cys Gly Ser Val Leu Asp Val Ser Ser Asp His Leu
    130                 135                 140

Pro His Thr Gly Thr Ser Phe Lys Cys Ile Ala Gly Tyr Arg Ala Glu
145                 150                 155                 160

Glu Ala Val Glu Met Leu Lys Thr Phe Tyr Lys Gln Glu Asn Pro Asn
                165                 170                 175

Ala Pro Lys Pro Lys Val Arg Lys Asp Ser Ile Asn Pro Gln Asp Gly
            180                 185                 190

Ala Ala Val Ile Gln Val Met Arg Gly Pro Pro Asp Glu Glu Thr Glu
        195                 200                 205

Thr Ile Ala His Leu Ser
    210

<210> SEQ ID NO 13
<211> LENGTH: 191
<212> TYPE: PRT
<213> ORGANISM: Bos taurus

<400> SEQUENCE: 13

Met Glu Ala Lys Ala Gly Pro Thr Ala Thr Asp Gly Ala Tyr Ser
1               5                   10                  15

Val Ser Ala Glu Glu Thr Glu Lys Trp Met Glu Gln Ala Met Gln Met
            20                  25                  30

Ala Lys Asp Ala Leu Asp Asn Thr Glu Val Pro Val Gly Cys Leu Met
        35                  40                  45

Val Tyr Asn Asn Glu Val Val Gly Lys Gly Arg Asn Glu Val Asn Gln
    50                  55                  60

Thr Lys Asn Ala Thr Arg His Ala Glu Met Val Ala Ile Asp Gln Ala
65                  70                  75                  80

Leu Asp Trp Cys Arg Arg Gly Arg Ser Pro Ser Glu Val Phe Glu
                85                  90                  95
```

His Thr Val Leu Tyr Val Thr Val Glu Pro Cys Ile Met Cys Ala Ala
                100                 105                 110

Ala Leu Arg Leu Met Arg Ile Pro Leu Val Val Tyr Gly Cys Gln Asn
            115                 120                 125

Glu Arg Phe Gly Gly Cys Gly Ser Val Leu Asp Ile Ala Ser Ala Asp
        130                 135                 140

Leu Pro Ser Thr Gly Lys Pro Phe Gln Cys Thr Pro Gly Tyr Arg Ala
145                 150                 155                 160

Glu Glu Ala Val Glu Met Leu Lys Thr Phe Tyr Lys Gln Glu Asn Pro
                165                 170                 175

Asn Ala Pro Lys Ser Lys Val Arg Lys Lys Glu Cys His Lys Ser
                180                 185                 190

<210> SEQ ID NO 14
<211> LENGTH: 191
<212> TYPE: PRT
<213> ORGANISM: Mus musculus

<400> SEQUENCE: 14

Met Glu Glu Lys Val Glu Ser Thr Thr Thr Pro Asp Gly Pro Cys Val
1               5                   10                  15

Val Ser Val Gln Glu Thr Glu Lys Trp Met Glu Ala Met Arg Met
            20                  25                  30

Ala Lys Glu Ala Leu Glu Asn Ile Glu Val Pro Val Gly Cys Leu Met
            35                  40                  45

Val Tyr Asn Asn Glu Val Val Gly Lys Gly Arg Asn Glu Val Asn Gln
        50                  55                  60

Thr Lys Asn Ala Thr Arg His Ala Glu Met Val Ala Ile Asp Gln Val
65                  70                  75                  80

Leu Asp Trp Cys His Gln His Gly Gln Ser Pro Ser Thr Val Phe Glu
                85                  90                  95

His Thr Val Leu Tyr Val Thr Val Glu Pro Cys Ile Met Cys Ala Ala
                100                 105                 110

Ala Leu Arg Leu Met Lys Ile Pro Leu Val Val Tyr Gly Cys Gln Asn
            115                 120                 125

Glu Arg Phe Gly Gly Cys Gly Ser Val Leu Asn Ile Ala Ser Ala Asp
        130                 135                 140

Leu Pro Asn Thr Gly Arg Pro Phe Gln Cys Ile Pro Gly Tyr Arg Ala
145                 150                 155                 160

Glu Glu Ala Val Glu Leu Leu Lys Thr Phe Tyr Lys Gln Glu Asn Pro
                165                 170                 175

Asn Ala Pro Lys Ser Lys Val Arg Lys Lys Asp Cys Gln Lys Ser
                180                 185                 190

<210> SEQ ID NO 15
<211> LENGTH: 191
<212> TYPE: PRT
<213> ORGANISM: Homo sapiens

<400> SEQUENCE: 15

Met Glu Ala Lys Ala Ala Pro Lys Pro Ala Ala Ser Gly Ala Cys Ser
1               5                   10                  15

Val Ser Ala Glu Glu Thr Glu Lys Trp Met Glu Glu Ala Met His Met
            20                  25                  30

Ala Lys Glu Ala Leu Glu Asn Thr Glu Val Pro Val Gly Cys Leu Met
            35                  40                  45

Val Tyr Asn Asn Glu Val Val Gly Lys Gly Arg Asn Glu Val Asn Gln
 50                  55                  60

Thr Lys Asn Ala Thr Arg His Ala Glu Met Val Ala Ile Asp Gln Val
 65                  70                  75                  80

Leu Asp Trp Cys Arg Gln Ser Gly Lys Ser Pro Ser Glu Val Phe Glu
                 85                  90                  95

His Thr Val Leu Tyr Val Thr Val Glu Pro Cys Ile Met Cys Ala Ala
            100                 105                 110

Ala Leu Arg Leu Met Lys Ile Pro Leu Val Val Tyr Gly Cys Gln Asn
        115                 120                 125

Glu Arg Phe Gly Gly Cys Gly Ser Val Leu Asn Ile Ala Ser Ala Asp
130                 135                 140

Leu Pro Asn Thr Gly Arg Pro Phe Gln Cys Ile Pro Gly Tyr Arg Ala
145                 150                 155                 160

Glu Glu Ala Val Glu Met Leu Lys Thr Phe Tyr Lys Gln Glu Asn Pro
                165                 170                 175

Asn Ala Pro Lys Ser Lys Val Arg Lys Lys Glu Cys Gln Lys Ser
            180                 185                 190

<210> SEQ ID NO 16
<211> LENGTH: 1774
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ser Glu Val Glu Phe Ser His Glu Tyr Trp Met Arg His Ala Leu
  1               5                  10                  15

Thr Leu Ala Lys Arg Ala Trp Asp Glu Arg Glu Val Pro Val Gly Ala
             20                  25                  30

Val Leu Val His Asn Asn Arg Val Ile Gly Glu Gly Trp Asn Arg Pro
         35                  40                  45

Ile Gly Arg His Asp Pro Thr Ala His Ala Glu Ile Met Ala Leu Arg
 50                  55                  60

Gln Gly Gly Leu Val Met Gln Asn Tyr Arg Leu Ile Asp Ala Thr Tyr
 65                  70                  75                  80

Val Thr Leu Glu Pro Cys Val Met Cys Ala Gly Ala Met Ile His Ser
                 85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Ser Glu Val Glu Phe Ser His Glu Tyr Trp
        195                 200                 205

Met Arg His Ala Leu Thr Leu Ala Lys Arg Ala Trp Asp Glu Arg Glu
210                 215                 220

```
Val Pro Val Gly Ala Val Leu Val Leu Asn Asn Arg Val Ile Gly Glu
225                 230                 235                 240

Gly Trp Asn Arg Ser Ile Gly Leu His Asp Pro Thr Ala His Ala Glu
            245                 250                 255

Ile Met Ala Leu Arg Gln Gly Leu Val Met Gln Asn Tyr Arg Leu
        260                 265                 270

Ile Asp Ala Thr Leu Tyr Val Thr Phe Glu Pro Cys Val Met Cys Ala
        275                 280                 285

Gly Ala Met Ile His Ser Arg Ile Gly Arg Val Val Phe Gly Val Arg
290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Arg Arg Gln Val
            340                 345                 350

Phe Asn Ala Gln Lys Lys Ala Gln Ser Ser Thr Asp Ser Gly Gly Ser
        355                 360                 365

Ser Gly Gly Ser Ser Gly Ser Glu Thr Pro Gly Thr Ser Glu Ser Ala
370                 375                 380

Thr Pro Glu Ser Ser Gly Gly Ser Ser Gly Gly Ser Asp Lys Lys Tyr
385                 390                 395                 400

Ser Ile Gly Leu Ala Ile Gly Thr Asn Ser Val Gly Trp Ala Val Ile
                405                 410                 415

Thr Asp Glu Tyr Lys Val Pro Ser Lys Lys Phe Lys Val Leu Gly Asn
        420                 425                 430

Thr Asp Arg His Ser Ile Lys Lys Asn Leu Ile Gly Ala Leu Leu Phe
        435                 440                 445

Asp Ser Gly Glu Thr Ala Glu Ala Thr Arg Leu Lys Arg Thr Ala Arg
450                 455                 460

Arg Arg Tyr Thr Arg Arg Lys Asn Arg Ile Cys Tyr Leu Gln Glu Ile
465                 470                 475                 480

Phe Ser Asn Glu Met Ala Lys Val Asp Asp Ser Phe Phe His Arg Leu
                485                 490                 495

Glu Glu Ser Phe Leu Val Glu Glu Asp Lys Lys His Glu Arg His Pro
            500                 505                 510

Ile Phe Gly Asn Ile Val Asp Glu Val Ala Tyr His Glu Lys Tyr Pro
        515                 520                 525

Thr Ile Tyr His Leu Arg Lys Lys Leu Val Asp Ser Thr Asp Lys Ala
        530                 535                 540

Asp Leu Arg Leu Ile Tyr Leu Ala Leu Ala His Met Ile Lys Phe Arg
545                 550                 555                 560

Gly His Phe Leu Ile Glu Gly Asp Leu Asn Pro Asp Asn Ser Asp Val
                565                 570                 575

Asp Lys Leu Phe Ile Gln Leu Val Gln Thr Tyr Asn Gln Leu Phe Glu
        580                 585                 590

Glu Asn Pro Ile Asn Ala Ser Gly Val Asp Ala Lys Ala Ile Leu Ser
        595                 600                 605

Ala Arg Leu Ser Lys Ser Arg Arg Leu Glu Asn Leu Ile Ala Gln Leu
610                 615                 620

Pro Gly Glu Lys Lys Asn Gly Leu Phe Gly Asn Leu Ile Ala Leu Ser
625                 630                 635                 640
```

```
Leu Gly Leu Thr Pro Asn Phe Lys Ser Asn Phe Asp Leu Ala Glu Asp
            645                 650                 655

Ala Lys Leu Gln Leu Ser Lys Asp Thr Tyr Asp Asp Leu Asp Asn
        660                 665                 670

Leu Leu Ala Gln Ile Gly Asp Gln Tyr Ala Asp Leu Phe Leu Ala Ala
            675                 680                 685

Lys Asn Leu Ser Asp Ala Ile Leu Leu Ser Asp Ile Leu Arg Val Asn
        690                 695                 700

Thr Glu Ile Thr Lys Ala Pro Leu Ser Ala Ser Met Ile Lys Arg Tyr
705                 710                 715                 720

Asp Glu His His Gln Asp Leu Thr Leu Leu Lys Ala Leu Val Arg Gln
                725                 730                 735

Gln Leu Pro Glu Lys Tyr Lys Glu Ile Phe Phe Asp Gln Ser Lys Asn
            740                 745                 750

Gly Tyr Ala Gly Tyr Ile Asp Gly Gly Ala Ser Gln Glu Glu Phe Tyr
        755                 760                 765

Lys Phe Ile Lys Pro Ile Leu Glu Lys Met Asp Gly Thr Glu Glu Leu
        770                 775                 780

Leu Val Lys Leu Asn Arg Glu Asp Leu Leu Arg Lys Gln Arg Thr Phe
785                 790                 795                 800

Asp Asn Gly Ser Ile Pro His Gln Ile His Leu Gly Glu Leu His Ala
                805                 810                 815

Ile Leu Arg Arg Gln Glu Asp Phe Tyr Pro Phe Leu Lys Asp Asn Arg
            820                 825                 830

Glu Lys Ile Glu Lys Ile Leu Thr Phe Arg Ile Pro Tyr Tyr Val Gly
            835                 840                 845

Pro Leu Ala Arg Gly Asn Ser Arg Phe Ala Trp Met Thr Arg Lys Ser
        850                 855                 860

Glu Glu Thr Ile Thr Pro Trp Asn Phe Glu Glu Val Val Asp Lys Gly
865                 870                 875                 880

Ala Ser Ala Gln Ser Phe Ile Glu Arg Met Thr Asn Phe Asp Lys Asn
                885                 890                 895

Leu Pro Asn Glu Lys Val Leu Pro Lys His Ser Leu Leu Tyr Glu Tyr
            900                 905                 910

Phe Thr Val Tyr Asn Glu Leu Thr Lys Val Lys Tyr Val Thr Glu Gly
        915                 920                 925

Met Arg Lys Pro Ala Phe Leu Ser Gly Glu Gln Lys Lys Ala Ile Val
        930                 935                 940

Asp Leu Leu Phe Lys Thr Asn Arg Lys Val Thr Val Lys Gln Leu Lys
945                 950                 955                 960

Glu Asp Tyr Phe Lys Lys Ile Glu Cys Phe Asp Ser Val Glu Ile Ser
                965                 970                 975

Gly Val Glu Asp Arg Phe Asn Ala Ser Leu Gly Thr Tyr His Asp Leu
            980                 985                 990

Leu Lys Ile Ile Lys Asp Lys Asp Phe Leu Asp Asn Glu Glu Asn Glu
        995                 1000                1005

Asp Ile Leu Glu Asp Ile Val Leu Thr Leu Thr Leu Phe Glu Asp
        1010                1015                1020

Arg Glu Met Ile Glu Glu Arg Leu Lys Thr Tyr Ala His Leu Phe
        1025                1030                1035

Asp Asp Lys Val Met Lys Gln Leu Lys Arg Arg Arg Tyr Thr Gly
        1040                1045                1050

Trp Gly Arg Leu Ser Arg Lys Leu Ile Asn Gly Ile Arg Asp Lys
```

-continued

```
              1055                1060                1065
Gln Ser  Gly Lys Thr Ile Leu Asp Phe Leu Lys Ser  Asp Gly Phe
     1070                1075                1080

Ala Asn  Arg Asn Phe Met Gln Leu Ile His Asp Asp  Ser Leu Thr
     1085                1090                1095

Phe Lys  Glu Asp Ile Gln Lys Ala Gln Val Ser Gly  Gln Gly Asp
     1100                1105                1110

Ser Leu  His Glu His Ile Ala Asn Leu Ala Gly Ser  Pro Ala Ile
     1115                1120                1125

Lys Lys  Gly Ile Leu Gln Thr Val Lys Val Val Asp  Glu Leu Val
     1130                1135                1140

Lys Val  Met Gly Arg His Lys Pro Glu Asn Ile Val  Ile Glu Met
     1145                1150                1155

Ala Arg  Glu Asn Gln Thr Thr Gln Lys Gly Gln Lys  Asn Ser Arg
     1160                1165                1170

Glu Arg  Met Lys Arg Ile Glu Glu Gly Ile Lys Glu  Leu Gly Ser
     1175                1180                1185

Gln Ile  Leu Lys Glu His Pro Val Glu Asn Thr Gln  Leu Gln Asn
     1190                1195                1200

Glu Lys  Leu Tyr Leu Tyr Tyr Leu Gln Asn Gly Arg  Asp Met Tyr
     1205                1210                1215

Val Asp  Gln Glu Leu Asp Ile Asn Arg Leu Ser Asp  Tyr Asp Val
     1220                1225                1230

Asp His  Ile Val Pro Gln Ser Phe Leu Lys Asp Asp  Ser Ile Asp
     1235                1240                1245

Asn Lys  Val Leu Thr Arg Ser Asp Lys Asn Arg Gly  Lys Ser Asp
     1250                1255                1260

Asn Val  Pro Ser Glu Glu Val Val Lys Lys Met Lys  Asn Tyr Trp
     1265                1270                1275

Arg Gln  Leu Leu Asn Ala Lys Leu Ile Thr Gln Arg  Lys Phe Asp
     1280                1285                1290

Asn Leu  Thr Lys Ala Glu Arg Gly Gly Leu Ser Glu  Leu Asp Lys
     1295                1300                1305

Ala Gly  Phe Ile Lys Arg Gln Leu Val Glu Thr Arg  Gln Ile Thr
     1310                1315                1320

Lys His  Val Ala Gln Ile Leu Asp Ser Arg Met Asn  Thr Lys Tyr
     1325                1330                1335

Asp Glu  Asn Asp Lys Leu Ile Arg Glu Val Lys Val  Ile Thr Leu
     1340                1345                1350

Lys Ser  Lys Leu Val Ser Asp Phe Arg Lys Asp Phe  Gln Phe Tyr
     1355                1360                1365

Lys Val  Arg Glu Ile Asn Asn Tyr His His Ala His  Asp Ala Tyr
     1370                1375                1380

Leu Asn  Ala Val Val Gly Thr Ala Leu Ile Lys Lys  Tyr Pro Lys
     1385                1390                1395

Leu Glu  Ser Glu Phe Val Tyr Gly Asp Tyr Lys Val  Tyr Asp Val
     1400                1405                1410

Arg Lys  Met Ile Ala Lys Ser Glu Gln Glu Ile Gly  Lys Ala Thr
     1415                1420                1425

Ala Lys  Tyr Phe Phe Tyr Ser Asn Ile Met Asn Phe  Phe Lys Thr
     1430                1435                1440

Glu Ile  Thr Leu Ala Asn Gly Glu Ile Arg Lys Arg  Pro Leu Ile
     1445                1450                1455
```

Glu Thr Asn Gly Glu Thr Gly Glu Ile Val Trp Asp Lys Gly Arg
    1460                1465                1470

Asp Phe Ala Thr Val Arg Lys Val Leu Ser Met Pro Gln Val Asn
    1475                1480                1485

Ile Val Lys Lys Thr Glu Val Gln Thr Gly Gly Phe Ser Lys Glu
    1490                1495                1500

Ser Ile Leu Pro Lys Arg Asn Ser Asp Lys Leu Ile Ala Arg Lys
    1505                1510                1515

Lys Asp Trp Asp Pro Lys Lys Tyr Gly Gly Phe Asp Ser Pro Thr
    1520                1525                1530

Val Ala Tyr Ser Val Leu Val Ala Lys Val Glu Lys Gly Lys
    1535                1540                1545

Ser Lys Lys Leu Lys Ser Val Lys Glu Leu Leu Gly Ile Thr Ile
    1550                1555                1560

Met Glu Arg Ser Ser Phe Glu Lys Asn Pro Ile Asp Phe Leu Glu
    1565                1570                1575

Ala Lys Gly Tyr Lys Glu Val Lys Lys Asp Leu Ile Ile Lys Leu
    1580                1585                1590

Pro Lys Tyr Ser Leu Phe Glu Leu Glu Asn Gly Arg Lys Arg Met
    1595                1600                1605

Leu Ala Ser Ala Gly Glu Leu Gln Lys Gly Asn Glu Leu Ala Leu
    1610                1615                1620

Pro Ser Lys Tyr Val Asn Phe Leu Tyr Leu Ala Ser His Tyr Glu
    1625                1630                1635

Lys Leu Lys Gly Ser Pro Glu Asp Asn Glu Gln Lys Gln Leu Phe
    1640                1645                1650

Val Glu Gln His Lys His Tyr Leu Asp Glu Ile Ile Glu Gln Ile
    1655                1660                1665

Ser Glu Phe Ser Lys Arg Val Ile Leu Ala Asp Ala Asn Leu Asp
    1670                1675                1680

Lys Val Leu Ser Ala Tyr Asn Lys His Arg Asp Lys Pro Ile Arg
    1685                1690                1695

Glu Gln Ala Glu Asn Ile Ile His Leu Phe Thr Leu Thr Asn Leu
    1700                1705                1710

Gly Ala Pro Ala Ala Phe Lys Tyr Phe Asp Thr Thr Ile Asp Arg
    1715                1720                1725

Lys Arg Tyr Thr Ser Thr Lys Glu Val Leu Asp Ala Thr Leu Ile
    1730                1735                1740

His Gln Ser Ile Thr Gly Leu Tyr Glu Thr Arg Ile Asp Leu Ser
    1745                1750                1755

Gln Leu Gly Gly Asp Ser Gly Gly Ser Pro Lys Lys Lys Arg Lys
    1760                1765                1770

Val

<210> SEQ ID NO 17
<211> LENGTH: 1775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ser Glu Val Glu Phe Ser His Glu Tyr Trp Met Arg His Ala Leu
1               5                   10                  15

```
Thr Leu Ala Lys Arg Ala Trp Asp Glu Arg Glu Val Pro Val Gly Ala
                20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
 50                  55                  60

Gln Gly Gly Leu Val Met Gln Asn Tyr Arg Leu Ile Asp Ala Thr Leu
 65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Leu Asp Glu Arg
            210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
            290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Asn Ala Leu Leu Cys Tyr Phe Phe Arg Met Arg Arg Gln
            340                 345                 350

Val Phe Asn Ala Gln Lys Lys Ala Gln Ser Ser Thr Asp Ser Gly Gly
            355                 360                 365

Ser Ser Gly Gly Ser Ser Gly Ser Glu Thr Pro Gly Thr Ser Glu Ser
            370                 375                 380

Ala Thr Pro Glu Ser Ser Gly Gly Ser Ser Gly Gly Ser Asp Lys Lys
385                 390                 395                 400

Tyr Ser Ile Gly Leu Ala Ile Gly Thr Asn Ser Val Gly Trp Ala Val
                405                 410                 415

Ile Thr Asp Glu Tyr Lys Val Pro Ser Lys Lys Phe Lys Val Leu Gly
            420                 425                 430
```

-continued

```
Asn Thr Asp Arg His Ser Ile Lys Lys Asn Leu Ile Gly Ala Leu Leu
            435                 440                 445

Phe Asp Ser Gly Glu Thr Ala Glu Ala Thr Arg Leu Lys Arg Thr Ala
450                 455                 460

Arg Arg Arg Tyr Thr Arg Arg Lys Asn Arg Ile Cys Tyr Leu Gln Glu
465                 470                 475                 480

Ile Phe Ser Asn Glu Met Ala Lys Val Asp Asp Ser Phe Phe His Arg
                485                 490                 495

Leu Glu Glu Ser Phe Leu Val Glu Asp Lys Lys His Glu Arg His
                500                 505                 510

Pro Ile Phe Gly Asn Ile Val Asp Glu Val Ala Tyr His Glu Lys Tyr
            515                 520                 525

Pro Thr Ile Tyr His Leu Arg Lys Lys Leu Val Asp Ser Thr Asp Lys
530                 535                 540

Ala Asp Leu Arg Leu Ile Tyr Leu Ala Leu Ala His Met Ile Lys Phe
545                 550                 555                 560

Arg Gly His Phe Leu Ile Glu Gly Asp Leu Asn Pro Asp Asn Ser Asp
                565                 570                 575

Val Asp Lys Leu Phe Ile Gln Leu Val Gln Thr Tyr Asn Gln Leu Phe
            580                 585                 590

Glu Glu Asn Pro Ile Asn Ala Ser Gly Val Asp Ala Lys Ala Ile Leu
            595                 600                 605

Ser Ala Arg Leu Ser Lys Ser Arg Arg Leu Glu Asn Leu Ile Ala Gln
        610                 615                 620

Leu Pro Gly Glu Lys Lys Asn Gly Leu Phe Gly Asn Leu Ile Ala Leu
625                 630                 635                 640

Ser Leu Gly Leu Thr Pro Asn Phe Lys Ser Asn Phe Asp Leu Ala Glu
                645                 650                 655

Asp Ala Lys Leu Gln Leu Ser Lys Asp Thr Tyr Asp Asp Asp Leu Asp
            660                 665                 670

Asn Leu Leu Ala Gln Ile Gly Asp Gln Tyr Ala Asp Leu Phe Leu Ala
            675                 680                 685

Ala Lys Asn Leu Ser Asp Ala Ile Leu Leu Ser Asp Ile Leu Arg Val
690                 695                 700

Asn Thr Glu Ile Thr Lys Ala Pro Leu Ser Ala Ser Met Ile Lys Arg
705                 710                 715                 720

Tyr Asp Glu His His Gln Asp Leu Thr Leu Leu Lys Ala Leu Val Arg
                725                 730                 735

Gln Gln Leu Pro Glu Lys Tyr Lys Glu Ile Phe Phe Asp Gln Ser Lys
            740                 745                 750

Asn Gly Tyr Ala Gly Tyr Ile Asp Gly Gly Ala Ser Gln Glu Glu Phe
            755                 760                 765

Tyr Lys Phe Ile Lys Pro Ile Leu Glu Lys Met Asp Gly Thr Glu Glu
770                 775                 780

Leu Leu Val Lys Leu Asn Arg Glu Asp Leu Leu Arg Lys Gln Arg Thr
785                 790                 795                 800

Phe Asp Asn Gly Ser Ile Pro His Gln Ile His Leu Gly Glu Leu His
                805                 810                 815

Ala Ile Leu Arg Arg Gln Glu Asp Phe Tyr Pro Phe Leu Lys Asp Asn
            820                 825                 830

Arg Glu Lys Ile Glu Lys Ile Leu Thr Phe Arg Ile Pro Tyr Tyr Val
            835                 840                 845

Gly Pro Leu Ala Arg Gly Asn Ser Arg Phe Ala Trp Met Thr Arg Lys
```

-continued

```
                850                 855                 860
Ser Glu Glu Thr Ile Thr Pro Trp Asn Phe Glu Val Val Asp Lys
865                 870                 875                 880

Gly Ala Ser Ala Gln Ser Phe Ile Glu Arg Met Thr Asn Phe Asp Lys
                    885                 890                 895

Asn Leu Pro Asn Glu Lys Val Leu Pro Lys His Ser Leu Leu Tyr Glu
                900                 905                 910

Tyr Phe Thr Val Tyr Asn Glu Leu Thr Lys Val Lys Tyr Val Thr Glu
            915                 920                 925

Gly Met Arg Lys Pro Ala Phe Leu Ser Gly Glu Gln Lys Lys Ala Ile
            930                 935                 940

Val Asp Leu Leu Phe Lys Thr Asn Arg Lys Val Thr Val Lys Gln Leu
945                 950                 955                 960

Lys Glu Asp Tyr Phe Lys Lys Ile Glu Cys Phe Asp Ser Val Glu Ile
                965                 970                 975

Ser Gly Val Glu Asp Arg Phe Asn Ala Ser Leu Gly Thr Tyr His Asp
            980                 985                 990

Leu Leu Lys Ile Ile Lys Asp Lys  Asp Phe Leu Asp Asn  Glu Glu Asn
            995                 1000                1005

Glu Asp  Ile Leu Glu Asp Ile  Val Leu Thr Leu Thr  Leu Phe Glu
    1010                1015                1020

Asp Arg  Glu Met Ile Glu Glu  Arg Leu Lys Thr Tyr  Ala His Leu
    1025                1030                1035

Phe Asp  Asp Lys Val Met Lys  Gln Leu Lys Arg Arg  Arg Tyr Thr
    1040                1045                1050

Gly Trp  Gly Arg Leu Ser Arg  Lys Leu Ile Asn Gly  Ile Arg Asp
    1055                1060                1065

Lys Gln  Ser Gly Lys Thr Ile  Leu Asp Phe Leu Lys  Ser Asp Gly
    1070                1075                1080

Phe Ala  Asn Arg Asn Phe Met  Gln Leu Ile His Asp  Asp Ser Leu
    1085                1090                1095

Thr Phe  Lys Glu Asp Ile Gln  Lys Ala Gln Val Ser  Gly Gln Gly
    1100                1105                1110

Asp Ser  Leu His Glu His Ile  Ala Asn Leu Ala Gly  Ser Pro Ala
    1115                1120                1125

Ile Lys  Lys Gly Ile Leu Gln  Thr Val Lys Val Val  Asp Glu Leu
    1130                1135                1140

Val Lys  Val Met Gly Arg His  Lys Pro Glu Asn Ile  Val Ile Glu
    1145                1150                1155

Met Ala  Arg Glu Asn Gln Thr  Thr Gln Lys Gly Gln  Lys Asn Ser
    1160                1165                1170

Arg Glu  Arg Met Lys Arg Ile  Glu Glu Gly Ile Lys  Glu Leu Gly
    1175                1180                1185

Ser Gln  Ile Leu Lys Glu His  Pro Val Glu Asn Thr  Gln Leu Gln
    1190                1195                1200

Asn Glu  Lys Leu Tyr Leu Tyr  Tyr Leu Gln Asn Gly  Arg Asp Met
    1205                1210                1215

Tyr Val  Asp Gln Glu Leu Asp  Ile Asn Arg Leu Ser  Asp Tyr Asp
    1220                1225                1230

Val Asp  His Ile Val Pro Gln  Ser Phe Leu Lys Asp  Asp Ser Ile
    1235                1240                1245

Asp Asn  Lys Val Leu Thr Arg  Ser Asp Lys Asn Arg  Gly Lys Ser
    1250                1255                1260
```

```
Asp Asn Val Pro Ser Glu Glu Val Val Lys Lys Met Lys Asn Tyr
    1265                1270                1275

Trp Arg Gln Leu Leu Asn Ala Lys Leu Ile Thr Gln Arg Lys Phe
    1280                1285                1290

Asp Asn Leu Thr Lys Ala Glu Arg Gly Gly Leu Ser Glu Leu Asp
    1295                1300                1305

Lys Ala Gly Phe Ile Lys Arg Gln Leu Val Glu Thr Arg Gln Ile
    1310                1315                1320

Thr Lys His Val Ala Gln Ile Leu Asp Ser Arg Met Asn Thr Lys
    1325                1330                1335

Tyr Asp Glu Asn Asp Lys Leu Ile Arg Glu Val Lys Val Ile Thr
    1340                1345                1350

Leu Lys Ser Lys Leu Val Ser Asp Phe Arg Lys Asp Phe Gln Phe
    1355                1360                1365

Tyr Lys Val Arg Glu Ile Asn Asn Tyr His His Ala His Asp Ala
    1370                1375                1380

Tyr Leu Asn Ala Val Val Gly Thr Ala Leu Ile Lys Lys Tyr Pro
    1385                1390                1395

Lys Leu Glu Ser Glu Phe Val Tyr Gly Asp Tyr Lys Val Tyr Asp
    1400                1405                1410

Val Arg Lys Met Ile Ala Lys Ser Glu Gln Glu Ile Gly Lys Ala
    1415                1420                1425

Thr Ala Lys Tyr Phe Phe Tyr Ser Asn Ile Met Asn Phe Phe Lys
    1430                1435                1440

Thr Glu Ile Thr Leu Ala Asn Gly Glu Ile Arg Lys Arg Pro Leu
    1445                1450                1455

Ile Glu Thr Asn Gly Glu Thr Gly Glu Ile Val Trp Asp Lys Gly
    1460                1465                1470

Arg Asp Phe Ala Thr Val Arg Lys Val Leu Ser Met Pro Gln Val
    1475                1480                1485

Asn Ile Val Lys Lys Thr Glu Val Gln Thr Gly Gly Phe Ser Lys
    1490                1495                1500

Glu Ser Ile Leu Pro Lys Arg Asn Ser Asp Lys Leu Ile Ala Arg
    1505                1510                1515

Lys Lys Asp Trp Asp Pro Lys Lys Tyr Gly Gly Phe Asp Ser Pro
    1520                1525                1530

Thr Val Ala Tyr Ser Val Leu Val Val Ala Lys Val Glu Lys Gly
    1535                1540                1545

Lys Ser Lys Lys Leu Lys Ser Val Lys Glu Leu Leu Gly Ile Thr
    1550                1555                1560

Ile Met Glu Arg Ser Ser Phe Glu Lys Asn Pro Ile Asp Phe Leu
    1565                1570                1575

Glu Ala Lys Gly Tyr Lys Glu Val Lys Lys Asp Leu Ile Ile Lys
    1580                1585                1590

Leu Pro Lys Tyr Ser Leu Phe Glu Leu Glu Asn Gly Arg Lys Arg
    1595                1600                1605

Met Leu Ala Ser Ala Gly Glu Leu Gln Lys Gly Asn Glu Leu Ala
    1610                1615                1620

Leu Pro Ser Lys Tyr Val Asn Phe Leu Tyr Leu Ala Ser His Tyr
    1625                1630                1635

Glu Lys Leu Lys Gly Ser Pro Glu Asp Asn Glu Gln Lys Gln Leu
    1640                1645                1650
```

-continued

```
Phe Val Glu Gln His Lys His Tyr Leu Asp Glu Ile Ile Glu Gln
1655                1660                1665

Ile Ser Glu Phe Ser Lys Arg Val Ile Leu Ala Asp Ala Asn Leu
    1670                1675                1680

Asp Lys Val Leu Ser Ala Tyr Asn Lys His Arg Asp Lys Pro Ile
1685                1690                1695

Arg Glu Gln Ala Glu Asn Ile Ile His Leu Phe Thr Leu Thr Asn
1700                1705                1710

Leu Gly Ala Pro Ala Ala Phe Lys Tyr Phe Asp Thr Thr Ile Asp
    1715                1720                1725

Arg Lys Arg Tyr Thr Ser Thr Lys Glu Val Leu Asp Ala Thr Leu
1730                1735                1740

Ile His Gln Ser Ile Thr Gly Leu Tyr Glu Thr Arg Ile Asp Leu
    1745                1750                1755

Ser Gln Leu Gly Gly Asp Ser Gly Gly Ser Pro Lys Lys Lys Arg
1760                1765                1770

Lys Val
1775

<210> SEQ ID NO 18
<211> LENGTH: 1775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
        195                 200                 205

Trp Met Arg His Ala Leu Thr Leu Ala Lys Arg Ala Leu Asp Glu Arg
    210                 215                 220
```

```
Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Met Gln Asn Tyr Arg
                260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
            290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Asn Ala Leu Leu Cys Tyr Phe Phe Arg Met Pro Arg Gln
                340                 345                 350

Val Phe Asn Ala Gln Lys Lys Ala Gln Ser Ser Thr Asp Ser Gly Gly
            355                 360                 365

Ser Ser Gly Gly Ser Ser Gly Ser Glu Thr Pro Gly Thr Ser Glu Ser
370                 375                 380

Ala Thr Pro Glu Ser Ser Gly Gly Ser Ser Gly Gly Ser Asp Lys Lys
385                 390                 395                 400

Tyr Ser Ile Gly Leu Ala Ile Gly Thr Asn Ser Val Gly Trp Ala Val
                405                 410                 415

Ile Thr Asp Glu Tyr Lys Val Pro Ser Lys Lys Phe Lys Val Leu Gly
                420                 425                 430

Asn Thr Asp Arg His Ser Ile Lys Lys Asn Leu Ile Gly Ala Leu Leu
            435                 440                 445

Phe Asp Ser Gly Glu Thr Ala Glu Ala Thr Arg Leu Lys Arg Thr Ala
450                 455                 460

Arg Arg Arg Tyr Thr Arg Arg Lys Asn Arg Ile Cys Tyr Leu Gln Glu
465                 470                 475                 480

Ile Phe Ser Asn Glu Met Ala Lys Val Asp Asp Ser Phe Phe His Arg
                485                 490                 495

Leu Glu Glu Ser Phe Leu Val Glu Glu Asp Lys Lys His Glu Arg His
            500                 505                 510

Pro Ile Phe Gly Asn Ile Val Asp Glu Val Ala Tyr His Glu Lys Tyr
            515                 520                 525

Pro Thr Ile Tyr His Leu Arg Lys Lys Leu Val Asp Ser Thr Asp Lys
            530                 535                 540

Ala Asp Leu Arg Leu Ile Tyr Leu Ala Leu Ala His Met Ile Lys Phe
545                 550                 555                 560

Arg Gly His Phe Leu Ile Glu Gly Asp Leu Asn Pro Asp Asn Ser Asp
                565                 570                 575

Val Asp Lys Leu Phe Ile Gln Leu Val Gln Thr Tyr Asn Gln Leu Phe
            580                 585                 590

Glu Glu Asn Pro Ile Asn Ala Ser Gly Val Asp Ala Lys Ala Ile Leu
            595                 600                 605

Ser Ala Arg Leu Ser Lys Ser Arg Arg Leu Glu Asn Leu Ile Ala Gln
            610                 615                 620

Leu Pro Gly Glu Lys Lys Asn Gly Leu Phe Gly Asn Leu Ile Ala Leu
625                 630                 635                 640
```

-continued

```
Ser Leu Gly Leu Thr Pro Asn Phe Lys Ser Asn Phe Asp Leu Ala Glu
                645                 650                 655

Asp Ala Lys Leu Gln Leu Ser Lys Asp Thr Tyr Asp Asp Leu Asp
            660                 665                 670

Asn Leu Leu Ala Gln Ile Gly Asp Gln Tyr Ala Asp Leu Phe Leu Ala
            675                 680                 685

Ala Lys Asn Leu Ser Asp Ala Ile Leu Leu Ser Asp Ile Leu Arg Val
    690                 695                 700

Asn Thr Glu Ile Thr Lys Ala Pro Leu Ser Ala Ser Met Ile Lys Arg
705                 710                 715                 720

Tyr Asp Glu His His Gln Asp Leu Thr Leu Leu Lys Ala Leu Val Arg
                725                 730                 735

Gln Gln Leu Pro Glu Lys Tyr Lys Glu Ile Phe Phe Asp Gln Ser Lys
            740                 745                 750

Asn Gly Tyr Ala Gly Tyr Ile Asp Gly Gly Ala Ser Gln Glu Glu Phe
            755                 760                 765

Tyr Lys Phe Ile Lys Pro Ile Leu Glu Lys Met Asp Gly Thr Glu Glu
    770                 775                 780

Leu Leu Val Lys Leu Asn Arg Glu Asp Leu Leu Arg Lys Gln Arg Thr
785                 790                 795                 800

Phe Asp Asn Gly Ser Ile Pro His Gln Ile His Leu Gly Glu Leu His
                805                 810                 815

Ala Ile Leu Arg Arg Gln Glu Asp Phe Tyr Pro Phe Leu Lys Asp Asn
            820                 825                 830

Arg Glu Lys Ile Glu Lys Ile Leu Thr Phe Arg Ile Pro Tyr Tyr Val
            835                 840                 845

Gly Pro Leu Ala Arg Gly Asn Ser Arg Phe Ala Trp Met Thr Arg Lys
    850                 855                 860

Ser Glu Glu Thr Ile Thr Pro Trp Asn Phe Glu Glu Val Val Asp Lys
865                 870                 875                 880

Gly Ala Ser Ala Gln Ser Phe Ile Glu Arg Met Thr Asn Phe Asp Lys
                885                 890                 895

Asn Leu Pro Asn Glu Lys Val Leu Pro Lys His Ser Leu Leu Tyr Glu
            900                 905                 910

Tyr Phe Thr Val Tyr Asn Glu Leu Thr Lys Val Lys Tyr Val Thr Glu
            915                 920                 925

Gly Met Arg Lys Pro Ala Phe Leu Ser Gly Glu Gln Lys Lys Ala Ile
    930                 935                 940

Val Asp Leu Leu Phe Lys Thr Asn Arg Lys Val Thr Val Lys Gln Leu
945                 950                 955                 960

Lys Glu Asp Tyr Phe Lys Lys Ile Glu Cys Phe Asp Ser Val Glu Ile
                965                 970                 975

Ser Gly Val Glu Asp Arg Phe Asn Ala Ser Leu Gly Thr Tyr His Asp
            980                 985                 990

Leu Leu Lys Ile Ile Lys Asp Lys Asp Phe Leu Asp Asn Glu Glu Asn
            995                 1000                1005

Glu Asp Ile Leu Glu Asp Ile Val Leu Thr Leu Thr Leu Phe Glu
    1010                1015                1020

Asp Arg Glu Met Ile Glu Glu Arg Leu Lys Thr Tyr Ala His Leu
    1025                1030                1035

Phe Asp Asp Lys Val Met Lys Gln Leu Lys Arg Arg Arg Tyr Thr
    1040                1045                1050

Gly Trp Gly Arg Leu Ser Arg Lys Leu Ile Asn Gly Ile Arg Asp
```

```
                1055                1060                1065
Lys Gln Ser Gly Lys Thr Ile Leu Asp Phe Leu Lys Ser Asp Gly
            1070                1075                1080
Phe Ala Asn Arg Asn Phe Met Gln Leu Ile His Asp Asp Ser Leu
            1085                1090                1095
Thr Phe Lys Glu Asp Ile Gln Lys Ala Gln Val Ser Gly Gln Gly
            1100                1105                1110
Asp Ser Leu His Glu His Ile Ala Asn Leu Ala Gly Ser Pro Ala
            1115                1120                1125
Ile Lys Lys Gly Ile Leu Gln Thr Val Lys Val Val Asp Glu Leu
            1130                1135                1140
Val Lys Val Met Gly Arg His Lys Pro Glu Asn Ile Val Ile Glu
            1145                1150                1155
Met Ala Arg Glu Asn Gln Thr Thr Gln Lys Gly Gln Lys Asn Ser
            1160                1165                1170
Arg Glu Arg Met Lys Arg Ile Glu Glu Gly Ile Lys Glu Leu Gly
            1175                1180                1185
Ser Gln Ile Leu Lys Glu His Pro Val Glu Asn Thr Gln Leu Gln
            1190                1195                1200
Asn Glu Lys Leu Tyr Leu Tyr Tyr Leu Gln Asn Gly Arg Asp Met
            1205                1210                1215
Tyr Val Asp Gln Glu Leu Asp Ile Asn Arg Leu Ser Asp Tyr Asp
            1220                1225                1230
Val Asp His Ile Val Pro Gln Ser Phe Leu Lys Asp Asp Ser Ile
            1235                1240                1245
Asp Asn Lys Val Leu Thr Arg Ser Asp Lys Asn Arg Gly Lys Ser
            1250                1255                1260
Asp Asn Val Pro Ser Glu Glu Val Val Lys Lys Met Lys Asn Tyr
            1265                1270                1275
Trp Arg Gln Leu Leu Asn Ala Lys Leu Ile Thr Gln Arg Lys Phe
            1280                1285                1290
Asp Asn Leu Thr Lys Ala Glu Arg Gly Gly Leu Ser Glu Leu Asp
            1295                1300                1305
Lys Ala Gly Phe Ile Lys Arg Gln Leu Val Glu Thr Arg Gln Ile
            1310                1315                1320
Thr Lys His Val Ala Gln Ile Leu Asp Ser Arg Met Asn Thr Lys
            1325                1330                1335
Tyr Asp Glu Asn Asp Lys Leu Ile Arg Glu Val Lys Val Ile Thr
            1340                1345                1350
Leu Lys Ser Lys Leu Val Ser Asp Phe Arg Lys Asp Phe Gln Phe
            1355                1360                1365
Tyr Lys Val Arg Glu Ile Asn Asn Tyr His His Ala His Asp Ala
            1370                1375                1380
Tyr Leu Asn Ala Val Val Gly Thr Ala Leu Ile Lys Lys Tyr Pro
            1385                1390                1395
Lys Leu Glu Ser Glu Phe Val Tyr Gly Asp Tyr Lys Val Tyr Asp
            1400                1405                1410
Val Arg Lys Met Ile Ala Lys Ser Glu Gln Glu Ile Gly Lys Ala
            1415                1420                1425
Thr Ala Lys Tyr Phe Phe Tyr Ser Asn Ile Met Asn Phe Phe Lys
            1430                1435                1440
Thr Glu Ile Thr Leu Ala Asn Gly Glu Ile Arg Lys Arg Pro Leu
            1445                1450                1455
```

Ile Glu Thr Asn Gly Glu Thr Gly Ile Val Trp Asp Lys Gly
1460                1465                1470

Arg Asp Phe Ala Thr Val Arg Lys Val Leu Ser Met Pro Gln Val
1475                1480                1485

Asn Ile Val Lys Lys Thr Glu Val Gln Thr Gly Gly Phe Ser Lys
1490                1495                1500

Glu Ser Ile Leu Pro Lys Arg Asn Ser Asp Lys Leu Ile Ala Arg
1505                1510                1515

Lys Lys Asp Trp Asp Pro Lys Lys Tyr Gly Gly Phe Asp Ser Pro
1520                1525                1530

Thr Val Ala Tyr Ser Val Leu Val Val Ala Lys Val Glu Lys Gly
1535                1540                1545

Lys Ser Lys Lys Leu Lys Ser Val Lys Glu Leu Leu Gly Ile Thr
1550                1555                1560

Ile Met Glu Arg Ser Ser Phe Glu Lys Asn Pro Ile Asp Phe Leu
1565                1570                1575

Glu Ala Lys Gly Tyr Lys Glu Val Lys Lys Asp Leu Ile Ile Lys
1580                1585                1590

Leu Pro Lys Tyr Ser Leu Phe Glu Leu Glu Asn Gly Arg Lys Arg
1595                1600                1605

Met Leu Ala Ser Ala Gly Glu Leu Gln Lys Gly Asn Glu Leu Ala
1610                1615                1620

Leu Pro Ser Lys Tyr Val Asn Phe Leu Tyr Leu Ala Ser His Tyr
1625                1630                1635

Glu Lys Leu Lys Gly Ser Pro Glu Asp Asn Glu Gln Lys Gln Leu
1640                1645                1650

Phe Val Glu Gln His Lys His Tyr Leu Asp Glu Ile Ile Glu Gln
1655                1660                1665

Ile Ser Glu Phe Ser Lys Arg Val Ile Leu Ala Asp Ala Asn Leu
1670                1675                1680

Asp Lys Val Leu Ser Ala Tyr Asn Lys His Arg Asp Lys Pro Ile
1685                1690                1695

Arg Glu Gln Ala Glu Asn Ile Ile His Leu Phe Thr Leu Thr Asn
1700                1705                1710

Leu Gly Ala Pro Ala Ala Phe Lys Tyr Phe Asp Thr Thr Ile Asp
1715                1720                1725

Arg Lys Arg Tyr Thr Ser Thr Lys Glu Val Leu Asp Ala Thr Leu
1730                1735                1740

Ile His Gln Ser Ile Thr Gly Leu Tyr Glu Thr Arg Ile Asp Leu
1745                1750                1755

Ser Gln Leu Gly Gly Asp Ser Gly Gly Ser Pro Lys Lys Lys Arg
1760                1765                1770

Lys Val
1775

<210> SEQ ID NO 19
<211> LENGTH: 1775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ser Glu Val Glu Phe Ser His Glu Tyr Trp Met Arg His Ala Leu

```
1               5                   10                  15
Thr Leu Ala Lys Arg Ala Trp Asp Glu Arg Glu Val Pro Val Gly Ala
                20                  25                  30
Val Leu Val His Asn Asn Arg Val Ile Gly Glu Gly Trp Asn Arg Pro
                35                  40                  45
Ile Gly Arg His Asp Pro Thr Ala His Ala Glu Ile Met Ala Leu Arg
            50                  55                  60
Gln Gly Gly Leu Val Met Gln Asn Tyr Arg Leu Ile Asp Ala Thr Leu
65                  70                  75                  80
Tyr Val Thr Leu Glu Pro Cys Val Met Cys Ala Gly Ala Met Ile His
                85                  90                  95
Ser Arg Ile Gly Arg Val Val Phe Gly Ala Arg Asp Ala Lys Thr Gly
                100                 105                 110
Ala Ala Gly Ser Leu Met Asp Val Leu His His Pro Gly Met Asn His
                115                 120                 125
Arg Val Glu Ile Thr Glu Gly Ile Leu Ala Asp Glu Cys Ala Ala Leu
            130                 135                 140
Leu Ser Asp Phe Phe Arg Met Arg Arg Gln Glu Ile Lys Ala Gln Lys
145                 150                 155                 160
Lys Ala Gln Ser Ser Thr Asp Ser Gly Gly Ser Gly Gly Ser Ser
                165                 170                 175
Gly Ser Glu Thr Pro Gly Thr Ser Glu Ser Ala Thr Pro Glu Ser Ser
                180                 185                 190
Gly Gly Ser Ser Gly Gly Ser Ser Glu Val Glu Phe Ser His Glu Tyr
                195                 200                 205
Trp Met Arg His Ala Leu Thr Leu Ala Lys Arg Ala Arg Asp Glu Arg
                210                 215                 220
Glu Val Pro Val Gly Ala Val Leu Val Leu Asn Asn Arg Val Ile Gly
225                 230                 235                 240
Glu Gly Trp Asn Arg Ala Ile Gly Leu His Asp Pro Thr Ala His Ala
                245                 250                 255
Glu Ile Met Ala Leu Arg Gln Gly Gly Leu Val Met Gln Asn Tyr Arg
                260                 265                 270
Leu Ile Asp Ala Thr Leu Tyr Val Thr Phe Glu Pro Cys Val Met Cys
            275                 280                 285
Ala Gly Ala Met Ile His Ser Arg Ile Gly Arg Val Val Phe Gly Val
                290                 295                 300
Arg Asn Ala Lys Thr Gly Ala Ala Gly Ser Leu Met Asp Val Leu His
305                 310                 315                 320
Tyr Pro Gly Met Asn His Arg Val Glu Ile Thr Glu Gly Ile Leu Ala
                325                 330                 335
Asp Glu Cys Ala Ala Leu Leu Cys Tyr Phe Phe Arg Met Pro Arg Gln
                340                 345                 350
Val Phe Asn Ala Gln Lys Lys Ala Gln Ser Ser Thr Asp Ser Gly Gly
                355                 360                 365
Ser Ser Gly Gly Ser Ser Gly Ser Glu Thr Pro Gly Thr Ser Glu Ser
            370                 375                 380
Ala Thr Pro Glu Ser Ser Gly Gly Ser Ser Gly Gly Ser Asp Lys Lys
385                 390                 395                 400
Tyr Ser Ile Gly Leu Ala Ile Gly Thr Asn Ser Val Gly Trp Ala Val
                405                 410                 415
Ile Thr Asp Glu Tyr Lys Val Pro Ser Lys Lys Phe Lys Val Leu Gly
                420                 425                 430
```

```
Asn Thr Asp Arg His Ser Ile Lys Lys Asn Leu Ile Gly Ala Leu Leu
            435                 440                 445

Phe Asp Ser Gly Glu Thr Ala Glu Ala Thr Arg Leu Lys Arg Thr Ala
450                 455                 460

Arg Arg Arg Tyr Thr Arg Arg Lys Asn Arg Ile Cys Tyr Leu Gln Glu
465                 470                 475                 480

Ile Phe Ser Asn Glu Met Ala Lys Val Asp Asp Ser Phe Phe His Arg
                485                 490                 495

Leu Glu Glu Ser Phe Leu Val Glu Asp Lys Lys His Glu Arg His
                500                 505                 510

Pro Ile Phe Gly Asn Ile Val Asp Glu Val Ala Tyr His Glu Lys Tyr
            515                 520                 525

Pro Thr Ile Tyr His Leu Arg Lys Lys Leu Val Asp Ser Thr Asp Lys
            530                 535                 540

Ala Asp Leu Arg Leu Ile Tyr Leu Ala Leu Ala His Met Ile Lys Phe
545                 550                 555                 560

Arg Gly His Phe Leu Ile Glu Gly Asp Leu Asn Pro Asp Asn Ser Asp
                565                 570                 575

Val Asp Lys Leu Phe Ile Gln Leu Val Gln Thr Tyr Asn Gln Leu Phe
            580                 585                 590

Glu Glu Asn Pro Ile Asn Ala Ser Gly Val Asp Ala Lys Ala Ile Leu
                595                 600                 605

Ser Ala Arg Leu Ser Lys Ser Arg Arg Leu Glu Asn Leu Ile Ala Gln
            610                 615                 620

Leu Pro Gly Glu Lys Lys Asn Gly Leu Phe Gly Asn Leu Ile Ala Leu
625                 630                 635                 640

Ser Leu Gly Leu Thr Pro Asn Phe Lys Ser Asn Phe Asp Leu Ala Glu
                645                 650                 655

Asp Ala Lys Leu Gln Leu Ser Lys Asp Thr Tyr Asp Asp Asp Leu Asp
                660                 665                 670

Asn Leu Leu Ala Gln Ile Gly Asp Gln Tyr Ala Asp Leu Phe Leu Ala
            675                 680                 685

Ala Lys Asn Leu Ser Asp Ala Ile Leu Leu Ser Asp Ile Leu Arg Val
            690                 695                 700

Asn Thr Glu Ile Thr Lys Ala Pro Leu Ser Ala Ser Met Ile Lys Arg
705                 710                 715                 720

Tyr Asp Glu His His Gln Asp Leu Thr Leu Leu Lys Ala Leu Val Arg
                725                 730                 735

Gln Gln Leu Pro Glu Lys Tyr Lys Glu Ile Phe Phe Asp Gln Ser Lys
            740                 745                 750

Asn Gly Tyr Ala Gly Tyr Ile Asp Gly Gly Ala Ser Gln Glu Glu Phe
            755                 760                 765

Tyr Lys Phe Ile Lys Pro Ile Leu Glu Lys Met Asp Gly Thr Glu Glu
770                 775                 780

Leu Leu Val Lys Leu Asn Arg Glu Asp Leu Leu Arg Lys Gln Arg Thr
785                 790                 795                 800

Phe Asp Asn Gly Ser Ile Pro His Gln Ile His Leu Gly Glu Leu His
                805                 810                 815

Ala Ile Leu Arg Arg Gln Glu Asp Phe Tyr Pro Phe Leu Lys Asp Asn
            820                 825                 830

Arg Glu Lys Ile Glu Lys Ile Leu Thr Phe Arg Ile Pro Tyr Tyr Val
835                 840                 845
```

-continued

```
Gly Pro Leu Ala Arg Gly Asn Ser Arg Phe Ala Trp Met Thr Arg Lys
    850                 855                 860
Ser Glu Glu Thr Ile Thr Pro Trp Asn Phe Glu Glu Val Val Asp Lys
865                 870                 875                 880
Gly Ala Ser Ala Gln Ser Phe Ile Glu Arg Met Thr Asn Phe Asp Lys
                885                 890                 895
Asn Leu Pro Asn Glu Lys Val Leu Pro Lys His Ser Leu Leu Tyr Glu
            900                 905                 910
Tyr Phe Thr Val Tyr Asn Glu Leu Thr Lys Val Lys Tyr Val Thr Glu
        915                 920                 925
Gly Met Arg Lys Pro Ala Phe Leu Ser Gly Glu Gln Lys Lys Ala Ile
    930                 935                 940
Val Asp Leu Leu Phe Lys Thr Asn Arg Lys Val Thr Val Lys Gln Leu
945                 950                 955                 960
Lys Glu Asp Tyr Phe Lys Lys Ile Glu Cys Phe Asp Ser Val Glu Ile
                965                 970                 975
Ser Gly Val Glu Asp Arg Phe Asn Ala Ser Leu Gly Thr Tyr His Asp
            980                 985                 990
Leu Leu Lys Ile Ile Lys Asp Lys Asp Phe Leu Asp Asn Glu Glu Asn
        995                 1000                1005
Glu Asp Ile Leu Glu Asp Ile Val Leu Thr Leu Thr Leu Phe Glu
    1010                1015                1020
Asp Arg Glu Met Ile Glu Glu Arg Leu Lys Thr Tyr Ala His Leu
    1025                1030                1035
Phe Asp Asp Lys Val Met Lys Gln Leu Lys Arg Arg Arg Tyr Thr
    1040                1045                1050
Gly Trp Gly Arg Leu Ser Arg Lys Leu Ile Asn Gly Ile Arg Asp
    1055                1060                1065
Lys Gln Ser Gly Lys Thr Ile Leu Asp Phe Leu Lys Ser Asp Gly
    1070                1075                1080
Phe Ala Asn Arg Asn Phe Met Gln Leu Ile His Asp Asp Ser Leu
    1085                1090                1095
Thr Phe Lys Glu Asp Ile Gln Lys Ala Gln Val Ser Gly Gln Gly
    1100                1105                1110
Asp Ser Leu His Glu His Ile Ala Asn Leu Ala Gly Ser Pro Ala
    1115                1120                1125
Ile Lys Lys Gly Ile Leu Gln Thr Val Lys Val Val Asp Glu Leu
    1130                1135                1140
Val Lys Val Met Gly Arg His Lys Pro Glu Asn Ile Val Ile Glu
    1145                1150                1155
Met Ala Arg Glu Asn Gln Thr Thr Gln Lys Gly Gln Lys Asn Ser
    1160                1165                1170
Arg Glu Arg Met Lys Arg Ile Glu Glu Gly Ile Lys Glu Leu Gly
    1175                1180                1185
Ser Gln Ile Leu Lys Glu His Pro Val Glu Asn Thr Gln Leu Gln
    1190                1195                1200
Asn Glu Lys Leu Tyr Leu Tyr Tyr Leu Gln Asn Gly Arg Asp Met
    1205                1210                1215
Tyr Val Asp Gln Glu Leu Asp Ile Asn Arg Leu Ser Asp Tyr Asp
    1220                1225                1230
Val Asp His Ile Val Pro Gln Ser Phe Leu Lys Asp Asp Ser Ile
    1235                1240                1245
Asp Asn Lys Val Leu Thr Arg Ser Asp Lys Asn Arg Gly Lys Ser
```

```
            1250                1255                1260

Asp Asn Val Pro Ser Glu Glu Val Val Lys Lys Met Lys Asn Tyr
            1265                1270                1275

Trp Arg Gln Leu Leu Asn Ala Lys Leu Ile Thr Gln Arg Lys Phe
            1280                1285                1290

Asp Asn Leu Thr Lys Ala Glu Arg Gly Gly Leu Ser Glu Leu Asp
            1295                1300                1305

Lys Ala Gly Phe Ile Lys Arg Gln Leu Val Glu Thr Arg Gln Ile
            1310                1315                1320

Thr Lys His Val Ala Gln Ile Leu Asp Ser Arg Met Asn Thr Lys
            1325                1330                1335

Tyr Asp Glu Asn Asp Lys Leu Ile Arg Glu Val Lys Val Ile Thr
            1340                1345                1350

Leu Lys Ser Lys Leu Val Ser Asp Phe Arg Lys Asp Phe Gln Phe
            1355                1360                1365

Tyr Lys Val Arg Glu Ile Asn Asn Tyr His His Ala His Asp Ala
            1370                1375                1380

Tyr Leu Asn Ala Val Val Gly Thr Ala Leu Ile Lys Lys Tyr Pro
            1385                1390                1395

Lys Leu Glu Ser Glu Phe Val Tyr Gly Asp Tyr Lys Val Tyr Asp
            1400                1405                1410

Val Arg Lys Met Ile Ala Lys Ser Glu Gln Glu Ile Gly Lys Ala
            1415                1420                1425

Thr Ala Lys Tyr Phe Phe Tyr Ser Asn Ile Met Asn Phe Phe Lys
            1430                1435                1440

Thr Glu Ile Thr Leu Ala Asn Gly Glu Ile Arg Lys Arg Pro Leu
            1445                1450                1455

Ile Glu Thr Asn Gly Glu Thr Gly Glu Ile Val Trp Asp Lys Gly
            1460                1465                1470

Arg Asp Phe Ala Thr Val Arg Lys Val Leu Ser Met Pro Gln Val
            1475                1480                1485

Asn Ile Val Lys Lys Thr Glu Val Gln Thr Gly Gly Phe Ser Lys
            1490                1495                1500

Glu Ser Ile Leu Pro Lys Arg Asn Ser Asp Lys Leu Ile Ala Arg
            1505                1510                1515

Lys Lys Asp Trp Asp Pro Lys Lys Tyr Gly Gly Phe Asp Ser Pro
            1520                1525                1530

Thr Val Ala Tyr Ser Val Leu Val Val Ala Lys Val Glu Lys Gly
            1535                1540                1545

Lys Ser Lys Lys Leu Lys Ser Val Lys Glu Leu Leu Gly Ile Thr
            1550                1555                1560

Ile Met Glu Arg Ser Ser Phe Glu Lys Asn Pro Ile Asp Phe Leu
            1565                1570                1575

Glu Ala Lys Gly Tyr Lys Glu Val Lys Lys Asp Leu Ile Ile Lys
            1580                1585                1590

Leu Pro Lys Tyr Ser Leu Phe Glu Leu Glu Asn Gly Arg Lys Arg
            1595                1600                1605

Met Leu Ala Ser Ala Gly Glu Leu Gln Lys Gly Asn Glu Leu Ala
            1610                1615                1620

Leu Pro Ser Lys Tyr Val Asn Phe Leu Tyr Leu Ala Ser His Tyr
            1625                1630                1635

Glu Lys Leu Lys Gly Ser Pro Glu Asp Asn Glu Gln Lys Gln Leu
            1640                1645                1650
```

Phe Val Glu Gln His Lys His Tyr Leu Asp Glu Ile Ile Glu Gln
            1655                1660                1665

Ile Ser Glu Phe Ser Lys Arg Val Ile Leu Ala Asp Ala Asn Leu
        1670                1675                1680

Asp Lys Val Leu Ser Ala Tyr Asn Lys His Arg Asp Lys Pro Ile
    1685                1690                1695

Arg Glu Gln Ala Glu Asn Ile Ile His Leu Phe Thr Leu Thr Asn
1700                1705                1710

Leu Gly Ala Pro Ala Ala Phe Lys Tyr Phe Asp Thr Thr Ile Asp
    1715                1720                1725

Arg Lys Arg Tyr Thr Ser Thr Lys Glu Val Leu Asp Ala Thr Leu
    1730                1735                1740

Ile His Gln Ser Ile Thr Gly Leu Tyr Glu Thr Arg Ile Asp Leu
    1745                1750                1755

Ser Gln Leu Gly Gly Asp Ser Gly Gly Ser Pro Lys Lys Lys Arg
    1760                1765                1770

Lys Val
    1775

<210> SEQ ID NO 20
<211> LENGTH: 1803
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Arg Thr Ala Asp Gly Ser Glu Phe Glu Ser Pro Lys Lys Lys
1               5                   10                  15

Arg Lys Val Ser Glu Val Glu Phe Ser His Glu Tyr Trp Met Arg His
                20                  25                  30

Ala Leu Thr Leu Ala Lys Arg Ala Trp Asp Glu Arg Glu Val Pro Val
            35                  40                  45

Gly Ala Val Leu Val His Asn Asn Arg Val Ile Gly Glu Gly Trp Asn
        50                  55                  60

Arg Pro Ile Gly Arg His Asp Pro Thr Ala His Ala Glu Ile Met Ala
65                  70                  75                  80

Leu Arg Gln Gly Gly Leu Val Met Gln Asn Tyr Arg Leu Ile Asp Ala
                85                  90                  95

Thr Leu Tyr Val Thr Leu Glu Pro Cys Val Met Cys Ala Gly Ala Met
            100                 105                 110

Ile His Ser Arg Ile Gly Arg Val Val Phe Gly Ala Arg Asp Ala Lys
        115                 120                 125

Thr Gly Ala Ala Gly Ser Leu Met Asp Val Leu His His Pro Gly Met
    130                 135                 140

Asn His Arg Val Glu Ile Thr Glu Gly Ile Leu Ala Asp Glu Cys Ala
145                 150                 155                 160

Ala Leu Leu Ser Asp Phe Phe Arg Met Arg Arg Gln Glu Ile Lys Ala
                165                 170                 175

Gln Lys Lys Ala Gln Ser Ser Thr Asp Ser Gly Gly Ser Ser Gly Gly
            180                 185                 190

Ser Ser Gly Ser Glu Thr Pro Gly Thr Ser Glu Ser Ala Thr Pro Glu
        195                 200                 205

Ser Ser Gly Gly Ser Ser Gly Gly Ser Ser Glu Val Glu Phe Ser His

```
            210                 215                 220
Glu Tyr Trp Met Arg His Ala Leu Thr Leu Ala Lys Arg Ala Arg Asp
225                 230                 235                 240

Glu Arg Glu Val Pro Val Gly Ala Val Leu Val Leu Asn Asn Arg Val
                245                 250                 255

Ile Gly Glu Gly Trp Asn Arg Ala Ile Gly Leu His Asp Pro Thr Ala
                260                 265                 270

His Ala Glu Ile Met Ala Leu Arg Gln Gly Gly Leu Val Met Gln Asn
            275                 280                 285

Tyr Arg Leu Ile Asp Ala Thr Leu Tyr Val Thr Phe Glu Pro Cys Val
290                 295                 300

Met Cys Ala Gly Ala Met Ile His Ser Arg Ile Gly Arg Val Val Phe
305                 310                 315                 320

Gly Val Arg Asn Ala Lys Thr Gly Ala Ala Gly Ser Leu Met Asp Val
                325                 330                 335

Leu His Tyr Pro Gly Met Asn His Arg Val Glu Ile Thr Glu Gly Ile
                340                 345                 350

Leu Ala Asp Glu Cys Ala Ala Leu Leu Cys Tyr Phe Phe Arg Met Pro
            355                 360                 365

Arg Gln Val Phe Asn Ala Gln Lys Lys Ala Gln Ser Ser Thr Asp Ser
370                 375                 380

Gly Gly Ser Ser Gly Gly Ser Ser Gly Ser Glu Thr Pro Gly Thr Ser
385                 390                 395                 400

Glu Ser Ala Thr Pro Glu Ser Ser Gly Gly Ser Ser Gly Gly Ser Asp
                405                 410                 415

Lys Lys Tyr Ser Ile Gly Leu Ala Ile Gly Thr Asn Ser Val Gly Trp
                420                 425                 430

Ala Val Ile Thr Asp Glu Tyr Lys Val Pro Ser Lys Lys Phe Lys Val
            435                 440                 445

Leu Gly Asn Thr Asp Arg His Ser Ile Lys Lys Asn Leu Ile Gly Ala
450                 455                 460

Leu Leu Phe Asp Ser Gly Glu Thr Ala Glu Ala Thr Arg Leu Lys Arg
465                 470                 475                 480

Thr Ala Arg Arg Arg Tyr Thr Arg Arg Lys Asn Arg Ile Cys Tyr Leu
                485                 490                 495

Gln Glu Ile Phe Ser Asn Glu Met Ala Lys Val Asp Asp Ser Phe Phe
                500                 505                 510

His Arg Leu Glu Glu Ser Phe Leu Val Glu Glu Asp Lys Lys His Glu
            515                 520                 525

Arg His Pro Ile Phe Gly Asn Ile Val Asp Glu Val Ala Tyr His Glu
530                 535                 540

Lys Tyr Pro Thr Ile Tyr His Leu Arg Lys Lys Leu Val Asp Ser Thr
545                 550                 555                 560

Asp Lys Ala Asp Leu Arg Leu Ile Tyr Leu Ala Leu Ala His Met Ile
                565                 570                 575

Lys Phe Arg Gly His Phe Leu Ile Glu Gly Asp Leu Asn Pro Asp Asn
                580                 585                 590

Ser Asp Val Asp Lys Leu Phe Ile Gln Leu Val Gln Thr Tyr Asn Gln
            595                 600                 605

Leu Phe Glu Glu Asn Pro Ile Asn Ala Ser Gly Val Asp Ala Lys Ala
610                 615                 620

Ile Leu Ser Ala Arg Leu Ser Lys Ser Arg Arg Leu Glu Asn Leu Ile
625                 630                 635                 640
```

-continued

```
Ala Gln Leu Pro Gly Glu Lys Asn Gly Leu Phe Gly Asn Leu Ile
            645                 650                 655

Ala Leu Ser Leu Gly Leu Thr Pro Asn Phe Lys Ser Asn Phe Asp Leu
        660                 665                 670

Ala Glu Asp Ala Lys Leu Gln Leu Ser Lys Asp Thr Tyr Asp Asp Asp
            675                 680                 685

Leu Asp Asn Leu Leu Ala Gln Ile Gly Asp Gln Tyr Ala Asp Leu Phe
    690                 695                 700

Leu Ala Ala Lys Asn Leu Ser Asp Ala Ile Leu Leu Ser Asp Ile Leu
705                 710                 715                 720

Arg Val Asn Thr Glu Ile Thr Lys Ala Pro Leu Ser Ala Ser Met Ile
                725                 730                 735

Lys Arg Tyr Asp Glu His His Gln Asp Leu Thr Leu Leu Lys Ala Leu
            740                 745                 750

Val Arg Gln Gln Leu Pro Glu Lys Tyr Lys Glu Ile Phe Phe Asp Gln
        755                 760                 765

Ser Lys Asn Gly Tyr Ala Gly Tyr Ile Asp Gly Gly Ala Ser Gln Glu
770                 775                 780

Glu Phe Tyr Lys Phe Ile Lys Pro Ile Leu Glu Lys Met Asp Gly Thr
785                 790                 795                 800

Glu Glu Leu Leu Val Lys Leu Asn Arg Glu Asp Leu Leu Arg Lys Gln
                805                 810                 815

Arg Thr Phe Asp Asn Gly Ser Ile Pro His Gln Ile His Leu Gly Glu
            820                 825                 830

Leu His Ala Ile Leu Arg Arg Gln Glu Asp Phe Tyr Pro Phe Leu Lys
        835                 840                 845

Asp Asn Arg Glu Lys Ile Glu Lys Ile Leu Thr Phe Arg Ile Pro Tyr
    850                 855                 860

Tyr Val Gly Pro Leu Ala Arg Gly Asn Ser Arg Phe Ala Trp Met Thr
865                 870                 875                 880

Arg Lys Ser Glu Glu Thr Ile Thr Pro Trp Asn Phe Glu Glu Val Val
                885                 890                 895

Asp Lys Gly Ala Ser Ala Gln Ser Phe Ile Glu Arg Met Thr Asn Phe
            900                 905                 910

Asp Lys Asn Leu Pro Asn Glu Lys Val Leu Pro Lys His Ser Leu Leu
        915                 920                 925

Tyr Glu Tyr Phe Thr Val Tyr Asn Glu Leu Thr Lys Val Lys Tyr Val
    930                 935                 940

Thr Glu Gly Met Arg Lys Pro Ala Phe Leu Ser Gly Glu Gln Lys Lys
945                 950                 955                 960

Ala Ile Val Asp Leu Leu Phe Lys Thr Asn Arg Lys Val Thr Val Lys
                965                 970                 975

Gln Leu Lys Glu Asp Tyr Phe Lys Lys Ile Glu Cys Phe Asp Ser Val
            980                 985                 990

Glu Ile Ser Gly Val Glu Asp Arg Phe Asn Ala Ser Leu Gly Thr Tyr
        995                 1000                1005

His Asp Leu Leu Lys Ile Ile Lys Asp Lys Asp Phe Leu Asp Asn
    1010                1015                1020

Glu Glu Asn Glu Asp Ile Leu Glu Asp Ile Val Leu Thr Leu Thr
    1025                1030                1035

Leu Phe Glu Asp Arg Glu Met Ile Glu Glu Arg Leu Lys Thr Tyr
    1040                1045                1050
```

```
Ala His Leu Phe Asp Asp Lys Val Met Lys Gln Leu Lys Arg Arg
1055            1060            1065

Arg Tyr Thr Gly Trp Gly Arg Leu Ser Arg Lys Leu Ile Asn Gly
1070            1075            1080

Ile Arg Asp Lys Gln Ser Gly Lys Thr Ile Leu Asp Phe Leu Lys
1085            1090            1095

Ser Asp Gly Phe Ala Asn Arg Asn Phe Met Gln Leu Ile His Asp
1100            1105            1110

Asp Ser Leu Thr Phe Lys Glu Asp Ile Gln Lys Ala Gln Val Ser
1115            1120            1125

Gly Gln Gly Asp Ser Leu His Glu His Ile Ala Asn Leu Ala Gly
1130            1135            1140

Ser Pro Ala Ile Lys Lys Gly Ile Leu Gln Thr Val Lys Val Val
1145            1150            1155

Asp Glu Leu Val Lys Val Met Gly Arg His Lys Pro Glu Asn Ile
1160            1165            1170

Val Ile Glu Met Ala Arg Glu Asn Gln Thr Thr Gln Lys Gly Gln
1175            1180            1185

Lys Asn Ser Arg Glu Arg Met Lys Arg Ile Glu Glu Gly Ile Lys
1190            1195            1200

Glu Leu Gly Ser Gln Ile Leu Lys Glu His Pro Val Glu Asn Thr
1205            1210            1215

Gln Leu Gln Asn Glu Lys Leu Tyr Leu Tyr Tyr Leu Gln Asn Gly
1220            1225            1230

Arg Asp Met Tyr Val Asp Gln Glu Leu Asp Ile Asn Arg Leu Ser
1235            1240            1245

Asp Tyr Asp Val Asp His Ile Val Pro Gln Ser Phe Leu Lys Asp
1250            1255            1260

Asp Ser Ile Asp Asn Lys Val Leu Thr Arg Ser Asp Lys Asn Arg
1265            1270            1275

Gly Lys Ser Asp Asn Val Pro Ser Glu Glu Val Val Lys Lys Met
1280            1285            1290

Lys Asn Tyr Trp Arg Gln Leu Leu Asn Ala Lys Leu Ile Thr Gln
1295            1300            1305

Arg Lys Phe Asp Asn Leu Thr Lys Ala Glu Arg Gly Gly Leu Ser
1310            1315            1320

Glu Leu Asp Lys Ala Gly Phe Ile Lys Arg Gln Leu Val Glu Thr
1325            1330            1335

Arg Gln Ile Thr Lys His Val Ala Gln Ile Leu Asp Ser Arg Met
1340            1345            1350

Asn Thr Lys Tyr Asp Glu Asn Asp Lys Leu Ile Arg Glu Val Lys
1355            1360            1365

Val Ile Thr Leu Lys Ser Lys Leu Val Ser Asp Phe Arg Lys Asp
1370            1375            1380

Phe Gln Phe Tyr Lys Val Arg Glu Ile Asn Asn Tyr His His Ala
1385            1390            1395

His Asp Ala Tyr Leu Asn Ala Val Val Gly Thr Ala Leu Ile Lys
1400            1405            1410

Lys Tyr Pro Lys Leu Glu Ser Glu Phe Val Tyr Gly Asp Tyr Lys
1415            1420            1425

Val Tyr Asp Val Arg Lys Met Ile Ala Lys Ser Glu Gln Glu Ile
1430            1435            1440

Gly Lys Ala Thr Ala Lys Tyr Phe Phe Tyr Ser Asn Ile Met Asn
```

```
            1445                1450                1455

Phe Phe Lys Thr Glu Ile Thr Leu Ala Asn Gly Glu Ile Arg Lys
        1460                1465                1470

Arg Pro Leu Ile Glu Thr Asn Gly Glu Thr Gly Glu Ile Val Trp
        1475                1480                1485

Asp Lys Gly Arg Asp Phe Ala Thr Val Arg Lys Val Leu Ser Met
        1490                1495                1500

Pro Gln Val Asn Ile Val Lys Lys Thr Glu Val Gln Thr Gly Gly
        1505                1510                1515

Phe Ser Lys Glu Ser Ile Leu Pro Lys Arg Asn Ser Asp Lys Leu
        1520                1525                1530

Ile Ala Arg Lys Lys Asp Trp Asp Pro Lys Lys Tyr Gly Gly Phe
        1535                1540                1545

Asp Ser Pro Thr Val Ala Tyr Ser Val Leu Val Val Ala Lys Val
        1550                1555                1560

Glu Lys Gly Lys Ser Lys Lys Leu Lys Ser Val Lys Glu Leu Leu
        1565                1570                1575

Gly Ile Thr Ile Met Glu Arg Ser Ser Phe Glu Lys Asn Pro Ile
        1580                1585                1590

Asp Phe Leu Glu Ala Lys Gly Tyr Lys Glu Val Lys Lys Asp Leu
        1595                1600                1605

Ile Ile Lys Leu Pro Lys Tyr Ser Leu Phe Glu Leu Glu Asn Gly
        1610                1615                1620

Arg Lys Arg Met Leu Ala Ser Ala Gly Glu Leu Gln Lys Gly Asn
        1625                1630                1635

Glu Leu Ala Leu Pro Ser Lys Tyr Val Asn Phe Leu Tyr Leu Ala
        1640                1645                1650

Ser His Tyr Glu Lys Leu Lys Gly Ser Pro Glu Asp Asn Glu Gln
        1655                1660                1665

Lys Gln Leu Phe Val Glu Gln His Lys His Tyr Leu Asp Glu Ile
        1670                1675                1680

Ile Glu Gln Ile Ser Glu Phe Ser Lys Arg Val Ile Leu Ala Asp
        1685                1690                1695

Ala Asn Leu Asp Lys Val Leu Ser Ala Tyr Asn Lys His Arg Asp
        1700                1705                1710

Lys Pro Ile Arg Glu Gln Ala Glu Asn Ile Ile His Leu Phe Thr
        1715                1720                1725

Leu Thr Asn Leu Gly Ala Pro Ala Ala Phe Lys Tyr Phe Asp Thr
        1730                1735                1740

Thr Ile Asp Arg Lys Arg Tyr Thr Ser Thr Lys Glu Val Leu Asp
        1745                1750                1755

Ala Thr Leu Ile His Gln Ser Ile Thr Gly Leu Tyr Glu Thr Arg
        1760                1765                1770

Ile Asp Leu Ser Gln Leu Gly Gly Asp Ser Gly Gly Ser Lys Arg
        1775                1780                1785

Thr Ala Asp Gly Ser Glu Phe Glu Pro Lys Lys Lys Arg Lys Val
        1790                1795                1800

<210> SEQ ID NO 21
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 21

```
Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Tyr Phe Phe Arg Met Pro Arg Gln Val Phe Asn Ala Gln Lys Lys
145                 150                 155                 160

Ala Gln Ser Ser Thr Asp
                165
```

<210> SEQ ID NO 22
<211> LENGTH: 365
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Gly Gly Ser Ser
                165                 170                 175
```

-continued

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
        195                 200                 205

Trp Met Arg His Ala Leu Thr Leu Ala Lys Arg Ala Arg Asp Glu Arg
210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
        275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp
        355                 360                 365

<210> SEQ ID NO 23
<211> LENGTH: 18
<212> TYPE: PRT
<213> ORGANISM: Unknown
<220> FEATURE:
<223> OTHER INFORMATION: Description of Unknown:
      Bipartite NLS sequence

<400> SEQUENCE: 23

Lys Arg Thr Ala Asp Gly Ser Glu Phe Glu Ser Pro Lys Lys Lys Arg
1               5                   10                  15

Lys Val

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Gly Ser
1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Gly Gly Ser

<210> SEQ ID NO 26
<211> LENGTH: 7
<212> TYPE: PRT
<213> ORGANISM: Simian virus 40

<400> SEQUENCE: 26

Pro Lys Lys Lys Arg Arg Val
1               5

<210> SEQ ID NO 27
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 27

Lys Arg Pro Ala Ala Thr Lys Lys Ala Gly Gln Ala Lys Lys Lys Lys
1               5                   10                  15

<210> SEQ ID NO 28
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 28
nnnnnnnnnn nnnnnnnnnn cgttttagag ctagaaatag caagttaaaa taaggctagt    60
ccgttatcaa cttgaaaaag tggcaccgag tcggtgcttt tttt                    104

<210> SEQ ID NO 29

<400> SEQUENCE: 29

000

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtcatcttag tcattacctg                                                20

<210> SEQ ID NO 31
<211> LENGTH: 1877
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Lys Arg Thr Ala Asp Gly Ser Glu Phe Glu Ser Pro Lys Lys Lys
1               5                   10                  15

```
Arg Lys Val Ser Glu Val Glu Phe Ser His Glu Tyr Trp Met Arg His
         20                  25                  30

Ala Leu Thr Leu Ala Lys Arg Ala Arg Asp Glu Arg Glu Val Pro Val
             35                  40                  45

Gly Ala Val Leu Val Leu Asn Asn Arg Val Ile Gly Glu Gly Trp Asn
 50                  55                  60

Arg Ala Ile Gly Leu His Asp Pro Thr Ala His Ala Glu Ile Met Ala
 65                  70                  75                  80

Leu Arg Gln Gly Gly Leu Val Met Gln Asn Tyr Arg Leu Ile Asp Ala
                 85                  90                  95

Thr Leu Tyr Val Thr Phe Glu Pro Cys Val Met Cys Ala Gly Ala Met
            100                 105                 110

Ile His Ser Arg Ile Gly Arg Val Val Phe Gly Val Arg Asn Ala Lys
        115                 120                 125

Thr Gly Ala Ala Gly Ser Leu Met Asp Val Leu His Tyr Pro Gly Met
130                 135                 140

Asn His Arg Val Glu Ile Thr Glu Gly Ile Leu Ala Asp Glu Cys Ala
145                 150                 155                 160

Ala Leu Leu Cys Tyr Phe Phe Arg Met Pro Arg Gln Val Phe Asn Ala
                165                 170                 175

Gln Lys Lys Ala Gln Ser Ser Thr Asp Ser Gly Gly Ser Ser Gly Gly
            180                 185                 190

Ser Ser Gly Ser Glu Thr Pro Gly Thr Ser Glu Ser Ala Thr Pro Glu
        195                 200                 205

Ser Ser Gly Gly Ser Ser Gly Ser Asp Lys Lys Tyr Ser Ile Gly
        210                 215                 220

Leu Ala Ile Gly Thr Asn Ser Val Gly Trp Ala Val Ile Thr Asp Glu
225                 230                 235                 240

Tyr Lys Val Pro Ser Lys Lys Phe Lys Val Leu Gly Asn Thr Asp Arg
                245                 250                 255

His Ser Ile Lys Lys Asn Leu Ile Gly Ala Leu Leu Phe Asp Ser Gly
            260                 265                 270

Glu Thr Ala Glu Ala Thr Arg Leu Lys Arg Thr Ala Arg Arg Arg Tyr
        275                 280                 285

Thr Arg Arg Lys Asn Arg Ile Cys Tyr Leu Gln Glu Ile Phe Ser Asn
290                 295                 300

Glu Met Ala Lys Val Asp Asp Ser Phe Phe His Arg Leu Glu Glu Ser
305                 310                 315                 320

Phe Leu Val Glu Glu Asp Lys Lys His Glu Arg His Pro Ile Phe Gly
                325                 330                 335

Asn Ile Val Asp Glu Val Ala Tyr His Glu Lys Tyr Pro Thr Ile Tyr
            340                 345                 350

His Leu Arg Lys Lys Leu Val Asp Ser Thr Asp Lys Ala Asp Leu Arg
        355                 360                 365

Leu Ile Tyr Leu Ala Leu Ala His Met Ile Lys Phe Arg Gly His Phe
370                 375                 380

Leu Ile Glu Gly Asp Leu Asn Pro Asp Asn Ser Asp Val Asp Lys Leu
385                 390                 395                 400

Phe Ile Gln Leu Val Gln Thr Tyr Asn Gln Leu Phe Glu Glu Asn Pro
                405                 410                 415

Ile Asn Ala Ser Gly Val Asp Ala Lys Ala Ile Leu Ser Ala Arg Leu
            420                 425                 430
```

```
Ser Lys Ser Arg Arg Leu Glu Asn Leu Ile Ala Gln Leu Pro Gly Glu
            435                 440                 445

Lys Lys Asn Gly Leu Phe Gly Asn Leu Ile Ala Leu Ser Leu Gly Leu
        450                 455                 460

Thr Pro Asn Phe Lys Ser Asn Phe Asp Leu Ala Glu Asp Ala Lys Leu
465                 470                 475                 480

Gln Leu Ser Lys Asp Thr Tyr Asp Asp Leu Asp Asn Leu Leu Ala
            485                 490                 495

Gln Ile Gly Asp Gln Tyr Ala Asp Leu Phe Leu Ala Ala Lys Asn Leu
            500                 505                 510

Ser Asp Ala Ile Leu Leu Ser Asp Ile Leu Arg Val Asn Thr Glu Ile
            515                 520                 525

Thr Lys Ala Pro Leu Ser Ala Ser Met Ile Lys Arg Tyr Asp Glu His
    530                 535                 540

His Gln Asp Leu Thr Leu Leu Lys Ala Leu Val Arg Gln Gln Leu Pro
545                 550                 555                 560

Glu Lys Tyr Lys Glu Ile Phe Phe Asp Gln Ser Lys Asn Gly Tyr Ala
                565                 570                 575

Gly Tyr Ile Asp Gly Gly Ala Ser Gln Glu Glu Phe Tyr Lys Phe Ile
            580                 585                 590

Lys Pro Ile Leu Glu Lys Met Asp Gly Thr Glu Glu Leu Leu Val Lys
    595                 600                 605

Leu Asn Arg Glu Asp Leu Leu Arg Lys Gln Arg Thr Phe Asp Asn Gly
    610                 615                 620

Ser Ile Pro His Gln Ile His Leu Gly Glu Leu His Ala Ile Leu Arg
625                 630                 635                 640

Arg Gln Glu Asp Phe Tyr Pro Phe Leu Lys Asp Asn Arg Glu Lys Ile
                645                 650                 655

Glu Lys Ile Leu Thr Phe Arg Ile Pro Tyr Tyr Val Gly Pro Leu Ala
            660                 665                 670

Arg Gly Asn Ser Arg Phe Ala Trp Met Thr Arg Lys Ser Glu Glu Thr
    675                 680                 685

Ile Thr Pro Trp Asn Phe Glu Glu Val Val Asp Lys Gly Ala Ser Ala
    690                 695                 700

Gln Ser Phe Ile Glu Arg Met Thr Asn Phe Asp Lys Asn Leu Pro Asn
705                 710                 715                 720

Glu Lys Val Leu Pro Lys His Ser Leu Leu Tyr Glu Tyr Phe Thr Val
                725                 730                 735

Tyr Asn Glu Leu Thr Lys Val Lys Tyr Val Thr Glu Gly Met Arg Lys
            740                 745                 750

Pro Ala Phe Leu Ser Gly Glu Gln Lys Lys Ala Ile Val Asp Leu Leu
    755                 760                 765

Phe Lys Thr Asn Arg Lys Val Thr Val Lys Gln Leu Lys Glu Asp Tyr
770                 775                 780

Phe Lys Lys Ile Glu Cys Phe Asp Ser Val Glu Ile Ser Gly Val Glu
785                 790                 795                 800

Asp Arg Phe Asn Ala Ser Leu Gly Thr Tyr His Asp Leu Leu Lys Ile
                805                 810                 815

Ile Lys Asp Lys Asp Phe Leu Asp Asn Glu Glu Asn Glu Asp Ile Leu
            820                 825                 830

Glu Asp Ile Val Leu Thr Leu Thr Leu Phe Glu Asp Arg Glu Met Ile
            835                 840                 845

Glu Glu Arg Leu Lys Thr Tyr Ala His Leu Phe Asp Asp Lys Val Met
```

```
                850             855            860
Lys Gln Leu Lys Arg Arg Tyr Thr Gly Trp Gly Arg Leu Ser Arg
865             870            875            880

Lys Leu Ile Asn Gly Ile Arg Asp Lys Gln Ser Gly Lys Thr Ile Leu
            885            890            895

Asp Phe Leu Lys Ser Asp Gly Phe Ala Asn Arg Asn Phe Met Gln Leu
            900            905            910

Ile His Asp Asp Ser Leu Thr Phe Lys Glu Asp Ile Gln Lys Ala Gln
            915            920            925

Val Ser Gly Gln Gly Asp Ser Leu His Glu His Ile Ala Asn Leu Ala
            930            935            940

Gly Ser Pro Ala Ile Lys Lys Gly Ile Leu Gln Thr Val Lys Val Val
945            950            955            960

Asp Glu Leu Val Lys Val Met Gly Arg His Lys Pro Glu Asn Ile Val
            965            970            975

Ile Glu Met Ala Arg Glu Asn Gln Thr Thr Gln Lys Gly Gln Lys Asn
            980            985            990

Ser Arg Glu Arg Met Lys Arg Ile Glu Glu Gly Ile Lys Glu Leu Gly
            995           1000           1005

Ser Gln Ile Leu Lys Glu His Pro Val Glu Asn Thr Gln Leu Gln
           1010           1015           1020

Asn Glu Lys Leu Tyr Leu Tyr Leu Gln Asn Gly Arg Asp Met
           1025           1030           1035

Tyr Val Asp Gln Glu Leu Asp Ile Asn Arg Leu Ser Asp Tyr Asp
           1040           1045           1050

Val Asp His Ile Val Pro Gln Ser Phe Leu Lys Asp Asp Ser Ile
           1055           1060           1065

Asp Asn Lys Val Leu Thr Arg Ser Asp Lys Asn Arg Gly Lys Ser
           1070           1075           1080

Asp Asn Val Pro Ser Glu Glu Val Val Lys Lys Met Lys Asn Tyr
           1085           1090           1095

Trp Arg Gln Leu Leu Asn Ala Lys Leu Ile Thr Gln Arg Lys Phe
           1100           1105           1110

Asp Asn Leu Thr Lys Ala Glu Arg Gly Gly Leu Ser Glu Leu Asp
           1115           1120           1125

Lys Ala Gly Phe Ile Lys Arg Gln Leu Val Glu Thr Arg Gln Ile
           1130           1135           1140

Thr Lys His Val Ala Gln Ile Leu Asp Ser Arg Met Asn Thr Lys
           1145           1150           1155

Tyr Asp Glu Asn Asp Lys Leu Ile Arg Glu Val Lys Val Ile Thr
           1160           1165           1170

Leu Lys Ser Lys Leu Val Ser Asp Phe Arg Lys Asp Phe Gln Phe
           1175           1180           1185

Tyr Lys Val Arg Glu Ile Asn Asn Tyr His His Ala His Asp Ala
           1190           1195           1200

Tyr Leu Asn Ala Val Val Gly Thr Ala Leu Ile Lys Lys Tyr Pro
           1205           1210           1215

Lys Leu Glu Ser Glu Phe Val Tyr Gly Asp Tyr Lys Val Tyr Asp
           1220           1225           1230

Val Arg Lys Met Ile Ala Lys Ser Glu Gln Glu Ile Gly Lys Ala
           1235           1240           1245

Thr Ala Lys Tyr Phe Phe Tyr Ser Asn Ile Met Asn Phe Phe Lys
           1250           1255           1260
```

```
Thr Glu Ile Thr Leu Ala Asn Gly Glu Ile Arg Lys Arg Pro Leu
    1265                1270                1275

Ile Glu Thr Asn Gly Glu Thr Gly Glu Ile Val Trp Asp Lys Gly
    1280                1285                1290

Arg Asp Phe Ala Thr Val Arg Lys Val Leu Ser Met Pro Gln Val
    1295                1300                1305

Asn Ile Val Lys Lys Thr Glu Val Gln Thr Gly Gly Phe Ser Lys
    1310                1315                1320

Glu Ser Ile Leu Pro Lys Arg Asn Ser Asp Lys Leu Ile Ala Arg
    1325                1330                1335

Lys Lys Asp Trp Asp Pro Lys Lys Tyr Gly Gly Phe Asp Ser Pro
    1340                1345                1350

Thr Val Ala Tyr Ser Val Leu Val Val Ala Lys Val Glu Lys Gly
    1355                1360                1365

Lys Ser Lys Lys Leu Lys Ser Val Lys Glu Leu Leu Gly Ile Thr
    1370                1375                1380

Ile Met Glu Arg Ser Ser Phe Glu Lys Asn Pro Ile Asp Phe Leu
    1385                1390                1395

Glu Ala Lys Gly Tyr Lys Glu Val Lys Lys Asp Leu Ile Ile Lys
    1400                1405                1410

Leu Pro Lys Tyr Ser Leu Phe Glu Leu Glu Asn Gly Arg Lys Arg
    1415                1420                1425

Met Leu Ala Ser Ala Gly Glu Leu Gln Lys Gly Asn Glu Leu Ala
    1430                1435                1440

Leu Pro Ser Lys Tyr Val Asn Phe Leu Tyr Leu Ala Ser His Tyr
    1445                1450                1455

Glu Lys Leu Lys Gly Ser Pro Glu Asp Asn Glu Gln Lys Gln Leu
    1460                1465                1470

Phe Val Glu Gln His Lys His Tyr Leu Asp Glu Ile Ile Glu Gln
    1475                1480                1485

Ile Ser Glu Phe Ser Lys Arg Val Ile Leu Ala Asp Ala Asn Leu
    1490                1495                1500

Asp Lys Val Leu Ser Ala Tyr Asn Lys His Arg Asp Lys Pro Ile
    1505                1510                1515

Arg Glu Gln Ala Glu Asn Ile Ile His Leu Phe Thr Leu Thr Asn
    1520                1525                1530

Leu Gly Ala Pro Ala Ala Phe Lys Tyr Phe Asp Thr Thr Ile Asp
    1535                1540                1545

Arg Lys Arg Tyr Thr Ser Thr Lys Glu Val Leu Asp Ala Thr Leu
    1550                1555                1560

Ile His Gln Ser Ile Thr Gly Leu Tyr Glu Thr Arg Ile Asp Leu
    1565                1570                1575

Ser Gln Leu Gly Gly Asp Ser Gly Gly Ser Lys Arg Thr Ala Asp
    1580                1585                1590

Gly Ser Glu Phe Glu Pro Lys Lys Lys Arg Lys Val Gly Ser Gly
    1595                1600                1605

Ala Thr Asn Phe Ser Leu Leu Lys Gln Ala Gly Asp Val Glu Glu
    1610                1615                1620

Asn Pro Gly Pro Met Val Ser Lys Gly Glu Glu Leu Phe Thr Gly
    1625                1630                1635

Val Val Pro Ile Leu Val Glu Leu Asp Gly Asp Val Asn Gly His
    1640                1645                1650
```

-continued

```
Lys Phe Ser Val Ser Gly Glu Gly Glu Gly Asp Ala Thr Tyr Gly
    1655                1660                1665

Lys Leu Thr Leu Lys Phe Ile Cys Thr Thr Gly Lys Leu Pro Val
    1670                1675                1680

Pro Trp Pro Thr Leu Val Thr Leu Thr Tyr Gly Val Gln Cys
    1685                1690                1695

Phe Ser Arg Tyr Pro Asp His Met Lys Gln His Asp Phe Phe Lys
    1700                1705                1710

Ser Ala Met Pro Glu Gly Tyr Val Gln Glu Arg Thr Ile Phe Phe
    1715                1720                1725

Lys Asp Asp Gly Asn Tyr Lys Thr Arg Ala Glu Val Lys Phe Glu
    1730                1735                1740

Gly Asp Thr Leu Val Asn Arg Ile Glu Leu Lys Gly Ile Asp Phe
    1745                1750                1755

Lys Glu Asp Gly Asn Ile Leu Gly His Lys Leu Glu Tyr Asn Tyr
    1760                1765                1770

Asn Ser His Asn Val Tyr Ile Met Ala Asp Lys Gln Lys Asn Gly
    1775                1780                1785

Ile Lys Val Asn Phe Lys Ile Arg His Asn Ile Glu Asp Gly Ser
    1790                1795                1800

Val Gln Leu Ala Asp His Tyr Gln Gln Asn Thr Pro Ile Gly Asp
    1805                1810                1815

Gly Pro Val Leu Leu Pro Asp Asn His Tyr Leu Ser Thr Gln Ser
    1820                1825                1830

Ala Leu Ser Lys Asp Pro Asn Glu Lys Arg Asp His Met Val Leu
    1835                1840                1845

Leu Glu Phe Val Thr Ala Ala Gly Ile Thr Leu Gly Met Asp Glu
    1850                1855                1860

Leu Tyr Lys Ser Gly Gly Ser Pro Lys Lys Lys Arg Lys Val
    1865                1870                1875

<210> SEQ ID NO 32
<211> LENGTH: 1877
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Lys Arg Thr Ala Asp Gly Ser Glu Phe Glu Ser Pro Lys Lys Lys
1               5                   10                  15

Arg Lys Val Ser Glu Val Glu Phe Ser His Glu Tyr Trp Met Arg His
            20                  25                  30

Ala Leu Thr Leu Ala Ala Ala Arg Asp Glu Arg Glu Val Pro Val
            35                  40                  45

Gly Ala Val Leu Val Leu Asn Asn Arg Val Ile Gly Glu Gly Trp Asn
        50                  55                  60

Arg Ala Ile Gly Leu His Asp Pro Thr Ala His Ala Glu Ile Met Ala
65                  70                  75                  80

Leu Arg Gln Gly Gly Leu Val Met Gln Asn Tyr Arg Leu Ile Asp Ala
                85                  90                  95

Thr Leu Tyr Val Thr Phe Glu Pro Cys Val Met Cys Ala Gly Ala Met
            100                 105                 110

Ile His Ser Arg Ile Gly Arg Val Val Phe Gly Val Arg Asn Ala Lys
            115                 120                 125
```

Thr Gly Ala Ala Gly Ser Leu Met Asp Val Leu His Tyr Pro Gly Met
130                 135                 140

Asn His Arg Val Glu Ile Thr Glu Gly Ile Leu Ala Asp Glu Cys Ala
145                 150                 155                 160

Ala Leu Leu Cys Tyr Phe Phe Arg Met Pro Arg Gln Val Phe Asn Ala
            165                 170                 175

Gln Lys Lys Ala Gln Ser Ser Thr Asp Ser Gly Gly Ser Ser Gly Gly
            180                 185                 190

Ser Ser Gly Ser Glu Thr Pro Gly Thr Ser Glu Ser Ala Thr Pro Glu
    195                 200                 205

Ser Ser Gly Gly Ser Ser Gly Gly Ser Asp Lys Lys Tyr Ser Ile Gly
    210                 215                 220

Leu Ala Ile Gly Thr Asn Ser Val Gly Trp Ala Val Ile Thr Asp Glu
225                 230                 235                 240

Tyr Lys Val Pro Ser Lys Lys Phe Lys Val Leu Gly Asn Thr Asp Arg
            245                 250                 255

His Ser Ile Lys Lys Asn Leu Ile Gly Ala Leu Leu Phe Asp Ser Gly
            260                 265                 270

Glu Thr Ala Glu Ala Thr Arg Leu Lys Arg Thr Ala Arg Arg Arg Tyr
    275                 280                 285

Thr Arg Arg Lys Asn Arg Ile Cys Tyr Leu Gln Glu Ile Phe Ser Asn
    290                 295                 300

Glu Met Ala Lys Val Asp Asp Ser Phe Phe His Arg Leu Glu Glu Ser
305                 310                 315                 320

Phe Leu Val Glu Glu Asp Lys Lys His Glu Arg His Pro Ile Phe Gly
            325                 330                 335

Asn Ile Val Asp Glu Val Ala Tyr His Glu Lys Tyr Pro Thr Ile Tyr
            340                 345                 350

His Leu Arg Lys Lys Leu Val Asp Ser Thr Asp Lys Ala Asp Leu Arg
    355                 360                 365

Leu Ile Tyr Leu Ala Leu Ala His Met Ile Lys Phe Arg Gly His Phe
370                 375                 380

Leu Ile Glu Gly Asp Leu Asn Pro Asp Asn Ser Asp Val Asp Lys Leu
385                 390                 395                 400

Phe Ile Gln Leu Val Gln Thr Tyr Asn Gln Leu Phe Glu Glu Asn Pro
            405                 410                 415

Ile Asn Ala Ser Gly Val Asp Ala Lys Ala Ile Leu Ser Ala Arg Leu
            420                 425                 430

Ser Lys Ser Arg Arg Leu Glu Asn Leu Ile Ala Gln Leu Pro Gly Glu
    435                 440                 445

Lys Lys Asn Gly Leu Phe Gly Asn Leu Ile Ala Leu Ser Leu Gly Leu
450                 455                 460

Thr Pro Asn Phe Lys Ser Asn Phe Asp Leu Ala Glu Asp Ala Lys Leu
465                 470                 475                 480

Gln Leu Ser Lys Asp Thr Tyr Asp Asp Asp Leu Asp Asn Leu Leu Ala
            485                 490                 495

Gln Ile Gly Asp Gln Tyr Ala Asp Leu Phe Leu Ala Ala Lys Asn Leu
            500                 505                 510

Ser Asp Ala Ile Leu Leu Ser Asp Ile Leu Arg Val Asn Thr Glu Ile
    515                 520                 525

Thr Lys Ala Pro Leu Ser Ala Ser Met Ile Lys Arg Tyr Asp Glu His
    530                 535                 540

```
His Gln Asp Leu Thr Leu Leu Lys Ala Leu Val Arg Gln Gln Leu Pro
545                 550                 555                 560

Glu Lys Tyr Lys Glu Ile Phe Phe Asp Gln Ser Lys Asn Gly Tyr Ala
            565                 570                 575

Gly Tyr Ile Asp Gly Gly Ala Ser Gln Glu Glu Phe Tyr Lys Phe Ile
            580                 585                 590

Lys Pro Ile Leu Glu Lys Met Asp Gly Thr Glu Glu Leu Leu Val Lys
            595                 600                 605

Leu Asn Arg Glu Asp Leu Leu Arg Lys Gln Arg Thr Phe Asp Asn Gly
        610                 615                 620

Ser Ile Pro His Gln Ile His Leu Gly Glu Leu His Ala Ile Leu Arg
625                 630                 635                 640

Arg Gln Glu Asp Phe Tyr Pro Phe Leu Lys Asp Asn Arg Glu Lys Ile
                645                 650                 655

Glu Lys Ile Leu Thr Phe Arg Ile Pro Tyr Tyr Val Gly Pro Leu Ala
            660                 665                 670

Arg Gly Asn Ser Arg Phe Ala Trp Met Thr Arg Lys Ser Glu Glu Thr
        675                 680                 685

Ile Thr Pro Trp Asn Phe Glu Glu Val Val Asp Lys Gly Ala Ser Ala
690                 695                 700

Gln Ser Phe Ile Glu Arg Met Thr Asn Phe Asp Lys Asn Leu Pro Asn
705                 710                 715                 720

Glu Lys Val Leu Pro Lys His Ser Leu Leu Tyr Glu Tyr Phe Thr Val
            725                 730                 735

Tyr Asn Glu Leu Thr Lys Val Lys Tyr Val Thr Glu Gly Met Arg Lys
        740                 745                 750

Pro Ala Phe Leu Ser Gly Glu Gln Lys Lys Ala Ile Val Asp Leu Leu
            755                 760                 765

Phe Lys Thr Asn Arg Lys Val Thr Val Lys Gln Leu Lys Glu Asp Tyr
770                 775                 780

Phe Lys Lys Ile Glu Cys Phe Asp Ser Val Glu Ile Ser Gly Val Glu
785                 790                 795                 800

Asp Arg Phe Asn Ala Ser Leu Gly Thr Tyr His Asp Leu Leu Lys Ile
            805                 810                 815

Ile Lys Asp Lys Asp Phe Leu Asp Asn Glu Glu Asn Glu Asp Ile Leu
        820                 825                 830

Glu Asp Ile Val Leu Thr Leu Thr Leu Phe Glu Asp Arg Glu Met Ile
            835                 840                 845

Glu Glu Arg Leu Lys Thr Tyr Ala His Leu Phe Asp Asp Lys Val Met
850                 855                 860

Lys Gln Leu Lys Arg Arg Arg Tyr Thr Gly Trp Gly Arg Leu Ser Arg
865                 870                 875                 880

Lys Leu Ile Asn Gly Ile Arg Asp Lys Gln Ser Gly Lys Thr Ile Leu
            885                 890                 895

Asp Phe Leu Lys Ser Asp Gly Phe Ala Asn Arg Asn Phe Met Gln Leu
        900                 905                 910

Ile His Asp Asp Ser Leu Thr Phe Lys Glu Asp Ile Gln Lys Ala Gln
            915                 920                 925

Val Ser Gly Gln Gly Asp Ser Leu His Glu His Ile Ala Asn Leu Ala
        930                 935                 940

Gly Ser Pro Ala Ile Lys Lys Gly Ile Leu Gln Thr Val Lys Val Val
945                 950                 955                 960

Asp Glu Leu Val Lys Val Met Gly Arg His Lys Pro Glu Asn Ile Val
```

```
              965             970             975
Ile Glu Met Ala Arg Glu Asn Gln Thr Thr Gln Lys Gly Gln Lys Asn
            980             985             990
Ser Arg Glu Arg Met Lys Arg Ile Glu Glu Gly Ile Lys Glu Leu Gly
        995             1000            1005
Ser Gln Ile Leu Lys Glu His Pro Val Glu Asn Thr Gln Leu Gln
    1010            1015            1020
Asn Glu Lys Leu Tyr Leu Tyr Tyr Leu Gln Asn Gly Arg Asp Met
    1025            1030            1035
Tyr Val Asp Gln Glu Leu Asp Ile Asn Arg Leu Ser Asp Tyr Asp
    1040            1045            1050
Val Asp His Ile Val Pro Gln Ser Phe Leu Lys Asp Asp Ser Ile
    1055            1060            1065
Asp Asn Lys Val Leu Thr Arg Ser Asp Lys Asn Arg Gly Lys Ser
    1070            1075            1080
Asp Asn Val Pro Ser Glu Glu Val Val Lys Lys Met Lys Asn Tyr
    1085            1090            1095
Trp Arg Gln Leu Leu Asn Ala Lys Leu Ile Thr Gln Arg Lys Phe
    1100            1105            1110
Asp Asn Leu Thr Lys Ala Glu Arg Gly Gly Leu Ser Glu Leu Asp
    1115            1120            1125
Lys Ala Gly Phe Ile Lys Arg Gln Leu Val Glu Thr Arg Gln Ile
    1130            1135            1140
Thr Lys His Val Ala Gln Ile Leu Asp Ser Arg Met Asn Thr Lys
    1145            1150            1155
Tyr Asp Glu Asn Asp Lys Leu Ile Arg Glu Val Lys Val Ile Thr
    1160            1165            1170
Leu Lys Ser Lys Leu Val Ser Asp Phe Arg Lys Asp Phe Gln Phe
    1175            1180            1185
Tyr Lys Val Arg Glu Ile Asn Asn Tyr His His Ala His Asp Ala
    1190            1195            1200
Tyr Leu Asn Ala Val Val Gly Thr Ala Leu Ile Lys Lys Tyr Pro
    1205            1210            1215
Lys Leu Glu Ser Glu Phe Val Tyr Gly Asp Tyr Lys Val Tyr Asp
    1220            1225            1230
Val Arg Lys Met Ile Ala Lys Ser Glu Gln Glu Ile Gly Lys Ala
    1235            1240            1245
Thr Ala Lys Tyr Phe Phe Tyr Ser Asn Ile Met Asn Phe Phe Lys
    1250            1255            1260
Thr Glu Ile Thr Leu Ala Asn Gly Glu Ile Arg Lys Arg Pro Leu
    1265            1270            1275
Ile Glu Thr Asn Gly Glu Thr Gly Glu Ile Val Trp Asp Lys Gly
    1280            1285            1290
Arg Asp Phe Ala Thr Val Arg Lys Val Leu Ser Met Pro Gln Val
    1295            1300            1305
Asn Ile Val Lys Lys Thr Glu Val Gln Thr Gly Gly Phe Ser Lys
    1310            1315            1320
Glu Ser Ile Leu Pro Lys Arg Asn Ser Asp Lys Leu Ile Ala Arg
    1325            1330            1335
Lys Lys Asp Trp Asp Pro Lys Lys Tyr Gly Gly Phe Asp Ser Pro
    1340            1345            1350
Thr Val Ala Tyr Ser Val Leu Val Val Ala Lys Val Glu Lys Gly
    1355            1360            1365
```

-continued

```
Lys Ser Lys Lys Leu Lys Ser  Val Lys Glu Leu Leu  Gly Ile Thr
    1370            1375              1380

Ile Met Glu Arg Ser Ser Phe  Glu Lys Asn Pro Ile  Asp Phe Leu
    1385            1390              1395

Glu Ala Lys Gly Tyr Lys Glu  Val Lys Lys Asp Leu  Ile Ile Lys
    1400            1405              1410

Leu Pro Lys Tyr Ser Leu Phe  Glu Leu Glu Asn Gly  Arg Lys Arg
    1415            1420              1425

Met Leu Ala Ser Ala Gly Glu  Leu Gln Lys Gly Asn  Glu Leu Ala
    1430            1435              1440

Leu Pro Ser Lys Tyr Val Asn  Phe Leu Tyr Leu Ala  Ser His Tyr
    1445            1450              1455

Glu Lys Leu Lys Gly Ser Pro  Glu Asp Asn Glu Gln  Lys Gln Leu
    1460            1465              1470

Phe Val Glu Gln His Lys His  Tyr Leu Asp Glu Ile  Ile Glu Gln
    1475            1480              1485

Ile Ser Glu Phe Ser Lys Arg  Val Ile Leu Ala Asp  Ala Asn Leu
    1490            1495              1500

Asp Lys Val Leu Ser Ala Tyr  Asn Lys His Arg Asp  Lys Pro Ile
    1505            1510              1515

Arg Glu Gln Ala Glu Asn Ile  Ile His Leu Phe Thr  Leu Thr Asn
    1520            1525              1530

Leu Gly Ala Pro Ala Ala Phe  Lys Tyr Phe Asp Thr  Thr Ile Asp
    1535            1540              1545

Arg Lys Arg Tyr Thr Ser Thr  Lys Glu Val Leu Asp  Ala Thr Leu
    1550            1555              1560

Ile His Gln Ser Ile Thr Gly  Leu Tyr Glu Thr Arg  Ile Asp Leu
    1565            1570              1575

Ser Gln Leu Gly Gly Asp Ser  Gly Gly Ser Lys Arg  Thr Ala Asp
    1580            1585              1590

Gly Ser Glu Phe Glu Pro Lys  Lys Lys Arg Lys Val  Gly Ser Gly
    1595            1600              1605

Ala Thr Asn Phe Ser Leu Leu  Lys Gln Ala Gly Asp  Val Glu Glu
    1610            1615              1620

Asn Pro Gly Pro Met Val Ser  Lys Gly Glu Glu Leu  Phe Thr Gly
    1625            1630              1635

Val Val Pro Ile Leu Val Glu  Leu Asp Gly Asp Val  Asn Gly His
    1640            1645              1650

Lys Phe Ser Val Ser Gly Glu  Gly Glu Gly Asp Ala  Thr Tyr Gly
    1655            1660              1665

Lys Leu Thr Leu Lys Phe Ile  Cys Thr Thr Gly Lys  Leu Pro Val
    1670            1675              1680

Pro Trp Pro Thr Leu Val Thr  Thr Leu Thr Tyr Gly  Val Gln Cys
    1685            1690              1695

Phe Ser Arg Tyr Pro Asp His  Met Lys Gln His Asp  Phe Phe Lys
    1700            1705              1710

Ser Ala Met Pro Glu Gly Tyr  Val Gln Glu Arg Thr  Ile Phe Phe
    1715            1720              1725

Lys Asp Asp Gly Asn Tyr Lys  Thr Arg Ala Glu Val  Lys Phe Glu
    1730            1735              1740

Gly Asp Thr Leu Val Asn Arg  Ile Glu Leu Lys Gly  Ile Asp Phe
    1745            1750              1755
```

```
Lys Glu Asp Gly Asn Ile Leu Gly His Lys Leu Glu Tyr Asn Tyr
    1760                1765                1770

Asn Ser His Asn Val Tyr Ile Met Ala Asp Lys Gln Lys Asn Gly
    1775                1780                1785

Ile Lys Val Asn Phe Lys Ile Arg His Asn Ile Glu Asp Gly Ser
1790                1795                1800

Val Gln Leu Ala Asp His Tyr Gln Gln Asn Thr Pro Ile Gly Asp
    1805                1810                1815

Gly Pro Val Leu Leu Pro Asp Asn His Tyr Leu Ser Thr Gln Ser
    1820                1825                1830

Ala Leu Ser Lys Asp Pro Asn Glu Lys Arg Asp His Met Val Leu
    1835                1840                1845

Leu Glu Phe Val Thr Ala Ala Gly Ile Thr Leu Gly Met Asp Glu
    1850                1855                1860

Leu Tyr Lys Ser Gly Gly Ser Pro Lys Lys Lys Arg Lys Val
    1865                1870                1875

<210> SEQ ID NO 33
<211> LENGTH: 1877
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Lys Arg Thr Ala Asp Gly Ser Glu Phe Glu Ser Pro Lys Lys Lys
1               5                   10                  15

Arg Lys Val Ser Glu Val Glu Phe Ser His Glu Tyr Trp Met Arg His
                20                  25                  30

Ala Leu Thr Leu Ala Lys Arg Ala Arg Asp Glu Arg Glu Val Pro Val
            35                  40                  45

Gly Ala Val Leu Val Leu Asn Asn Arg Val Ile Gly Glu Gly Trp Asn
        50                  55                  60

Arg Ala Ile Gly Leu His Asp Pro Thr Ala His Ala Glu Ile Met Ala
65                  70                  75                  80

Leu Arg Gln Gly Gly Leu Val Met Gln Asn Tyr Arg Leu Ile Asp Ala
                85                  90                  95

Thr Leu Tyr Gly Thr Phe Glu Pro Cys Val Met Cys Ala Gly Ala Met
            100                 105                 110

Ile His Ser Arg Ile Gly Arg Val Phe Gly Val Arg Asn Ala Lys
        115                 120                 125

Thr Gly Ala Ala Gly Ser Leu Met Asp Val Leu His Tyr Pro Gly Met
130                 135                 140

Asn His Arg Val Glu Ile Thr Glu Gly Ile Leu Ala Asp Glu Cys Ala
145                 150                 155                 160

Ala Leu Leu Cys Tyr Phe Phe Arg Met Pro Arg Gln Val Phe Asn Ala
                165                 170                 175

Gln Lys Lys Ala Gln Ser Ser Thr Asp Ser Gly Gly Ser Gly Gly
            180                 185                 190

Ser Ser Gly Ser Glu Thr Pro Gly Thr Ser Glu Ser Ala Thr Pro Glu
        195                 200                 205

Ser Ser Gly Gly Ser Ser Gly Gly Ser Asp Lys Lys Tyr Ser Ile Gly
        210                 215                 220

Leu Ala Ile Gly Thr Asn Ser Val Gly Trp Ala Val Ile Thr Asp Glu
225                 230                 235                 240
```

-continued

```
Tyr Lys Val Pro Ser Lys Lys Phe Lys Val Leu Gly Asn Thr Asp Arg
            245                 250                 255

His Ser Ile Lys Lys Asn Leu Ile Gly Ala Leu Leu Phe Asp Ser Gly
            260                 265                 270

Glu Thr Ala Glu Ala Thr Arg Leu Lys Arg Thr Ala Arg Arg Arg Tyr
            275                 280                 285

Thr Arg Arg Lys Asn Arg Ile Cys Tyr Leu Gln Glu Ile Phe Ser Asn
        290                 295                 300

Glu Met Ala Lys Val Asp Asp Ser Phe Phe His Arg Leu Glu Glu Ser
305                 310                 315                 320

Phe Leu Val Glu Glu Asp Lys Lys His Glu Arg His Pro Ile Phe Gly
                325                 330                 335

Asn Ile Val Asp Glu Val Ala Tyr His Glu Lys Tyr Pro Thr Ile Tyr
            340                 345                 350

His Leu Arg Lys Lys Leu Val Asp Ser Thr Asp Lys Ala Asp Leu Arg
            355                 360                 365

Leu Ile Tyr Leu Ala Leu Ala His Met Ile Lys Phe Arg Gly His Phe
        370                 375                 380

Leu Ile Glu Gly Asp Leu Asn Pro Asp Asn Ser Asp Val Asp Lys Leu
385                 390                 395                 400

Phe Ile Gln Leu Val Gln Thr Tyr Asn Gln Leu Phe Glu Glu Asn Pro
                405                 410                 415

Ile Asn Ala Ser Gly Val Asp Ala Lys Ala Ile Leu Ser Ala Arg Leu
            420                 425                 430

Ser Lys Ser Arg Arg Leu Glu Asn Leu Ile Ala Gln Leu Pro Gly Glu
            435                 440                 445

Lys Lys Asn Gly Leu Phe Gly Asn Leu Ile Ala Leu Ser Leu Gly Leu
        450                 455                 460

Thr Pro Asn Phe Lys Ser Asn Phe Asp Leu Ala Glu Asp Ala Lys Leu
465                 470                 475                 480

Gln Leu Ser Lys Asp Thr Tyr Asp Asp Asp Leu Asp Asn Leu Leu Ala
                485                 490                 495

Gln Ile Gly Asp Gln Tyr Ala Asp Leu Phe Leu Ala Ala Lys Asn Leu
            500                 505                 510

Ser Asp Ala Ile Leu Leu Ser Asp Ile Leu Arg Val Asn Thr Glu Ile
            515                 520                 525

Thr Lys Ala Pro Leu Ser Ala Ser Met Ile Lys Arg Tyr Asp Glu His
        530                 535                 540

His Gln Asp Leu Thr Leu Leu Lys Ala Leu Val Arg Gln Gln Leu Pro
545                 550                 555                 560

Glu Lys Tyr Lys Glu Ile Phe Phe Asp Gln Ser Lys Asn Gly Tyr Ala
                565                 570                 575

Gly Tyr Ile Asp Gly Gly Ala Ser Gln Glu Glu Phe Tyr Lys Phe Ile
            580                 585                 590

Lys Pro Ile Leu Glu Lys Met Asp Gly Thr Glu Glu Leu Leu Val Lys
        595                 600                 605

Leu Asn Arg Glu Asp Leu Leu Arg Lys Gln Arg Thr Phe Asp Asn Gly
610                 615                 620

Ser Ile Pro His Gln Ile His Leu Gly Glu Leu His Ala Ile Leu Arg
625                 630                 635                 640

Arg Gln Glu Asp Phe Tyr Pro Phe Leu Lys Asp Asn Arg Glu Lys Ile
                645                 650                 655
```

```
Glu Lys Ile Leu Thr Phe Arg Ile Pro Tyr Tyr Val Gly Pro Leu Ala
            660                 665                 670

Arg Gly Asn Ser Arg Phe Ala Trp Met Thr Arg Lys Ser Glu Glu Thr
            675                 680                 685

Ile Thr Pro Trp Asn Phe Glu Glu Val Val Asp Lys Gly Ala Ser Ala
            690                 695                 700

Gln Ser Phe Ile Glu Arg Met Thr Asn Phe Asp Lys Asn Leu Pro Asn
705                 710                 715                 720

Glu Lys Val Leu Pro Lys His Ser Leu Leu Tyr Glu Tyr Phe Thr Val
            725                 730                 735

Tyr Asn Glu Leu Thr Lys Val Lys Tyr Val Thr Glu Gly Met Arg Lys
            740                 745                 750

Pro Ala Phe Leu Ser Gly Glu Gln Lys Lys Ala Ile Val Asp Leu Leu
            755                 760                 765

Phe Lys Thr Asn Arg Lys Val Thr Val Lys Gln Leu Lys Glu Asp Tyr
            770                 775                 780

Phe Lys Lys Ile Glu Cys Phe Asp Ser Val Glu Ile Ser Gly Val Glu
785                 790                 795                 800

Asp Arg Phe Asn Ala Ser Leu Gly Thr Tyr His Asp Leu Leu Lys Ile
            805                 810                 815

Ile Lys Asp Lys Asp Phe Leu Asp Asn Glu Glu Asn Glu Asp Ile Leu
            820                 825                 830

Glu Asp Ile Val Leu Thr Leu Thr Leu Phe Glu Asp Arg Glu Met Ile
            835                 840                 845

Glu Glu Arg Leu Lys Thr Tyr Ala His Leu Phe Asp Asp Lys Val Met
850                 855                 860

Lys Gln Leu Lys Arg Arg Arg Tyr Thr Gly Trp Gly Arg Leu Ser Arg
865                 870                 875                 880

Lys Leu Ile Asn Gly Ile Arg Asp Lys Gln Ser Gly Lys Thr Ile Leu
            885                 890                 895

Asp Phe Leu Lys Ser Asp Gly Phe Ala Asn Arg Asn Phe Met Gln Leu
            900                 905                 910

Ile His Asp Asp Ser Leu Thr Phe Lys Glu Asp Ile Gln Lys Ala Gln
            915                 920                 925

Val Ser Gly Gln Gly Asp Ser Leu His Glu His Ile Ala Asn Leu Ala
930                 935                 940

Gly Ser Pro Ala Ile Lys Lys Gly Ile Leu Gln Thr Val Lys Val Val
945                 950                 955                 960

Asp Glu Leu Val Lys Val Met Gly Arg His Lys Pro Glu Asn Ile Val
            965                 970                 975

Ile Glu Met Ala Arg Glu Asn Gln Thr Thr Gln Lys Gly Gln Lys Asn
            980                 985                 990

Ser Arg Glu Arg Met Lys Arg Ile Glu Glu Gly Ile Lys Glu Leu Gly
            995                 1000                1005

Ser Gln Ile Leu Lys Glu His Pro Val Glu Asn Thr Gln Leu Gln
            1010                1015                1020

Asn Glu Lys Leu Tyr Leu Tyr Tyr Leu Gln Asn Gly Arg Asp Met
            1025                1030                1035

Tyr Val Asp Gln Glu Leu Asp Ile Asn Arg Leu Ser Asp Tyr Asp
            1040                1045                1050

Val Asp His Ile Val Pro Gln Ser Phe Leu Lys Asp Asp Ser Ile
            1055                1060                1065

Asp Asn Lys Val Leu Thr Arg Ser Asp Lys Asn Arg Gly Lys Ser
```

```
                1070                1075                1080
Asp Asn Val Pro Ser Glu Glu Val Val Lys Lys Met Lys Asn Tyr
    1085                1090                1095
Trp Arg Gln Leu Leu Asn Ala Lys Leu Ile Thr Gln Arg Lys Phe
    1100                1105                1110
Asp Asn Leu Thr Lys Ala Glu Arg Gly Gly Leu Ser Glu Leu Asp
    1115                1120                1125
Lys Ala Gly Phe Ile Lys Arg Gln Leu Val Glu Thr Arg Gln Ile
    1130                1135                1140
Thr Lys His Val Ala Gln Ile Leu Asp Ser Arg Met Asn Thr Lys
    1145                1150                1155
Tyr Asp Glu Asn Asp Lys Leu Ile Arg Glu Val Lys Val Ile Thr
    1160                1165                1170
Leu Lys Ser Lys Leu Val Ser Asp Phe Arg Lys Asp Phe Gln Phe
    1175                1180                1185
Tyr Lys Val Arg Glu Ile Asn Asn Tyr His His Ala His Asp Ala
    1190                1195                1200
Tyr Leu Asn Ala Val Val Gly Thr Ala Leu Ile Lys Lys Tyr Pro
    1205                1210                1215
Lys Leu Glu Ser Glu Phe Val Tyr Gly Asp Tyr Lys Val Tyr Asp
    1220                1225                1230
Val Arg Lys Met Ile Ala Lys Ser Glu Gln Glu Ile Gly Lys Ala
    1235                1240                1245
Thr Ala Lys Tyr Phe Phe Tyr Ser Asn Ile Met Asn Phe Phe Lys
    1250                1255                1260
Thr Glu Ile Thr Leu Ala Asn Gly Glu Ile Arg Lys Arg Pro Leu
    1265                1270                1275
Ile Glu Thr Asn Gly Glu Thr Gly Glu Ile Val Trp Asp Lys Gly
    1280                1285                1290
Arg Asp Phe Ala Thr Val Arg Lys Val Leu Ser Met Pro Gln Val
    1295                1300                1305
Asn Ile Val Lys Lys Thr Glu Val Gln Thr Gly Gly Phe Ser Lys
    1310                1315                1320
Glu Ser Ile Leu Pro Lys Arg Asn Ser Asp Lys Leu Ile Ala Arg
    1325                1330                1335
Lys Lys Asp Trp Asp Pro Lys Lys Tyr Gly Gly Phe Asp Ser Pro
    1340                1345                1350
Thr Val Ala Tyr Ser Val Leu Val Val Ala Lys Val Glu Lys Gly
    1355                1360                1365
Lys Ser Lys Lys Leu Lys Ser Val Lys Glu Leu Leu Gly Ile Thr
    1370                1375                1380
Ile Met Glu Arg Ser Ser Phe Glu Lys Asn Pro Ile Asp Phe Leu
    1385                1390                1395
Glu Ala Lys Gly Tyr Lys Glu Val Lys Lys Asp Leu Ile Ile Lys
    1400                1405                1410
Leu Pro Lys Tyr Ser Leu Phe Glu Leu Glu Asn Gly Arg Lys Arg
    1415                1420                1425
Met Leu Ala Ser Ala Gly Glu Leu Gln Lys Gly Asn Glu Leu Ala
    1430                1435                1440
Leu Pro Ser Lys Tyr Val Asn Phe Leu Tyr Leu Ala Ser His Tyr
    1445                1450                1455
Glu Lys Leu Lys Gly Ser Pro Glu Asp Asn Glu Gln Lys Gln Leu
    1460                1465                1470
```

-continued

```
Phe Val Glu Gln His Lys His Tyr Leu Asp Glu Ile Ile Glu Gln
    1475            1480                1485

Ile Ser Glu Phe Ser Lys Arg Val Ile Leu Ala Asp Ala Asn Leu
    1490            1495                1500

Asp Lys Val Leu Ser Ala Tyr Asn Lys His Arg Asp Lys Pro Ile
    1505            1510                1515

Arg Glu Gln Ala Glu Asn Ile Ile His Leu Phe Thr Leu Thr Asn
    1520            1525                1530

Leu Gly Ala Pro Ala Ala Phe Lys Tyr Phe Asp Thr Thr Ile Asp
    1535            1540                1545

Arg Lys Arg Tyr Thr Ser Thr Lys Glu Val Leu Asp Ala Thr Leu
    1550            1555                1560

Ile His Gln Ser Ile Thr Gly Leu Tyr Glu Thr Arg Ile Asp Leu
    1565            1570                1575

Ser Gln Leu Gly Gly Asp Ser Gly Gly Ser Lys Arg Thr Ala Asp
    1580            1585                1590

Gly Ser Glu Phe Glu Pro Lys Lys Lys Arg Lys Val Gly Ser Gly
    1595            1600                1605

Ala Thr Asn Phe Ser Leu Leu Lys Gln Ala Gly Asp Val Glu Glu
    1610            1615                1620

Asn Pro Gly Pro Met Val Ser Lys Gly Glu Glu Leu Phe Thr Gly
    1625            1630                1635

Val Val Pro Ile Leu Val Glu Leu Asp Gly Asp Val Asn Gly His
    1640            1645                1650

Lys Phe Ser Val Ser Gly Glu Gly Glu Gly Asp Ala Thr Tyr Gly
    1655            1660                1665

Lys Leu Thr Leu Lys Phe Ile Cys Thr Thr Gly Lys Leu Pro Val
    1670            1675                1680

Pro Trp Pro Thr Leu Val Thr Thr Leu Thr Tyr Gly Val Gln Cys
    1685            1690                1695

Phe Ser Arg Tyr Pro Asp His Met Lys Gln His Asp Phe Phe Lys
    1700            1705                1710

Ser Ala Met Pro Glu Gly Tyr Val Gln Glu Arg Thr Ile Phe Phe
    1715            1720                1725

Lys Asp Asp Gly Asn Tyr Lys Thr Arg Ala Glu Val Lys Phe Glu
    1730            1735                1740

Gly Asp Thr Leu Val Asn Arg Ile Glu Leu Lys Gly Ile Asp Phe
    1745            1750                1755

Lys Glu Asp Gly Asn Ile Leu Gly His Lys Leu Glu Tyr Asn Tyr
    1760            1765                1770

Asn Ser His Asn Val Tyr Ile Met Ala Asp Lys Gln Lys Asn Gly
    1775            1780                1785

Ile Lys Val Asn Phe Lys Ile Arg His Asn Ile Glu Asp Gly Ser
    1790            1795                1800

Val Gln Leu Ala Asp His Tyr Gln Gln Asn Thr Pro Ile Gly Asp
    1805            1810                1815

Gly Pro Val Leu Leu Pro Asp Asn His Tyr Leu Ser Thr Gln Ser
    1820            1825                1830

Ala Leu Ser Lys Asp Pro Asn Glu Lys Arg Asp His Met Val Leu
    1835            1840                1845

Leu Glu Phe Val Thr Ala Ala Gly Ile Thr Leu Gly Met Asp Glu
    1850            1855                1860
```

```
Leu Tyr Lys Ser Gly Gly Ser Pro Lys Lys Lys Arg Lys Val
    1865                1870                1875
```

<210> SEQ ID NO 34
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
            20                  25                  30

Val Leu Val Leu Asn Asn Arg Val Ile Gly Glu Gly Trp Asn Arg Ala
        35                  40                  45

Ile Gly Leu His Asp Pro Thr Ala His Ala Glu Ile Met Ala Leu Arg
50                  55                  60

Gln Gly Gly Leu Val Met Gln Asn Tyr Arg Leu Ile Asp Ala Thr Leu
65                  70                  75                  80

Tyr Val Thr Phe Glu Pro Cys Val Met Cys Ala Gly Ala Met Ile His
                85                  90                  95

Ser Arg Ile Gly Arg Val Val Phe Gly Val Arg Asn Ala Lys Thr Gly
            100                 105                 110

Ala Ala Gly Ser Leu Met Asp Val Leu His Tyr Pro Gly Met Asn His
        115                 120                 125

Arg Val Glu Ile Thr Glu Gly Ile Leu Ala Asp Glu Cys Ala Ala Leu
    130                 135                 140

Leu Cys Tyr Phe Phe Arg Met Pro Arg Gln Val Phe Asn Ala Gln Lys
145                 150                 155                 160

Lys Ala Gln Ser Ser Thr Asp
                165
```

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 35

```
His His His His His His
1               5
```

<210> SEQ ID NO 36
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ala, Glu or Gly
<220> FEATURE:
<221> NAME/KEY: MOD_RES
<222> LOCATION: (10)..(10)
<223> OTHER INFORMATION: Ala, Thr or Glu
<220> FEATURE:
<221> NAME/KEY: MOD_RES

```
<222> LOCATION: (11)..(11)
<223> OTHER INFORMATION: Ala, Pro, Lys, Thr or Ser
<220> FEATURE:
<221> NAME/KEY: MOD_RES
<222> LOCATION: (12)..(12)
<223> OTHER INFORMATION: Ser, Asp or Asn
<220> FEATURE:
<221> NAME/KEY: MOD_RES
<222> LOCATION: (15)..(15)
<223> OTHER INFORMATION: Met, Cys, Leu, Tyr, Pro, Glu or Thr
<220> FEATURE:
<221> NAME/KEY: MOD_RES
<222> LOCATION: (19)..(19)
<223> OTHER INFORMATION: Glu, Ala, Val, Asp, Thr, Cys, Met or Leu
<220> FEATURE:
<221> NAME/KEY: MOD_RES
<222> LOCATION: (24)..(24)
<223> OTHER INFORMATION: Tyr, Lys, Thr or Asn
<220> FEATURE:
<221> NAME/KEY: MOD_RES
<222> LOCATION: (28)..(28)
<223> OTHER INFORMATION: His, Glu, Lys, Gln, Phe or Leu
<220> FEATURE:
<221> NAME/KEY: MOD_RES
<222> LOCATION: (30)..(30)
<223> OTHER INFORMATION: Leu, Met, Phe, His, or Ile
<220> FEATURE:
<221> NAME/KEY: MOD_RES
<222> LOCATION: (35)..(35)
<223> OTHER INFORMATION: Arg, Glu, Asp, Leu or Lys
<220> FEATURE:
<221> NAME/KEY: MOD_RES
<222> LOCATION: (41)..(41)
<223> OTHER INFORMATION: Glu, Ile or not present

<400> SEQUENCE: 36

Met Glu Ala Lys Ala Xaa Pro Thr Pro Xaa Xaa Xaa Gly Ala Xaa Ser
1               5                   10                  15

Val Ser Xaa Glu Glu Thr Glu Xaa Trp Met Glu Xaa Ala Xaa Gln Met
            20                  25                  30

Ala Lys Xaa Ala Leu Glu Asn Gly Xaa Val Pro Val
        35                  40

<210> SEQ ID NO 37
<211> LENGTH: 30
<212> TYPE: PRT
<213> ORGANISM: Escherichia coli

<400> SEQUENCE: 37

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val
            20                  25                  30

<210> SEQ ID NO 38
<211> LENGTH: 46
<212> TYPE: PRT
<213> ORGANISM: Homo sapiens

<400> SEQUENCE: 38

Met Glu Ala Lys Ala Ala Pro Lys Pro Ala Ala Ser Gly Ala Cys Ser
1               5                   10                  15

Val Ser Ala Glu Glu Thr Glu Lys Trp Met Glu Ala Met His Met
            20                  25                  30

Ala Lys Glu Ala Leu Glu Asn Thr Glu Val Pro Val Gly Cys
        35                  40                  45

<210> SEQ ID NO 39
```

<211> LENGTH: 46
<212> TYPE: PRT
<213> ORGANISM: Mus musculus

<400> SEQUENCE: 39

Met Glu Glu Lys Val Glu Ser Thr Thr Thr Pro Asp Gly Pro Cys Val
1               5                   10                  15

Val Ser Val Gln Glu Thr Glu Lys Trp Met Glu Glu Ala Met Arg Met
            20                  25                  30

Ala Lys Glu Ala Leu Glu Asn Ile Glu Val Pro Val Gly Cys
        35                  40                  45

<210> SEQ ID NO 40
<211> LENGTH: 43
<212> TYPE: PRT
<213> ORGANISM: Danio rerio

<400> SEQUENCE: 40

Met Gln Glu Val Gly Val Asp Pro Glu Lys Asn Asp Phe Leu Gln Pro
1               5                   10                  15

Ser Asp Ser Glu Val Gln Thr Trp Met Ala Lys Ala Phe Asp Met Ala
            20                  25                  30

Val Glu Ala Leu Glu Asn Gly Glu Val Pro Val
        35                  40

<210> SEQ ID NO 41
<211> LENGTH: 44
<212> TYPE: PRT
<213> ORGANISM: Bos taurus

<400> SEQUENCE: 41

Met Glu Ala Lys Ala Gly Pro Thr Ala Ala Thr Asp Gly Ala Tyr Ser
1               5                   10                  15

Val Ser Ala Glu Glu Thr Glu Lys Trp Met Glu Gln Ala Met Gln Met
            20                  25                  30

Ala Lys Asp Ala Leu Asp Asn Thr Glu Val Pro Val
        35                  40

<210> SEQ ID NO 42
<211> LENGTH: 32
<212> TYPE: PRT
<213> ORGANISM: Xenopus laevis

<400> SEQUENCE: 42

Met Glu Pro Leu Gln Ile Thr Glu Glu Ile Gln Asn Trp Met His Lys
1               5                   10                  15

Ala Phe Gln Met Ala Gln Asp Ala Leu Asn Asn Gly Glu Val Pro Val
            20                  25                  30

<210> SEQ ID NO 43
<211> LENGTH: 27
<212> TYPE: PRT
<213> ORGANISM: Xenopus tropicalis

<400> SEQUENCE: 43

Met Thr Glu Glu Ile Gln Asn Trp Met His Lys Ala Phe Gln Met Ala
1               5                   10                  15

Gln Asp Ala Leu Asn Asn Gly Glu Val Pro Val
            20                  25

<210> SEQ ID NO 44

-continued

```
<211> LENGTH: 31
<212> TYPE: PRT
<213> ORGANISM: Arabidopsis thaliana

<400> SEQUENCE: 44

Met Glu Glu Asp His Cys Glu Asp Ser His Asn Tyr Met Gly Phe Ala
1               5                   10                  15

Leu His Gln Ala Lys Leu Ala Leu Glu Ala Leu Glu Val Pro Val
            20                  25                  30

<210> SEQ ID NO 45
<211> LENGTH: 48
<212> TYPE: PRT
<213> ORGANISM: Schizosaccharomyces pombe

<400> SEQUENCE: 45

Gln Asp Ile Leu Ala Glu Met Asn Lys Thr Ser Ser Asn Thr Val
1               5                   10                  15

Lys Tyr Asp Thr Gln His Glu Thr Tyr Met Lys Leu Ala His Glu Ile
            20                  25                  30

Leu Asn Leu Gly Pro Tyr Phe Val Ile Gln Pro Arg Ser Pro Gly Ser
        35                  40                  45

<210> SEQ ID NO 46
<211> LENGTH: 32
<212> TYPE: PRT
<213> ORGANISM: Salmonella typhi

<400> SEQUENCE: 46

Met Ser Asp Val Glu Leu Asp His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

<210> SEQ ID NO 47
<211> LENGTH: 28
<212> TYPE: PRT
<213> ORGANISM: Staphylococcus aureus

<400> SEQUENCE: 47

Met Thr Asn Asp Ile Tyr Phe Met Thr Leu Ala Ile Glu Glu Ala Lys
1               5                   10                  15

Lys Ala Ala Gln Leu Gly Glu Val Pro Ile Gly Ala
            20                  25

<210> SEQ ID NO 48
<211> LENGTH: 30
<212> TYPE: PRT
<213> ORGANISM: Streptococcus pyogenes

<400> SEQUENCE: 48

Met Pro Tyr Ser Leu Glu Glu Gln Thr Tyr Phe Met Gln Glu Ala Leu
1               5                   10                  15

Lys Glu Ala Glu Lys Ser Leu Gln Lys Ala Glu Ile Pro Ile
            20                  25                  30

<210> SEQ ID NO 49
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (38)..(38)
<223> OTHER INFORMATION: Met, Arg, His, Glu, Gln, Pro, Gly, or Asn
<220> FEATURE:
<221> NAME/KEY: MOD_RES
<222> LOCATION: (39)..(39)
<223> OTHER INFORMATION: Gln, Leu, Arg, Met, Lys, Ala, Ser, Thr or Asn
<220> FEATURE:
<221> NAME/KEY: MOD_RES
<222> LOCATION: (45)..(45)
<223> OTHER INFORMATION: Asp, His, Gln, Asn, Lys, Glu or Gly
<220> FEATURE:
<221> NAME/KEY: MOD_RES
<222> LOCATION: (60)..(60)
<223> OTHER INFORMATION: Gly, Ala, Ser, or Tyr
<220> FEATURE:
<221> NAME/KEY: MOD_RES
<222> LOCATION: (75)..(75)
<223> OTHER INFORMATION: Arg, Gln, Lys, Pro, Gly, Leu, Asp or Ser
<220> FEATURE:
<221> NAME/KEY: MOD_RES
<222> LOCATION: (89)..(89)
<223> OTHER INFORMATION: Ala, Asp, Gly, Leu or not present
<220> FEATURE:
<221> NAME/KEY: MOD_RES
<222> LOCATION: (105)..(105)
<223> OTHER INFORMATION: Leu, Arg, Gln, Met, Phe or Pro

<400> SEQUENCE: 49

Leu Val Tyr Asn Asn Glu Val Ile Gly Lys Gly Arg Asn Glu Val Asn
1               5                   10                  15

Glu Thr Lys Asn Ala Thr Arg His Ala Glu Met Val Ala Ile Asp Gln
            20                  25                  30

Val Leu Asp Trp Cys Xaa Xaa Arg Gly Val Phe Glu Xaa Thr Val Leu
        35                  40                  45

Tyr Val Thr Val Glu Pro Cys Ile Met Cys Ala Xaa Ala Leu Arg Leu
    50                  55                  60

Leu Arg Ile Pro Leu Val Val Tyr Gly Cys Xaa Asn Glu Arg Phe Gly
65                  70                  75                  80

Gly Cys Gly Ser Val Leu Asn Ile Xaa Asp Leu Pro Asn Thr Gly His
                85                  90                  95

Arg Phe Lys Cys Ile Pro Gly Tyr Xaa Ala Glu Glu Ala Val Glu Leu
            100                 105                 110

Leu Lys Thr Phe Tyr Lys Gln Glu Asn Pro Asn Ala Pro Lys Ser Lys
        115                 120                 125

Val Arg Lys Lys Glu
    130

<210> SEQ ID NO 50
<211> LENGTH: 136
<212> TYPE: PRT
<213> ORGANISM: Escherichia coli

<400> SEQUENCE: 50

Ala Val Leu Val His Asn Asn Arg Val Ile Gly Glu Gly Trp Asn Arg
1               5                   10                  15

Pro Ile Gly Arg His Asp Pro Thr Ala His Ala Glu Ile Met Ala Leu
            20                  25                  30

Arg Gln Gly Gly Leu Val Met Gln Asn Tyr Arg Leu Ile Asp Ala Thr
        35                  40                  45

Leu Tyr Val Thr Leu Glu Pro Cys Val Met Cys Ala Gly Ala Met Ile
    50                  55                  60

His Ser Arg Ile Gly Arg Val Val Phe Gly Ala Arg Asp Ala Lys Thr
```

```
                65                  70                  75                  80
Gly Ala Ala Gly Ser Leu Met Asp Val Leu His His Pro Gly Met Asn
                    85                  90                  95

His Arg Val Glu Ile Thr Glu Gly Ile Leu Ala Asp Glu Cys Ala Ala
            100                 105                 110

Leu Leu Ser Asp Phe Phe Arg Met Arg Arg Gln Glu Ile Lys Ala Gln
        115                 120                 125

Lys Lys Ala Gln Ser Ser Thr Asp
130                 135

<210> SEQ ID NO 51
<211> LENGTH: 140
<212> TYPE: PRT
<213> ORGANISM: Homo sapiens

<400> SEQUENCE: 51

Met Val Tyr Asn Asn Glu Val Val Gly Lys Gly Arg Asn Glu Val Asn
1               5                   10                  15

Gln Thr Lys Asn Ala Thr Arg His Ala Glu Met Val Ala Ile Asp Gln
            20                  25                  30

Val Leu Asp Trp Cys Arg Gln Ser Gly Lys Ser Pro Ser Glu Val Phe
        35                  40                  45

Glu His Thr Val Leu Tyr Val Thr Val Glu Pro Cys Ile Met Cys Ala
    50                  55                  60

Ala Ala Leu Arg Leu Met Lys Ile Pro Leu Val Val Tyr Gly Cys Gln
65                  70                  75                  80

Asn Glu Arg Phe Gly Gly Cys Gly Ser Val Leu Asn Ile Ala Ser Ala
                85                  90                  95

Asp Leu Pro Asn Thr Gly Arg Pro Phe Gln Cys Ile Pro Gly Tyr Arg
            100                 105                 110

Ala Glu Glu Ala Val Glu Met Leu Lys Thr Phe Tyr Lys Gln Glu Asn
        115                 120                 125

Pro Asn Ala Pro Lys Ser Lys Val Arg Lys Lys Glu
    130                 135                 140

<210> SEQ ID NO 52
<211> LENGTH: 140
<212> TYPE: PRT
<213> ORGANISM: Mus musculus

<400> SEQUENCE: 52

Met Val Tyr Asn Asn Glu Val Val Gly Lys Gly Arg Asn Glu Val Asn
1               5                   10                  15

Gln Thr Lys Asn Ala Thr Arg His Ala Glu Met Val Ala Ile Asp Gln
            20                  25                  30

Val Leu Asp Trp Cys His Gln His Gly Gln Ser Pro Ser Thr Val Phe
        35                  40                  45

Glu His Thr Val Leu Tyr Val Thr Val Glu Pro Cys Ile Met Cys Ala
    50                  55                  60

Ala Ala Leu Arg Leu Met Lys Ile Pro Leu Val Val Tyr Gly Cys Gln
65                  70                  75                  80

Asn Glu Arg Phe Gly Gly Cys Gly Ser Val Leu Asn Ile Ala Ser Ala
                85                  90                  95

Asp Leu Pro Asn Thr Gly Arg Pro Phe Gln Cys Ile Pro Gly Tyr Arg
            100                 105                 110

Ala Glu Glu Ala Val Glu Leu Leu Lys Thr Phe Tyr Lys Gln Glu Asn
```

115                 120                 125
Pro Asn Ala Pro Lys Ser Lys Val Arg Lys Lys Asp
    130                 135                 140

<210> SEQ ID NO 53
<211> LENGTH: 142
<212> TYPE: PRT
<213> ORGANISM: Danio rerio

<400> SEQUENCE: 53

Cys Leu Met Val Tyr Asn Asn Glu Ile Ile Gly Lys Gly Arg Asn Glu
1               5                   10                  15

Val Asn Glu Thr Lys Asn Ala Thr Arg His Ala Glu Met Val Ala Leu
            20                  25                  30

Asp Gln Val Leu Asp Trp Cys Arg Leu Arg Glu Lys Asp Cys Lys Glu
        35                  40                  45

Val Cys Glu Gln Thr Val Leu Tyr Val Thr Val Glu Pro Cys Ile Met
    50                  55                  60

Cys Ala Ala Ala Leu Arg Leu Arg Ile Pro Phe Val Val Tyr Gly
65                  70                  75                  80

Cys Lys Asn Glu Arg Phe Gly Gly Cys Gly Ser Val Leu Asp Val Ser
                85                  90                  95

Ser Asp His Leu Pro His Thr Gly Thr Ser Phe Lys Cys Ile Ala Gly
            100                 105                 110

Tyr Arg Ala Glu Glu Ala Val Glu Met Leu Lys Thr Phe Tyr Lys Gln
        115                 120                 125

Glu Asn Pro Asn Ala Pro Lys Pro Lys Val Arg Lys Asp Ser
    130                 135                 140

<210> SEQ ID NO 54
<211> LENGTH: 142
<212> TYPE: PRT
<213> ORGANISM: Bos taurus

<400> SEQUENCE: 54

Cys Leu Met Val Tyr Asn Asn Glu Val Val Gly Lys Gly Arg Asn Glu
1               5                   10                  15

Val Asn Gln Thr Lys Asn Ala Thr Arg His Ala Glu Met Val Ala Ile
            20                  25                  30

Asp Gln Ala Leu Asp Trp Cys Arg Arg Gly Arg Ser Pro Ser Glu
        35                  40                  45

Val Phe Glu His Thr Val Leu Tyr Val Thr Val Glu Pro Cys Ile Met
    50                  55                  60

Cys Ala Ala Ala Leu Arg Leu Met Arg Ile Pro Leu Val Val Tyr Gly
65                  70                  75                  80

Cys Gln Asn Glu Arg Phe Gly Gly Cys Gly Ser Val Leu Asp Ile Ala
                85                  90                  95

Ser Ala Asp Leu Pro Ser Thr Gly Lys Pro Phe Gln Cys Thr Pro Gly
            100                 105                 110

Tyr Arg Ala Glu Glu Ala Val Glu Met Leu Lys Thr Phe Tyr Lys Gln
        115                 120                 125

Glu Asn Pro Asn Ala Pro Lys Ser Lys Val Arg Lys Lys Glu
    130                 135                 140

<210> SEQ ID NO 55
<211> LENGTH: 142
<212> TYPE: PRT

<213> ORGANISM: Xenopus laevis

<400> SEQUENCE: 55

Cys Leu Met Val Tyr Gly Asn Gln Val Val Gly Lys Gly Arg Asn Glu
1               5                   10                  15

Val Asn Glu Thr Lys Asn Ala Thr Gln His Ala Glu Met Val Ala Ile
            20                  25                  30

Asp Gln Val Leu Asp Trp Cys Glu Met Asn Ser Lys Lys Ser Thr Asp
        35                  40                  45

Val Phe Glu Asn Ile Val Leu Tyr Val Thr Val Glu Pro Cys Ile Met
    50                  55                  60

Cys Ala Gly Ala Leu Arg Leu Leu Lys Ile Pro Leu Val Val Tyr Gly
65                  70                  75                  80

Cys Arg Asn Glu Arg Phe Gly Gly Cys Gly Ser Val Leu Asn Val Ser
                85                  90                  95

Gly Asp Asp Ile Pro Asp Thr Gly Thr Lys Phe Lys Cys Ile Gly Gly
            100                 105                 110

Tyr Gln Ala Glu Lys Ala Ile Glu Leu Leu Lys Thr Phe Tyr Lys Gln
        115                 120                 125

Glu Asn Pro Asn Ala Pro Lys Ser Lys Val Arg Lys Lys Glu
    130                 135                 140

<210> SEQ ID NO 56
<211> LENGTH: 142
<212> TYPE: PRT
<213> ORGANISM: Xenopus tropicalis

<400> SEQUENCE: 56

Cys Leu Met Val Tyr Asp Asn Gln Val Val Gly Lys Gly Arg Asn Glu
1               5                   10                  15

Val Asn Glu Thr Lys Asn Ala Thr Arg His Ala Glu Met Val Ala Ile
            20                  25                  30

Asp Gln Val Leu Asp Trp Cys Glu Lys Asn Ser Lys Lys Ser Arg Asp
        35                  40                  45

Val Phe Glu Asn Ile Val Leu Tyr Val Thr Val Glu Pro Cys Ile Met
    50                  55                  60

Cys Ala Gly Ala Leu Arg Leu Leu Lys Ile Pro Leu Val Val Tyr Gly
65                  70                  75                  80

Cys Arg Asn Glu Arg Phe Gly Gly Cys Gly Ser Val Leu Asn Val Ala
                85                  90                  95

Gly Asp Asn Ile Pro Asp Thr Gly Thr Glu Phe Lys Tyr Ile Gly Gly
            100                 105                 110

Tyr Gln Ala Glu Lys Ala Val Glu Leu Leu Lys Thr Phe Tyr Lys Gln
        115                 120                 125

Glu Asn Pro Asn Ala Pro Arg Ser Lys Val Arg Lys Lys Glu
    130                 135                 140

<210> SEQ ID NO 57
<211> LENGTH: 145
<212> TYPE: PRT
<213> ORGANISM: Arabidopsis thaliana

<400> SEQUENCE: 57

Val Phe Leu Glu Asp Gly Lys Val Ile Ala Ser Gly Arg Asn Arg Thr
1               5                   10                  15

Asn Glu Thr Arg Asn Ala Thr Arg His Ala Glu Met Glu Ala Ile Asp
            20                  25                  30

```
Gln Leu Val Gly Gln Trp Gln Lys Asp Gly Leu Ser Pro Ser Gln Val
            35                  40                  45

Ala Glu Lys Phe Ser Lys Cys Val Leu Tyr Val Thr Cys Glu Pro Cys
 50                  55                  60

Ile Met Cys Ala Ser Ala Leu Ser Phe Leu Gly Ile Lys Glu Val Tyr
 65                  70                  75                  80

Tyr Gly Cys Pro Asn Asp Lys Phe Gly Gly Cys Gly Ser Ile Leu Ser
                     85                  90                  95

Leu His Leu Gly Ser Glu Glu Ala Gln Arg Gly Lys Gly Tyr Lys Cys
                100                 105                 110

Arg Gly Gly Ile Met Ala Glu Ala Val Ser Leu Phe Lys Cys Phe
                115                 120                 125

Tyr Glu Gln Gly Asn Pro Asn Ala Pro Lys Pro His Arg Pro Val Val
                130                 135                 140

Gln
145

<210> SEQ ID NO 58
<211> LENGTH: 134
<212> TYPE: PRT
<213> ORGANISM: Schizosaccharomyces pombe

<400> SEQUENCE: 58

Cys Val Phe Val Tyr Lys Gly Glu Val Ile Gly Arg Gly Phe Asn Glu
 1               5                  10                  15

Thr Asn Cys Ser Leu Ser Gly Ile Arg His Ala Glu Leu Ile Ala Ile
                 20                  25                  30

Glu Lys Ile Leu Glu His Tyr Pro Ala Ser Val Phe Lys Glu Thr Thr
             35                  40                  45

Leu Tyr Val Thr Val Glu Pro Cys Leu Met Cys Ala Ala Ala Leu Lys
 50                  55                  60

Gln Leu His Ile Lys Ala Val Tyr Phe Gly Cys Gly Asn Asp Arg Phe
 65                  70                  75                  80

Gly Gly Cys Gly Ser Val Phe Ser Ile Asn Lys Asp Gln Ser Ile Asp
                 85                  90                  95

Pro Ser Tyr Pro Val Tyr Pro Gly Leu Phe Tyr Ser Glu Ala Val Met
            100                 105                 110

Leu Met Arg Glu Phe Tyr Val Gln Glu Asn Val Lys Ala Pro Val Pro
            115                 120                 125

Gln Ser Lys Lys Gln Arg
130

<210> SEQ ID NO 59
<211> LENGTH: 143
<212> TYPE: PRT
<213> ORGANISM: Saccharomyces cerevisiae

<400> SEQUENCE: 59

His Thr Pro Thr Gly Gln Val Met Ala Tyr Gly Met Asn Asp Thr Asn
 1               5                  10                  15

Lys Ser Leu Thr Gly Val Ala His Ala Glu Phe Met Gly Ile Asp Gln
                 20                  25                  30

Ile Lys Ala Met Leu Gly Ser Arg Gly Val Val Asp Val Phe Lys Asp
             35                  40                  45

Ile Thr Leu Tyr Val Thr Val Glu Pro Cys Ile Met Cys Ala Ser Ala
 50                  55                  60
```

Leu Lys Gln Leu Asp Ile Gly Lys Val Val Phe Gly Cys Gly Asn Glu
 65                  70                  75                  80

Arg Phe Gly Gly Asn Gly Thr Val Leu Ser Val Asn His Asp Thr Cys
                 85                  90                  95

Thr Leu Val Pro Lys Asn Asn Ser Ala Ala Gly Tyr Glu Ser Ile Pro
            100                 105                 110

Gly Ile Leu Arg Lys Glu Ala Ile Met Leu Leu Arg Tyr Phe Tyr Val
            115                 120                 125

Arg Gln Asn Glu Arg Ala Pro Lys Pro Arg Ser Lys Ser Asp Arg
            130                 135                 140

<210> SEQ ID NO 60
<211> LENGTH: 125
<212> TYPE: PRT
<213> ORGANISM: Aquifex aeolicus

<400> SEQUENCE: 60

Ala Ile Ile Val Lys Glu Gly Glu Ile Ile Ser Lys Ala His Asn Ser
 1                   5                  10                  15

Val Glu Glu Leu Lys Asp Pro Thr Ala His Ala Glu Met Leu Ala Ile
                 20                  25                  30

Lys Glu Ala Cys Arg Arg Leu Asn Thr Lys Tyr Leu Glu Gly Cys Glu
             35                  40                  45

Leu Tyr Val Thr Leu Glu Pro Cys Ile Met Cys Ser Tyr Ala Leu Val
         50                  55                  60

Leu Ser Arg Ile Glu Lys Val Ile Phe Ser Ala Leu Asp Lys Lys His
 65                  70                  75                  80

Gly Gly Val Val Ser Val Phe Asn Ile Leu Asp Glu Pro Thr Leu Asn
                 85                  90                  95

His Arg Val Lys Trp Glu Tyr Tyr Pro Leu Glu Glu Ala Ser Glu Leu
            100                 105                 110

Leu Ser Glu Phe Phe Lys Lys Leu Arg Asn Asn Ile Ile
            115                 120                 125

<210> SEQ ID NO 61
<211> LENGTH: 133
<212> TYPE: PRT
<213> ORGANISM: Salmonella typhi

<400> SEQUENCE: 61

Val His Asn His Arg Val Ile Gly Glu Gly Trp Asn Arg Pro Ile Gly
 1                   5                  10                  15

Arg His Asp Pro Thr Ala His Ala Glu Ile Met Ala Leu Arg Gln Gly
                 20                  25                  30

Gly Leu Val Leu Gln Asn Tyr Arg Leu Leu Asp Thr Thr Leu Tyr Val
             35                  40                  45

Thr Leu Glu Pro Cys Val Met Cys Ala Gly Ala Met Val His Ser Arg
         50                  55                  60

Ile Gly Arg Val Val Phe Gly Ala Arg Asp Ala Lys Thr Gly Ala Ala
 65                  70                  75                  80

Gly Ser Leu Ile Asp Val Leu His Pro Gly Met Asn His Arg Val Glu
                 85                  90                  95

Glu Ile Ile Glu Gly Val Leu Arg Asp Glu Cys Ala Thr Leu Leu Ser
            100                 105                 110

Asp Phe Phe Arg Met Arg Arg Gln Glu Ile Lys Ala Leu Lys Lys Ala
            115                 120                 125

Asp Arg Ala Glu Gly
            130

<210> SEQ ID NO 62
<211> LENGTH: 126
<212> TYPE: PRT
<213> ORGANISM: Staphylococcus aureus

<400> SEQUENCE: 62

Thr Lys Asp Asp Glu Val Ile Ala Arg Ala His Asn Leu Arg Glu Thr
1               5                   10                  15

Leu Gln Gln Pro Thr Ala His Ala Glu His Ile Ala Ile Glu Arg Ala
            20                  25                  30

Ala Lys Val Leu Gly Ser Trp Arg Leu Glu Gly Cys Thr Leu Tyr Val
        35                  40                  45

Thr Leu Glu Pro Cys Val Met Cys Ala Gly Thr Ile Val Met Ser Arg
    50                  55                  60

Ile Pro Arg Val Val Tyr Gly Ala Asp Asp Pro Lys Gly Gly Cys Ser
65                  70                  75                  80

Gly Ser Leu Met Asn Leu Leu Gln Gln Ser Asn Phe Asn His Arg Ala
                85                  90                  95

Ile Val Asp Lys Gly Val Leu Lys Glu Ala Cys Ser Thr Leu Leu Thr
            100                 105                 110

Thr Phe Phe Lys Asn Leu Arg Ala Asn Lys Lys Ser Thr Asn
        115                 120                 125

<210> SEQ ID NO 63
<211> LENGTH: 135
<212> TYPE: PRT
<213> ORGANISM: Streptococcus pyogenes

<400> SEQUENCE: 63

Cys Val Ile Val Lys Asp Gly Glu Ile Ile Gly Arg Gly His Asn Ala
1               5                   10                  15

Arg Glu Glu Ser Asn Gln Ala Ile Met His Ala Glu Met Met Ala Ile
            20                  25                  30

Asn Glu Ala Asn Ala His Glu Gly Asn Trp Arg Leu Leu Asp Thr Thr
        35                  40                  45

Leu Phe Val Thr Ile Glu Pro Cys Val Met Cys Ser Gly Ala Ile Gly
    50                  55                  60

Leu Ala Arg Ile Pro His Val Ile Tyr Gly Ala Ser Asn Gln Lys Phe
65                  70                  75                  80

Gly Gly Ala Asp Ser Leu Tyr Gln Ile Leu Thr Asp Glu Arg Leu Asn
                85                  90                  95

His Arg Val Gln Val Glu Arg Gly Leu Leu Ala Ala Asp Cys Ala Asn
            100                 105                 110

Ile Met Gln Thr Phe Phe Arg Gln Gly Arg Glu Arg Lys Lys Ile Ala
        115                 120                 125

Lys His Leu Ile Lys Glu Gln
    130                 135

<210> SEQ ID NO 64
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

```
<220> FEATURE:
<221> NAME/KEY: modified_base
<222> LOCATION: (1)..(20)
<223> OTHER INFORMATION: a, c, t, g, unknown or other

<400> SEQUENCE: 64
nnnnnnnnnn nnnnnnnnnn gttttagagc tagaaatagc aagttaaaat aaggctagtc      60
cgttatcaac ttgaaaaagt ggcaccgagt cggtgctttt ttt                       103

<210> SEQ ID NO 65
<211> LENGTH: 21
<212> TYPE: DNA
<213> ORGANISM: Unknown
<220> FEATURE:
<223> OTHER INFORMATION: Description of Unknown:
      Target gene sequence

<400> SEQUENCE: 65
ggagacgatt aatgcgtctc c                                                21

<210> SEQ ID NO 66
<211> LENGTH: 23
<212> TYPE: DNA
<213> ORGANISM: Homo sapiens

<400> SEQUENCE: 66
gaacacaaag catagactgc ggg                                              23

<210> SEQ ID NO 67
<211> LENGTH: 23
<212> TYPE: DNA
<213> ORGANISM: Homo sapiens

<400> SEQUENCE: 67
ggctaaagac catagactgt ggg                                              23

<210> SEQ ID NO 68
<211> LENGTH: 23
<212> TYPE: DNA
<213> ORGANISM: Homo sapiens

<400> SEQUENCE: 68
gggaataaat catagaatcc tgg                                              23

<210> SEQ ID NO 69
<211> LENGTH: 22
<212> TYPE: DNA
<213> ORGANISM: Homo sapiens

<400> SEQUENCE: 69
cacacacact tagaatctgt gg                                               22

<210> SEQ ID NO 70
<211> LENGTH: 23
<212> TYPE: DNA
<213> ORGANISM: Homo sapiens

<400> SEQUENCE: 70
gtcatcttag tcattacctg agg                                              23

<210> SEQ ID NO 71
<211> LENGTH: 58
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 71
acactctttc cctacacgac gctcttccga tctacaagac ctggctgagc taactgtg          58

<210> SEQ ID NO 72
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
acactctttc cctacacgac gctcttccga tctagtgttg ggattacagc ctga              54

<210> SEQ ID NO 73
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acactctttc cctacacgac gctcttccga tcttctctat ccacctggaa tgagttt           57

<210> SEQ ID NO 74
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
acactctttc cctacacgac gctcttccga tctatctcag cgctttcgtc cac               53

<210> SEQ ID NO 75
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
acactctttc cctacacgac gctcttccga tcttgtgcag acaaacggaa ctcaacc           57

<210> SEQ ID NO 76
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acactctttc cctacacgac gctcttccga tctcatggca tgagggtctc catgg             55

<210> SEQ ID NO 77
<211> LENGTH: 56
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 77
acactctttc cctacacgac gctcttccga tctgatgtga gggtgcaggt agaggg          56

<210> SEQ ID NO 78
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
acactctttc cctacacgac gctcttccga tctagattttt ggtaattccc cattgcatcg     60

<210> SEQ ID NO 79
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
acactctttc cctacacgac gctcttccga tctcagaacc ccctggcaga tgttc           55

<210> SEQ ID NO 80
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
acactctttc cctacacgac gctcttccga tctattgcca acactcctga tagctgaatg     60

<210> SEQ ID NO 81
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acactctttc cctacacgac gctcttccga tctgaagtag acaacacgca gcctcttg        58

<210> SEQ ID NO 82
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gactggagtt cagacgtgtg ctcttccgat ctccagcccc atctgtcaaa ctgtg           55

<210> SEQ ID NO 83
<211> LENGTH: 52
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 83
gactggagtt cagacgtgtg ctcttccgat ctaacctgaa gcctttcccc aa        52

<210> SEQ ID NO 84
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gactggagtt cagacgtgtg ctcttccgat ctcagcaatc cagcaacacg c         51

<210> SEQ ID NO 85
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gactggagtt cagacgtgtg ctcttccgat ctctcatttc cccactccct cc        52

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gactggagtt cagacgtgtg ctcttccgat ctccaacata cagaagtcag gaatgcttga    60

<210> SEQ ID NO 87
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gactggagtt cagacgtgtg ctcttccgat ctgcgctacc acccggacaa g         51

<210> SEQ ID NO 88
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gactggagtt cagacgtgtg ctcttccgat ctgggattcg ttcaagctca cagcc     55

<210> SEQ ID NO 89
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gactggagtt cagacgtgtg ctcttccgat ctcctgaata gcttcttcca ctgttgcc        58

<210> SEQ ID NO 90
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gactggagtt cagacgtgtg ctcttccgat cttcctcaga ccagccatgg gg              52

<210> SEQ ID NO 91
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gactggagtt cagacgtgtg ctcttccgat ctgacttgca ggtctccact cccg            54

<210> SEQ ID NO 92
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gactggagtt cagacgtgtg ctcttccgat ctccattgac attcgccgga tggag           55

<210> SEQ ID NO 93
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
acaagacctg gctgagctaa ctgtgacagc atgtggtaat tttccagccc gctggccctg       60
taaaggaaac tggaacacaa agcatagact gcggggcggg ccagcctgaa tagctgcaaa      120
caagtgcaga atatctgatg atgtcatacg cacagtttga cagatggggc tgg             173

<210> SEQ ID NO 94
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
aacctgaagc ctttccccaa accatttgga tgcttgaaga actcaatagg catctggaga       60
gactgggcta aagaccatag actgtgggaa tgaaactcac acattgagtg cttgtacttt     120
ccttatgcca agtgtcacac aggttagaga atactccatc tttggccggg cacggtggct     180
caggctgtaa tcccaacact                                                 200

<210> SEQ ID NO 95
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
cagcaatcca gcaacacgcg gggaggtgga gagaggatgt tttgcttatc cagaaaaggg      60
agtgattgct tccaggggcc tcaggggaat aaatcataga atcctggaca aggtttgaag     120
gacaggtagg atttgggtgg gtggaggagg gtgcatgggg tcagaattgt aaccgaaaac     180
tcattccagg tggatagagc                                                 200

<210> SEQ ID NO 96
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
atctcagcgc tttcgtccac cacccctcta cacacacaca gacacacaca cacttagaat      60
ctgtgggagt ggagcccagc aatctgtgtt tgcacaaacc ctccagggaa ttctgatgcc     120
cgctgaagtt tgagaactag aggtaaacta tacctttctg caggcgagaa cctggaccaa     180
ggagggagtg gggaaatgag                                                 200

<210> SEQ ID NO 97
<211> LENGTH: 209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
ccaacataca gaagtcagga atgcttgaat ataaatttat tattactcta tgttctattt      60 aagtttcat gttctaaaaa tgtatcccag tttacacgtc tcatatgccc cttggcagtc     120
atcttagtca ttacctgagg tgttcgttgt aactcatata aactgagttc ccatgttttg     180
cttaatggtt gagttccgtt tgtctgcac                                       209

<210> SEQ ID NO 98
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gcgctaccac ccggacaaga acaaggagcc cggcgccgag gagaagttca aggagatcgc      60
tgaggcctac gacgtgctca gcgacccgcg caagcgcgat atcttcgacc gctacgggga     120
ggaaggccta aagggagtg gcccccagtgg cggtagcggc ggtggtgcca atggtacctc     180
tttcagctac acattccatg gagaccctca tgccatg                              217

<210> SEQ ID NO 99

<211> LENGTH: 226
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
gggattcgtt caagctcaca gccagcagcc aagcgtcaga aactaaaccc agctgatgcc      60
cccaatcctg tggtgtttgt ggccacaaag gataccaggg ccctacggaa ggctctgacc     120
catctggaaa tgcggcgagc tgctcgccga cccaacttgc ccctgaaggt gaagccaacg     180
ctgattgcag tgcggccccc tgtccctcta cctgcaccct cacatc                    226

<210> SEQ ID NO 100
<211> LENGTH: 236
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
agattttggt aattccccat tgcatcgttt taagaaacct ggatccaaaa attttcaaaa      60 cattttcct ccttctgcca cccttcacct atctaatatc cctccatcag tagcagaaga     120
ggatctacga acactgttcg ctaacactgg gggcactgtg aaagcattta agttttttca     180
aagagatcac aaaatggctc ttcttcagat ggcaacagtg gaagaagcta ttcagg        236

<210> SEQ ID NO 101
<211> LENGTH: 220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
cagaaccccc tggcagatgt tcaaatcact tgcaagacaa gatccagaag ctttatgaac      60
gaaagataaa ggagggaatg gatatgaact acattatcca aaggaagaaa gaatttcgga     120
accctagcat ctacgagaag ctgatccagt tctgtgccat tgacgagctt ggcaccaact     180
acccaaagga tatgtttgat ccccatggct ggtctgagga                          220

<210> SEQ ID NO 102
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
attgccaaca ctcctgatag ctgaatgtgt gctggtttac atgactccag agcagtccgc      60
aaacctcctg aagtgggcag ccaacagttt tgagagagcc atgttcataa actacgaaca     120
ggtgaacatg ggtgatcggt ttgggcagat catgattgaa aacctgcgga gacgccagtg     180
tgacctggcg ggagtggaga cctgcaagtc                                      210

<210> SEQ ID NO 103
<211> LENGTH: 206
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 103
ctccatccgg cgaatgtcaa tggctagcag acctgaacaa gcgactgccc cctgaggcct     60
gcctgccctc agccaagcca gtgggacagc caacgcgcta cgagcggcag ctggctgtga    120
ggccgtccac accccacacc atcacgttgc agccgtcttc cttccgaaac ctgcggctcc    180
ccaagaggct gcgtgttgtc tacttc                                        206

<210> SEQ ID NO 104
<211> LENGTH: 10
<212> TYPE: DNA
<213> ORGANISM: Homo sapiens

<400> SEQUENCE: 104
gattgaccca                                                           10

<210> SEQ ID NO 105
<211> LENGTH: 11
<212> TYPE: DNA
<213> ORGANISM: Homo sapiens

<400> SEQUENCE: 105
taaacaaagc a                                                         11

<210> SEQ ID NO 106
<211> LENGTH: 11
<212> TYPE: DNA
<213> ORGANISM: Homo sapiens

<400> SEQUENCE: 106
tagaaaaagt a                                                         11
```

ADENINE DNA BASE EDITOR VARIANTS WITH REDUCED OFF-TARGET RNA EDITING

CROSS-REFERENCE TO RELATED APPLICATIONS

This application claims the benefit of U.S. Provisional Application Ser. No. 62/800,974, filed on Feb. 4, 2019 and U.S. Provisional Application Ser. No. 62/844,717, filed on May 7, 2019. The entire contents of the foregoing are incorporated herein by reference.

FEDERALLY SPONSORED RESEARCH OR DEVELOPMENT

This invention was made with Government support under Grant Nos. HG009490 and GM118158 awarded by the National Institutes of Health and HR0011-17-2-0042 awarded by the Defense Advanced Research Projects Agency (DARPA). The Government has certain rights in the invention.

SEQUENCE LISTING

The instant application contains a Sequence Listing which has been filed electronically in ASCII format and is hereby incorporated by reference in its entirety. Said ASCII copy, created on Mar. 27, 2020, is named 29539-0387001_SL.txt and is 201,290 bytes in size.

TECHNICAL FIELD

Described herein are variants of wild type and engineered *E. coli* TadA domains of the adenine DNA base editor (ABE) that have reduced unwanted off-target RNA editing activity.

BACKGROUND

Base editors represent a new genome editing platform that allows efficient installation of single base substitutions in DNA (Rees, H. A. & Liu, D. R. Base editing: precision chemistry on the genome and transcriptome of living cells. *Nat. Rev. Genet.* (2018); Komor, A. C., et al., Programmable editing of a target base in genomic DNA without double-stranded DNA cleavage, Nature (2016); Gaudelli, N. M. et al., Programmable base editing of A•T to G•C in genomic DNA without DNA cleavage. Nature 551, 464-471 (2017)). Adenine base editors (ABEs) are fusions of programmable DNA-binding domains (e.g, catalytically impaired RNA-guided CRISPR-Cas nucleases) linked to engineered adenosine deaminases that can induce programmable adenosine (A) to inosine (I) edits in single-stranded DNA that in turn result in A-to-G transitions after DNA repair or replication. In instances where the programmable DNA-binding domain is a CRISPR-Cas nuclease, targeted adenines lie within an "editing window" in the single-stranded (ss) DNA bubble (R-loop) induced by the CRISPR-Cas RNA-protein complex. The most commonly used ABEs comprise an adenosine deaminase heterodimer consisting of *E. coli* TadA (wild type) fused to an engineered *E. coli* TadA variant, as well as a nickase Cas9 and nuclear localization sequences (NLS)(Gaudelli, N. M. et al. Programmable base editing of A•T to G•C in genomic DNA without DNA cleavage. *Nature* 551, 464-471 (2017)). ABEs have been used successfully for installation of A-to-G substitutions in multiple cell types and organisms and could potentially reverse a large number of mutations known to be associated with human disease (Rees, H. A. & Liu, D. R. Base editing: precision chemistry on the genome and transcriptome of living cells. *Nat. Rev. Genet.* (2018)).

SUMMARY

Described herein are adenine base editors (ABEs) having reduced RNA editing activity. These ABEs comprise a programmable DNA-binding domain fused to an adenosine deaminase, e.g. TadA or previously described engineered TadA variants (e.g. ABEs 0.1, 0.2, 1.1, 1.2, 2.1, 2.2, 2.3, 2.4, 2.5, 2.6, 2.7, 2.8, 2.9, 2.10, 2.11, 2.12, 3.1, 3.2, 3.3, 3.4, 3.5, 3.6, 3.7, 3.8, 4.1, 4.2, 4.3, 5.2, 5.3, 5.4, 5.5, 5.6, 5.7, 5.8, 5.9, 5.10, 5.11, 5.12, 5.13, 5.14, 6.1, 6.2, 6.3, 6.4, 6.5, 6.6, 7.1, 7.2, 7.3, 7.4, 7.5, 7.6, 7.7, 7.8, 7.9, 7.10, ABEmax as described in Gaudelli et al., Nature. 2017 Nov. 23; 551 (7681): 464-471 and Koblan et al., Nat Biotechnol. 2018 October; 36(9):843-846), with one or more amino acid substitutions may decrease RNA editing activity while still preserving DNA editing activity (RRE or Reduced RNA Editing variants). The substitutions in *E. coli* TadA (SEQ ID NO:1) or its engineered derivatives described herein are at the amino acid positions indicated in Table A. In some embodiments, the ABE comprises one or more mutations corresponding to a mutation listed in Table A.

In one aspect, the present disclosure relates to an adenine base editor (ABE) variant including an adenosine deaminase and a programmable DNA binding domain, the adenosine deaminase including one or more *E. coli* TadA monomers, where at least one of the one or more *E. coli* TadA monomers include one or more mutations that decrease RNA editing activity while preserving DNA editing activity.

In one embodiment, the adenosine deaminase includes a wild type or engineered *E. coli* TadA monomer, or a variation of homo- or heterodimers thereof.

In one embodiment, the adenosine deaminase includes ABE 0.1, ABE 0.2, ABE 1.1, ABE 1.2, ABE 2.1, ABE 2.2, ABE 2.3, ABE 2.4, ABE 2.5, ABE 2.6, ABE 2.7, ABE 2.8, ABE 2.9, ABE 2.10, ABE 2.11, ABE 2.12, ABE 3.1, ABE 3.2, ABE 3.3, ABE 3.4, ABE 3.5, ABE 3.6, ABE 3.7, ABE 3.8, ABE 4.1, ABE 4.2, ABE 4.3, ABE 5.1, ABE 5.2, ABE 5.3, ABE 5.4, ABE 5.5, ABE 5.6, ABE 5.7, ABE 5.8, ABE 5.9, ABE 5.10, ABE 5.11, ABE 5.12, ABE 5.13, ABE 5.14, ABE 6.1, ABE 6.2, ABE 6.3, ABE 6.4, ABE 6.5, ABE 6.6, ABE 7.1, ABE 7.2, ABE 7.3, ABE 7.4, ABE 7.5, ABE 7.6, ABE 7.7, ABE 7.8, ABE 7.9, ABE 7.10, or ABEmax.

In one embodiment, the one or more mutations include one or more mutations at amino acid positions that correspond to residues of wild type *E. coli* TadA (SEQ ID NO:1) or *E. coli* TadA deaminase monomer with ABE 7.10 mutations (SEQ ID: 34) as listed in Table A.

In one embodiment, the one or more mutations are at amino acid positions that correspond to residues Y10, W11, R13, T17, K20, R21, R23, E25, R26, A48, 149, A56, A58, Q71, N72, R74, D77, V82, V106, R107, N108, A109, K110, T111, H122, Y123, H128, R129, A138, D139, E140, A142, A143, F148, and/or R150, R153, V155 of wild type *E. coli* TadA (SEQ ID NO:1) or *E. coli* TadA deaminase monomer with ABE 7.10 mutations (SEQ ID: 34).

In one embodiment, the one or more mutations include mutations that correspond to Y10A, W11A, R13A, T17A, K20A, R21A, R23A, R23W, E25A, R26A, A48G, 149A, A56G, A58A, Q71A, N72A, R74A, D77A, V82G, V106G, V106W, R107A, N108A, A109G, A109W, K110A, T111A, H122A, Y123A, H128A, R129A, A138W, A138G, D139A, E140A, A142W, A142G, A143G, F148A, R150A, R153A, V155G, and/or V155W of wild type *E. coli* TadA (SEQ ID NO:1) or *E. coli* TadA deaminase monomer with ABE 7.10 mutations (SEQ ID: 34).

In one embodiment, the at least one of the one or more *E. coli* TadA monomers include mutations that correspond to: R13A; T17A; K20A and R21A; K20A, R21A, and R23A; R23W; E25A; R26A; A48G; 149A; A56G; R74A; D77A; V82G; W11A; V106G; N108A; A109W; K110A; T111A; A138G; D139A and E140A; A142G; A143G; R153A; V155G; V155W; A58G; N72A; V106W; K110A; H128A and R129A; A138W; D139A and E140A; A142W; F148A; or R150A of wild type *E. coli* TadA (SEQ ID NO:1) or *E. coli* TadA deaminase monomer with ABE 7.10 mutations (SEQ ID: 34).

In one embodiment, the ABE variant described herein further includes one or more nuclear localization sequences (NLS).

In one embodiment, the ABE variant described herein includes a linker between the adenosine deaminase monomers and/or between the adenosine deaminase monomer or between a single-chain dimer and the programmable DNA binding domain.

In one embodiment, the programmable DNA binding domain is a engineered C2H2 zinc-finger, a transcription activator effector-like effector (TALE), or a Clustered Regularly Interspaced Short Palindromic Repeats (CRISPR) Cas RNA-guided nucleases (CRISPR-Cas nuclease), or a variant thereof.

In one embodiment, the CRISPR-Cas nuclease is a single strand DNA (ssDNA) nickase or is catalytically inactive.

In one embodiment, the CRISPR-Cas nuclease is a Cas9 or Cas12a that has ssDNA nickase activity or is catalytically inactive.

In one aspect, the present disclosure relates to a base editing system including: (i) an ABE variant described herein, where the programmable DNA binding domain is a CRISPR Cas RGN or a variant thereof; and (ii) at least one guide RNA compatible with the base editor that directs the base editor to a target sequence.

In one aspect, the present disclosure relates to an isolated nucleic acid encoding an ABE variant disclosed herein.

In one aspect, the present disclosure relates to a vector including an isolated nucleic acid described herein.

In one aspect, the present disclosure relates to an isolated host cell, preferably a mammalian host cell, including a nucleic acid described herein.

In one embodiment, the isolated host cell described herein expresses any one of the ABE variant described herein.

In one aspect, the present disclosure relates to a method of deaminating a selected adenine in a nucleic acid, the method including contacting the nucleic acid with an ABE variant or a base editing system described herein.

In one embodiment, the nucleic acid is in a cell.

In one embodiment, the cell is in a living subject.

In one embodiment, the living subject is a mammal.

In one aspect, the present disclosure relates to a composition including a purified ABE variant or a base editing system described herein.

In one embodiment, the composition described herein includes one or more ribonucleoprotein (RNP) complexes.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-C. Schematic illustrating activities of wild-type *E. coli* TadA adenosine deaminase and engineered adenine base editors (ABEs). (A) Schematic illustrating wild-type TadA targeting adenosine 34 in *E. coli* tRNA and inducing an A-to-I substitution by deamination of adenosine 34. (B) Schematic illustrating an ABE, which in this example comprises a heterodimer of wild-type (WT) and an engineered TadA fused to a nickase Cas9 (nCas9)-gRNA complex that directs A to I deamination in the ssDNA generated by nCas9-induced R-loop formation. (C) Schematic illustrating potential off-target A-to-I deamination of adenosine in an RNA by ABE.

FIG. 5 discloses SEQ ID NOS 36-63, respectively, in order of appearance.

FIG. 7A discloses SEQ ID NOS 104-106, respectively, in order of appearance. For (b), A-to-G editing efficiencies for only the most highly edited adenine for each gRNA on-target site are reported; error bars represent standard deviation (SD).

FIG. 13. Self-editing generates a diverse range of heterogeneously edited ABE transcript sequences in HEK293T cells Scatterplots showing A-to-I self-editing induced by expression of ABEmax, miniABEmax, miniABEmax-K20A/R21A, and miniABEmax-V82G (sorted for all GFP-positive cells) with gRNAs targeting HEK site 2, ABE site 16, and a non-targeting gRNA (NT) in HEK293T cells for 2 other replicates. Each dot represents an edited A and the color of the dot indicates the predicted type of mutation caused by a A-to-I edit at that position. The y-axis shows editing efficiencies for each A-to-I modification and the x-axis represents the position of each A within the ABE coding sequence (with the architecture of the editor shown schematically below but not displaying the NLS and linkers). n=total number of modified As.

Figure 15A:
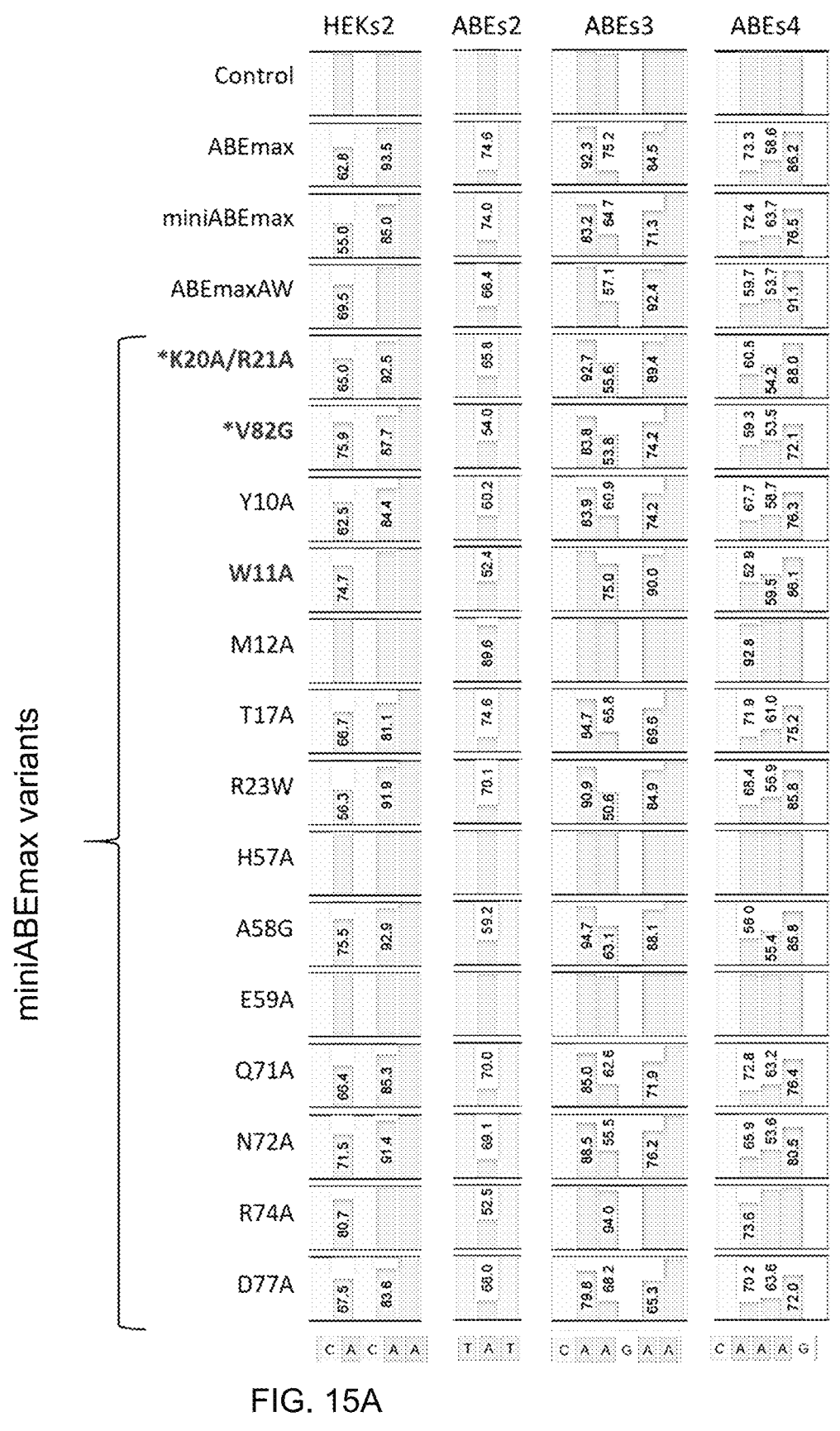
Figure 15C:
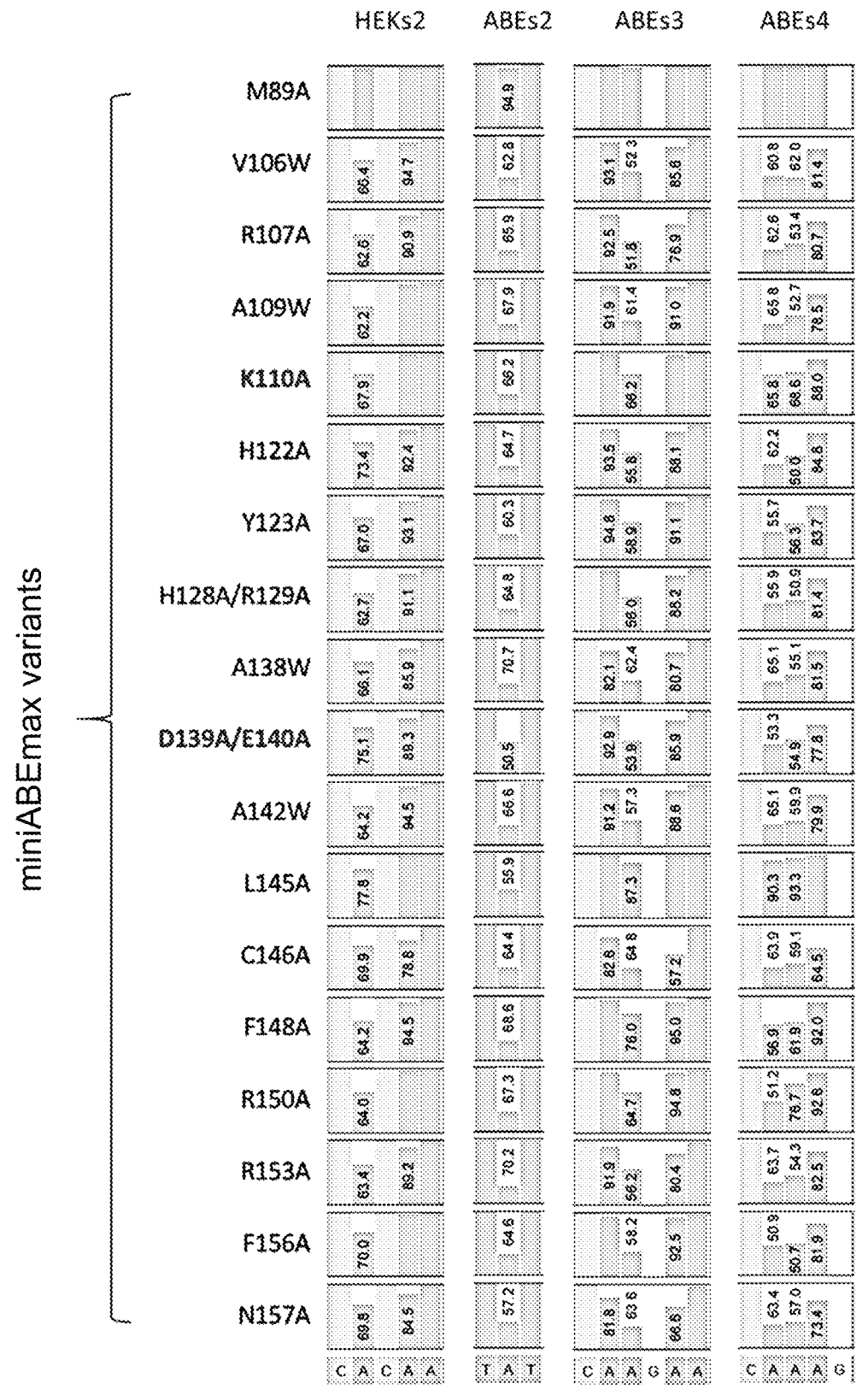

FIGS. 15A-D. Overlay bar plots of 1 replicate of 32 miniABEmax variants for their on-target DNA editing (A-to-G) and off-target RNA editing (A-to-1) activities. On-target DNA editing was assessed with four different gRNAs and off-target RNA alterations were screened on six RNA adenines previously identified as being efficiently modified by ABEmax. Control=nCas9(D10A). ABEmax=codon optimized adenine base editor. miniABEmax=ABEmax without N-terminal wild type TadA domain. ABEmaxAW=ABEmax variant described by Rees et al, Sci. Adv., 2019. Amino acid abbreviations are according to IUPAC nomenclature and residue numbering is based on the amino acid position in E. coli TadA. Promising variants (including K20A/R21A and V82G as previously published) with comparable DNA on-target and highly reduced RNA off-target editing are highlighted. Orange=Cytosine; green=Adenine; purple=Thymine; yellow=Guanine.

FIGS. 16A-B. Average DNA on-target A-to-G editing (of 2 replicates) and average RNA off-target A-to-I editing (of 4 replicates) of 32 miniABEmax variants. (A) On-target DNA editing was assessed at 4 sites and higher desired DNA editing was shown as darker shade (four tables on the left). (B) Off-target RNA editing was assessed at 6 sites and higher unwanted RNA editing was shown as darker shade (right-most table). Control=nCas9(D10A). ABEmax=codon optimized adenine base editor. miniABEmax=ABEmax without N-terminal wild type TadA domain. ABEmaxAW=ABEmax variant described by Rees et al, Sci. Adv., 2019. Amino acid abbreviations are according to IUPAC nomenclature and residue numbering is based on the amino acid position in E. coli TadA. Some promising variants (including K20A/R21A and V82G as previously published) with comparable DNA on-target and highly reduced RNA off-target are highlighted.

DETAILED DESCRIPTION

Figure 2A:
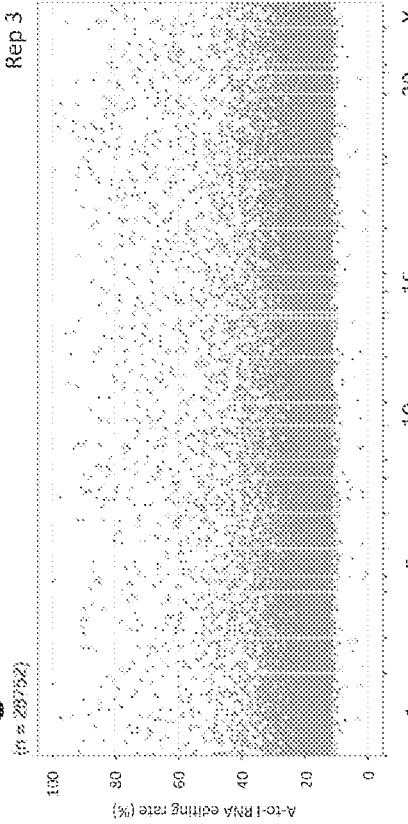
FIG. 2A-D. High expression of ABEmax induces transcriptome-wide off-target RNA editing in human HEK293T cells. (A) RNA of HEK293T cells transiently transfected with ABEmax (codon- and NLS-optimized variant of ABE7.10, Koblan et al, *Nat Biotechnol*. 2018 October; 36(9): 843-846) and flow-sorted for the highest GFP signal (top 5%) shows tens of thousands of A-to-I RNA edits in three replicate experiments. (B) Transcriptome-wide distribution of A-to-I RNA editing for replicate 3 from (A). (C) Histograms showing the distribution of RNA editing frequencies of adenines from the triplicate experiments shown in (A). Dashed line shows the median, solid line represents the mean. (D) Core sequence motif around adenines that are edited in RNA.

ABEs efficiently install A-to-G transitions in DNA (Gaudelli, N. M. et al. Programmable base editing of A•T to G•C in genomic DNA without DNA cleavage. Nature 551, 464-471 (2017); Koblan, L. W. et al., Improving cytidine and adenine base editors by expression optimization and ancestral reconstruction, SUPPLEMENTS. Nat. Biotechnol. 36, 843-848 (2018)). However, the E. coli TadA protein (present in all commonly used ABEs) was originally discovered as a tRNA-specific adenosine deaminase (FIG. 1A) (Wolf, J. tadA, an essential tRNA-specific adenosine deaminase from Escherichia coli. EMBO J. 21, 3841-3851 (2002); Kim, J. et al. Structural and kinetic characterization of Escherichia coli TadA, the wobble-Specific tRNA deaminase. Biochemistry 45, 6407-6416 (2006)). Directed evolution and protein engineering were used to generate an enzyme that is capable of programmable A-to-I deamination on ssDNA, when fused to a catalytically impaired CRISPR/Cas mutant (Gaudelli, N. M. et al. Programmable base editing of A•T to G•C in genomic DNA without DNA cleavage. Nature 551, 464-471 (2017)).

We sought to investigate if the RNA editing capability of the TadA enzyme might have been preserved or even expanded (e.g., to other RNA species) when present in an ABE context (FIGS. 1B&C).

Thus, described herein are variants of wild type and engineered (ABE0.1-7.10 and ABEmax) TadA domains, each as monomers and/or combined as single-chain homodimers and/or single-chain heterodimers, bearing mutations that may exhibit reduced RNA editing (RRE) activities while preserving DNA deamination activities, optionally fused to an engineered DNA binding domain such as a CRISPR-Cas nuclease modified to either be a nickase or catalytically inactive, to enable DNA adenine base editing with reduced RNA mutation profiles. These SElective Curbing of Unwanted RNA Editing (SECURE)-ABE variants exhibit substantially reduced unwanted RNA editing activities while retaining robust and more precise on-target DNA editing.

Herein are described structure-guided engineering of SECURE-ABE variants that not only possess reduced off-target RNA editing with comparable on-target DNA activities but are also the smallest Streptococcus pyogenes Cas9 (SpCas9) base editors described to date. Finally, we discovered the important finding that ABEs that exhibit off-target editing activities can also self-edit their own transcripts. This hitherto unappreciated activity leads to substantial heterogeneity in base editor coding sequences and provides strong additional motivation for using variants with reduced RNA editing activities. In sum, our work describes broadly useful SECURE-ABE base editors, defines a new class of unintended alterations caused by base editor self-editing, and reinforces the importance of minimizing RNA editing activities of DNA base editors for research and therapeutic applications.

The work described here extends our understanding of the off-target RNA editing activities of DNA base editors, expands the options available to minimize these unwanted effects, and provides novel SECURE base editor architectures with other desirable properties. The successful engineering of SECURE-ABE variants shows that it is possible to minimize unwanted RNA editing while retaining efficient on-target DNA editing for an ABE. In the process of engineering these variants, we discovered a more extended consensus sequence motif for adenines edited with high efficiencies by ABEmax (CUACGAA) that appears to be recognized by the wild-type TadA part of this fusion. Deletion of this TadA domain abolished recognition of these high efficiency sites and also resulted in the generation of the smallest SpCas9 base editors (1605 amino acids in length) described to date. Our findings further expand the toolbox of base editors that can be used without inducing high-level RNA editing.

Our description of self-editing by DNA base editors provides yet another strong motivation to avoid the use of base editors that possess off-target RNA editing activities. Self-editing by ABEs potentially creates a heterogeneous population of base editor-encoding transcripts in human cells including missense mutations that might lead to the generation of novel epitopes or other gain/loss-of-function effects. The potential impacts of creating diverse mutated forms of base editor proteins in cells are particularly important to consider because these fusions will be highly overexpressed for most applications. One possibility is that these truncated forms might further exacerbate RNA editing activity levels because these proteins would still be expected to induce off-target RNA editing but not on-target DNA editing. Thus, the existence of self-editing further underscores the importance of using DNA base editors with reduced RNA editing activities for both research and therapeutic applications.

Figure 5:
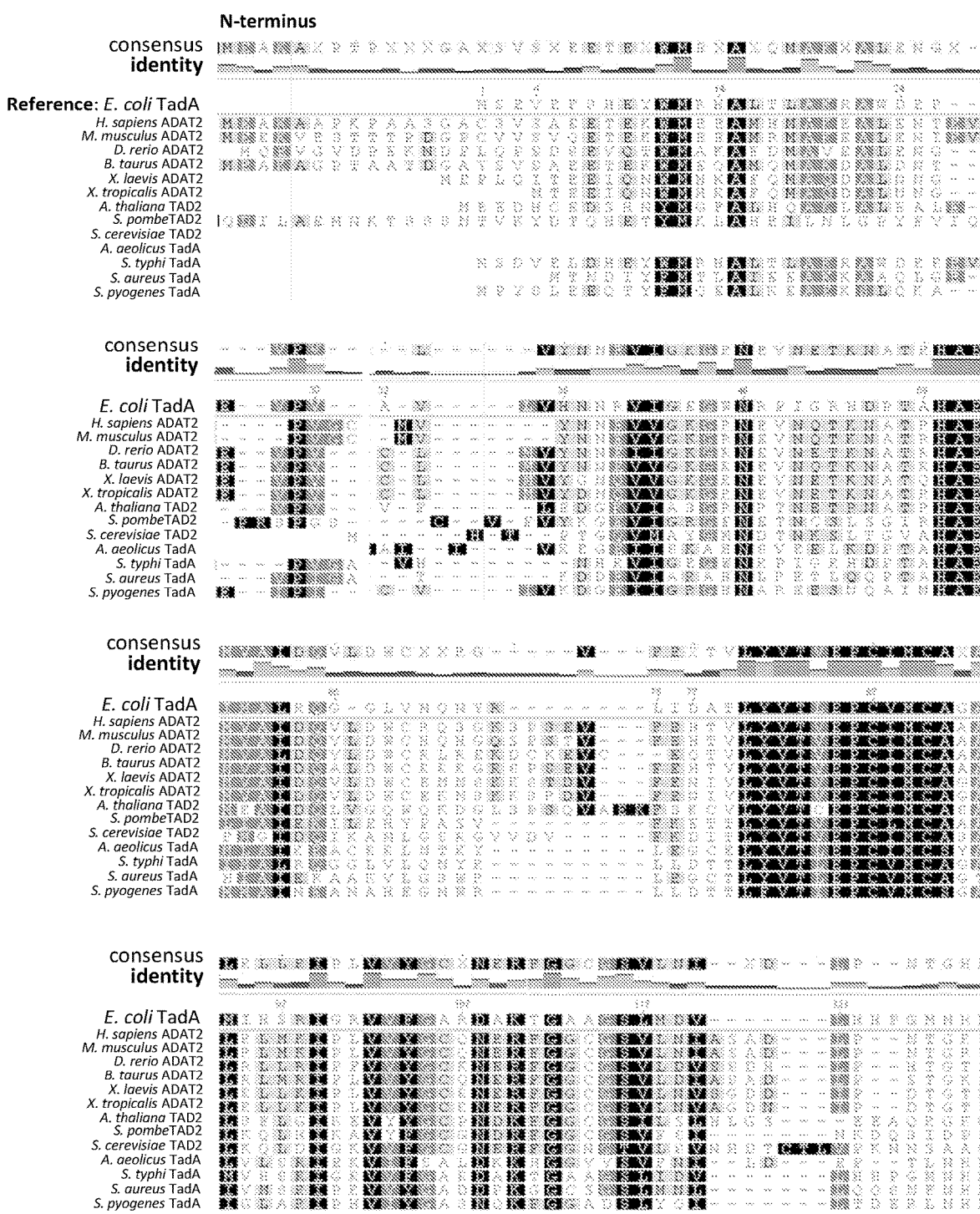
FIG. 5. Alignment of TadA orthologues. Various TadA orthologues and homologous tRNA-specific adenosine deaminases were obtained from the uniprot platform (Table B) and aligned to the amino acid sequence of *E. coli* TadA. Sequence homology is displayed by darker coloring of amino acids. The considerable sequence homology displayed enables extrapolation of amino acid substitutions that should confer an RRE phenotype to analogous positions in other adenosine deaminase orthologues and homologues.
Figure 5:
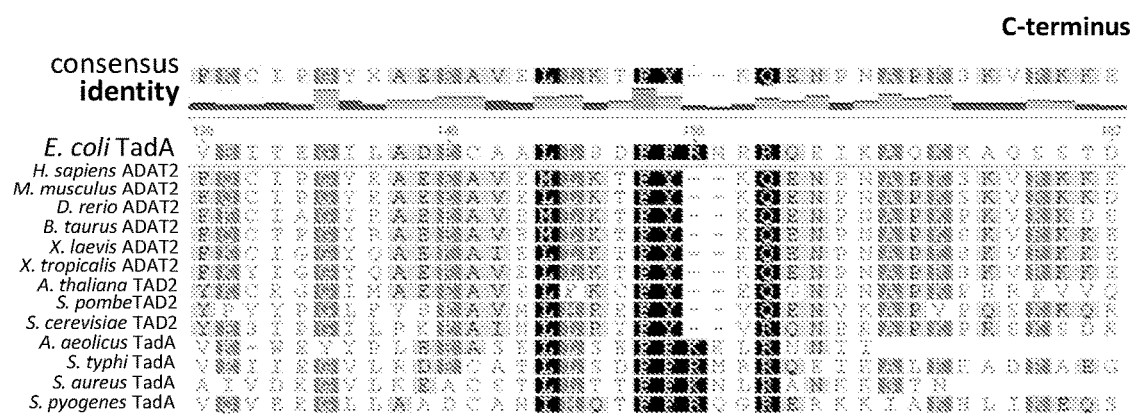

In some embodiments, the adenosine deaminase is TadA from *E. coli*, or an orthologue from a different prokaryote, e.g. *S. aureus*, or a homologue from the eukaryotic domain, such as yeast TAD1/2 or a mammalian species such as human (e.g. ADAT2). The tRNA-specific adenosine deaminase family members have high sequence homology. FIG. 5 shows the alignment of exemplary tRNA-specific adenosine deaminase orthologues and homologues across different domains, kingdoms and species listed in the uniprot database that are compatible with one or more of the amino acid substitutions in *E. coli* TadA expected to cause an RRE phenotype and described in this application.

Reduced RNA Editing (RRE) Base Editor Variants

Thus described herein are base editors comprising adenosine deaminases with one or more mutations to reduce undesirable RNA editing activity. In general, these base editors have one or more mutations as described herein. In some embodiments, they have mutations shown in Table A that correspond to residues in wild type (SEQ ID NO: 1) or engineered *E. coli* TadA (e.g. ABEs 0.1, 0.2, 1.1, 1.2, 2.1, 2.2, 2.3, 2.4, 2.5, 2.6, 2.7, 2.8, 2.9, 2.10, 2.11, 2.12, 3.1, 3.2, 3.3, 3.4, 3.5, 3.6, 3.7, 3.8, 4.1, 4.2, 4.3, 5.1, 5.2, 5.3, 5.4, 5.5, 5.6, 5.7, 5.8, 5.9, 5.10, 5.11, 5.12, 5.13, 5.14, 6.1, 6.2, 6.3, 6.4, 6.5, 6.6, 7.1, 7.2, 7.3, 7.4, 7.5, 7.6, 7.7, 7.8, 7.9, 7.10, ABEmax as described in Gaudelli et al., Nature. 2017 Nov. 23; 551(7681): 464-471 (especially supplementary sequences 3 thereof) and Koblan et al., *Nat Biotechnol.* 2018 October; 36(9):843-846). Alternatively, or in addition, they may have mutations in either one of the WT or engineered monomers solely and separately fused to a DNA binding protein such as nickase Cas9, or they might have the same mutations introduced to one or both TadA monomers which are then linked to each other, generating single-chain homo- or heterodimers that in turn are fused to a DNA binding domain.

TABLE A

Amino acid substitutions predicted to generate ABE variants with reduced RNA editing. This table lists the residue changes in either or both TadA domains of the TadA-heterodimer (present in e.g. ABE7.10) predicted to cause an RRE phenotype, next to the reasoning behind the proposed changes.

| Residues to Change | | Rationale | |
| --- | --- | --- | --- |
| Wild type (WT) TadA | Engineered TadA | Protein structure | Binding prediction |
| S7 | S205 | | x |
| H8 | H206 | | x |
| E9 | E207 | | x |
| Y10 | Y208 | | x |
| W11 | W209 | | x |
| M12 | M210 | | x |
| R13 | R211 | x | x |
| H14 | H212 | | x |
| T17 | T215 | | x |
| K20 | K218 | x | x |
| R21 | R219 | x | x |
| W23 | R221 | x | |
| E25 | E223 | x | x |
| R26 | R224 | x | x |
| E27 | E225 | x | |
| V28 | V226 | x | x |
| P29 | P227 | | x |
| V30 | V228 | x | |
| G31 | G229 | | x |
| H36 | L234 | | x |
| N37 | N235 | | x |
| N38 | N236 | | x |
| N46 | N244 | x | |
| R47 | R245 | | x |
| P48 | A246 | x | |
| I49 | I247 | x | |
| G50 | G248 | | x |
| R51 | I249 | | x |
| H52 | H250 | | x |
| D53 | D251 | | x |
| P54 | P252 | | x |
| T55 | T253 | | x |
| A56 | A254 | x | |
| H57 | H255 | x | x |
| A58 | A256 | x | |
| E59 | E257 | x | |
| R64 | R262 | | x |
| Q65 | Q263 | | x |
| G67 | G265 | | x |
| L68 | L266 | | x |
| Q71 | Q269 | | x |
| N72 | N270 | | x |
| R74 | R272 | | x |
| I76 | I274 | | x |
| D77 | D275 | | x |
| Y81 | Y279 | | x |
| V82 | V280 | x | |
| T83 | T281 | | x |
| L84 | F282 | x | |
| E85 | E283 | | x |

TABLE A-continued

Amino acid substitutions predicted to generate ABE variants with reduced RNA editing. This table lists the residue changes in either or both TadA domains of the TadA-heterodimer (present in e.g. ABE7.10) predicted to cause an RRE phenotype, next to the reasoning behind the proposed changes.

| Residues to Change | | Rationale | |
| --- | --- | --- | --- |
| Wild type (WT) TadA | Engineered TadA | Protein structure | Binding prediction |
| P86 | P284 | x | x |
| C87 | C285 | x | x |
| V88 | V286 | | x |
| M89 | M287 | | x |
| C90 | C288 | x | x |
| R98 | R296 | | x |
| G100 | G298 | | x |
| R101 | R299 | | x |
| A106 | V304 | x | |
| R107 | R305 | x | |
| D108 | N306 | x | |
| A109 | A307 | x | |
| K110 | K308 | x | |
| T111 | T309 | x | |
| D119 | D317 | | x |
| H122 | H320 | | x |
| H123 | Y321 | | x |
| P124 | P322 | | x |
| G125 | G323 | | x |
| M126 | M324 | | x |
| N127 | N325 | | x |
| H128 | H326 | | x |
| R129 | R327 | | x |
| V130 | V328 | | x |
| E131 | E329 | | x |
| I132 | I330 | | x |
| T133 | T331 | | x |
| E134 | E332 | | x |
| G135 | G333 | | x |
| L137 | L335 | | x |
| A138 | A336 | x | x |
| D139 | D337 | | x |
| E140 | E338 | | x |
| C141 | C339 | x | x |
| A142 | A340 | x | x |
| A143 | A341 | x | x |
| L144 | L342 | | x |
| L145 | L343 | x | x |
| S146 | C344 | x | |
| D147 | Y345 | | x |
| F148 | F346 | x | x |
| F149 | F347 | x | x |
| R150 | R348 | x | x |
| M151 | M349 | | x |
| R152 | P350 | x | x |
| R153 | R351 | x | |
| Q154 | Q352 | | x |
| E155 | V353 | x | x |
| I156 | F354 | | x |
| K157 | N355 | | x |
| K160 | K358 | | x |
| K161 | K359 | | x |

The mutations can include substitution with any other amino acid other than the WT amino acid; in some embodiments the substitution is with alanine or glycine.

TABLE B

Exemplary TadA proteins. Some or all residues listed in Table A as well as combinations thereof might also be introduced in any of these TadA orthologues or tRNA adenosine deaminase homologues (same proteins were aligned in FIG. 5).

| tRNA-specific adenosine deaminase | Uniprot accession number | Sequence version # | Seq. ID |
| --- | --- | --- | --- |
| E. coli TadA | P68398 | 2 | 1 |
| S. aureus TadA | Q99W51 | 1 | 2 |
| S. pyogenes TadA | Q5XE14 | 2 | 3 |
| S. typhi TadA | Q8XGY4 | 2 | 4 |
| A. aeolicus TadA | O67050 | 1 | 5 |
| S. pombe TAD2 | O94642 | 2 | 6 |
| S. cerevisiae TAD1 | P53065 | 1 | 7 |
| S. cerevisiae TAD2 | P47058 | 1 | 8 |
| A. thaliana TAD2 | Q6IDB6 | 1 | 9 |
| X. laevis ADAT2 | Q4V7V8 | 1 | 10 |
| X. tropicalis ADAT2 | Q0P4H0 | 1 | 11 |
| D. rerio ADAT2 | Q5RIV4 | 2 | 12 |
| B. taurus ADAT2 | Q5E9J7 | 1 | 13 |
| M. musculus ADAT2 | Q6P6J0 | 1 | 14 |
| H. sapiens ADAT2 | Q7Z6V5 | 1 | 15 |

The wild type sequence of wild type E. coli TadA, available in uniprot at P68398, is as follows:

(SEQ ID NO: 1)
MSEVEFSHEYWMRHALTLAKRAWDEREVPVGAVLVHNNRVIGEGWNRPIG

RHDPTAHAEIMALRQGGLVMQNYRLIDATLYVTLEPCVMCAGAMIHSRIG

RVVFGARDAKTGAAGSLMDVLHHPGMNHRVEITEGILADECAALLSDFFR

MRRQEIKAQKKAQSSTD.

The engineered E. coli TadA sequence present in ABE7.10 and ABEmax is as follows:

(SEQ ID NO: 21)
SEVEFSHEYWMRHALTLAKRARDEREVPVGAVLVLNNRVIGEGWNRAIGL

HDPTAHAEIMALRQGGLVMQNYRLIDATLYVTFEPCVMCAGAMIHSRIGR

VVFGVRNAKTGAAGSLMDVLHYPGMNHRVEITEGILADECAALLCYFFRM

PRQVFNAQKKAQSSTD.

In the most commonly used ABEs (ABE7.10 and ABEmax), these two proteins are fused using a 32 amino acid linker (bolded in sequence below), forming a heterodimer, the sequence of which is as follows:

(SEQ ID NO: 22)
MSEVEFSHEYWMRHALTLAKRAWDEREVPVGAVLVHNNRVIGEGWNRPIG

RHDPTAHAEIMALRQGGLVMQNYRLIDATLYVTLEPCVMCAGAMIHSRIG

RVVFGARDAKTGAAGSLMDVLHHPGMNHRVEITEGILADECAALLSDFFR

MRRQEIKAQKKAQSSTDSGGSSGGSSGSETPGTSESATPESSGGSSGGSS

EVEFSHEYWMRHALTLAKRARDEREVPVGAVLVLNNRVIGEGWNRAIGLH

DPTAHAEIMALRQGGLVMQNYRLIDATLYVTFEPCVMCAGAMIHSRIGRV

VFGVRNAKTGAAGSLMDVLHYPGMNHRVEITEGILADECAALLCYFFRMP

RQVFNAQKKAQSSTD.

Other exemplary sequences are shown in the list below as well as aligned to E. coli TadA in FIG. 5. These tRNA-specific adenosine deaminase orthologues and homologues also represent candidates for inclusion of the abovementioned mutations at analogous positions in these proteins.

In some embodiments, the base editors do not include catalytically dead adenine deaminase variants, e.g. E59A. (Gaudelli et al, 2017, PMID: 29160308).

Programmable DNA Binding Domain

In some embodiments, the base editors include programmable DNA binding domains such as engineered C2H2 zinc-fingers, transcription activator effector-like effectors (TALEs), and Clustered Regularly Interspaced Short Palindromic Repeats (CRISPR) Cas RNA-guided nucleases (RGNs) and their variants, including ssDNA nickases (nCas9) or their analogs and catalytically inactive dead Cas9 (dCas9) and its analogs (e.g., as shown in Table C), and any engineered protospacer-adjacent motif (PAM) or high-fidelity variants (e.g., as shown in Table D). A programmable DNA binding domain is one that can be engineered to bind to a selected target sequence.

CRISPR-Cas Nucleases

Although herein we refer to Cas9, in general any Cas9-like nickase could be used (including the related Cpf1/Cas12a enzyme classes), unless specifically indicated.

(2013); Jinek et al., *Elife* 2, e00471 (2013); Hwang et al., *Nat Biotechnol* 31, 227-229 (2013); Cong et al., *Science* 339, 819-823 (2013); Mali et al., *Science* 339, 823-826 (2013c); Cho et al., *Nat Biotechnol* 31, 230-232 (2013); Jinek et al., *Science* 337, 816-821 (2012)). The engineered CRISPR from *Prevotella* and *Francisella* 1 (Cpf1, also known as Cas12a) nuclease can also be used, e.g., as described in Zetsche et al., *Cell* 163, 759-771 (2015); Schunder et al., *Int J Med Microbiol* 303, 51-60 (2013); Makarova et al., *Nat Rev Microbiol* 13, 722-736 (2015); Fagerlund et al., *Genome Biol* 16, 251 (2015). Unlike SpCas9, Cpf1/Cas12a requires only a single 42-nt crRNA, which has 23 nt at its 3' end that are complementary to the protospacer of the target DNA sequence (Zetsche et al., 2015). Furthermore, whereas SpCas9 recognizes an NGG PAM sequence that is 3' of the protospacer, AsCpf1 and LbCp1 recognize TTTN PAMs that are found 5' of the protospacer (Id.).

In some embodiments, the present system utilizes a wild type or variant Cas9 protein from *S. pyogenes* or *Staphylococcus aureus*, or a wild type or variant Cpf1 protein from Acidaminococcus sp. BV3L6 or Lachnospiraceae *bacterium* ND2006 either as encoded in bacteria or codon-optimized

TABLE C

List of Exemplary Cas9 or Cas12a Orthologs

| Ortholog | UniProt or GenBank Accession Number | Nickase Mutations/Catalytic residues |
|---|---|---|
| *S. pyogenes* Cas9 (SpCas9) | Q99ZW2.1 | D10A, E762A, H840A, N854A, N863A, D986A[17] |
| *S. aureus* Cas9 (SaCas9) | J7RUA5.1 | D10A and N580[18] |
| *S. thermophilus* Cas9 (St1Cas9) | G3ECR1.2 | D31A and N891A[19] |
| *S. pasteurianus* Cas9 (SpaCas9) | BAK30384.1 | D10, H599* |
| *C. jejuni* Cas9 (CjCas9) | Q0P897.1 | D8A, H559A[20] |
| *F. novicida* Cas9 (FnCas9) | A0Q5Y3.1 | D11, N995[21] |
| *P. lavamentivorans* Cas9 (PlCas9) | A7HP89.1 | D8, H601* |
| *C. lari* Cas9 (ClCas9) | G1UFN3.1 | D7, H567* |
| *Pasteurella multocida* Cas9 | Q9CLT2.1 | |
| *F. novicida* Cpf1 (FnCpf1) | A0Q7Q2.1 | D917, E1006, D1255[21] |
| *M. bovoculi* Cpf1 (MbCpf1) | WP_052585281.1 | D986A** |
| *A.* sp. BV3L6 Cpf1 (AsCpf1) | U2UMQ6.1 | D908, 993E, Q1226, D1263[23] |
| *L. bacterium* N2006 (LbCpf1) | A0A182DWE3.1 | D832A[24] |

*predicted based on UniRule annotation on the UniProt database.
**Unpublished but deposited at addgene by Ervin Welker: pTE4565 (Addgene plasmid # 88903)

These orthologs, and mutants and variants thereof as known in the art, can be used in any of the fusion proteins described herein. See, e.g., WO 2017/040348 (which describes variants of SaCas9 and SpCas 9 with increased specificity) and WO 2016/141224 (which describes variants of SaCas9 and SpCas 9 with altered PAM specificity).

The Cas9 nuclease from *S. pyogenes* (hereafter simply Cas9) can be guided via simple base pair complementarity between 17-20 nucleotides of an engineered guide RNA (gRNA), e.g., a single guide RNA or crRNA/tracrRNA pair, and the complementary strand of a target genomic DNA sequence of interest that lies next to a protospacer adjacent motif (PAM), e.g., a PAM matching the sequence NGG or NAG (Shen et al., *Cell Res* (2013); Dicarlo et al., *Nucleic Acids Res* (2013); Jiang et al., *Nat Biotechnol* 31, 233-239 for expression in mammalian cells and/or modified in its PAM recognition specificity and/or its genome-wide specificity. A number of variants have been described; see, e.g., WO 2016/141224, PCT/US2016/049147, Kleinstiver et al., *Nat Biotechnol*. 2016 August; 34(8):869-74; Tsai and Joung, *Nat Rev Genet*. 2016 May; 17(5):300-12; Kleinstiver et al., *Nature*. 2016 Jan. 28; 529(7587):490-5; Shmakov et al., *Mol Cell*. 2015 Nov. 5; 60(3):385-97; Kleinstiver et al., *Nat Biotechnol*. 2015 December; 33(12):1293-1298; Dahlman et al., *Nat Biotechnol*. 2015 November; 33(11):1159-61; Kleinstiver et al., *Nature*. 2015 Jul. 23; 523(7561):481-5; Wyvekens et al., *Hum Gene Ther.* 2015 July; 26(7):425-31; Hwang et al., *Methods Mol Biol*. 2015; 1311:317-34; Osborn et al., *Hum Gene Ther.* 2015 February; 26(2):114-26; Konermann et al., *Nature*. 2015 Jan. 29; 517(7536):583-8; Fu et al.,

*Methods Enzymol.* 2014; 546:21-45; and Tsai et al., *Nat Biotechnol.* 2014 June; 32(6):569-76, inter alia. Concerning rAPOBEC1 itself, a number of variants have been described, e.g. Chen et al, *RNA.* 2010 May; 16(5):1040-52; Chester et al, *EMBO J.* 2003 Aug. 1; 22(15):3971-82: Teng et al, *J Lipid Res.* 1999 April; 40(4):623-35; Navaratnam et al, *Cell.* 1995 Apr. 21; 81(2):187-95; MacGinnitie et al, *J Biol Chem.* 1995 Jun. 16; 270(24):14768-75; Yamanaka et al, *J Biol Chem.* 1994 Aug. 26; 269(34):21725-34. The guide RNA is expressed or present in the cell together with the Cas9 or Cpf1. Either the guide RNA or the nuclease, or both, can be expressed transiently or stably in the cell or introduced as a purified protein or nucleic acid.

In some embodiments, the Cas9 also includes one of the following mutations, which reduce nuclease activity of the Cas9; e.g., for SpCas9, mutations at D10A or H840A (which creates a single-strand nickase).

In some embodiments, the SpCas9 variants also include mutations at one of each of the two sets of the following amino acid positions, which together destroy the nuclease activity of the Cas9: D10, E762, D839, H983, or D986 and H840 or N863, e.g., D10A/D10N and H840A/H840N/H840Y, to render the nuclease portion of the protein catalytically inactive; substitutions at these positions could be alanine (as they are in Nishimasu al., Cell 156, 935-949 (2014)), or other residues, e.g., glutamine, asparagine, tyrosine, serine, or aspartate, e.g., E762Q, H983N, H983Y, D986N, N863D, N863S, or N863H (see WO 2014/152432).

In some embodiments, the Cas9 is fused to one or more SV40 or bipartite (bp) nuclear localization sequences (NLSs) protein sequences; an exemplary (bp)NLS sequence is as follows: (KRTADGSEFES)PKKKRKV (SEQ ID NO: 23). Typically, the NLSs are at the N- and C-termini of an ABEmax fusion protein, but can also be positioned at the N- or C-terminus in other ABEs, or between the DNA binding domain and the deaminase domain. Linkers as known in the art can be used to separate domains.

TABLE D

List of Exemplary High Fidelity and/or PAM-relaxed RGN Orthologs

| Published HF/PAM-RGN variants | PMID | Mutations* |
|---|---|---|
| *S. pyogenes* Cas9 (SpCas9) eSpCas9 | 26628643 | K810A/K1003A/R1060A (1.0); K848A/K1003A/R1060A(1.1) |
| *S. pyogenes* Cas9 (SpCas9) evoCas9 | 29431739 | M495V/Y515N/K526E/R661Q; (M495V/Y515N/K526E/R661S; M495V/Y515N/K526E/R661L) |
| *S. pyogenes* Cas9 (SpCas9) HF1 | 26735016 | N497A/R661A/Q695A/Q926A |
| *S. pyogenes* Cas9 (SpCas9) HiFi Cas9 | 30082871 | R691A |
| *S. pyogenes* Cas9 (SpCas9) HypaCas9 | 28931002 | N692A, M694A, Q695A, H698A |
| *S. pyogenes* Cas9 (SpCas9) Sniper-Cas9 | 30082838 | F539S, M763I, K890N |
| *S. pyogenes* Cas9 (SpCas9) xCas9 | 29512652 | A262T, R324L, S409I, E480K, E543D, M694I, E1219V |
| *S. pyogenes* Cas9 (SpCas9) SpCas9-NG | 30166441 | R1335V, L1111R, D1135V, G1218R, E1219F, A1322R, T1337R |
| *S. pyogenes* Cas9 (SpCas9) VQR/VRER | 26098369 | D1135V, R1335Q, T1337R; D1135V/G1218R/R1335E/T1337R |
| *S. aureus* Cas9 (SaCas9)-KKH | 26524662 | E782K/N968K/R1015H |
| enAsCas12a | USSN 15/960,271 | One or more of: E174R, S170R, S542R, K548R, K548V, N551R, N552R, K607R, K607H, e.g., E174R/S542R/K548R, E174R/S542R/K607R, E174R/S542R/K548V/N552R, S170R/S542R/K548R, S170R/E174R, E174R/S542R, S170R/S542R, E174R/S542R/K548R/N551R, E174R/S542R/K607H, S170R/S542R/K607R, or S170R/S542R/K548V/N552R |
| enAsCas12a-HF | USSN 15/960,271 | One or more of: E174R, S542R, K548R, e.g., E174R/S542R/K548R, E174R/S542R/K607R, E174R/S542R/K548V/N552R, S170R/S542R/K548R, S170R/E174R, E174R/S542R, S170R/S542R, E174R/S542R/K548R/N551R, E174R/S542R/K607H, S170R/S542R/K607R, or S170R/S542R/K548V/N552R, with the addition of one or more of: N282A, T315A, N515A and K949A |
| enLbCas12a(HF) | USSN 15/960,271 | One or more of T152R, T152K, D156R, D156K, Q529K, G532R, G532K, G532Q, K538R, K538V, D541R, Y542R, M592A, K595R, K595H, K595S or K595Q, e.g., D156R/G532R/K538R, D156R/G532R/K595R, |

TABLE D-continued

List of Exemplary High Fidelity and/or PAM-relaxed RGN Orthologs

| Published HF/PAM-RGN variants | PMID | Mutations* |
|---|---|---|
| | | D156R/G532R/K538V/Y542R, T152R/G532R/K538R, T152R/D156R, D156R/G532R, T152R/G532R, D156R/G532R/K538R/D541R, D156R/G532R/K595H, T152R/G532R/K595R, T152R/G532R/K538V/Y542R, optionally with the addition of one or more of: N260A, N256A, K514A, D505A, K881A, S286A, K272A, K897A |
| enFnCas12a(HF) | USSN 15/960,271 | One or more of T177A, K180R, K180K, E184R, E184K, T604K, N607R, N607K, N607Q, K613R, K613V, D616R, N617R, M668A, K671R, K671H, K671S, or K671Q, e.g., E184R/N607R/K613R, E184R/N607R/K671R, E184R/N607R/K613V/N617R, K180R/N607R/K613R, K180R/E184R, E184R/N607R, K180R/N607R, E184R/N607R/K613R/D616R, E184R/N607R/K671H, K180R/N607R/K671R, K180R/N607R/K613V/N617R, optionally with the addition of one or more of: N305A, N301A, K589A, N580A, K962A, S334A, K320A, K978A |

*predicted based on UniRule annotation on the UniProt database.

TAL Effector Repeat Arrays

Transcription activator like effectors (TALEs) of plant pathogenic bacteria in the genus *Xanthomonas* play important roles in disease, or trigger defense, by binding host DNA and activating effector-specific host genes. Specificity depends on an effector-variable number of imperfect, typically ~33-35 amino acid repeats. Polymorphisms are present primarily at repeat positions 12 and 13, which are referred to herein as the repeat variable-diresidue (RVD). The RVDs of TAL effectors correspond to the nucleotides in their target sites in a direct, linear fashion, one RVD to one nucleotide, with some degeneracy and no apparent context dependence. In some embodiments, the polymorphic region that grants nucleotide specificity may be expressed as a triresidue or triplet.

Each DNA binding repeat can include a RVD that determines recognition of a base pair in the target DNA sequence, wherein each DNA binding repeat is responsible for recognizing one base pair in the target DNA sequence. In some embodiments, the RVD can comprise one or more of: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

TALE proteins may be useful in research and biotechnology as targeted chimeric nucleases that can facilitate homologous recombination in genome engineering (e.g., to add or enhance traits useful for biofuels or biorenewables in plants). These proteins also may be useful as, for example, transcription factors, and especially for therapeutic applications requiring a very high level of specificity such as therapeutics against pathogens (e.g., viruses) as non-limiting examples.

Methods for generating engineered TALE arrays are known in the art, see, e.g., the fast ligation-based automatable solid-phase high-throughput (FLASH) system described in U.S. Ser. No. 61/610,212, and Reyon et al., *Nature Biotechnology* 30, 460-465 (2012); as well as the methods described in Bogdanove & Voytas, *Science* 333, 1843-1846 (2011); Bogdanove et al., *Curr Opin Plant Biol* 13, 394-401 (2010); Scholze & Boch, *J. Curr Opin Microbiol* (2011); Boch et al., *Science* 326, 1509-1512 (2009); Moscou & Bogdanove, *Science* 326, 1501 (2009); Miller et al., *Nat Biotechnol* 29, 143-148 (2011); Morbitzer et al., *T. Proc Natl Acad Sci USA* 107, 21617-21622 (2010); Morbitzer et al., *Nucleic Acids Res* 39, 5790-5799 (2011); Zhang et al., *Nat Biotechnol* 29, 149-153 (2011); Geissler et al., *PLoS ONE* 6, e19509 (2011); Weber et al., *PLoS ONE* 6, e19722 (2011); Christian et al., *Genetics* 186, 757-761 (2010); Li et al., *Nucleic Acids Res* 39, 359-372 (2011); Mahfouz et al., *Proc Natl Acad Sci USA* 108, 2623-2628 (2011); Mussolino et al., *Nucleic Acids Res* (2011); Li et al., *Nucleic Acids Res* 39, 6315-6325 (2011); Cermak et al., *Nucleic Acids Res* 39, e82 (2011); Wood et al., *Science* 333, 307 (2011); Hockemeye et al. *Nat Biotechnol* 29, 731-734 (2011); Tesson et al., *Nat Biotechnol* 29, 695-696 (2011); Sander et al., *Nat Biotechnol* 29, 697-698 (2011); Huang et al., *Nat Biotechnol* 29, 699-700 (2011); and Zhang et al., *Nat Biotechnol* 29, 149-153 (2011); all of which are incorporated herein by reference in their entirety.

Zinc Fingers

Zinc finger (ZF) proteins are DNA-binding proteins that contain one or more zinc fingers, independently folded zinc-containing mini-domains, the structure of which is well known in the art and defined in, for example, Miller et al., 1985, *EMBO J.*, 4:1609; Berg, 1988, *Proc. Natl. Acad. Sci. USA*, 85:99; Lee et al., 1989, *Science.* 245:635; and Klug, 1993, *Gene*, 135:83. Crystal structures of the zinc finger protein Zif268 and its variants bound to DNA show a semi-conserved pattern of interactions, in which typically three amino acids from the alpha-helix of the zinc finger contact three adjacent base pairs or a "subsite" in the DNA (Pavletich et al., 1991, *Science*, 252:809; Elrod-Erickson et al., 1998, *Structure,* 6:451). Thus, the crystal structure of Zif268 suggested that zinc finger DNA-binding domains might function in a modular manner with a one-to-one interaction between a zinc finger and a three-base-pair "subsite" in the DNA sequence. In naturally occurring zinc finger transcription factors, multiple zinc fingers are typically linked together in a tandem array to achieve sequence-specific recognition of a contiguous DNA sequence (Klug, 1993, *Gene* 135:83).

Multiple studies have shown that it is possible to artificially engineer the DNA binding characteristics of individual zinc fingers by randomizing the amino acids at the alpha-helical positions involved in DNA binding and using selection methodologies such as phage display to identify desired variants capable of binding to DNA target sites of interest (Rebar et al., 1994, *Science,* 263:671; Choo et al., 1994 *Proc. Natl. Acad. Sci. USA,* 91:11163; Jamieson et al., 1994, *Biochemistry* 33:5689; Wu et al., 1995 *Proc. Natl. Acad. Sci. USA,* 92: 344). Such recombinant zinc finger proteins can be fused to functional domains, such as transcriptional activators, transcriptional repressors, methylation domains, and nucleases to regulate gene expression, alter DNA methylation, and introduce targeted alterations into genomes of model organisms, plants, and human cells (Carroll, 2008, 15:1463—*Gene Ther* 68; Cathomen, 2008, *Mol. Ther.,* 16:1200-07; Wu et al., 2007, *Cell. Mol. Life Sci.,* 64:2933-44).

One existing method for engineering zinc finger arrays, known as "modular assembly," advocates the simple joining together of pre-selected zinc finger modules into arrays (Segal et al., 2003, *Biochemistry,* 42:2137-48; Beerli et al., 2002, *Nat. Biotechnol.,* 20:135-141; Mandell et al., 2006, *Nucleic Acids Res.,* 34:W516-523; Carroll et al., 2006, *Nat. Protoc.* 1:1329-41; Liu et al., 2002, *J. Biol. Chem.,* 277: 3850-56; Bae et al., 2003, *Nat. Biotechnol.,* 21:275-280; Wright et al., 2006, *Nat. Protoc.,* 1:1637-52). Although straightforward enough to be practiced by any researcher, recent reports have demonstrated a high failure rate for this method, particularly in the context of zinc finger nucleases (Ramirez et al., 2008, *Nat. Methods,* 5:374-375; Kim et al., 2009, *Genome Res.* 19:1279-88), a limitation that typically necessitates the construction and cell-based testing of very large numbers of zinc finger proteins for any given target gene (Kim et al., 2009, *Genome Res.* 19:1279-88).

Combinatorial selection-based methods that identify zinc finger arrays from randomized libraries have been shown to have higher success rates than modular assembly (Maeder et al., 2008, *Mol. Cell,* 31:294-301; Joung et al., 2010, *Nat. Methods,* 7:91-92; Isalan et al., 2001, *Nat. Biotechnol.,* 19:656-660). In preferred embodiments, the zinc finger arrays are described in, or are generated as described in, WO 2011/017293 and WO 2004/099366. Additional suitable zinc finger DBDs are described in U.S. Pat. Nos. 6,511,808, 6,013,453, 6,007,988, and 6,503,717 and U.S. patent application 2002/0160940.

Variants

In some embodiments, the components of the fusion proteins are at least 80%, e.g., at least 85%, 90%, 95%, 97%, or 99% identical to the amino acid sequence of an exemplary sequence (e.g., a TadA or DBD as provided herein), e.g., have differences at up to 1%, 2%, 5%, 10%, 15%, or 20% of the residues of the exemplary sequence replaced, e.g., with conservative mutations, e.g., including or in addition to the mutations described herein. In preferred embodiments, the variant retains a desired activity of the parent, e.g., deaminase activity, and/or the ability to interact with a guide RNA and/or target DNA, optionally with improved specificity or altered substrate specificity.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, *Advances in Applied Mathematics,* 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) *J Mol Biol* 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Also provided herein are isolated nucleic acids encoding the base editor fusion proteins, vectors comprising the isolated nucleic acids, optionally operably linked to one or more regulatory domains for expressing the variant proteins, and host cells, e.g., mammalian host cells, comprising the nucleic acids, and optionally expressing the variant proteins. In some embodiments, the host cells are stem cells, e.g., hematopoietic stem cells.

In some embodiments, the fusion proteins include a linker between the DNA binding domain (e.g., ZFN, TALE, or nCas9) and the BE domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:24) or GGGGS (SEQ ID NO:25), e.g., two, three, four, or more repeats of the GGGS (SEQ ID NO:24) or GGGGS (SEQ ID NO:25) unit. Other linker sequences can also be used.

In some embodiments, the deaminase fusion protein includes a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton FL 2002); El-Andaloussi et al., (2005) Curr Pharm Des. 11(28):3597-611; and Deshayes et al., (2005) Cell Mol Life Sci. 62(16):1839-49.

Cell penetrating peptides (CPPs) are short peptides that facilitate the movement of a wide range of biomolecules across the cell membrane into the cytoplasm or other organelles, e.g. the mitochondria and the nucleus. Examples of molecules that can be delivered by CPPs include therapeutic drugs, plasmid DNA, oligonucleotides, siRNA, peptide-nucleic acid (PNA), proteins, peptides, nanoparticles, and liposomes. CPPs are generally 30 amino acids or less, are derived from naturally or non-naturally occurring protein or chimeric sequences, and contain either a high relative abundance of positively charged amino acids, e.g. lysine or arginine, or an alternating pattern of polar and non-polar amino acids. CPPs that are commonly used in the art include Tat (Frankel et al., (1988) Cell. 55:1189-1193, Vives et al., (1997) J. Biol. Chem. 272:16010-16017), penetratin (Derossi et al., (1994) J. Biol. Chem. 269:10444-10450), polyarginine peptide sequences (Wender et al., (2000) Proc. Natl. Acad. Sci. USA 97:13003-13008, Futaki et al., (2001) J. Biol. Chem. 276:5836-5840), and transportan (Pooga et al., (1998) Nat. Biotechnol. 16:857-861).

CPPs can be linked with their cargo through covalent or non-covalent strategies. Methods for covalently joining a CPP and its cargo are known in the art, e.g. chemical cross-linking (Stetsenko et al., (2000) J. Org. Chem. 65:4900-4909, Gait et al. (2003) Cell. Mol. Life. Sci. 60:844-853) or cloning a fusion protein (Nagahara et al., (1998) Nat. Med. 4:1449-1453). Non-covalent coupling between the cargo and short amphipathic CPPs comprising polar and non-polar domains is established through electrostatic and hydrophobic interactions.

CPPs have been utilized in the art to deliver potentially therapeutic biomolecules into cells. Examples include cyclosporine linked to polyarginine for immunosuppression (Rothbard et al., (2000) Nature Medicine 6(11):1253-1257), siRNA against cyclin B1 linked to a CPP called MPG for inhibiting tumorigenesis (Crombez et al., (2007) Biochem Soc. Trans. 35:44-46), tumor suppressor p53 peptides linked to CPPs to reduce cancer cell growth (Takenobu et al., (2002) Mol. Cancer Ther. 1(12):1043-1049, Snyder et al., (2004) PLoS Biol. 2:E36), and dominant negative forms of Ras or phosphoinositol 3 kinase (PI3K) fused to Tat to treat asthma (Myou et al., (2003) J. Immunol. 171:4399-4405).

CPPs have been utilized in the art to transport contrast agents into cells for imaging and biosensing applications. For example, green fluorescent protein (GFP) attached to Tat has been used to label cancer cells (Shokolenko et al., (2005) DNA Repair 4(4):511-518). Tat conjugated to quantum dots have been used to successfully cross the blood-brain barrier for visualization of the rat brain (Santra et al., (2005) Chem. Commun. 3144-3146). CPPs have also been combined with magnetic resonance imaging techniques for cell imaging (Liu et al., (2006) Biochem. and Biophys. Res. Comm. 347(1):133-140). See also Ramsey and Flynn, Pharmacol Ther. 2015 Jul. 22. pii: S0163-7258(15)00141-2.

Alternatively or in addition, the deaminase fusion proteins can include a nuclear localization sequence, e.g., SV40 large T antigen NLS (PKKKRRV (SEQ ID NO:26)) and nucleoplasmin NLS (KRPAATKKAGQAKKKK (SEQ ID NO:27)). Other NLSs are known in the art; see, e.g., Cokol et al., EMBO Rep. 2000 Nov. 15; 1(5): 411-415; Freitas and Cunha, Curr Genomics. 2009 December; 10(8): 550-557.

In some embodiments, the deaminase fusion proteins include a moiety that has a high affinity for a ligand, for example GST, FLAG or hexahistidine (SEQ ID NO: 35) sequences. Such affinity tags can facilitate the purification of recombinant deaminase fusion proteins.

The deaminase fusion proteins described herein can be used for altering the genome of a cell. The methods generally include expressing or contacting the deaminase fusion proteins in the cells; in versions using one or two Cas9s, the methods include using a guide RNA having a region complementary to a selected portion of the genome of the cell. Methods for selectively altering the genome of a cell are known in the art, see, e.g., U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US20160024529; US20160024524; US20160024523; US20160024510; US20160017366; US20160017301; US20150376652; US20150356239; US20150315576; US20150291965; US20150252358; US20150247150; US20150232883; US20150232882; US20150203872; US20150191744; US20150184139; US20150176064; US20150167000; US20150166969; US20150159175; US20150159174; US20150093473; US20150079681; US20150067922; US20150056629; US20150044772; US20150024500; US20150024499; US20150020223; US20140356867; US20140295557; US20140273235; US20140273226; US20140273037; US20140189896; US20140113376; US20140093941; US20130330778; US20130288251; US20120088676; US20110300538; US20110236530; US20110217739; US20110002889; US20100076057; US20110189776; US20110223638; US20130130248; US20150050699; US20150071899; US20150050699; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; WO/2008/108989; WO/2010/054108; WO/2012/164565; WO/2013/098244; WO/2013/176772; US 20150071899; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea"

482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302. For methods in which the deaminase fusion proteins are delivered to cells, the proteins can be produced using any method known in the art, e.g., by in vitro translation, or expression in a suitable host cell from nucleic acid encoding the deaminase fusion protein; a number of methods are known in the art for producing proteins. For example, the proteins can be produced in and purified from yeast, E. coli, insect cell lines, plants, transgenic animals, or cultured mammalian cells; see, e.g., Palomares et al., "Production of Recombinant Proteins: Challenges and Solutions," Methods Mol Biol. 2004; 267:15-52. In addition, the deaminase fusion proteins can be linked to a moiety that facilitates transfer into a cell, e.g., a lipid nanoparticle, optionally with a linker that is cleaved once the protein is inside the cell. See, e.g., LaFountaine et al., Int J Pharm. 2015 Aug. 13; 494(1):180-194.

Expression Systems

To use the deaminase fusion proteins described herein, it may be desirable to express them from a nucleic acid that encodes them. This can be performed in a variety of ways. For example, the nucleic acid encoding the deaminase fusion can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the deaminase fusion for production of the deaminase fusion protein. The nucleic acid encoding the deaminase fusion protein can also be cloned into an expression vector, for administration to a plant cell, animal cell, preferably a mammalian cell or a human cell, fungal cell, bacterial cell, or protozoan cell.

To obtain expression, a sequence encoding a deaminase fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., E. coli, Bacillus sp., and Salmonella (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the deaminase fusion protein is to be administered in vivo for gene regulation, either a constitutive or an inducible promoter can be used, depending on the particular use of the deaminase fusion protein. In addition, a preferred promoter for administration of the deaminase fusion protein can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the deaminase fusion protein, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the deaminase fusion protein, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMT010/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the deaminase fusion protein can include RNA Pol III promoters to drive expression of the guide RNAs, e.g., the H1, U6 or 7SK promoters. These human promoters allow for expression of deaminase fusion protein in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the deaminase fusion protein.

In methods wherein the fusion proteins include a Cas9 domain, the methods also include delivering at least one gRNA that interacts with the Cas9, or a nucleic acid that encodes a gRNA.

Alternatively, the methods can include delivering the deaminase fusion protein and guide RNA together, e.g., as a complex. For example, the deaminase fusion protein and gRNA can be can be overexpressed in a host cell and purified, then complexed with the guide RNA (e.g., in a test tube) to form a ribonucleoprotein (RNP), and delivered to cells. In some embodiments, the deaminase fusion protein can be expressed in and purified from bacteria through the use of bacterial expression plasmids. For example, His-tagged deaminase fusion protein can be expressed in bacterial cells and then purified using nickel affinity chromatography. The use of RNPs circumvents the necessity of delivering plasmid DNAs encoding the nuclease or the guide, or encoding the nuclease as an mRNA. RNP delivery may also improve specificity, presumably because the half-life of the RNP is shorter and there's no persistent expression of the nuclease and guide (as you'd get from a plasmid). The RNPs can be delivered to the cells in vivo or in vitro, e.g., using lipid-mediated transfection or electroporation. See, e.g., Liang et al. "Rapid and highly efficient mammalian cell engineering via Cas9 protein transfection." Journal of biotechnology 208 (2015): 44-53; Zuris, John A., et al. "Cationic lipid-mediated delivery of proteins enables efficient protein-based genome editing in vitro and in vivo." Nature biotechnology 33.1 (2015): 73-80; Kim et al. "Highly efficient RNA-guided genome editing in human cells via delivery of purified Cas9 ribonucleoproteins." Genome research 24.6 (2014): 1012-1019.

The present invention also includes the vectors and cells comprising the vectors, as well as kits comprising the proteins and nucleic acids described herein, e.g., for use in a method described herein.

Methods of Use

The base editors described herein can be used to deaminate a selected adenine in a nucleic acid sequence, e.g., in a cell, e.g., a cell in an animal (e.g., a mammal such as a human or veterinary subject), or a synthetic nucleic acid substrate. The methods include contacting the nucleic acid with a base editor as described herein. Where the base editor includes a CRISPR Cas9 or Cas12a protein, the methods further include the use of one or more guide RNAs that direct binding of the base editor to a sequence to be deaminated.

For example, the base editors described herein can be used for in vitro, in vivo or in situ directed evolution, e.g., to engineer polypeptides or proteins based on a synthetic selection framework, e.g. antibiotic resistance in E. coli or resistance to anti-cancer therapeutics being assayed in mammalian cells (e.g. CRISPR-X Hess et al, PMID: 27798611 or BE-plus systems Jiang et al, PMID: 29875396).

EXAMPLES

The invention is further described in the following examples, which do not limit the scope of the invention described in the claims.

Methods

The following materials and methods were used in the Examples set forth herein.

Molecular Cloning

Expression plasmids are constructed by selectively amplifying desired DNA sequences using the PCR method such that they have significant overlapping ends and using isothermal assembly (or "Gibson Assembly", NEB) to assemble them in the desired order in a CAG or CMV expression vector. PCR is conducted using Phusion HF polymerase (NEB). Cas9 gRNAs is cloned into the pUC19-based entry vector BPK1520 (via BsmBI) under control of a U6 promoter.

Guide RNAs

All gRNAs are of the form 5'-NNNNNNNNNNNNNNNNNNNNCGTTT-TAGAGCTAGAAATAGCAAGT-TAAAATAAGGCTAGTC CGTTATCAACTT-GAAAAAGTGGCACCGAGTCGGTGCTTTTTTT-3'.
(SEQ ID NO:28) Shown below are the protospacer regions (NNNNNNNNNNNNNNNNNNNN in SEQ ID NO:28) for these gRNAs (all written 5' to 3').

Cas9 guide RNA protospacer, RNF2 site 1: GTCATCT-TAGTCATTACCTG (SEQ ID NO:30)
Cas9 guide RNA protospacer, RNF2 site 1: GTCATCT-TAGTCATTACCTG (SEQ ID NO:30)

Cell Culture and Transfections

HEK293T cells (CRL-3216, ATCC) are grown in culture using Dulbeccos Modified Medium (Gibco) supplemented with 10% FBS (Gibco) and 1% penicillin-streptomycin solution (Gibco). Cells are passaged at ~80% confluency every 2-3 days to maintain an actively growing population. HepG2 cells (HB80-65, ATCC) are grown in Eagle's Minimum Essential Medium (ATCC) supplemented with 10% FBS and 0.5% penicillin-streptomycin solution (Gibco). Cells are passaged at ~80% confluency every 4 days. Both cell lines are used for experiments until passage 20 for HEK293T and passage 12 for HepG2. Cells are tested for *Mycoplasma* bi-weekly.

For sorting experiments, transfections with 50 ug of transfection quality DNA (Qiagen Maxiprep) encoding desired ABEmax-P2A-EGFP fusion proteins or controls (same construct, lacking TadA-TadA* heterodimer, * marks the engineered variants, e.g. 7.10) and gRNAs (75:25%) were conducted by seeding $6 \times 10^6$ HEK293T or $15 \times 10^6$ HepG2 into TC-treated 150 mm plates 18-24h prior to transfection to yield ~80% confluency on the day of transfection. Cells are transfected at 60-80% confluency using TransIT-293 (HEK293T, Mirus) or tranfeX (HepG2, ATCC) reagents according to the manufacturers' protocols. To ensure maximal correlation of negative controls to ABE overexpression, cells of the same passage are transfected with bpNLS-32AAlinker-nCas9-bpNLS (negative control) and adenine base editors in parallel. RNA and gDNA is harvested after cell sorting. For experiments validating DNA on-target activity of ABE or ABEmax-RRE variants, 1.5× $10^4$ HEK293T cells are seeded into the wells of a 96-well plate and transfected 18-24h after seeding with 220 ng DNA (ABE/nCas9-NLS control:gRNA ration of 75:25%). For these experiments, gDNA is harvested 72h post-transfection.

FACS & RNA/DNA Harvest

Sorting of negative control and BE expressing cells as well as RNA/DNA harvest is carried out on the same day. Cells are sorted on a BD FACSARIAII 36-40h after transfection. We gate on the cell population on forward/sideward scatter after exclusion of doublets. We then sort all GFP-positive cells and/or top 5% of cells with the highest FITC signal into pre-chilled 100% FBS and 5% of mean fluorescence intensity (MFI)-matched cells for nCas9-NLS negative controls, matching the MFI/GeoMean of top 5% of ABE or ABEmax-transfected cells. We use MFI-matching for these controls, as the bpNLS-32AAlinker-nCas9-bpNLS-P2A-EGFP (control) plasmid is smaller than ABEmax-P2A-EGFP—due to the lack of the TadA-TadA* heterodimer—and thus yields higher transfection efficiency and overall higher FITC signal. After sorting, cells are spun down, lysed using DNA lysis buffer (Laird et al, 1991) with DTT and Proteinase K or RNA lysis buffer (Macherey-Nagel). gDNA is extracted using magnetic beads (made from FisherSci Sera-Mag SpeedBeads Carboxyl Magnetic Beads, hydrophobic according to Rohland & Reich, 2012), after overnight lysis. RNA then is extracted with Macherey-Nagel's NucleoSpin RNA Plus kit.

High-Throughput Amplicon Sequencing, RT-PCR & Base Editing Data Analysis

Genomic DNA is amplified using gene-specific DNA primers flanking desired target sequence. These primers include illumina-compatible adapter-flaps. The amplicons are molecularly indexed with NEBNext Dual Index Primers (NEB) or index primers with the same or similar sequence ordered from IDT. Samples are combined into libraries and sequenced on the Illumina MiSeq machine using the MiSeq Reagent Kit v2 or Micro Kit v2 (Illumina). Sequencing results are analyzed using a batch version of the software CRISPResso 2.0 (crispresso.rocks). Reverse transcription is performed using the High Capacity RNA-to-cDNA kit (Thermo Fisher) following the manufacturer's instructions. Amplicon PCR and library preparation for Next-Generation Sequencing (NGS) off of cDNA is done as described above for gDNA. If possible, we use exon-exon junction spanning primers to exclude amplification of gDNA.

RNA-Seq and Single Nucleotide Variant Calling

RNA library preparation is performed using Illumina's TruSeq Stranded Total RNA Gold Kit with initial input of ~500 ng of extracted RNA per sample, using SuperScript III for first-strand synthesis (Thermo Fisher). rRNA depletion is confirmed during library preparation by fluorometric quantitation using the Qubit HS RNA kit before and after depletion (Thermo Fisher). For indexing, we use IDT-Illumina Unique Dual Indeces (Illumina). Libraries are pooled based on qPCR quantification (NEBNext Library Quant Kit for Illumina) and loaded onto a NextSeq (at MGH Cancer Center, PE 2×150, 500/550 MidOutput Cartridge) or HiSeq2500 in High Output mode (Broad Institute, PE 2×76). Illumina fastq sequencing reads are aligned to the human hg38 reference genome with STAR (Dobin et al., 2013, PMID: 23104886) and processed with GATK best practices (McKenna et al., 2010, PMID: 20644199: DePristo et al., 2011, PMID: 21478889). RNA variants are called using HaplotypeCaller, and empirical editing efficiencies are established on PCR-de-duplicated alignment data.

Variant loci in ABE/ABEmax overexpression experiments are further required to have comparable read coverage in the corresponding control experiment (read coverage for SNV in control >90th percentile of read coverage across all SNVs in overexpression). Additionally, the above loci are required to have a consensus of at least 99% of reads calling the reference allele in control.

Protein Structure Analysis and DNA/RNA Binding Prediction

We access the crystal structures of E. coli (1Z3A, DOI: 10.2210/pdb1Z3A/pdb) and S. aureus TadA (2B3J, DOI: 10.2210/pdb2B3J/pdb; NDB: PRO180), only the latter of which is in complex with RNA, from the protein databank PDB (rcsb.org). Using the software PyMOL (Schrödinger), the two three-dimensional crystal structures are aligned and residues in these two crystal structures are analyzed regarding proximity to RNA and the modeled enzymatic pocket adenosine deamination is localized at. DNA and RNA binding is predicted using the DRNApred interface (Yan&Kurgan, NAR 2017).

Alignment of tRNA Adenosine Deaminase Homologues and Orthologues

The amino acid sequence of E. coli TadA is aligned to other tRNA adenosine deaminase homologues or orthologues using Geneious 7 software. Amino acid sequences are obtained from the uniprot platform (uniprot.org).

Figure 2B:
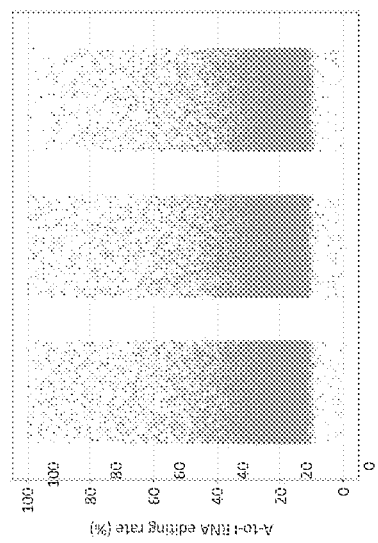
Figure 2D:
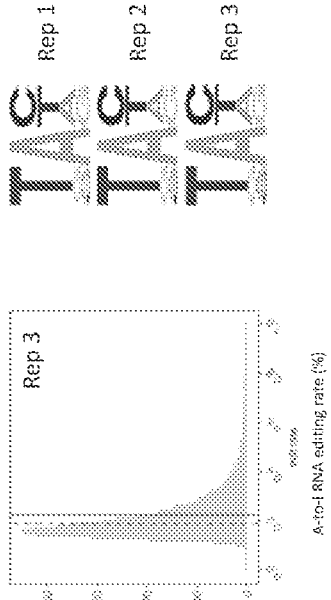
Figure 2C:
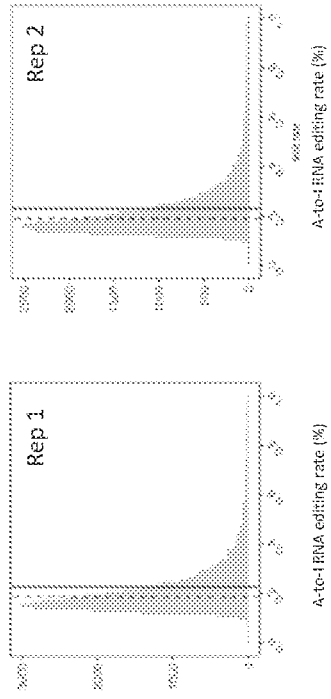

Example 1. Adenine Base Editors (ABEmax) Comprised of E. coli TadA (WT Fused to Engineered TadA) Induce Unwanted A-to-I Edits in RNA To test whether ABEs might be capable of editing adenines in RNA, we assessed whether this base editor fusion could edit adenines transcriptome-wide using RNA-seq. To do this, we transfected human HEK293T cells with a plasmid that expressed an ABEmax-P2A-EGFP fusion protein (the P2A sequence mediates a post-translational cleavage that releases EGFP from the ABEmax part of the fusion) (Methods). At 36 hours after transfection, we then used flow cytometry to sort out the cells with the highest (top 5%) GFP/FITC signal and isolated total RNA from these cells. As a negative control, we transfected HEK293T cells in parallel with a plasmid that expressed a bpNLS-32AA-linker-nickase Cas9 (nCas9)-bpNLS-P2A-EGFP (called nCas9-NLS below) fusion protein (i.e., a plasmid identical to the ABEmax-P2A-EGFP expression plasmid but lacking the TadA-TadA* heterodimer within the ABEmax part of the fusion protein) and also sorted these for the top 5% GFP signal and isolated total RNA. We used a gRNA targeting a genomic site in the RNF2 gene and on-target DNA base editing was high (~70% A-to-G, data not shown). Using RNA-seq, we found that ABEmax edited tens of thousands of adenosines in RNA with high efficiency (FIG. 2A-C). These experiments were done in triplicate and each ABEmax sample was RNA-sequenced with a matching negative control. The fraction of A-to-I changes with respect to all possible substitutions was >99.5% in all replicates (Table C).

TABLE C

Total numbers of A-to-I RNA edits
induced by ABEmax overexpression

| Cell Line | Guide RNA | Replicate No. | A-to-I mutations in RNA | |
|---|---|---|---|---|
| | | | % of detected variants | total |
| 293T | RNF2, site1 | #1 | 99.76 | 37,061 |
| | | #2 | 99.79 | 31,821 |
| | | #3 | 99.83 | 28,752 |

Total transcriptome-wide numbers of edited adenosines in different biological replicates Cells were transfected 18-24h after seeding and sorted 36-40h after transfection for top 5% FITC signal (Methods).

These edited As were distributed throughout the human genome and had considerable editing efficiencies (FIGS. 2B-C). Sequence logos derived from edited As in each of these experiments showed the high prevalence of a T preceding the edited A (FIG. 2D), which is similar to the sequence context of adenosine 34 which gets physiologically edited on tRNA by TadA. Subsequent experiments are focused on determining the impact of ABE expression levels, the use of different gRNAs as well as potential differences in off-target A-to-I RNA editing induced by ABEs in different cell lines.

Example 2. ABE Variants with Reduced RNA Editing Activities

Figure 3:
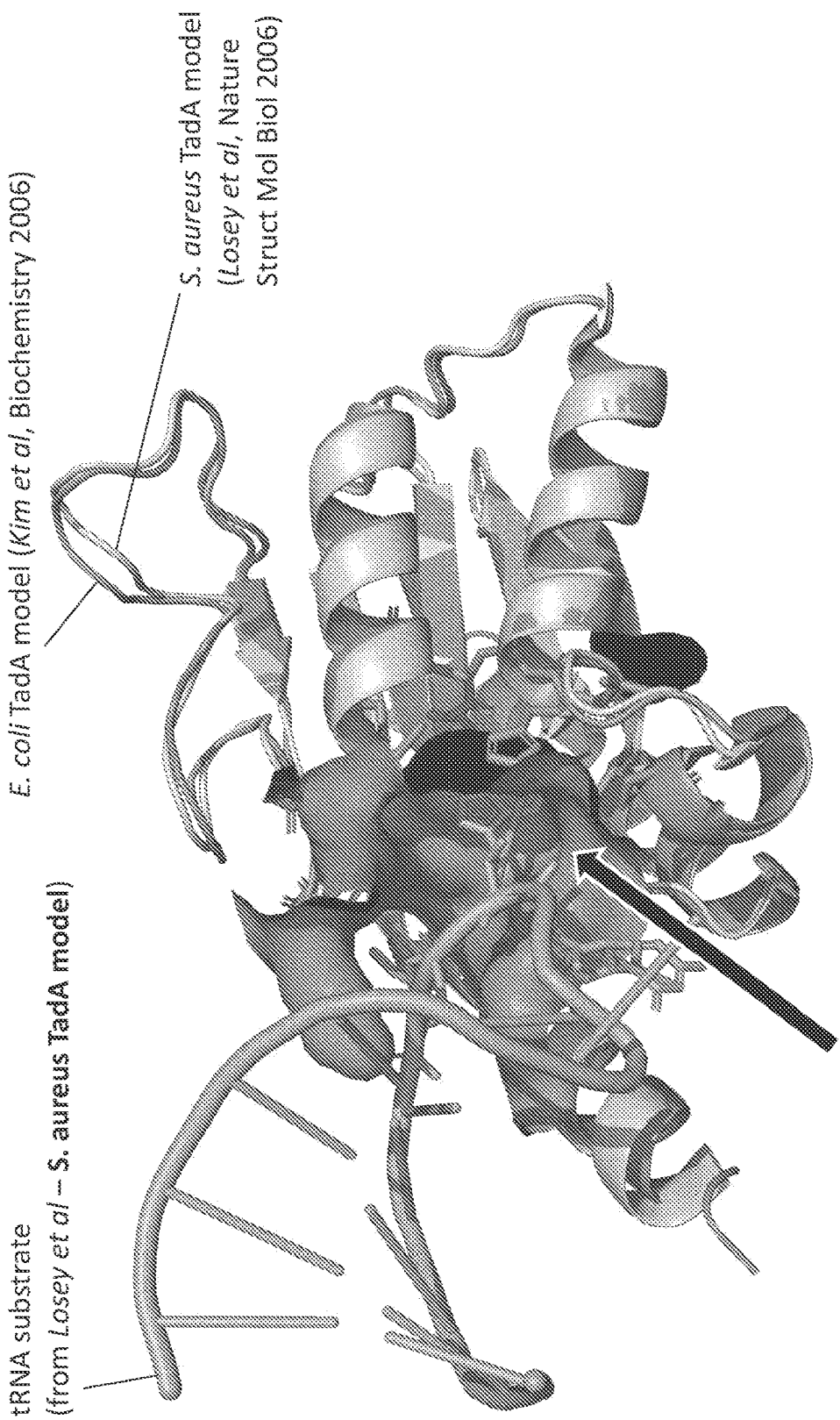
FIG. 3. Ribbon diagram of molecular structures of *E. coli* and *S. aureus* TadA showing the RNA editing pocket proximal to adenosine 34 on the target tRNA substrate. Illustration shows the structural overlap between the two adenosine deaminase structures. Structural data of *S. aureus* TadA bound to RNA enables derivation of possible TadA-RNA contacts in *E. coli* TadA, the structure of which is not available in complex with RNA.
Figure 4:
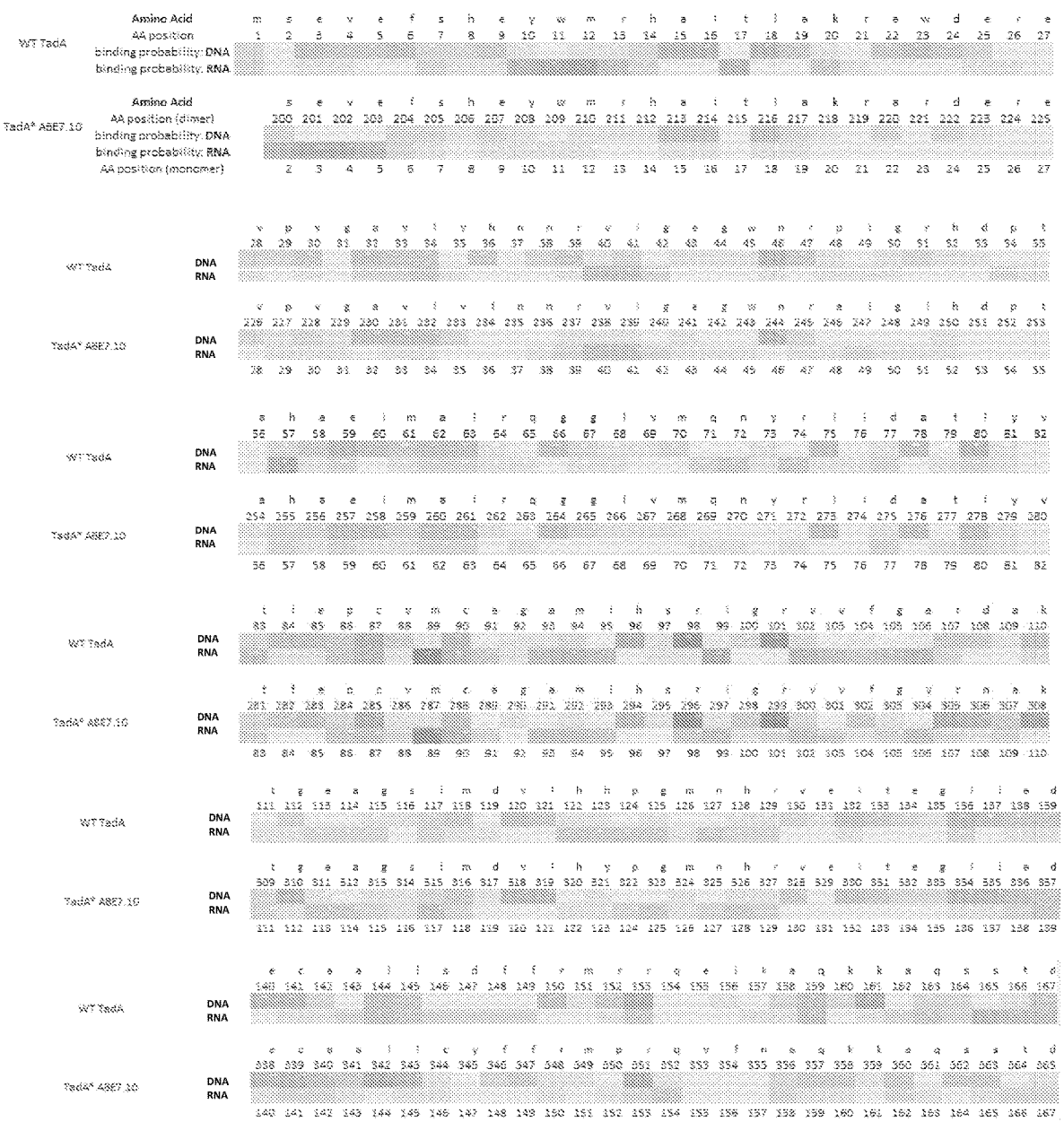
FIG. 4. Differential DNA and RNA binding prediction of individual residues of the *E. coli* TadA heterodimer present in ABE7.10 and ABEmax. We used the DRNApred tool (Yan and Kurgan, *Nucleic Acids Res*. 2017 Jun. 2; 45(10): e84; PMID 28132027) to predict DNA and RNA binding probabilities of individual residues across the *E. coli* TadA heterodimer present in ABE7.10. The heatmap illustrates binding probabilities at indicated amino acid positions for both WT (SEQ ID NO: 1) and engineered TadA (SEQ ID NO: 21). Green coloring represents low, yellow intermediate and red high binding probability.

Given the transcriptome-wide RNA editing induced by ABEmax, it is desirable to create variants of the adenine base editor that would diminish this unwanted activity while retaining the desired capability to perform targeted DNA base editing (RRE or Reduced RNA Editing variants). We reasoned that the introduction of mutations into the TadA-TadA* part (* marking the engineered variant of E. coli TadA of the adenine base editor) of an ABE, either in one or both monomers, might accomplish this. We also reasoned that mutations might also be introduced into the TadA* part of an ABE harboring only a single adenine deaminase domain. To identify potential positions to alter, we first aligned the structures of S. aureus TadA bound to RNA and E. coli TadA on its own (no structure is available for this TadA bound to RNA) using PyMol software. All residues in proximity of the enzymatic pocket in which A34 gets deaminated, or residues which could establish contacts with the RNA near the TadA structure were identified using this structure-guided strategy (FIG. 3) and we reasoned that these are candidate positions at which to introduce amino acid substitutions that might have an RRE phenotype. To generate additional positions that might be mutated to achieve an RRE phenotype, we used DRNApred to predict differential DNA and RNA binding of positions in the TadA-TadA* single-chain heterodimer. Using this tool, we were able to identify residues that may predominantly bind to one or the other or both types of nucleic acids (i.e., DNA or RNA) (FIG. 4). Positions predicted to predominantly bind RNA are candidate residues at which amino acid substitutions may generate adenine deaminases with an RRE phenotype (FIG. 4). Table A lists all amino acid positions identified with these two orthogonal approaches. To test these variants with amino acid substitutions at these positions for an RRE phenotype, we generate variants of ABE with mutations at the one or more of the positions listed in Table A and test them in three steps: (1) testing for on-target DNA editing capabilities in cells using gRNAs targeted to 4 genomic sites, (2) all variants that preserve high and precise on-target DNA editing capabilities are then assayed for off-target RNA editing on 4 commonly RNA-edited transcriptomic sites determined using RNA-seq data from Example 1, and (3). the variants showing most promising on/off-target profiles are assayed using deep RNA-seq to validate reduction of transcriptome-wide RNA editing activity.

Example 3. CRISPR Adenine and Cytosine Base Editors with Reduced Self-Editing and RNA Off-Target Activities Methods:

The following materials and methods were used in Example 3.

PyMOL Analysis of TadA structures. *Escherichia coli* tRNA-specific adenosine deaminase (TadA, PDB 1Z3A) and *Staphylococcus aureus* TadA with tRNA (PDB 2B3J) structures were downloaded from the Protein Data Bank and visualized with PyMOL version 2.2.2. Subunit A (monomer) of *S. aureus* TadA with tRNA was superimposed with subunit A of *E. coli* TadA using the "super" command. All figures were generated with PyMOL (Schrödinger).

Plasmid cloning. All ABE constructs were cloned using the backbone and the P2A-EGFP-NLS fragment of ABEmax-P2A-EGFP-NLS (AgeI/NotI digest; Addgene ID 112101). ABEmax and variants were expressed under the control of a pCMV promoter. For the P2A-EGFP fragments in these constructs, we used BPK4335 (pCMV-BE3-P2A-EGFP) as a template. Guide RNA (gRNA) plasmids were cloned using the SpCas9 gRNA entry vector BPK1520 (pUC19 backbone; BsmBI cassette, Addgene ID 65777). All remaining constructs were generated using isothermal amplification (Gibson assembly, NEB). All gRNA and ABE plasmids were midi or maxi prepped using the Qiagen Midi/Maxi Plus kits.

Cell culture. HEK293T cells (CRL-3216) and HepG2 cells (HB-8065) were purchased from and STR-authenticated by ATCC. Cells were cultured in Dulbecco's Modified Eagle Medium (DMEM, Gibco) supplemented with 10% (v/v) fetal bovine serum (FBS, Gibco) and 1% (v/v) penicillin-streptomycin (Gibco) or Eagle's Minimum Essential Medium with 10% (v/v) FBS and 0.5% (v/v) penicillin. Cells were passaged every 2-3 days when reaching around 80-90% confluency. Both cell lines were used only until passage 20 for all experiments, and the media was tested every two weeks for *Mycoplasma*.

Transfections. For ABE DNA on-target screening experiments, $2 \times 10^4$ HEK293T cells were seeded into 96-well Flat Bottom Cell Culture plates (Corning), transfected 24h post seeding with 165 ng base editor or negative control (bpNLS-32AA linker-nCas9(D10A)-bpNLS), 55 ng guide RNA expression plasmid, and 0.66 µL TransIT-293 (Mirus), and harvested 72h after transfection for DNA. For ABE RNA off-target screening experiments, $2 \times 10^5$ HEK293T cells were seeded into 12-well Cell Culture plates (Corning), transfected 24h post seeding with 1.65 µg base editor or negative control, 0.55 µg guide RNA, and 6.6 µL TransIT-293, and harvested 36h after transfection for RNA. For experiments with FACS-sorted cells, $6.5-7 \times 10^6$ HEK293T cells were seeded into 150 mm Cell Culture dishes (Corning), transfected 24h post seeding with 37.5 µg base editor or an appropriate negative control fused to P2A-EGFP, 12.5 µg guide RNA, and 150 µL TransIT-293. Sorting took place 36-40h post transfection.

Fluorescence-activated cell sorting (FACS). Cells were prepared for sorting by diluting to $1 \times 10^7$ cells per ml with 1× Phosphate Buffer Saline (PBS, Corning) supplemented with 10% FBS and filtering through 35 µm cell strainer caps (Corning). Cells were sorted on a FACSAria II (BD Biosciences) using FACSDiva version 6.1.3 (BD Biosciences) after gating for single live cells. Cells treated with base editor were sorted for either all GFP signal (standard expression) or top 5% of cells with the highest GFP (FITC) signal (overexpression) into FBS; cells treated with nCas9 negative controls were sorted for either all GFP positive cells or the 5% of cells with a mean fluorescence intensity (MFI) matching that of the top 5% of cells treated with base editor.

DNA extraction. For ABE DNA on-target experiments, cells were lysed for DNA 72h post-transfection with freshly prepared 43.5 µL DNA lysis buffer (50 mM Tris HCl pH 8.0, 100 mM NaCl, 5 mM EDTA, 0.05% SDS, adapted from ref. 15), 5.25 µL Proteinase K (NEB), and 1.25 µL 1M DTT (Sigma). For experiments with sorted cells, cells were centrifuged (200 g, 8 min) and lysed with 174 µL DNA lysis buffer, 21 µL Proteinase K, and 5 µL 1M DTT. Lysates were incubated at 55° C. on a plate shaker overnight, then gDNA were extracted with 2× paramagnetic beads (as described in ref. 16), washed 3 times with 70% EtOH, and eluted in 30 µL 0.1×EB buffer (Qiagen).

RNA extraction & reverse transcription. Cells were lysed for RNA 36h-40h post-transfection with 350 µL RNA lysis buffer LBP (Macherey-Nagel), and RNA were extracted with the NucleoSpin RNA Plus kit (Macherey-Nagel) following the manufacturer's instructions. RNA was then reverse transcribed into cDNA with the High Capacity RNA-to-cDNA kit (Thermo Fisher) following the manufacturer's instructions.

Library preparation for DNA or cDNA targeted amplicon sequencing. Next-generation sequencing (NGS) of DNA or cDNA was performed as previously described[5]. In summary, the first PCR was performed to amplify genomic or transcriptomic sites of interested with primers containing Illumina forward and reverse adapter sequences (see FIG. 6G, Supplementary Table 2 for primers and amplicons used in this study), following NEB Phusion High-Fidelity DNA Polymerase instructions. The first PCR products were cleaned with 0.7× paramagnetic beads, then the second PCR was performed to add barcodes with primers containing unique sets of p5/p7 Illumina barcodes (analogous to TruSeq CD indexes). The second PCR products were again cleaned with 0.7× paramagnetic beads. The libraries were then pooled based on concentrations measured with the QuantiFluor dsDNA System (Promega) and Synergy HT microplate reader (BioTek) at 485/528 nm. The final pool was quantified by qPCR with the NEBNext Library Quant Kit for Illumina (NEB) and sequenced paired-end (PE) 2×150 on the Illumina MiSeq machine using 300-cycle MiSeq Reagent Kit v2 or Micro Kit v2 (Illumina). FASTQs (post-demultiplexing) were downloaded from Illumina BaseSpace and analyzed using a batch version of CRISPResso 2.

RNA library preparation & sequencing. RNA-seq experiments were performed as previously described[5]. Briefly, RNA libraries were prepared with the TruSeq Stranded Total RNA Library Prep Gold kit (Illumina) following the manufacturer's instructions. SuperScript III (Invitrogen) was used for first-strand synthesis, and IDT for Illumina TruSeq RNA unique dual indexes (96 indexes) were used to avoid index hopping. The libraries were pooled based on qPCR measurements with the NEBNext Library Quant Kit for Illumina. The final pool was sequenced PE 2×76 on the Illumina HiSeq2500 machine (for the ABE experiment shown in FIG. 6b) or PE 2×100 on the NovaSeq6000 machine (for all remaining ABE experiments) at the Broad Institute of Harvard and MIT (Cambridge, MA). To account for variable sequencing depths, all RNA-seq libraries sequenced on the NovaSeq were uniformly downsampled to 100 million reads per library using seqtk version 1.0-r82-dirty (github.com/lh3/seqtk).

Amplicon sequencing analysis. Amplicon sequencing data was analyzed with CRISPResso2 v.2.0.27[17]. The heatmaps for the SECURE-ABE screening in FIG. 6f display the highest edited adenine at the target site. Editing efficiency values were $\log_2$ transformed with a pseudocount of 1, averaged over quadruplicates, and normalized to ABEmax. The remaining heatmaps showing ABE on-target DNA editing (FIG. 7 and FIG. 9) show an editing window that includes the edited Cs and a grey background for editing efficiencies smaller than 2%.

RNA Variant Calling Pipeline

All bioinformatic analysis was performed in concordance with GATK Best Practices[18,19] for RNA-seq mutation calling as we have previously described[5]. Briefly, raw sequencing reads were two-pass aligned to the reference hg38 reference genome with STAR[20] with parameters to discard multi-mapping reads. After PCR duplicate removal and base recalibration, mutations in RNA-seq libraries were called using GATK HaplotypeCaller. RNA edits in ABE overexpression experiments were identified using a downstream modification of the GATK pipeline output as we have previously described[5]. Specifically, mutation positions called by HaplotypeCaller were further filtered to include only those satisfying the following criteria with reference to the corresponding control experiments: (1) Read coverage for a given edit in control experiment should be greater than the 90th percentile of read coverage across all edits in the overexpression experiment. (2) 99% of reads covering each edit in the control experiment were required to contain the reference allele. Edits were further filtered to exclude those with fewer than 10 reads or 0% alternate allele frequencies. A-G edits include A-G edits identified on the positive strand as well as T-C edits identified on the negative strand.

Six A-to-I edits identified from the above pipeline were chosen to test SECURE ABE variants based on the following criteria. These were sites that had (1) read coverage of at least 50 in all replicates of control and overexpression experiments, (2) 99% reads in all control experiments containing reference allele and (3) at least 60% alternate allele frequencies in all replicates. From this list, primers were tested for the top 15 edited sites that were also within 150 bases of an exon-exon junction and the 6 highest edited sites with robust amplification from cDNA were chosen.

To identify self-edits occurring on the base-editing construct, we generated a modified hg38 reference genome with additional contigs for the gRNA and base editor constructs. These additional contigs were appended to the reference genome, and each library was re-processed using GATK best practices, including variant calling with HaplotypeCaller. Variants were then further filtered using a similar process as described above for the transcriptome (i.e. filtering for no more than 1% editing in the negative control) with the exception that positions poorly covered in the control due to differences in the construct design (i.e. the deaminase domain) were not filtered out. We note that since both control and BE constructs were expressed from plasmids, the overall expression of these transcripts is much higher than most detected genes which supersedes the control of coverage between control and BE expression in this analysis (see part 1 of transcriptome variant calling above). Editing efficiencies per position were computed based on the abundance of Gs (ABE) over total coverage from bam-readcount estimated on the PCR deduplicated .bam files. Edits were further filtered to exclude those with fewer than 50 reads or 0% alternate allele frequencies.

Results

Figure 6:
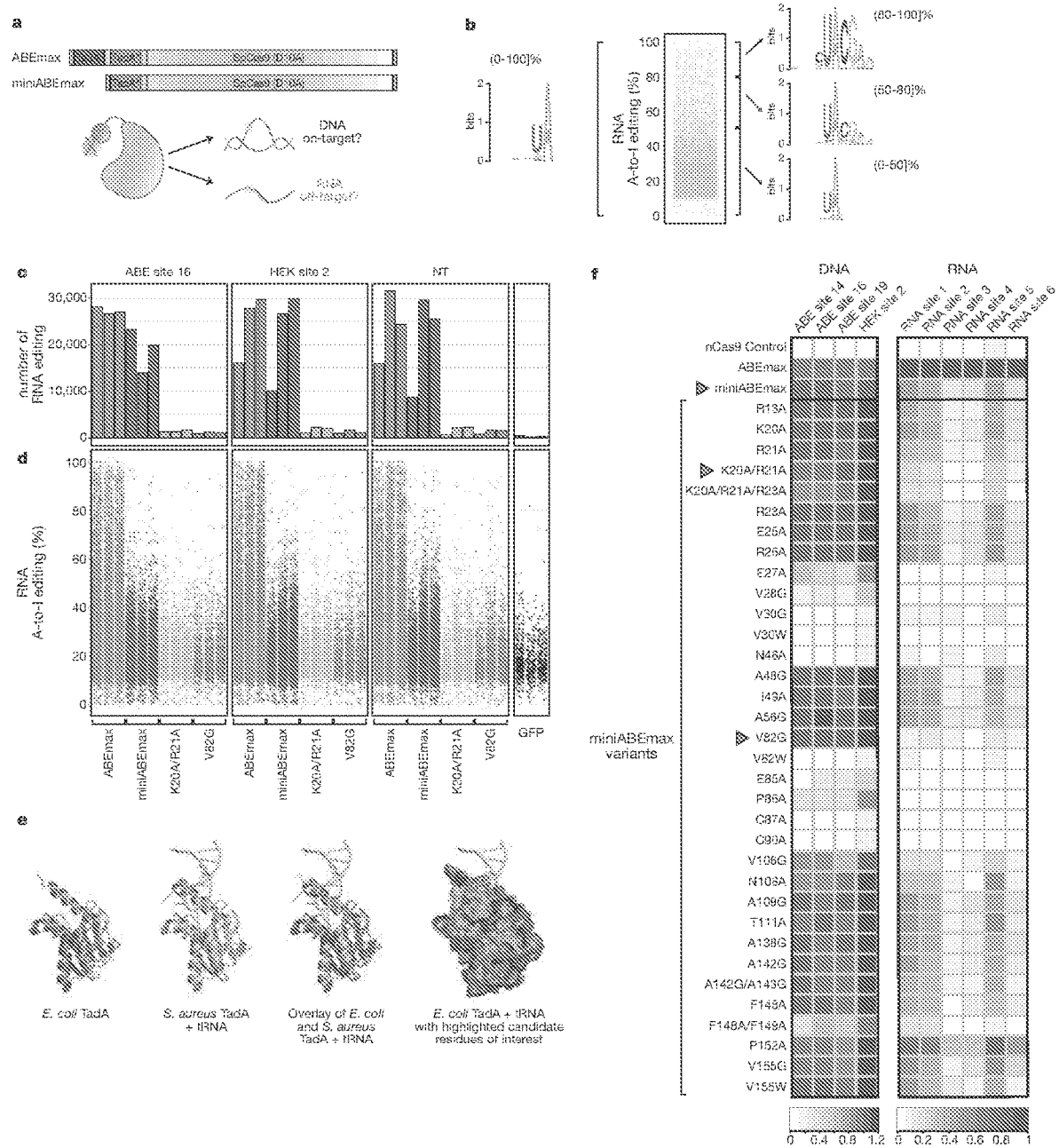
FIG. 6A-G. Engineering of SECURE-ABE variants with reduced off-target RNA editing activities (a) Schematic illustration of ABEmax and miniABEmax architectures and overview of experimental testing of miniABEmax for on-target DNA and off-target RNA editing. Left-most and right-most boxes=bipartite NLS at N- and C-termini, TadA*=mutant TadA 7·10³, and small grey boxes (between TadA and TadA*, or TadA* and SpCas9(D10A))=32AA flanked XTEN linkers. nCas9 (SpCas9 D10A)=grey shape, TadA WT and mutant monomers=circles. Halo=sites of potential adenine deamination on DNA and RNA. (b) Unstratified sequence logo (left) and stratified sequence logos for RNA adenines edited with high (80-100 1%, middle (50-80 1%, and low (0-50 1% efficiencies by ABEmax. RNA-seq data shown in the Jitter plot was obtained from HEK293T cells in an earlier published study. (c) Bar plots showing the number of RNA A-to-I edits observed in RNA-seq experiments in HEK293T cells with expression of ABEmax, miniABEmax, miniABEmax-K20A/R21A, or miniABEmax-V82G each with three different gRNAs (ABE site 16, HEK site 2, and non-targeting (NT)) and performed in independent biological replicates (n=3). GFP negative control also performed in independent biological replicates (n=3) is also shown. (d) Jitter plot showing the efficiencies of RNA A-to-I edits from the RNA-seq experiments shown in c. Each dot represents an edited adenine position in RNA. (e) Structural representations of *E. coli* TadA (PDB 1Z3A), structural representation of *S. aureus* TadA in complex with tRNA (PDB 2B3J), overlaid structures from *E. coli* TadA and *S. aureus* TadA, and surface representation of *E. coli* TadA in dark gray with backbone carbons of amino acid positions proximal to the predicted deaminase catalytic site highlighted in light gray. Target adenine on tRNA (A34) marked in green. All graphical representations generated with PyMol (Methods). (f) Testing of 34 miniABEmax variants for their on-target DNA editing (A-to-G) and off-target RNA editing (A-to-I) activities. (g) Supplementary Table 2, sequences of primers and amplicons used in the present study. On-target DNA editing was assessed with four different gRNAs and off-target RNA alterations were screened on six RNA adenines previously identified as being efficiently modified by ABEmax[5]. Efficiencies are shown in heat map format (log-fold changes), with each box representing the mean of four independent biological replicates normalized to the edit efficiency observed with ABEmax for each target DNA or RNA site. Arrows indicate three variants that were chosen for further analysis. Amino acid abbreviations are according to IUPAC nomenclature and residue numbering is based on the amino acid position in *E. coli* TadA. A=adenine; I=inosine. ABEmax=codon optimized adenine base editor. miniABEmax=ABEmax without N-terminal wild type TadA domain and the proximal 32AA linker.
Figure 7:
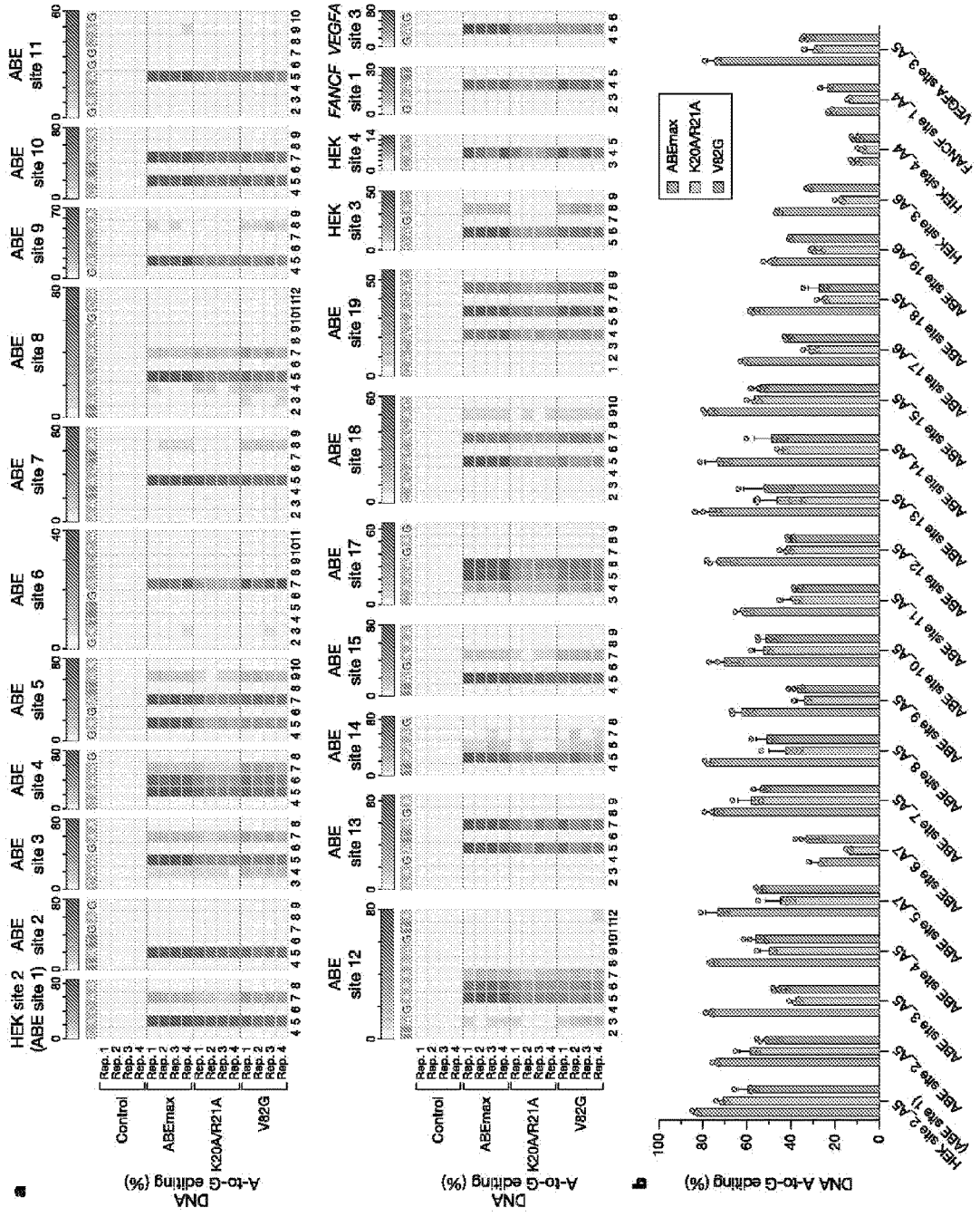
FIG. 7A-B. On-target DNA editing activities of ABEmax, miniABEmax-K20A/R21A, and miniABEmax-V82G in HEK293T cells Heat maps (a) and bar plots (b) showing the on-target DNA A-to-G editing efficiencies of nCas9 (Control), ABEmax, miniABEmax-K20A/R21A, and miniABEmax-V82G with 22 gRNAs (n=4 independent replicates). For (a), editing window shown includes only the most highly edited adenines and not the entire spacer sequence. A-to-G editing efficiencies are shown in heatmap format. Numbering at the bottom represents spacer position with 1 being the most PAM-distal location.

To engineer SECURE-ABE variants, we first used a protein truncation strategy to reduce the RNA recognition capability of the widely used ABEmax fusion. ABEmax harbors a single-chain heterodimer of the wild type (WT) *E. coli* TadA adenosine deaminase monomer (which deaminates adenines on tRNA) fused to an engineered *E. coli* TadA monomer that was modified by directed evolution to deaminate DNA adenines[3,6,7] (FIG. 6a). We hypothesized that the WT TadA monomer should still be capable of recognizing its tRNA substrate and therefore might recruit ABEmax to deaminate RNA adenines that lie in the same or a similar sequence motif to that present in the tRNA. Consistent with this idea, a re-analysis of our previously published RNA-seq data[5] revealed that adenines that are edited at the highest efficiencies (80-100%) are embedded in a more extended CUACGAA motif, which contrasts to the shorter UA sequence observed across all edits (FIG. 6b). Importantly, the CUACGAA motif is a perfect match to the sequence surrounding the adenine deaminated in the tRNA substrate of the WT *E. coli* TadA enzyme[6]. We reasoned that removing the WT TadA domain from ABEmax might reduce its RNA editing activity and we therefore generated a smaller ABEmax variant lacking this domain that we refer to as miniABEmax (FIG. 6a).

Figure 9:
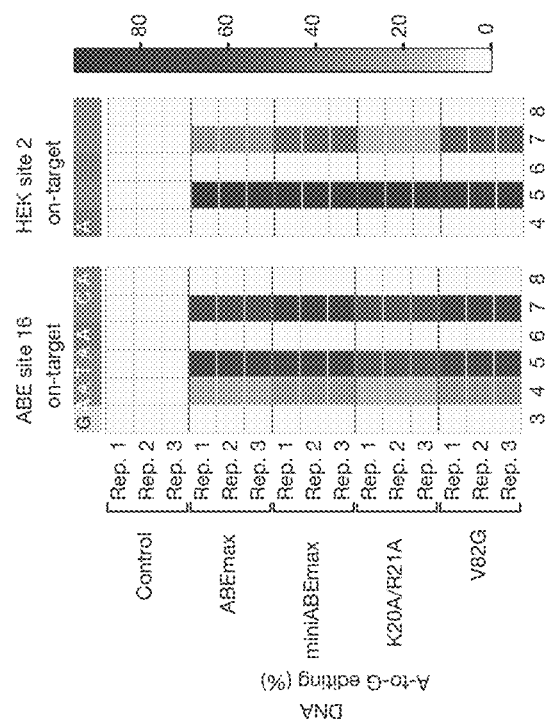
FIG. 9. On-target DNA editing activities of ABEmax, miniABEmax, and SECURE-ABE variants in HEK293T cells Heat maps showing the on-target DNA editing efficiencies of nCas9 (Control), ABEmax, miniABEmax, miniABEmax-K20A/R21A, and miniABEmax-V82G each assessed with two gRNAs targeted to ABE site 16 and HEK site 2 and performed in triplicate. Note that these were performed with the same transfected cells used for the RNA-seq experiments shown in FIGS. 6c and d). Editing windows shown include only the most highly edited adenines and not the entire spacer sequence. Numbering at the bottom represents spacer position with 1 being the most PAM distal location.
Figure 10:
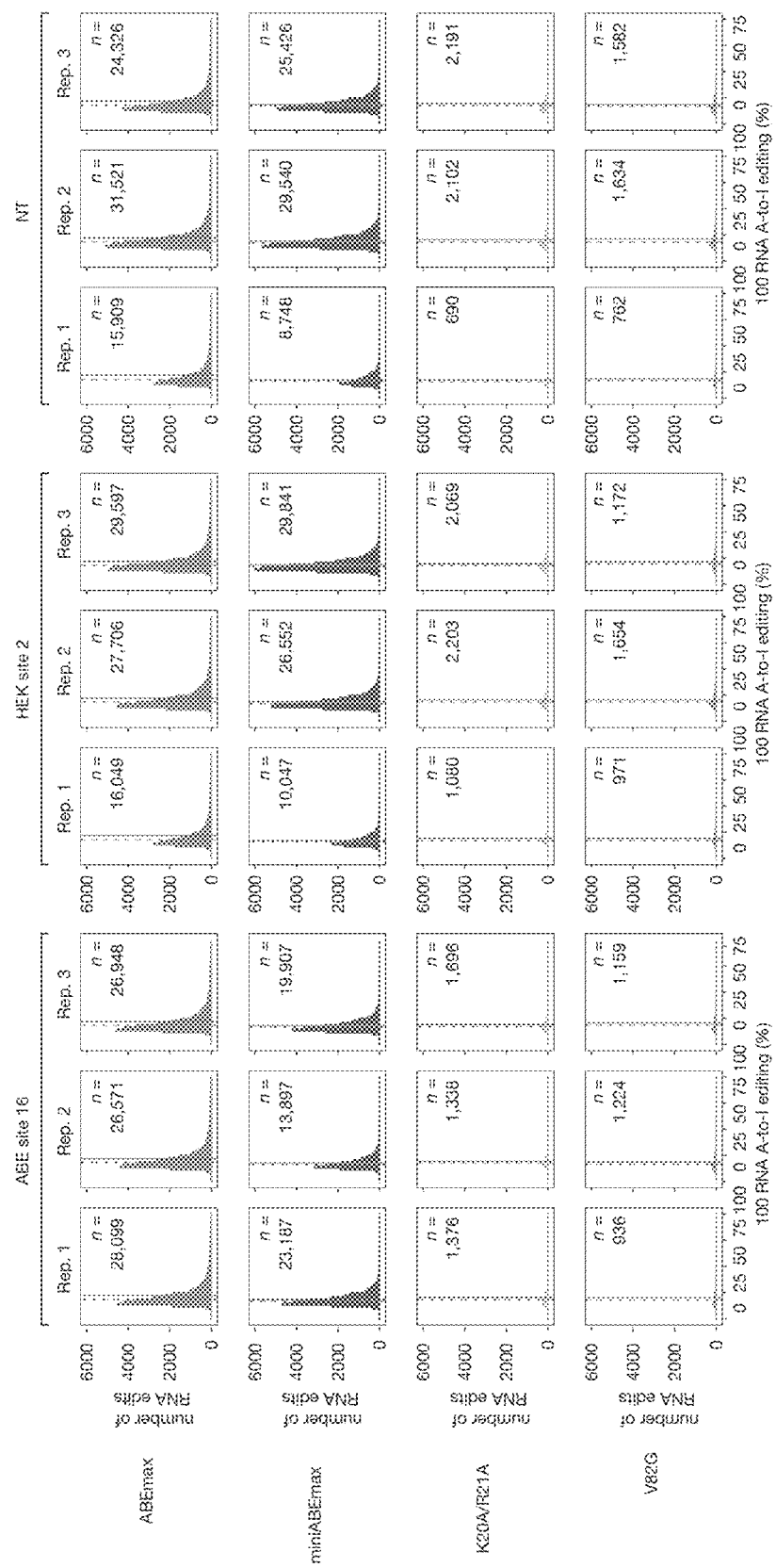
FIG. 10. Additional data on the off-target RNA editing activities of ABEmax, miniABEmax, and SECURE-ABE in HEK293T cells Histograms showing the total number of RNA A-to-I edits observed (y-axis) for different editing efficiencies (x-axis) for ABEmax, miniABEmax, miniABEmax-K20A/R21A, and miniABEmax-V82G each tested with the ABE site 16, HEK site 2, and NT gRNAs. n=number of modified adenines. Experiments were performed in biological triplicate (data is derived from the same experiments as FIGS. 6c and d). Dashed line=median; solid line=mean. Rep.=Replicate.
Figure 11:
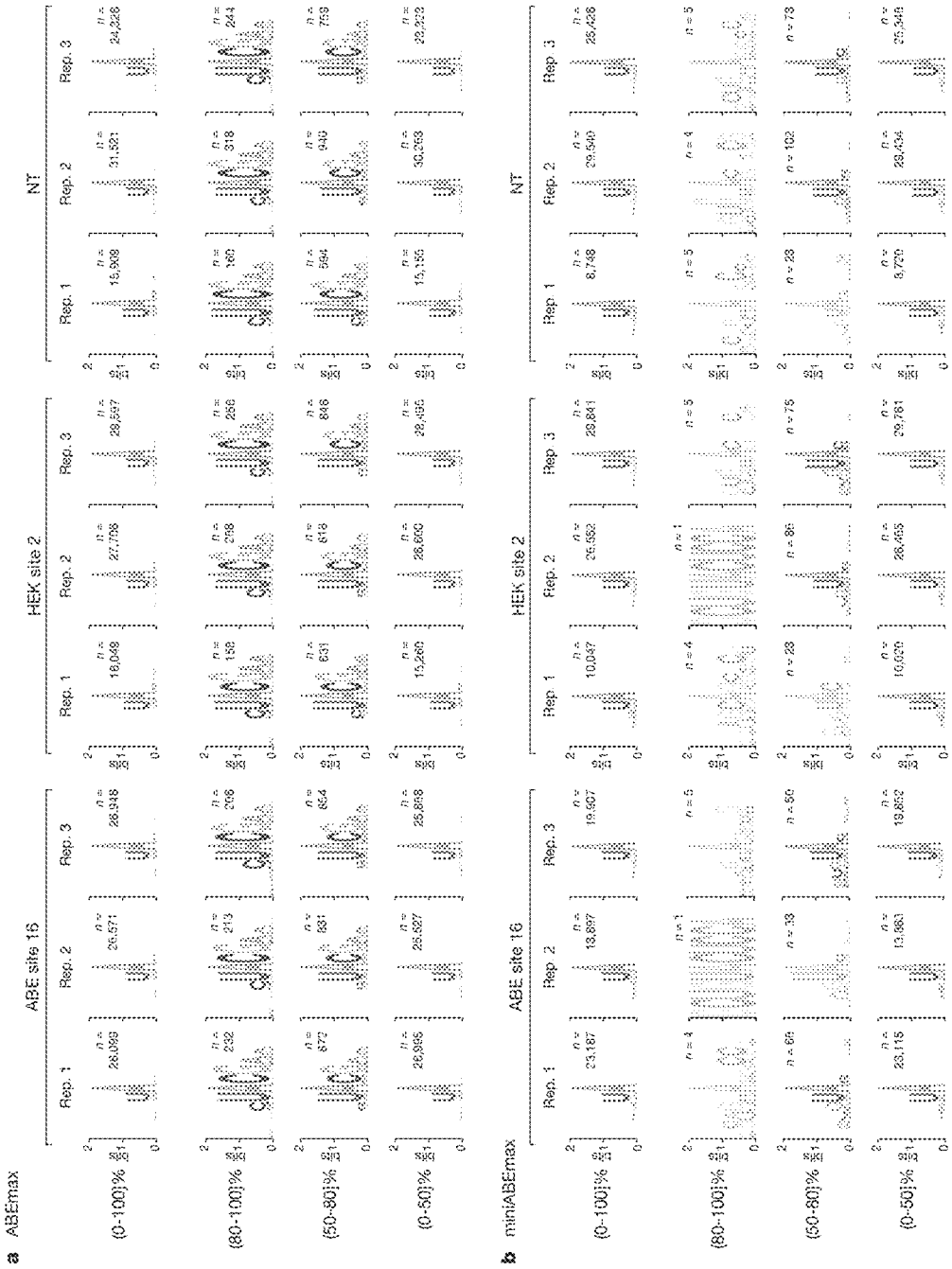
FIG. 11A-B. Sequence logos for RNA adenines edited by ABEmax and miniABEmax in HEK293T cells Sequence logos derived using all RNA-edited adenines (0-100 1% or stratified RNA-edited adenines with high (80-100 1%, middle (50-80 1%, or low (0-50 1% edit efficiencies induced by (a) ABEmax co-expressed with an ABE site 16, HEK site 2 or NT (non-targeting) gRNA or (b) miniABEmax co-expressed with an ABE site 16, HEK site 2, or NT gRNA. Logos are shown for biological triplicates from the same RNA-seq experiments displayed FIGS. 6c and d. n=total number of modified adenines. For strata that contained <25 edited adenines, we considered the motif analysis as not sufficiently powered and therefore presented these logos in a semi-transparent fashion.

We used RNA-seq to compare the transcriptome-wide off-target RNA editing activities of miniABEmax to ABEmax in HEK293T cells. Both editors and a nickase Cas9 (nCas9) control were each assayed in biological triplicate with three different gRNAs: two targeted to endogenous human gene sites (HEK site 2 and ABE site 16)[3] and one to a site that does not occur in the human genome (NT)[5]. We performed these studies by sorting for GFP-positive cells (ABEmax was expressed as a P2A fusion with the base editor or nCas9 (Methods)). As an internal control, we first confirmed that ABEmax and miniABEmax both induced comparable on-target DNA editing efficiencies with HEK site 2 and ABE site 16 gRNAs (FIG. 9). Edited RNA adenines were identified as previously described[5] by filtering out background editing observed with read-count-matched negative controls (Methods). Surprisingly, the total number of edited adenines induced with miniABEmax expression was not consistently lower than what we observed with ABEmax—the two editors induced on average 80-fold and 54-fold more edited adenines relative to background (determined with a GFP-only negative control) (FIG. 6c and Table 1). However, the overall distribution of individual RNA adenine edit efficiencies induced by miniABEmax were generally shifted to lower values (FIG. 6d and FIG. 10). In addition, the sequence logos of the adenines edited by miniABEmax now appear to be shorter GUA or UA motifs, in contrast to the more extended CUACGAA motif characteristic of ABEmax (FIGS. 11a and 11b).

TABLE 1

Summary of numbers of RNA edits observed in all RNA-seq experiments

| FIG. | Cell | BE | gRNA | Sort | Replicate | A-to-I (for ABE) or C-to-U (for CBE) | Other | A-to-I or C-to-U (%) |
|---|---|---|---|---|---|---|---|---|
| FIG. 1b | HEK293T | ABEmax | HEK site 2 | Top 5% | Rep. 1 | 37,061 | 88 | 99.763 |
|  | HEK293T | ABEmax | ABE site 16 | All GFP | Rep. 1 | 28,099 | 197 | 99.304 |
|  |  |  |  |  | Rep. 2 | 26,571 | 238 | 99.112 |
|  |  |  |  |  | Rep. 3 | 26,948 | 238 | 99.125 |
|  |  | miniABEmax | ABE site 16 | All GFP | Rep. 1 | 23,187 | 216 | 99.077 |
|  |  |  |  |  | Rep. 2 | 13,897 | 202 | 98.567 |
|  |  |  |  |  | Rep. 3 | 19,907 | 232 | 98.848 |
|  |  | miniABEmax-K20A/R21A | ABE site 16 | All GFP | Rep. 1 | 1,376 | 292 | 82.494 |
|  |  |  |  |  | Rep. 2 | 1,338 | 291 | 82.136 |
|  |  |  |  |  | Rep. 3 | 1,696 | 295 | 85.183 |
|  |  | miniABEmax-V82G | ABE site 16 | All GFP | Rep. 1 | 936 | 243 | 79.389 |
|  |  |  |  |  | Rep. 2 | 1,224 | 336 | 78.462 |
|  |  |  |  |  | Rep. 3 | 1,159 | 269 | 81.162 |
| FIG. 1c & d | HEK293T | ABEmax | HEK site 2 | All GFP | Rep. 1 | 16,049 | 201 | 98.763 |
|  |  |  |  |  | Rep. 2 | 27,706 | 246 | 99.120 |
|  |  |  |  |  | Rep. 3 | 29,597 | 193 | 99.352 |
|  |  | miniABEmax | HEK site 2 | All GFP | Rep. 1 | 10,047 | 231 | 97.752 |
|  |  |  |  |  | Rep. 2 | 26,552 | 251 | 99.064 |
|  |  |  |  |  | Rep. 3 | 29,841 | 177 | 99.410 |
|  |  | miniABEmax-K20A/R21A | HEK site 2 | All GFP | Rep. 1 | 1,080 | 238 | 81.942 |
|  |  |  |  |  | Rep. 2 | 2,203 | 383 | 85.189 |
|  |  |  |  |  | Rep. 3 | 2,069 | 315 | 86.787 |
|  |  | miniABEmax-V82G | HEK site 2 | All GFP | Rep. 1 | 971 | 216 | 81.803 |
|  |  |  |  |  | Rep. 2 | 1,654 | 333 | 83.241 |
|  |  |  |  |  | Rep. 3 | 1,172 | 276 | 80.939 |
|  | HEK293T | ABEmax | NT | All GFP | Rep. 1 | 15,909 | 202 | 98.746 |
|  |  |  |  |  | Rep. 2 | 31,521 | 229 | 99.279 |
|  |  |  |  |  | Rep. 3 | 24,326 | 196 | 99.201 |
|  |  | miniABEmax | NT | All GFP | Rep. 1 | 8,748 | 379 | 95.847 |
|  |  |  |  |  | Rep. 2 | 29,540 | 244 | 99.181 |
|  |  |  |  |  | Rep. 3 | 25,426 | 261 | 98.984 |
|  |  | miniABEmax-K20A/R21A | NT | All GFP | Rep. 1 | 690 | 206 | 77.009 |
|  |  |  |  |  | Rep. 2 | 2,102 | 325 | 86.609 |
|  |  |  |  |  | Rep. 3 | 2,191 | 265 | 89.210 |
|  |  | miniABEmax-V82G | NT | All GFP | Rep. 1 | 762 | 143 | 84.199 |
|  |  |  |  |  | Rep. 2 | 1,634 | 304 | 84.314 |
|  |  |  |  |  | Rep. 3 | 1,582 | 282 | 84.871 |

TABLE 1-continued

Summary of numbers of RNA edits observed in all RNA-seq experiments

| FIG. | Cell | BE | gRNA | Sort | Replicate | A-to-I (for ABE) or C-to-U (for CBE) | Other | A-to-I or C-to-U (%) |
|---|---|---|---|---|---|---|---|---|
| | HEK293T | GFP | — | All GFP | Rep. 1 | 423 | 202 | 67.680 |
| | | | | | Rep. 2 | 270 | 175 | 60.674 |
| | | | | | Rep. 3 | 363 | 168 | 68.362 |
| FIG. 2b | HEK293T | GFP | — | MFI-matched to top 5% BE3 expression | Rep. 1 | 31 | 131 | 19.136 |
| | | hA3A-BE3 | RNF2 | Top 5% | Rep. 1 | 30,435 | 8 | 99.974 |
| | | | | | Rep. 2 | 27,190 | 8 | 99.971 |
| | | | | | Rep. 3 | 32,402 | 11 | 99.966 |
| | | eA3A-BE3 | RNF2 | Top 5% | Rep. 1 | 98 | 101 | 49.246 |
| | | | | | Rep. 2 | 72 | 87 | 45.283 |
| | | | | | Rep. 3 | 113 | 78 | 59.162 |
| | | hAID-BE3 | RNF2 | Top 5% | Rep. 1 | 45 | 201 | 18.293 |
| | | | | | Rep. 2 | 34 | 144 | 19.101 |
| | | | | | Rep. 3 | 70 | 234 | 23.026 |

Figure 12:
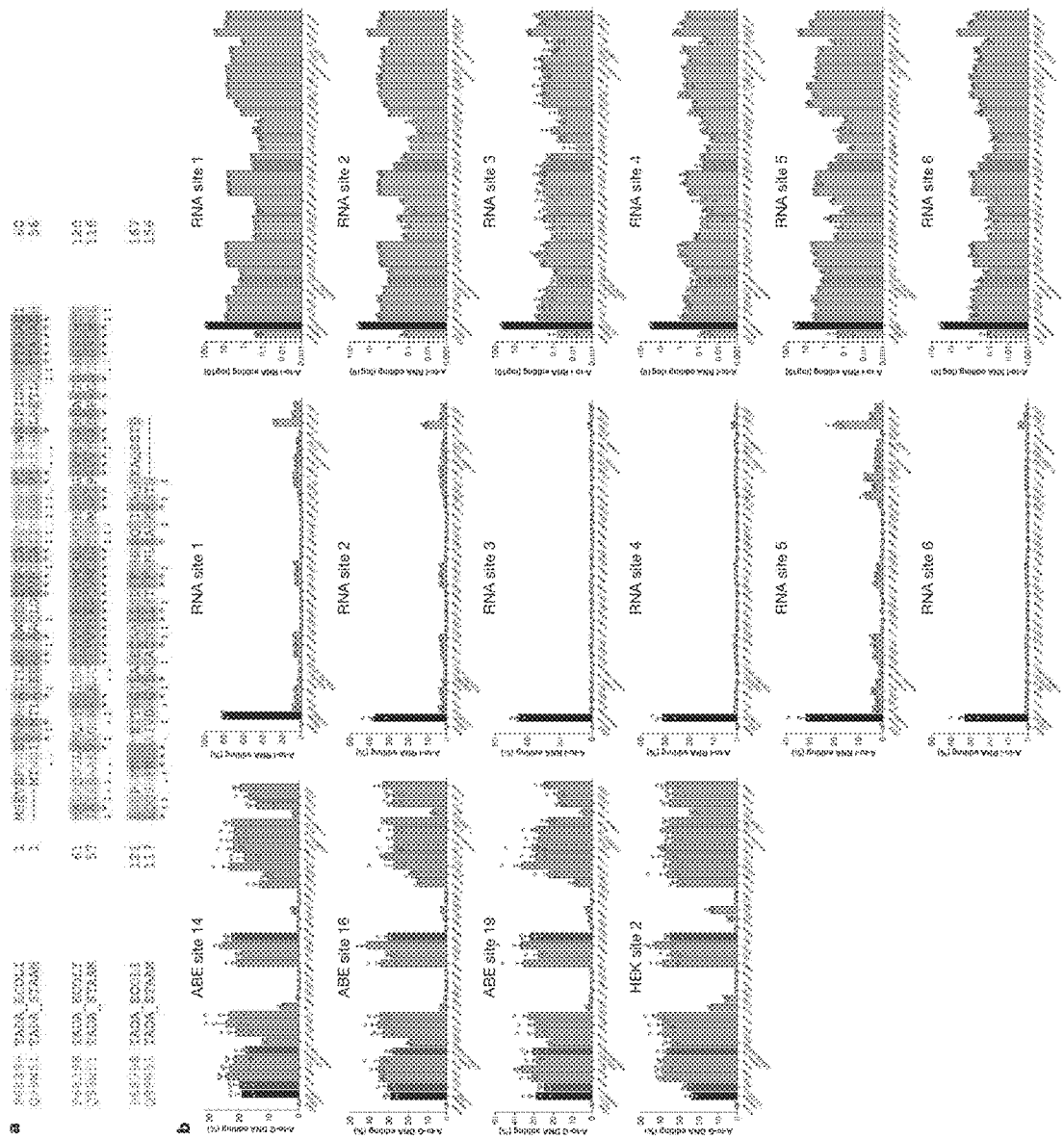
FIG. 12A-B. Engineering of miniABEmax variants with reduced off-target RNA adenine editing activities and preserved on-target DNA editing activities (a) Alignment of E. coli and S. aureus TadA amino acid sequences (SEQ ID NOS 1-2, respectively, in order of appearance) showing 39.5% identity (Uniprot alignment function). Stars represent 66 identical residues, dots and colons represent 54 residues of lower and higher similarity. Negative charges highlighted in red, positive charges highlighted in green. (b) Bar graphs of the data shown in FIG. 6f. On-target DNA editing (left bar graphs) and off-target RNA editing (right bar graphs) efficiencies observed with negative control, ABEmax, miniABEmax, and 34 miniABEmax variants are shown for four on-target DNA sites (left panel, linear y-axis scale) and six RNA adenines previously shown to be edited by ABEmax (middle panel with linear y-axis scale and right panel with log 10 y-axis scale). Means of four replicates are shown with individual quadruplicate biological replicate values (n=4) overlaid as dots and error bars representing S.E.M. A=adenine; G=guanine; I=inosine.

We reasoned we might further reduce the off-target RNA editing activity of miniABEmax by altering amino acid residues within the remaining engineered *E. coli* TadA domain that could potentially mediate RNA recognition. However, although a crystal structure of isolated *E. coli* TadA has previously been solved 8 (PDB 1Z3A; FIG. 6e), no structural information was available to delineate how this protein might recognize its RNA substrate. To overcome this, we exploited the availability of a *S. aureus* TadA-tRNA co-crystal structures (PDB 2B3J) (FIG. 6e and Methods). Although *E. coli* and *S. aureus* TadA share only partial amino acid sequence homology (39.5% identity; FIG. 12a), we found, that these two proteins share a high degree of structural homology (FIG. 6e). This similarity enabled us to overlay the two structures and thereby to infer 31 amino acid residues in *E. coli* TadA that likely lie near the enzymatic pocket around the substrate tRNA (FIG. 6e). In addition, we mutated three positively charged residues (R13, K20, and R21) in TadA* that we imagined might make contacts to the phosphate backbone of an RNA substrate.

We generated a total of 34 miniABEmax variants bearing various substitutions at the amino acid positions described above and screened each editor for on-target DNA editing and off-target RNA editing activities in HEK293T cells. To assess on-target DNA editing, we examined the efficiencies of A-to-G edits induced by each of the 34 variants with four gRNAs targeted to different endogenous gene sequences. To screen for off-target RNA editing activities, we quantified editing by each of the 34 variants at six RNA adenines using standard plasmid expression conditions (i.e., without sorting for GFP expression; see Methods); these six adenines were previously identified as being highly edited with ABEmax overexpression in HEK293T cells[5]. These experiments revealed that 23 of the 34 variants induced robust on-target DNA editing at least comparable to that observed with miniABEmax and ABEmax (FIG. 6f and FIG. 12b). In addition, 14 of the 34 variants showed reduced editing activities on at least three of the six RNA adenines we examined relative to that observed with miniABEmax (FIG. 6f, FIG. 12b). Importantly, three of the 34 variants (miniABEmax-K20A/R21A, -K20A/R21A/R23A, and -V82G) showed both robust on-target DNA editing activity and substantially reduced RNA editing activities (FIG. 6f and FIG. 12b and Table 2). Based on their DNA/RNA editing ratios, we chose to carry forward two miniABEmax variants (K20A/R21A and V82G) for more comprehensive characterization.

TABLE 2

Statistical tests for data on miniABEmax variant activities

| DNA | ABEmax vs miniABEmax | ABEmax vs K20A/R21A | ABEmax vs V82G | miniABEmax vs K20A/R21A | miniABEmax vs V82G |
|---|---|---|---|---|---|
| ABE site14 | 0.78601 | 0.69378 | 0.23183 | 0.45035 | 0.29956 |
| ABE site16 | 0.58244 | 0.65370 | 0.62989 | 0.32954 | 0.90884 |
| ABE site19 | 0.27139 | 0.67921 | 0.45482 | 0.11499 | 0.05184 |
| HEK site2 | 0.16276 | 0.00461 | 0.00737 | 0.01031 | 0.01829 |

| RNA | ABEmax vs miniABEmax | nCas9 Control vs miniABEmax | ABEmax vs K20A/R21A | ABEmax vs V82G | miniABEmax vs K20A/R21A | miniABEmax vs V82G |
|---|---|---|---|---|---|---|
| RNA site1 | 0.00001 | 0.00003 | 0.00001 | 0.00001 | 0.00002 | 0.00004 |
| RNA site2 | 0.00067 | 0.00215 | 0.00064 | 0.00061 | 0.00523 | 0.00215 |
| RNA site3 | 0.00011 | 0.01602 | 0.00011 | 0.00011 | 0.01714 | 0.19767 |
| RNA site4 | 0.00063 | 0.00891 | 0.00061 | 0.00060 | 0.00865 | 0.00824 |
| RNA site5 | 0.00287 | 0.00115 | 0.00253 | 0.00239 | 0.00746 | 0.00419 |
| RNA site6 | 0.00162 | 0.01755 | 0.00178 | 0.00178 | 0.06036 | 0.05016 | p-values generated with two-tailed t-test (type 3)

We characterized the transcriptome-wide off-target RNA editing profiles of the miniABEmax K20A/R21A and V82G variants using RNA-seq. The two variants were assessed in biological triplicate with the HEK site 2, ABE site 16, and NT gRNAs. In contrast to what we observed with miniABEmax, the K20A/R21A and V82G variants both induced substantially reduced numbers of edited adenines relative to ABEmax but still approximately four-fold and three-fold higher numbers, respectively, than background (determined with the GFP-only negative control) (FIG. 6c). In addition, the distribution of individual RNA adenine editing efficiencies for the two variants was shifted lower with both variants relative to ABEmax and miniABEmax (FIG. 6d and FIG. 10). Overall, these results demonstrate the feasibility of separating unwanted off-target RNA editing from desired on-target DNA editing activities with an ABE.

Figure 8:
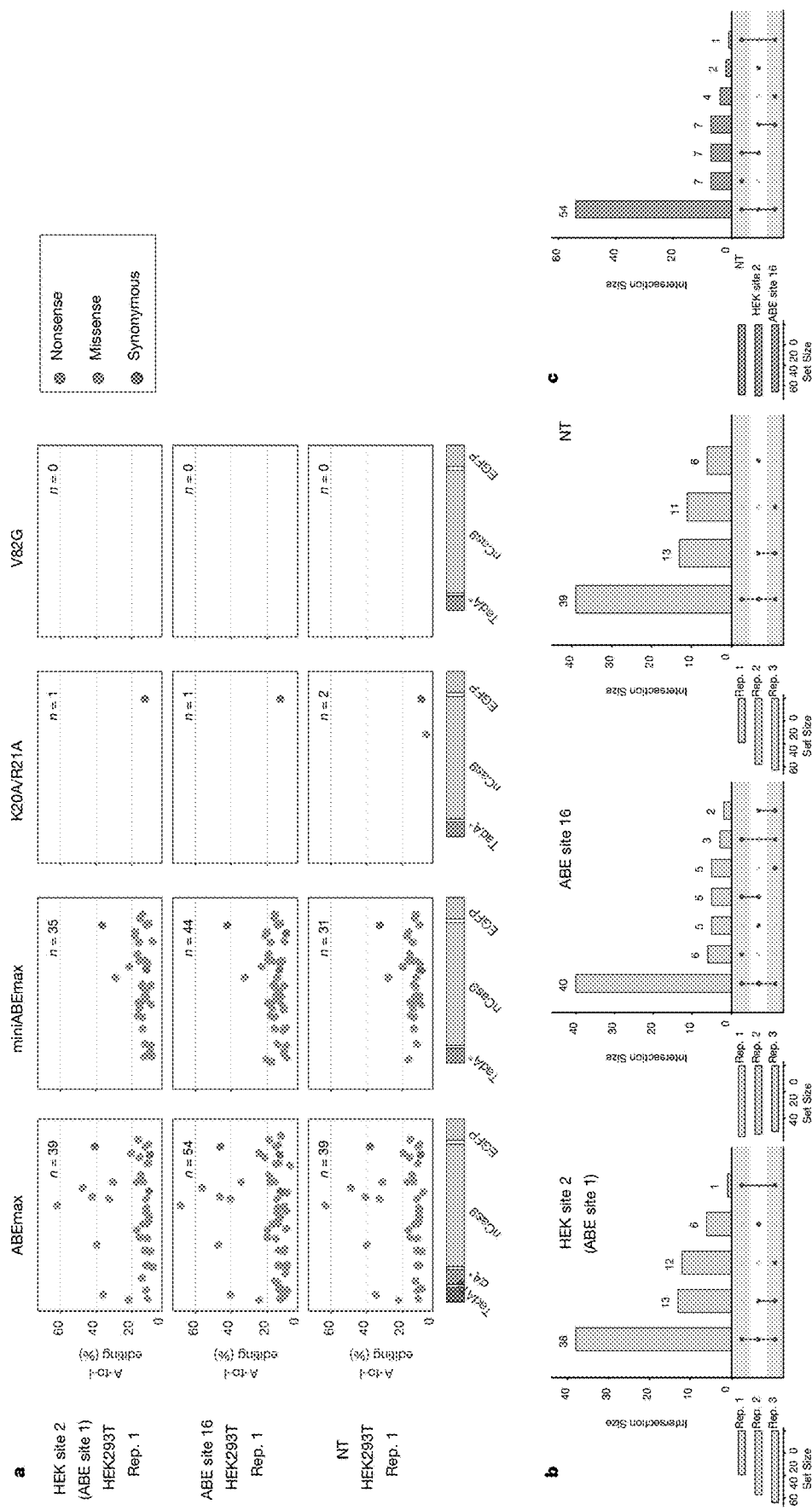
FIG. 8A-C. Self-editing generates a diverse range of heterogeneously edited ABE transcript sequences in HEK293T cells (a) Scatterplots showing A-to-I self-editing induced by expression of ABEmax, miniABEmax, miniABEmax-K20A/R21A, and miniABEmax-V82G (sorted for all GFP-positive cells) with gRNAs targeting HEK site 2, ABE site 16, and a non-targeting gRNA (NT) in HEK293T cells. Each dot represents an edited A and the color of the dot indicates the predicted type of mutation caused by a A-to-I edit at that position. The y-axis shows editing efficiencies for each A-to-I modification and the x-axis represents the position of each A within the ABE coding sequence (with the architecture of the editor shown schematically below but not displaying the NLS and linkers). n=total number of modified As. (b) UpSet plots showing the intersections of RNA A-to-I self-edits induced by ABEmax on its own transcript across three replicates. Each plot shows data from co-expression of ABEmax with one of three different gRNAs. (c) UpSet plots showing the intersection of RNA A-to-I self-edits induced by ABEmax across three different gRNAs. For each gRNA, we used A-to-I edits that represent the union of all such edits across the three replicates.
Figure 13:
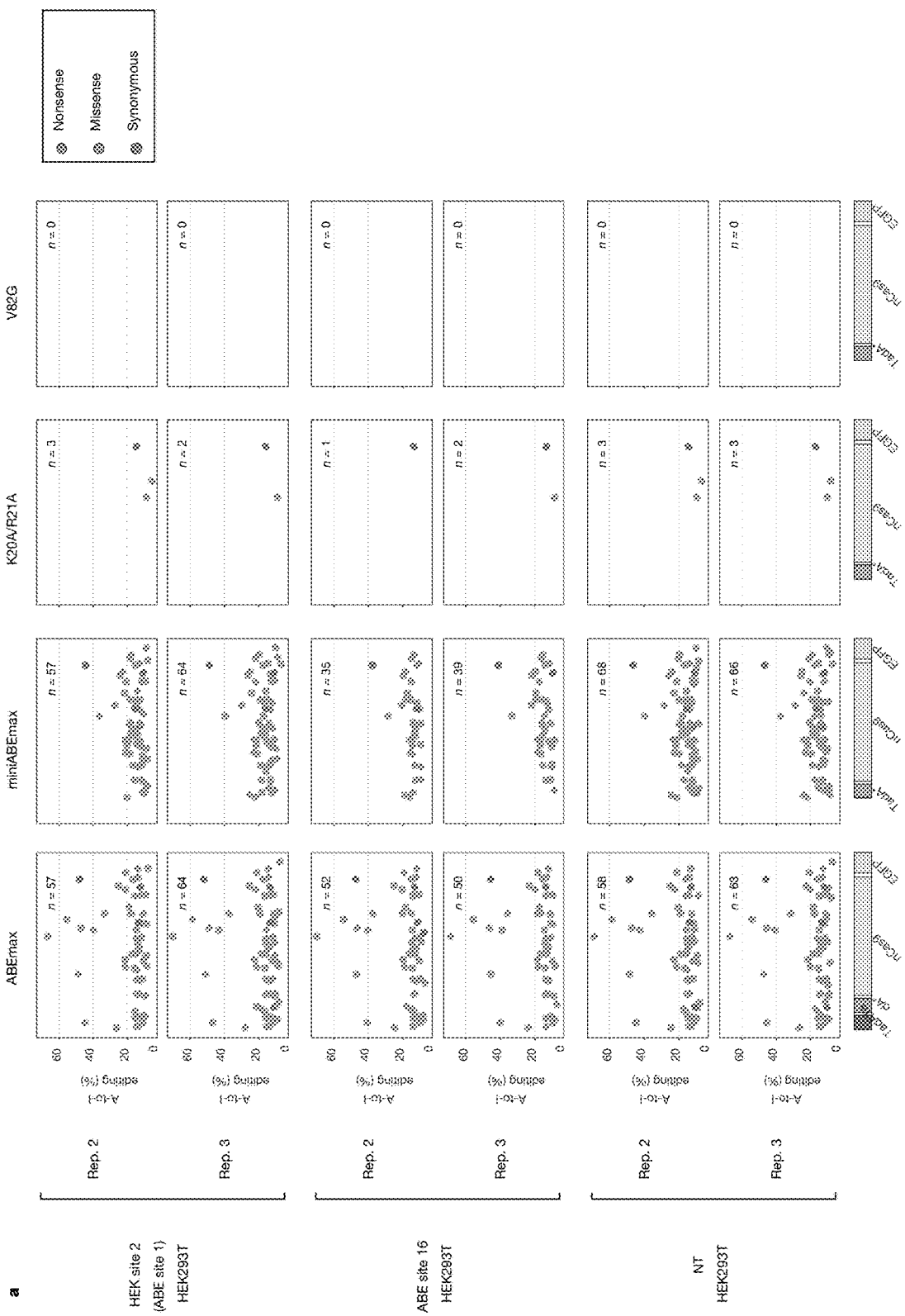
Figure 14:
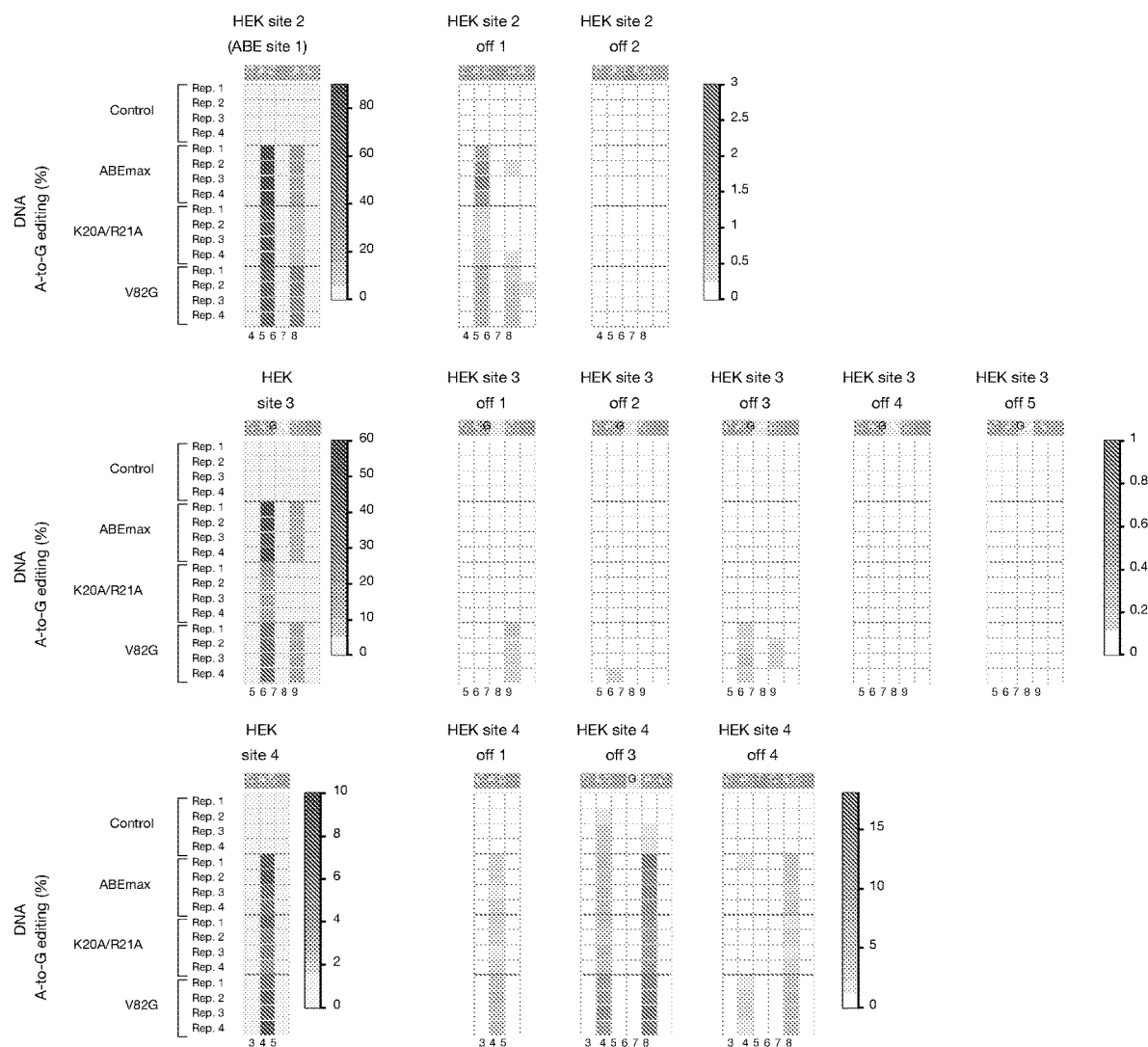
FIG. 14. DNA off-target activities of ABEmax, miniABEmax-K20A/R21A, and miniABEmax-V82G in HEK293T cells Heat maps showing A-to-G DNA on-target (left) and A-to-G DNA off-target (right) editing efficiencies of nCas9 (Control), ABEmax, miniABEmax-K20A/R21A, and miniABEmax-V82G each co-expressed with HEK site 2, HEK site 3, or HEK site 4 gRNAs (n=4 independent replicates). Editing windows shown include the most highly edited adenines. Numbering at the bottom represents spacer position with 1 being the most PAM-distal location.
Figure 15B:
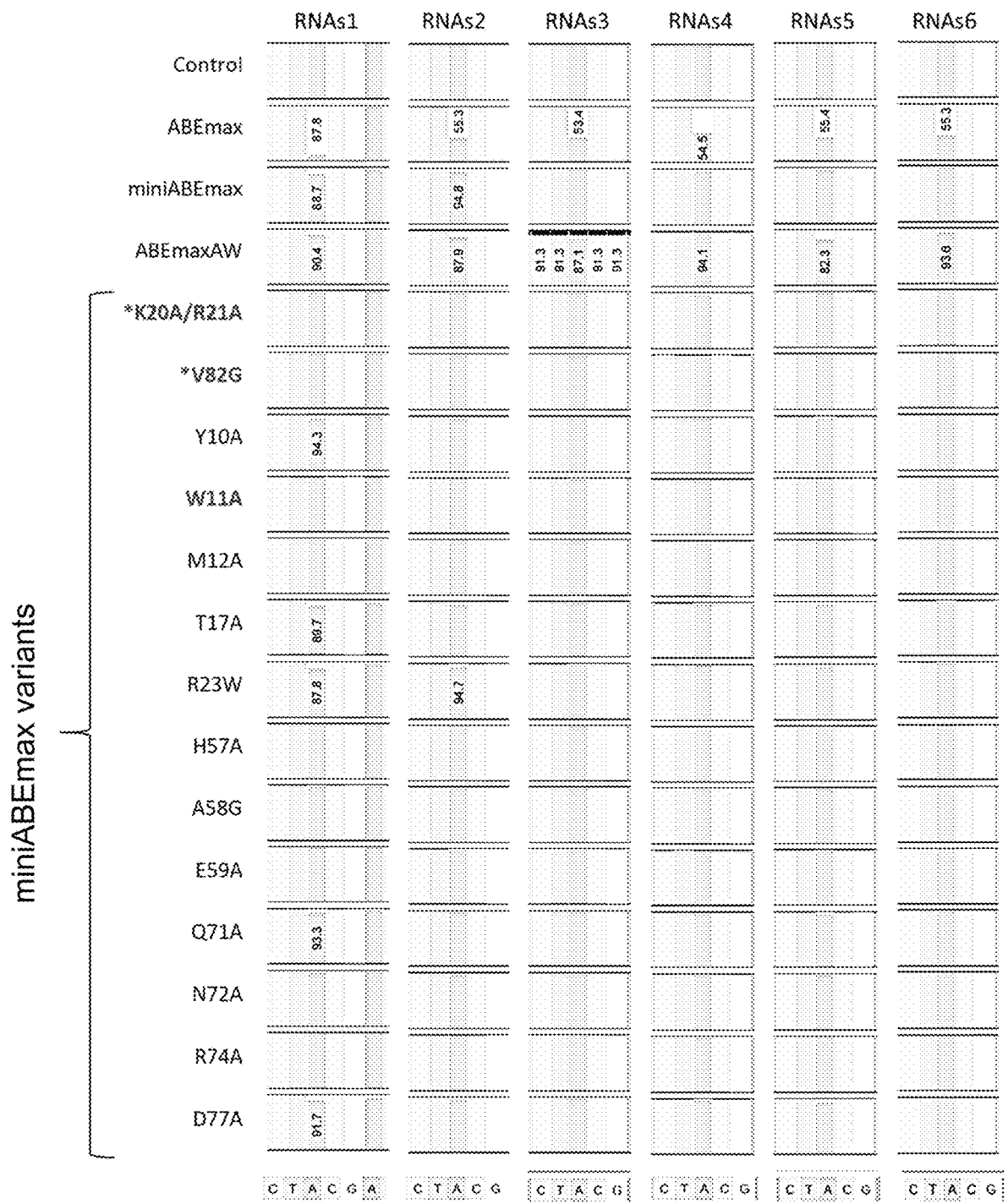
Figure 15D:
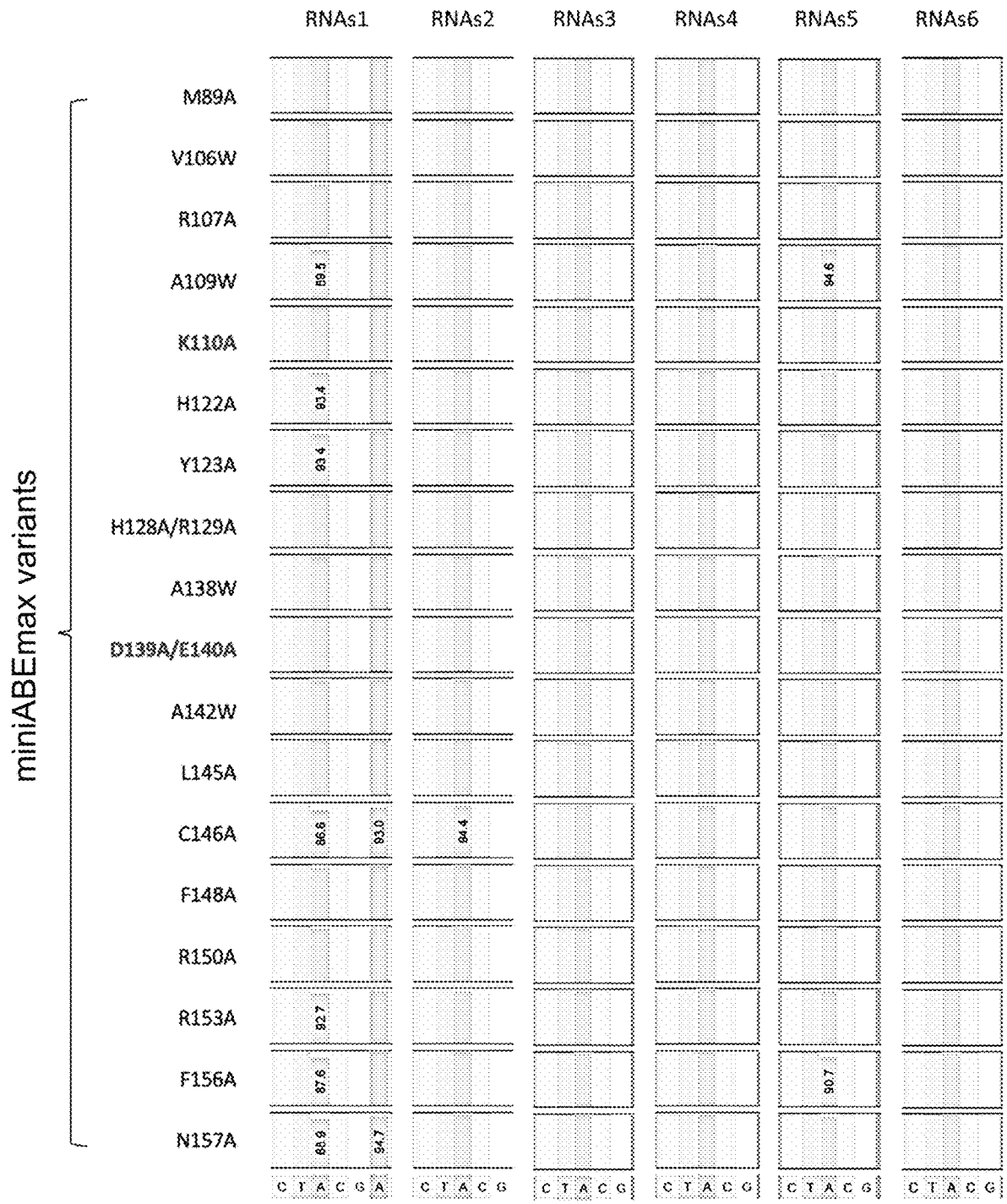

Finally, given their abilities to edit RNA transcripts, we wondered whether ABEs might also self-edit their own transcripts, thereby potentially generating a set of heterogeneous base editor proteins. To assess this, we applied our analysis pipeline to quantify self-edit events in our previously published RNA-seq data 5 obtained with BE3 expressed at standard or overexpression levels in HEK293T cells. These data showed ABEmax and miniABEmax both inducing dozens (29 to 67) of A-to-I changes throughout their own transcripts with editing efficiencies ranging from 7.3% to 58.7% among replicates performed with three different gRNAs (FIG. 8a; FIG. 13; Table 3). Nearly all of the edits induced by the ABEs may induce missense mutations (Table 3). On average, 53% of adenines self-edited by ABEmax appeared to be edited across all three replicates (FIG. 8c). Comparing the unions of self-edits from different gRNAs shows 68% of overlap between edits across the three gRNAs, suggesting that self-editing is independent of the gRNA with which the ABE was co-expressed (FIG. 8). Notably, the two miniABEmax variants showed substantially reduced self-editing activities: K20A/R21A induced only small numbers (range 1 to 3) of self-edits and V82G did not induce any detectable self-edits (FIG. 3d; FIG. 13; Table 3).

TABLE 3

Numbers of RNA self-edit alterations by CBEs and ABEs expected to generate synonymous, missense, and nonsense mutations

| Cell | BE | gRNA | Sort | Replicate | Nonsense | Missense | Synonymous | Total |
|---|---|---|---|---|---|---|---|---|
| HEK293T | WT BE3 | RNF2 | All GFP | Rep. 1 | 11 | 48 | 70 | 129 |
| | | | | Rep. 2 | 8 | 27 | 51 | 86 |
| | | | | Rep. 3 | 10 | 40 | 56 | 106 |
| | WT BE3 | EMX1 | All GFP | Rep. 1 | 6 | 36 | 55 | 97 |
| | | | | Rep. 2 | 9 | 31 | 45 | 85 |
| | | | | Rep. 3 | 6 | 32 | 51 | 89 |
| HEK293T | WT BE3 | RNF2 | Top 5% | Rep. 1 | 14 | 57 | 80 | 151 |
| | | | | Rep. 2 | 15 | 73 | 95 | 183 |
| | | | | Rep. 3 | 15 | 62 | 79 | 156 |
| | BE3-R33A | RNF2 | Top 5% | Rep. 1 | 0 | 0 | 0 | 0 |
| | | | | Rep. 2 | 0 | 0 | 0 | 0 |
| | | | | Rep. 3 | 0 | 0 | 0 | 0 |
| | BE3-R33A/K34A | RNF2 | Top 5% | Rep. 1 | 0 | 0 | 0 | 0 |
| | | | | Rep. 2 | 0 | 0 | 0 | 0 |
| | | | | Rep. 3 | 0 | 0 | 0 | 0 |
| HepG2 | WT BE3 | RNF2 | Top 5% | Rep. 1 | 10 | 38 | 66 | 114 |
| | | | | Rep. 2 | 10 | 37 | 55 | 102 |
| | | | | Rep. 3 | 9 | 48 | 61 | 118 |
| | BE3-R33A | RNF2 | Top 5% | Rep. 1 | 0 | 0 | 0 | 0 |
| | | | | Rep. 2 | 0 | 0 | 0 | 0 |
| | | | | Rep. 3 | 0 | 0 | 0 | 0 |
| | BE3-R33A/K34A | RNF2 | Top 5% | Rep. 1 | 0 | 0 | 0 | 0 |
| | | | | Rep. 2 | 0 | 0 | 0 | 0 |
| | | | | Rep. 3 | 0 | 0 | 0 | 0 |
| HEK293T | hA3A-BE3 | RNF2 | Top 5% | Rep. 1 | 6 | 7 | 16 | 29 |
| | | | | Rep. 2 | 6 | 7 | 15 | 28 |
| | | | | Rep. 3 | 6 | 8 | 17 | 31 |
| | eA3A-BE3 | RNF2 | Top 5% | Rep. 1 | 0 | 0 | 0 | 0 |
| | | | | Rep. 2 | 0 | 0 | 0 | 0 |
| | | | | Rep. 3 | 0 | 0 | 0 | 0 |
| HEK293T | ABEmax | ABE site 16 | All GFP | Rep. 1 | — | 41 | 0 | 41 |
| | | | | Rep. 2 | — | 38 | 0 | 38 |
| | | | | Rep. 3 | — | 39 | 0 | 39 |
| | miniABEmax | ABE site 16 | All GFP | Rep. 1 | — | 43 | 1 | 44 |
| | | | | Rep. 2 | — | 33 | 1 | 34 |
| | | | | Rep. 3 | — | 39 | 1 | 40 |
| | miniABEmax-K20A/R21A | ABE site 16 | All GFP | Rep. 1 | — | 0 | 1 | 1 |
| | | | | Rep. 2 | — | 0 | 1 | 1 |
| | | | | Rep. 3 | — | 1 | 1 | 2 |
| | miniABEmax-V82G | ABE site 16 | All GFP | Rep. 1 | — | 0 | 0 | 0 |
| | | | | Rep. 2 | — | 0 | 0 | 0 |
| | | | | Rep. 3 | — | 0 | 0 | 0 |
| HEK293T | ABEmax | HEK site 2 | All GFP | Rep. 1 | — | 30 | 0 | 30 |
| | | | | Rep. 2 | — | 45 | 0 | 45 |
| | | | | Rep. 3 | — | 47 | 0 | 47 |
| | miniABEmax | HEK site 2 | All GFP | Rep. 1 | — | 35 | 1 | 36 |
| | | | | Rep. 2 | — | 57 | 1 | 58 |
| | | | | Rep. 3 | — | 63 | 1 | 64 |
| | miniABEmax-K20A/R21A | HEK site 2 | All GFP | Rep. 1 | — | 0 | 1 | 1 |
| | | | | Rep. 2 | — | 2 | 1 | 3 |
| | | | | Rep. 3 | — | 1 | 1 | 2 |

TABLE 3-continued

Numbers of RNA self-edit alterations by CBEs and ABEs expected to generate synonymous, missense, and nonsense mutations

| Cell | BE | gRNA | Sort | Replicate | Nonsense | Missense | Synonymous | Total |
|---|---|---|---|---|---|---|---|---|
| | miniABEmax-V82G | HEK site 2 | All GFP | Rep. 1 | — | 0 | 0 | 0 |
| | | | | Rep. 2 | — | 0 | 0 | 0 |
| | | | | Rep. 3 | — | 0 | 0 | 0 |
| HEK293T | ABEmax | NT | All GFP | Rep. 1 | — | 29 | 0 | 29 |
| | | | | Rep. 2 | — | 42 | 0 | 42 |
| | | | | Rep. 3 | — | 48 | 0 | 48 |
| | miniABEmax | NT | All GFP | Rep. 1 | — | 30 | 1 | 31 |
| | | | | Rep. 2 | — | 66 | 1 | 67 |
| | | | | Rep. 3 | — | 65 | 1 | 66 |
| | miniABEmax-K20A/R21A | NT | All GFP | Rep. 1 | — | 1 | 1 | 2 |
| | | | | Rep. 2 | — | 2 | 1 | 3 |
| | | | | Rep. 3 | — | 2 | 1 | 3 |
| | miniABEmax-V82G | NT | All GFP | Rep. 1 | — | 0 | 0 | 0 |
| | | | | Rep. 2 | — | 0 | 0 | 0 |
| | | | | Rep. 3 | — | 0 | 0 | 0 |

Example 4: Additional SECURE-ABE Variants

To screen for additional SECURE-ABE variants with minimized unwanted RNA editing activities that maintain efficient DNA on-target editing, we engineered 30 more miniABEmax variants and assessed their DNA and RNA editing efficiencies. In this second screen, we included two SECURE-ABE variants (miniABEmax-K20A/R21A and -V82G) with reduce RNA off-target editing. DNA on-target editing was examined with four gRNAs targeted to different endogenous gene sequences (HEK site 2, ABE site 2, site 3 and site 4), and 25 out of 30 variants induced DNA editing comparable to that observed with miniABEmax and ABEmax. RNA off-target editing was examined on six RNA sites that were previously identified to be highly edited with ABEmax and were used for first round of screening, and 24 out of 30 variants showed reduced RNA editing compared to miniABEmax on all 6 sites tested. Based on both DNA and RNA editing profiles (see FIGS. 16A-B), miniABEmax-W11A, -K110A, and -D139A/E140A showed the most promising characteristics to become SECURE-ABE variants, while A58G, N72A, V106W, K110A, H128A/R129A, A138W, D139A/E140A, A142W, F148A, and R150A all showed promising reductions of RNA off-targets as well, with reasonably maintained DNA on-target editing capabilities.

REFERENCES

1 Rees, H. A. & Liu, D. R. Base editing: precision chemistry on the genome and transcriptome of living cells. Nat Rev Genet 19, 770-788, doi:10.1038/s41576-018-0059-1 (2018).
2 Komor, A. C., Kim, Y. B., Packer, M. S., Zuris, J. A. & Liu, D. R. Programmable editing of a target base in genomic DNA without double-stranded DNA cleavage. Nature 533, 420-424, doi:10.1038/nature17946 (2016).
3 Gaudelli, N. M. et al. Programmable base editing of A*T to G*C in genomic DNA without DNA cleavage. Nature 551, 464-471, doi:10.1038/nature24644 (2017).
4 Nishida, K. et al. Targeted nucleotide editing using hybrid prokaryotic and vertebrate adaptive immune systems. Science 353, doi:10.1126/science.aaf8729 (2016).
5 Grunewald, J. et al. Transcriptome-wide off-target RNA editing induced by CRISPR-guided DNA base editors. Nature, doi:10.1038/s41586-019-1161-z (2019).
6 Wolf, J., Gerber, A. P. & Keller, W. tadA, an essential tRNA-specific adenosine deaminase from Escherichia coli. EMBO J 21, 3841-3851, doi:10.1093/emboj/cdf362 (2002).
7 Koblan, L. W. et al. Improving cytidine and adenine base editors by expression optimization and ancestral reconstruction. Nat Biotechnol 36, 843-846, doi:10.1038/nbt.4172 (2018).
8 Kim, J. et al. Structural and kinetic characterization of Escherichia coli TadA, the wobble-specific tRNA deaminase. Biochemistry 45, 6407-6416, doi:10.1021/bi0522394 (2006).
9 Losey, H. C., Ruthenburg, A. J. & Verdine, G. L. Crystal structure of Staphylococcus aureus tRNA adenosine deaminase TadA in complex with RNA. Nat Struct Mol Biol 13, 153-159, doi:10.1038/nsmb1047 (2006).
10 Wang, X. et al. Efficient base editing in methylated regions with a human APOBEC3A-Cas9 fusion. Nat Biotechnol, doi:10.1038/nbt.4198 (2018).
11 Gehrke, J. M. et al. An APOBEC3A-Cas9 base editor with minimized bystander and off-target activities. Nat Biotechnol 36, 977-982, doi:10.1038/nbt.4199 (2018).
12 Komor, A. C. et al. Improved base excision repair inhibition and bacteriophage Mu Gam protein yields C:G-to-T:A base editors with higher efficiency and product purity. Sci Adv 3, eaao4774, doi:10.1126/sciadv.aao4774 (2017).
13 Sharma, S., Patnaik, S. K., Kemer, Z. & Baysal, B. E. Transient overexpression of exogenous APOBEC3A causes C-to-U RNA editing of thousands of genes. RNA Biol 14, 603-610, doi:10.1080/15476286.2016.1184387 (2017).
14 Fritz, E. L. et al. A comprehensive analysis of the effects of the deaminase AID on the transcriptome and methylome of activated B cells. Nat Immunol 14, 749-755, doi:10.1038/ni.2616 (2013).
15 Laird, P. W. et al. Simplified mammalian DNA isolation procedure. Nucleic Acids Res 19, 4293 (1991).
16 Rohland, N. & Reich, D. Cost-effective, high-throughput DNA sequencing libraries for multiplexed target capture. Genome Res 22, 939-946, doi:10.1101/gr.128124.111 (2012).

17 Clement, K. et al. CRISPResso2 provides accurate and rapid genome editing sequence analysis. *Nat Biotechnol* 37, 224-226, doi:10.1038/s41587-019-0032-3 (2019).
18 McKenna, A. et al. The Genome Analysis Toolkit: a MapReduce framework for analyzing next-generation DNA sequencing data. *Genome Res* 20, 1297-1303, doi: 10.1101/gr.107524.110 (2010).
19 DePristo, M. A. et al. A framework for variation discovery and genotyping using next-generation DNA sequencing data. *Nat Genet* 43, 491-498, doi:10.1038/ng.806 (2011).
20 Dobin, A. et al. STAR: ultrafast universal RNA-seq aligner. *Bioinformatics* 29, 15-21, doi:10.1093/bioinformatics/bts635 (2013).

```
SEQUENCES LISTINGS
E. coli TadA,
                                                                SEQ ID: 1
MSEVEFSHEYWMRHALTLAKRAWDEREVPVGAVLVHNNRVIGEGWNRPIGRHDPTAHAEIMA

LRQGGLVMQNYRLIDATLYVTLEPCVMCAGAMIHSRIGRVVFGARDAKTGAAGSLMDVLHHPG

MNHRVEITEGILADECAALLSDFFRMRRQEIKAQKKAQSSTD

S. aureus TadA,
                                                                SEQ ID: 2
MTNDIYFMTLAIEEAKKAAQLGEVPIGAIITKDDEVIARAHNLRETLQQPTAHAEHIAIERAAKVLG

SWRLEGCTLYVTLEPCVMCAGTIVMSRIPRVVYGADDPKGGCSGSLMNLLQQSNFNHRAIVDK

GVLKEACSTLLTTFFKNLRANKKSTN

S. pyogenes TadA,
                                                                SEQ ID: 3
MPYSLEEQTYFMQEALKEAEKSLQKAEIPIGCVIVKDGEIIGRGHNAREESNQAIMHAEMMAINE

ANAHEGNWRLLDTTLFVTIEPCVMCSGAIGLARIPHVIYGASNQKFGGADSLYQILTDERLNHRV

QVERGLLAADCANIMQTFFRQGRERKKIAKHLIKEQSDPFD

S. typhi TadA,
                                                                SEQ ID: 4
MSDVELDHEYWMRHALTLAKRAWDEREVPVGAVLVHNHRVIGEGWNRPIGRHDPTAHAEIMA

LRQGGLVLQNYRLLDTTLYVTLEPCVMCAGAMVHSRIGRVVFGARDAKTGAAGSLIDVLHHPG

MNHRVEIIEGVLRDECATLLSDFFRMRRQEIKALKKADRAEGAGPAV

A. aeolicus TadA,
                                                                SEQ ID: 5
MGKEYFLKVALREAKRAFEKGEVPVGAIIVKEGEIISKAHNSVEELKDPTAHAEMLAIKEACRRL

NTKYLEGCELYVTLEPCIMCSYALVLSRIEKVIFSALDKKHGGVVSVFNILDEPTLNHRVKWEYY

PLEEASELLSEFFKKLRNNII

S. pombe TAD2,
                                                                SEQ ID: 6
MAGDSVKSAIIGIAGGPFSGKTQLCEQLLERLKSSAPSTFSKLIHLTSFLYPNSVDRYALSSYDIE

AFKKVLSLISQGAEKICLPDGSCIKLPVDQNRIILIEGYYLLLPELLPYYTSKIFVYEDADTRLERCV

LQRVKAEKGDLTKVLNDFVTLSKPAYDSSIHPTRENADIILPQKENIDTALLFVSQHLQDILAEMN

KTSSSNTVKYDTQHETYMKLAHEILNLGPYFVIQPRSPGSCVFVYKGEVIGRGFNETNCSLSGI

RHAELIAIEKILEHYPASVFKETTLYVTVEPCLMCAAALKQLHIKAVYFGCGNDRFGGCGSVFSIN

KDQSIDPSYPVYPGLFYSEAVMLREFYVQENVKAPVPQSKKQRVLKREVKSLDLSRFK

S. cerevisiae TAD1,
                                                                SEQ ID: 7
MVSCQGTRPCIVNLLTMPSEDKLGEEISTRVINEYSKLKSACRPIIRPSGIREWTILAGVAAINRD

GGANKIEILSIATGVKALPDSELQRSEGKILHDCHAEILALRGANTVLLNRIQNYNPSSGDKFIQH

NDEIPARFNLKENWELALYISRLPCGDASMSFLNDNCKNDDFKIEDSDEFQYVDRSVKTILRGR

LNFNRRNVVRTKPGRYDSNITLSKSCSDKLLMKQRSSVLNCLNYELFEKPVFLKYIVIPNLEDET

KHHLEQSFHTRLPNLDNEIKFLNCLKPFYDDKLDEEDVPGLMCSVKLFMDDFSTEEAILNGVRN

GFYTKSSKPLRKHCQSQVSRFAQWELFKKIRPEYEGISYLEFKSRQKKRSQLIIAIKNILSPDGWI

PTRTDDVK
```

*S. cerevisiae* TAD2, SEQ ID: 8

MQHIKHMRTAVRLARYALDHDETPVACIFVHTPTGQVMAYGMNDTNKSLTGVAHAEFMGIDQI

KAMLGSRGVVDVFKDITLYVTVEPCIMCASALKQLDIGKVVFGCGNERFGGNGTVLSVNHDTC

TLVPKNNSAAGYESIPGILRKEAIMLLRYFYVRQNERAPKPRSKSDRVLDKNTFPPMEWSKYLN

EEAFIETFGDDYRTCFANKVDLSSNSVDWDLIDSHQDNIIQELEEQCKMFKFNVHKKSKV

*A. thaliana* TAD2, SEQ ID: 9

MEEDHCEDSHNYMGFALHQAKLALEALEVPVGCVFLEDGKVIASGRNRTNETRNATRHAEME

AIDQLVGQWQKDGLSPSQVAEKFSKCVLYVTCEPCIMCASALSFLGIKEVYYGCPNDKFGGCG

SILSLHLGSEEAQRGKGYKCRGGIMAEEAVSLFKCFYEQGNPNAPKPHRPVVQRERT

*X. laevis* ADAT2, SEQ ID: 10

MEPLQITEEIQNWMHKAFQMAQDALNNGEVPVGCLMVYGNQVVGKGRNEVNETKNATQHAE

MVAIDQVLDWCEMNSKKSTDVFENIVLYVTVEPCIMCAGALRLLKIPLVVYGCRNERFGGCGSV

LNVSGDDIPDTGTKFKCIGGYQAEKAIELLKTFYKQENPNAPKSKVRKKE

*X. tropicalis* ADAT2, SEQ ID: 11

MTEEIQNWMHKAFQMAQDALNNGEVPVGCLMVYDNQVVGKGRNEVNETKNATRHAEMVAID

QVLDWCEKNSKKSRDVFENIVLYVTVEPCIMCAGALRLLKIPLVVYGCRNERFGGCGSVLNVA

GDNIPDTGTEFKYIGGYQAEKAVELLKTFYKQENPNAPRSKVRKKE

*D. rerio* ADAT2, SEQ ID: 12

MQEVGVDPEKNDFLQPSDSEVQTWMAKAFDMAVEALENGEVPVGCLMVYNNEIIGKGRNEV

NETKNATRHAEMVALDQVLDWCRLREKDCKEVCEQTVLYVTVEPCIMCAAALRLLRIPFVVYG

CKNERFGGCGSVLDVSSDHLPHTGTSFKCIAGYRAEEAVEMLKTFYKQENPNAPKPKVRKDSI

NPQDGAAVIQVMRGPPDEETETIAHLS

*B. Taurus* ADAT2, SEQ ID: 13

MEAKAGPTAATDGAYSVSAEETEKWMEQAMQMAKDALDNTEVPVGCLMVYNNEVVGKGRN

EVNQTKNATRHAEMVAIDQALDWCRRRGRSPSEVFEHTVLYVTVEPCIMCAAALRLMRIPLVV

YGCQNERFGGCGSVLDIASADLPSTGKPFQCTPGYRAEEAVEMLKTFYKQENPNAPKSKVRK

KECHKS

*M. musculus* ADAT2, SEQ ID: 14

MEEKVESTTTPDGPCVVSVQETEKWMEEAMRMAKEALENIEVPVGCLMVYNNEVVGKGRNE

VNQTKNATRHAEMVAIDQVLDWCHQHGQSPSTVFEHTVLYVTVEPCIMCAAALRLMKIPLVVY

GCQNERFGGCGSVLNIASADLPNTGRPFQCIPGYRAEEAVELLKTFYKQENPNAPKSKVRKKD

CQKS

*H. sapiens* ADAT2 SEQ ID: 15

MEAKAAPKPAASGACSVSAEETEKWMEEAMHMAKEALENTEVPVGCLMVYNNEVVGKGRNE

VNQTKNATRHAEMVAIDQVLDWCRQSGKSPSEVFEHTVLYVTVEPCIMCAAALRLMKIPLVVY

GCQNERFGGCGSVLNIASADLPNTGRPFQCIPGYRAEEAVEMLKTFYKQENPNAPKSKVRKKE

CQKS

ABE6.3, SEQ ID: 16

MSEVEFSHEYWMRHALTLAKRAWDEREVPVGAVLVHNNRVIGEGWNRPIGRHDPTAHAEIMA

LRQGGLVMQNYRLIDATYVTLEPCVMCAGAMIHSRIGRVVFGARDAKTGAAGSLMDVLHHPG

MNHRVEITEGILADECAALLSDFFRMRRQEIKAQKKAQSSTDSGGSSGGSSGSETPGTSESAT

-continued

PESSGGSSGGSSEVEFSHEYVVMRHALTLAKRAWDEREVPVGAVLVLNNRVIGEGWNRSIGLH

DPTAHAEIMALRQGGLVMQNYRLIDATLYVTFEPCVMCAGAMIHSRIGRVVFGVRNAKTGAAG

SLMDVLHYPGMNHRVEITEGILADECAALLCYFFRMRRQVFNAQKKAQSSTDSGGSSGGSSG

SETPGTSESATPESSGGSSGGS

DKKYSIGLAIGTNSVGWAVITDEYKVPSKKFKVLGNTDRHSIKKNLIGALLFDSGETAEATRLKRT

ARRRYTRRKNRICYLQEIFSNEMAKVDDSFFHRLEESFLVEEDKKHERHPIFGNIVDEVAYHEK

YPTIYHLRKKLVDSTDKADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSLGLTPNFKSNFDLAEDAK

LQLSKDTYDDDLDNLLAQIGDQYADLFLAAKNLSDAILLSDILRVNTEITKAPLSASMIKRYDEHH

QDLTLLKALVRQQLPEKYKEIFFDQSKNGYAGYIDGGASQEEFYKFIKPILEKMDGTEELLVKLN

REDLLRKQRTFDNGSIPHQIHLGELHAILRRQEDFYPFLKDNREKIEKILTFRIPYYVGPLARGNS

RFAWMTRKSEETITPWNFEEVVDKGASAQSFIERMTNFDKNLPNEKVLPKHSLLYEYFTVYNEL

TKVKYVTEGMRKPAFLSGEQKKAIVDLLFKTNRKVTVKQLKEDYFKKIECFDSVEISGVEDRFNA

SLGTYHDLLKIIKDKDFLDNEENEDILEDIVLTLTLFEDREMIEERLKTYAHLFDDKVMKQLKRRR

YTGWGRLSRKLINGIRDKQSGKTILDFLKSDGFANRNFMQLIHDDSLTFKEDIQKAQVSGQGDS

LHEHIANLAGSPAIKKGILQTVKVVDELVKVMGRHKPENIVIEMARENQTTQKGQKNSRERMKRI

EEGIKELGSQILKEHPVENTQLQNEKLYLYYLQNGRDMYVDQELDINRLSDYDVDHIVPQSFLK

DDSIDNKVLTRSDKNRGKSDNVPSEEVVKKMKNYWRQLLNAKLITQRKFDNLTKAERGGLSEL

DKAGFIKRQLVETRQITKHVAQILDSRMNTKYDENDKLIREVKVITLKSKLVSDFRKDFQFYKVR

EINNYHHAHDAYLNAVVGTALIKKYPKLESEFVYGDYKVYDVRKMIAKSEQEIGKATAKYFFYSN

IMNFFKTEITLANGEIRKRPLIETNGETGEIVWDKGRDFATVRKVLSMPQVNIVKKTEVQTGGFS

KESILPKRNSDKLIARKKDWDPKKYGGFDSPTVAYSVLVVAKVEKGKSKKLKSVKELLGITIMER

SSFEKNPIDFLEAKGYKEVKKDLIIKLPKYSLFELENGRKRMLASAGELQKGNELALPSKYVNFL

YLASHYEKLKGSPEDNEQKQLFVEQHKHYLDEIIEQISEFSKRVILADANLDKVLSAYNKHRDKPI

REQAENIIHLFTLTNLGAPAAFKYFDTTIDRKRYTSTKEVLDATLIHQSITGLYETRIDLSQLGGDS

GGSPKKKRKV

ABE7.8, SEQ ID: 17

MSEVEFSHEYWMRHALTLAKRAWDEREVPVGAVLVHNNRVIGEGWNRPIGRHDPTAHAEIMA

LRQGGLVMQNYRLIDATLYVTLEPCVMCAGAMIHSRIGRVVFGARDAKTGAAGSLMDVLHHPG

MNHRVEITEGILADECAALLSDFFRMRRQEIKAQKKAQSSTDSGGSSGGSSGSETPGTSESAT

PESSGGSSGGSSEVEFSHEYWMRHALTLAKRALDEREVPVGAVLVLNNRVIGEGWNRAIGLH

DPTAHAEIMALRQGGLVMQNYRLIDATLYVTFEPCVMCAGAMIHSRIGRVVFGVRNAKTGAAG

SLMDVLHYPGMNHRVEITEGILADECNALLCYFFRMRRQVFNAQKKAQSSTDSGGSSGGSSG

SETPGTSESATPESSGGSSGGSDKKYSIGLAIGTNSVGWAVITDEYKVPSKKFKVLGNTDRHSI

KKNLIGALLFDSGETAEATRLKRTARRRYTRRKNRICYLQEIFSNEMAKVDDSFFHRLEESFLVE

EDKKHERHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKKNGLFG

NLIALSLGLTPNFKSNFDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKNGYAGYIDGGASQE

EFYKFIKPILEKMDGTEELLVKLNREDLLRKQRTFDNGSIPHQIHLGELHAILRRQEDFYPFLKDN

-continued

REKIEKILTFRIPYYVGPLARGNSRFAVVMTRKSEETITPWNFEEVVDKGASAQSFIERMTNFDK

NLPNEKVLPKHSLLYEYFTVYNELTKVKYVTEGMRKPAFLSGEQKKAIVDLLFKTNRKVTVKQL

KEDYFKKIECFDSVEISGVEDRFNASLGTYHDLLKIIKDKDFLDNEENEDILEDIVLTLTLFEDREM

IEERLKTYAHLFDDKVMKQLKRRRYTGWGRLSRKLINGIRDKQSGKTILDFLKSDGFANRNFMQ

LIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYV

DQELDINRLSDYDVDHIVPQSFLKDDSIDNKVLTRSDKNRGKSDNVPSEEVVKKMKNYWRQLL

NAKLITQRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYGDYKVYD

VRKMIAKSEQEIGKATAKYFFYSNIMNFFKTEITLANGEIRKRPLIETNGETGEIVWDKGRDFATV

RKVLSMPQVNIVKKTEVQTGGFSKESILPKRNSDKLIARKKDWDPKKYGGFDSPTVAYSVLVVA

KVEKGKSKKLKSVKELLGITIMERSSFEKNPIDFLEAKGYKEVKKDLIIKLPKYSLFELENGRKRM

LASAGELQKGNELALPSKYVNFLYLASHYEKLKGSPEDNEQKQLFVEQHKHYLDEIIEQISEFSK

RVILADANLDKVLSAYNKHRDKPIREQAENIIHLFTLTNLGAPAAFKYFDTTIDRKRYTSTKEVLD

ATLIHQSITGLYETRIDLSQLGGDSGGSPKKKRKV

ABE7.9,
SEQ ID: 18
MSEVEFSHEYWMRHALTLAKRAWDEREVPVGAVLVHNNRVIGEGWNRPIGRHDPTAHAEIMA

LRQGGLVMQNYRLIDATLYVTLEPCVMCAGAMIHSRIGRVVFGARDAKTGAAGSLMDVLHHPG

MNHRVEITEGILADECAALLSDFFRMRRQEIKAQKKAQSSTDSGGSSGGSSGSETPGTSESAT

PESSGGSSGGSSEVEFSHEYWMRHALTLAKRALDEREVPVGAVLVLNNRVIGEGWNRAIGLH

DPTAHAEIMALRQGGLVMQNYRLIDATLYVTFEPCVMCAGAMIHSRIGRVVFGVRNAKTGAAG

SLMDVLHYPGMNHRVEITEGILADECNALLCYFFRMPRQVFNAQKKAQSSTDSGGSSGGSSG

SETPGTSESATPESSGGSSGGSDKKYSIGLAIGTNSVGWAVITDEYKVPSKKFKVLGNTDRHSI

KKNLIGALLFDSGETAEATRLKRTARRRYTRRKNRICYLQEIFSNEMAKVDDSFFHRLEESFLVE

EDKKHERHPIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGEKKNGLFG

NLIALSLGLTPNF

KSNFDLAEDAKLQLSKDTYDDDLDNLLAQIGDQYADLFLAAKNLSDAILLSDILRVNTEITKAPLS

ASMIKRYDEHHQDLTLLKALVRQQLPEKYKEIFFDQSKNGYAGYIDGGASQEEFYKFIKPILEKM

DGTEELLVKLNREDLLRKQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDKNLPNEKVLPKHSL

LYEYFTVYNELTKVKYVTEGMRKPAFLSGEQKKAIVDLLFKTNRKVTVKQLKEDYFKKIECFDSV

EISGVEDRFNASLGTYHDLLKIIKDKDFLDNEENEDILEDIVLTLTLFEDREMIEERLKTYAHLFDD

KVMKQLKRRRYTGWGRLSRKLINGIRDKQSGKTILDFLKSDGFANRNFMQLIHDDSLTFKEDIQ

KAQVSGQGDSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQELDINRLSDYD

VDHIVPQSFLKDDSIDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIREVKVITLKSKLVSDFR

KDFQFYKVREINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSMPQVNIVKK

TEVQTGGFSKESILPKRNSDKLIARKKDWDPKKYGGFDSPTVAYSVLVVAKVEKGKSKKLKSVK

ELLGITIMERSSFEKNPIDFLEAKGYKEVKKDLIIKLPKYSLFELENGRKRMLASAGELQKGNELA
LPSKYVNFLYLASHYEKLKGSPEDNEQKQLFVEQHKHYLDEIIEQISEFSKRVILADANLDKVLSA
YNKHRDKPIREQAENIIHLFTLTNLGAPAAFKYFDTTIDRKRYTSTKEVLDATLIHQSITGLYETRI
DLSQLGGDSGGSPKKKRKV

ABE7.10, SEQ ID: 19

MSEVEFSHEYWMRHALTLAKRAWDEREVPVGAVLVHNNRVIGEGWNRPIGRHDPTAHAEIMA
LRQGGLVMQNYRLIDATLYVTLEPCVMCAGAMIHSRIGRVVFGARDAKTGAAGSLMDVLHHPG
MNHRVEITEGILADECAALLSDFFRMRRQEIKAQKKAQSSTDSGGSSGGSSGSETPGTSESAT
PESSGGSSGGSSEVEFSHEYWMRHALTLAKRARDEREVPVGAVLVLNNRVIGEGWNRAIGLH
DPTAHAEIMALRQGGLVMQNYRLIDATLYVTFEPCVMCAGAMIHSRIGRVVFGVRNAKTGAAG
SLMDVLHYPGMNHRVEITEGILADECAALLCYFFRMPRQVFNAQKKAQSSTDSGGSSGGSSG
SETPGTSESATPESSGGSSGGSDKKYSIGLAIGTNSVGWAVITDEYKVPSKKFKVLGNTDRHSI
KKNLIGALLFDSGETAEATRLKRTARRRYTRRKNRICYLQEIFSNEMAKVDDSFFHRLEESFLVE
EDKKHERHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKKNGLFG
NLIALSLGLTPNFKSNFDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKNGYAGYIDGGASQE
EFYKFIKPILEKMDGTEELLVKLNREDLLRKQRTFDNGSIPHQIHLGELHAILRRQEDFYPFLKDN
REKIEKILTFRIPYYVGPLARGNSRFAVVMTRKSEETITPWNFEEVVDKGASAQSFIERMTNFDK
NLPNEKVLPKHSLLYEYFTVYNELTKVKYVTEGMRKPAFLSGEQKKAIVDLLFKTNRKVTVKQL
KEDYFKKIECFDSVEISGVEDRFNASLGTYHDLLKIIKDKDFLDNEENEDILEDIVLTLTLFEDREM
IEERLKTYAHLFDDKVMKQLKRRRYTGWGRLSRKLINGIRDKQSGKTILDFLKSDGFANRNFMQ
LIHDDSLTFKEDIQKAQVSGQGDSLHEHIANLAGSPAIKKGILQTVKVVDELVKVMGRHKPENIVI
EMARENQTTQKGQKNSRERMKRIEEGIKELGSQILKEHPVENTQLQNEKLYLYYLQNGRDMYV
DQELDINRLSDYDVDHIVPQSFLKDDSIDNKVLTRSDKNRGKSDNVPSEEVVKKMKNYWRQLL
NAKLITQRKFDNLTKAERGGLSELDKAGFIKRQLVETRQITKHVAQILDSRMNTKYDENDKLIRE
VKVITLKSKLVSDFRKDFQFYKVREINNYHHAHDAYLNAVVGTALIKKYPKLESEFVYGDYKVYD
VRKMIAKSEQEIGKATAKYFFYSNIMNFFKTEITLANGEIRKRPLIETNGETGEIVWDKGRDFATV
RKVLSMPQVNIVKKTEVQTGGFSKESILPKRNSDKLIARKKDWDPKKYGGFDSPTVAYSVLVVA
KVEKGKSKKLKSVKELLGITIMERSSFEKNPIDFLEAKGYKEVKKDLIIKLPKYSLFELENGRKRM
LASAGELQKGNELALPSKYVNFLYLASHYEKLKGSPEDNEQKQLFVEQHKHYLDEIIEQISEFSK
RVILADANLDKVLSAYNKHRDKPIREQAENIIHLFTLTNLGAPAAFKYFDTTIDRKRYTSTKEVLD
ATLIHQSITGLYETRIDLSQLGGDSGGSPKKKRKV

ABEmax, SEQ ID: 20

MKRTADGSEFESPKKKRKVSEVEFSHEYWMRHALTLAKRAWDEREVPVGAVLVHNNRVIGEG
WNRPIGRHDPTAHAEIMALRQGGLVMQNYRLIDATLYVTLEPCVMCAGAMIHSRIGRVVFGAR
DAKTGAAGSLMDVLHHPGMNHRVEITEGILADECAALLSDFFRMRRQEIKAQKKAQSSTDSGG
SSGGSSGSETPGTSESATPESSGGSSGGSSEVEFSHEYWMRHALTLAKRARDEREVPVGAV
LVLNNRVIGEGWNRAIGLHDPTAHAEIMALRQGGLVMQNYRLIDATLYVTFEPCVMCAGAMIHS
RIGRVVFGVRNAKTGAAGSLMDVLHYPGMNHRVEITEGILADECAALLCYFFRMPRQVFNAQK

-continued

KAQSSTDSGGSSGGSSGSETPGTSESATPESSGGSSGGSDKKYSIGLAIGTNSVGWAVITDEY

KVPSKKFKVLGNTDRHSIKKNLIGALLFDSGETAEATRLKRTARRRYTRRKNRICYLQEIFSNEM

AKVDDSFFHRLEESFLVEEDKKHERHPIFGNIVDEVAYHEKYPTIYHLRKKLVDSTDKADLRLIYL

ALAHMIKFRGHFLIEGDLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYDDDLDNLLAQIGDQYA

DLFLAAKNLSDAILLSDILRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQRTFDNGSIPHQIHLGEL

HAILRRQEDFYPFLKDNREKIEKILTFRIPYYVGPLARGNSRFAVVMTRKSEETITPWNFEEVVDK

GASAQSFIERMTNFDKNLPNEKVLPKHSLLYEYFTVYNELTKVKYVTEGMRKPAFLSGEQKKAI

VDLLFKTNRKVTVKQLKEDYFKKIECFDSVEISGVEDRFNASLGTYHDLLKIIKDKDFLDNEENED

ILEDIVLTLTLFEDREMIEERLKTYAHLFDDKVMKQLKRRRYTGWGRLSRKLINGIRDKQSGKTIL

DFLKSDGFANRNFMQLIHDDSLTFKEDIQKAQVSGQGDSLHEHIANLAGSPAIKKGILQTVKVVD

ELVKVMGRHKPENIVIEMARENQTTQKGQKNSRERMKRIEEGIKELGSQILKEHPVENTQLQNE

KLYLYYLQNGRDMYVDQELDINRLSDYDVDHIVPQSFLKDDSIDNKVLTRSDKNRGKSDNVPSE

EVVKKMKNYWRQLLNAKLITQRKFDNLTKAERGGLSELDKAGFIKRQLVETRQITKHVAQILDS

RMNTKYDENDKLIREVKVITLKSKLVSDFRKDFQFYKVREINNYHHAHDAYLNAVVGTALIKKYP

KLESEFVYGDYKVYDVRKMIAKSEQEIGKATAKYFFYSNIMNFFKTEITLANGEIRKRPLIETNGE

TGEIVWDKGRDFATVRKVLSMPQVNIVKKTEVQTGGFSKESILPKRNSDKLIARKKDWDPKKY

GGFDSPTVAYSVLVVAKVEKGKSKKLKSVKELLGITIMERSSFEKNPIDFLEAKGYKEVKKDLIIK

LPKYSLFELENGRKRMLASAGELQKGNELALPSKYVNFLYLASHYEKLKGSPEDNEQKQLFVE

QHKHYLDEIIEQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSGGSKRTADGSEFEPKKKRKV miniABEmax,
SEQ ID: 31
NLS-tadA(7.10)-32AA linker*-hSpCas9n(D10A)-NLS-P2A-EGFP-NLS
MKRTADGSEFESPKKKRKVSEVEFSHEYWMRHALTLAKRARDEREVPVGAVLVLNNRVIGEG

WNRAIGLHDPTAHAEIMALRQGGLVMQNYRLIDATLYVTFEPCVMCAGAMIHSRIGRVVFGVR

NAKTGAAGSLMDVLHYPGMNHRVEITEGILADECAALLCYFFRMPRQVFNAQKKAQSSTDSG

GSSGGSSGSETPGTSESATPESSGGSSGGSDKKYSIGLAIGTNSVGWAVITDEYKVPSKKFKV

LGNTDRHSIKKNLIGALLFDSGETAEATRLKRTARRRYTRRKNRICYLQEIFSNEMAKVDDSFFH

RLEESFLVEEDKKHERHPIFGNIVDEVAYHEKYPTIYHLRKKLVDSTDKADLRLIYLALAHMIKFR

GHFLIEGDLNPDNSDVDKLFIQLVQTYNQLFEENPINASGVDAKAILSARLSKSRRLENLIAQLPG

EKKNGLFGNLIALSLGLTPNFKSNFDLAEDAKLQLSKDTYDDDLDNLLAQIGDQYADLFLAAKNL

SDAILLSDILRVNTEITKAPLSASMIKRYDEHHQDLTLLKALVRQQLPEKYKEIFFDQSKNGYAGY

IDGGASQEEFYKFIKPILEKMDGTEELLVKLNREDLLRKQRTFDNGSIPHQIHLGELHAILRRQED

FYPFLKDNREKIEKILTFRIPYYVGPLARGNSRFAWMTRKSEETITPWNFEEVVDKGASAQSFIE

RMTNFDKNLPNEKVLPKHSLLYEYFTVYNELTKVKYVTEGMRKPAFLSGEQKKAIVDLLFKTNR

KVTVKQLKEDYFKKIECFDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFLKSDGF

ANRNFMQLIHDDSLTFKEDIQKAQVSGQGDSLHEHIANLAGSPAIKKGILQTVKVVDELVKVMG

RHKPENIVIEMARENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKSDNVPSEEVVKKM

-continued

KNYWRQLLNAKLITQRKFDNLTKAERGGLSELDKAGFIKRQLVETRQITKHVAQILDSRMNTKY

DENDKLIREVKVITLKSKLVSDFRKDFQFYKVREINNYHHAHDAYLNAVVGTALIKKYPKLESEFV

YGDYKVYDVRKMIAKSEQEIGKATAKYFFYSNIMNFFKTEITLANGEIRKRPLIETNGETGEIVWD

KGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQHKHYLDE

IIEQISEFSKRVILADANLDKVLSAYNKHRDKPIREQAENIIHLFTLTNLGAPAAFKYFDTTIDRKRY

TSTKEVLDATLIHQSITGLYETRIDLSQLGGDSGGSKRTADGSEFEPKKKRKVGSGATNFSLLK

QAGDVEENPGPMVSKGEELFTGVVPILVELDGDVNGHKFSVSGEGEGDATYGKLTLKFICTTG

KLPVPWPTLVTTLTYGVQCFSRYPDHMKQHDFFKSAMPEGYVQERTIFFKDDGNYKTRAEVKF

EGDTLVNRIELKGIDFKEDGNILGHKLEYNYNSHNVYIMADKQKNGIKVNFKIRHNIEDGSVQLA

DHYQQNTPIGDGPVLLPDNHYLSTQSALSKDPNEKRDHMVLLEFVTAAGITLGMDELYKSGGS

PKKKRKV

MiniABEmax K20A/R21A,
SEQ ID: 32
NLS-tadA(K20A/R21A)-32AA linker*-hSpCas9n(D10A)-NLS-P2A-EGFP-NLS
MKRTADGSEFESPKKKRKVSEVEFSHEYWMRHALTLAAAARDEREVPVGAVLVLNNRVIGEG

WNRAIGLHDPTAHAEIMALRQGGLVMQNYRLIDATLYVTFEPCVMCAGAMIHSRIGRVVFGVR

NAKTGAAGSLMDVLHYPGMNHRVEITEGILADECAALLCYFFRMPRQVFNAQKKAQSSTDSG

GSSGGSSGSETPGTSESATPESSGGSSGGSDKKYSIGLAIGTNSVGWAVITDEYKVPSKKFKV

LGNTDRHSIKKNLIGALLFDSGETAEATRLKRTARRRYTRRKNRICYLQEIFSNEMAKVDDSFFH

RLEESFLVEEDKKHERHPIFGNIVDEVAYHEKYPTIYHLRKKLVDSTDKADLRLIYLALAHMIKFR

GHFLIEGDLNPDNSDVDKLFIQLVQTYNQLFEENPINASGVDAKAILSARLSKSRRLENLIAQLPG

EKKNGLFGNLIALSLGLTPNFKSNFDLAEDAKLQLSKDTYDDDLDNLLAQIGDQYADLFLAAKNL

SDAILLSDILRVNTEITKAPLSASMIKRYDEHHQDLTLLKALVRQQLPEKYKEIFFDQSKNGYAGY

IDGGASQEEFYKFIKPILEKMDGTEELLVKLNREDLLRKQRTFDNGSIPHQIHLGELHAILRRQED

FYPFLKDNREKIEKILTFRIPYYVGPLARGNSRFAWMTRKSEETITPWNFEEVVDKGASAQSFIE

RMTNFDKNLPNEKVLPKHSLLYEYFTVYNELTKVKYVTEGMRKPAFLSGEQKKAIVDLLFKTNR

KVTVKQLKEDYFKKIECFDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFLKSDGF

ANRNFMQLIHDDSLTFKEDIQKAQVSGQGDSLHEHIANLAGSPAIKKGILQTVKVVDELVKVMG

RHKPENIVIEMARENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKSDNVPSEEVVKKM

KNYWRQLLNAKLITQRKFDNLTKAERGGLSELDKAGFIKRQLVETRQITKHVAQILDSRMNTKY

DENDKLIREVKVITLKSKLVSDFRKDFQFYKVREINNYHHAHDAYLNAVVGTALIKKYPKLESEFV

YGDYKVYDVRKMIAKSEQEIGKATAKYFFYSNIMNFFKTEITLANGEIRKRPLIETNGETGEIVWD

KGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQHKHYLDE

IIEQISEFSKRVILADANLDKVLSAYNKHRDKPIREQAENIIHLFTLTNLGAPAAFKYFDTTIDRKRY

TSTKEVLDATLIHQSITGLYETRIDLSQLGGDSGGSKRTADGSEFEPKKKRKVGSGATNFSLLK

QAGDVEENPGPMVSKGEELFTGVVPILVELDGDVNGHKFSVSGEGEGDATYGKLTLKFICTTG

```
KLPVPWPTLVTTLTYGVQCFSRYPDHMKQHDFFKSAMPEGYVQERTIFFKDDGNYKTRAEVKF

EGDTLVNRIELKGIDFKEDGNILGHKLEYNYNSHNVYIMADKQKNGIKVNFKIRHNIEDGSVQLA

DHYQQNTPIGDGPVLLPDNHYLSTQSALSKDPNEKRDHMVLLEFVTAAGITLGMDELYKSGGS

PKKKRKV

MiniABEmax V82G,                                                     SEQ ID: 33
NLS-tadA(V82G)-32AA linker*-hSpCas9n(D10A)-NLS-P2A-EGFP-NLS
MKRTADGSEFESPKKKRKVSEVEFSHEYWMRHALTLAKRARDEREVPVGAVLVLNNRVIGEG

WNRAIGLHDPTAHAEIMALRQGGLVMQNYRLIDATLYGTFEPCVMCAGAMIHSRIGRVVFGVR

NAKTGAAGSLMDVLHYPGMNHRVEITEGILADECAALLCYFFRMPRQVFNAQKKAQSSTDSG

GSSGGSSGSETPGTSESATPESSGGSSGGSDKKYSIGLAIGTNSVGWAVITDEYKVPSKKFKV

LGNTDRHSIKKNLIGALLFDSGETAEATRLKRTARRRYTRRKNRICYLQEIFSNEMAKVDDSFFH

RLEESFLVEEDKKHERHPIFGNIVDEVAYHEKYPTIYHLRKKLVDSTDKADLRLIYLALAHMIKFR

GHFLIEGDLNPDNSDVDKLFIQLVQTYNQLFEENPINASGVDAKAILSARLSKSRRLENLIAQLPG

EKKNGLFGNLIALSLGLTPNFKSNFDLAEDAKLQLSKDTYDDDLDNLLAQIGDQYADLFLAAKNL

SDAILLSDILRVNTEITKAPLSASMIKRYDEHHQDLTLLKALVRQQLPEKYKEIFFDQSKNGYAGY

IDGGASQEEFYKFIKPILEKMDGTEELLVKLNREDLLRKQRTFDNGSIPHQIHLGELHAILRRQED

FYPFLKDNREKIEKILTFRIPYYVGPLARGNSRFAWMTRKSEETITPWNFEEVVDKGASAQSFIE

RMTNFDKNLPNEKVLPKHSLLYEYFTVYNELTKVKYVTEGMRKPAFLSGEQKKAIVDLLFKTNR

KVTVKQLKEDYFKKIECFDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFLKSDGF

ANRNFMQLIHDDSLTFKEDIQKAQVSGQGDSLHEHIANLAGSPAIKKGILQTVKVVDELVKVMG

RHKPENIVIEMARENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKSDNVPSEEVVKKM

KNYWRQLLNAKLITQRKFDNLTKAERGGLSELDKAGFIKRQLVETRQITKHVAQILDSRMNTKY

DENDKLIREVKVITLKSKLVSDFRKDFQFYKVREINNYHHAHDAYLNAVVGTALIKKYPKLESEFV

YGDYKVYDVRKMIAKSEQEIGKATAKYFFYSNIMNFFKTEITLANGEIRKRPLIETNGETGEIVWD

KGRDFATVRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQHKHYLDE

IIEQISEFSKRVILADANLDKVLSAYNKHRDKPIREQAENIIHLFTLTNLGAPAAFKYFDTTIDRKRY

TSTKEVLDATLIHQSITGLYETRIDLSQLGGDSGGSKRTADGSEFEPKKKRKVGSGATNFSLLK

QAGDVEENPGPMVSKGEELFTGVVPILVELDGDVNGHKFSVSGEGEGDATYGKLTLKFICTTG

KLPVPWPTLVTTLTYGVQCFSRYPDHMKQHDFFKSAMPEGYVQERTIFFKDDGNYKTRAEVKF

EGDTLVNRIELKGIDFKEDGNILGHKLEYNYNSHNVYIMADKQKNGIKVNFKIRHNIEDGSVQLA

DHYQQNTPIGDGPVLLPDNHYLSTQSALSKDPNEKRDHMVLLEFVTAAGITLGMDELYKSGGS

PKKKRKV

E. coli TadA deaminase monomer with ABE 7.10 mutations,              SEQ ID: 34
MSEVEFSHEYWMRHALTLAKRARDEREVPVGAVLVLNNRVIGEGWNRAIGLHDPTAHAEIMAL

RQGGLVMQNYRLIDATLYVTFEPCVMCAGAMIHSRIGRVVFGVRNAKTGAAGSLMDVLHYPG

MNHRVEITEGILADECAALLCYFFRMPRQVFNAQKKAQSSTD
```

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An adenine base editor (ABE) variant capable of deaminating adenine in DNA comprising an adenosine deaminase and a programmable DNA binding domain, wherein the adenosine deaminase comprises one or more *Escherichia coli* TadA monomers, wherein each *E. coli* TadA monomer has at least 90% sequence identity to the amino acid sequence of SEQ ID NO: 1 or the amino acid sequence of SEQ ID NO: 34, and wherein at least one of the one or more *E. coli* TadA monomers comprise one or more mutations at amino acid residue positions that correspond to amino acid residues 10, 11, 13, 21, 25, 26, 49, 58, 71, 72, 74, 77, 82, 109, 111, 122, 128, 129, 139, 140, 143, 148, 150, or 153 of the amino acid sequence of SEQ ID NO: 1 or the amino acid sequence of SEQ ID NO: 34.

2. The ABE variant of claim 1, wherein the one or more mutations comprise mutations at amino acid residue positions that correspond to amino acid residues 11A, 13A, 20A, 21A, 25A, 26A, 49A, 58G, 71A, 72A, 74A, 77A, 82G, 109G, 109W, 111A, 122A, 128A, 129A, 139A, 140A, 143G, 148A, 150A, and/or 153A of the amino acid sequence of SEQ ID NO: 1 or the amino acid sequence of SEQ ID NO: 34.

3. The ABE variant of claim 2, wherein the at least one of the one or more *E. coli* TadA monomers comprise mutations at amino acid residue positions that correspond to amino acid residues:

R13A;
20A and 21A;
21A, and 23A;
26A;
49A;
74A;
77A;
82G;
11A;
109W;
111A;
139A and 140A;
143G;
153A;
58G;
72A;
128A and 129A;
139A and 140A;
148A; or
150A
of the amino acid sequence of SEQ ID NO: 1 or the amino acid sequence of SEQ ID NO: 34.

4. The ABE variant of claim 1, further comprising one or more nuclear localization sequences (NLS).

5. The ABE variant of claim 1, further comprising a linker between the adenosine deaminase monomers and/or between the adenosine deaminase monomer or between a single-chain dimer and the programmable DNA binding domain.

6. The ABE variant of claim 1, wherein the programmable DNA binding domain is an engineered C2H2 zinc-finger, a transcription activator effector-like effector (TALE), or a Clustered Regularly Interspaced Short Palindromic Repeats (CRISPR) Cas RNA-guided nucleases (CRISPR-Cas nuclease).

7. The ABE variant of claim 6, wherein the CRISPR-Cas nuclease is a single strand DNA (ssDNA) nickase or is a catalytically inactive CRISPR-Cas nuclease.

8. The ABE variant of claim 7, wherein the CRISPR-Cas nuclease is a Cas9 or Cas12a that has ssDNA nickase activity or is a catalytically inactive Cas9 or Cas12a.

9. A base editing system comprising:
   (i) the ABE variant of claim 1, wherein the programmable DNA binding domain is a CRISPR-Cas RNA guided nuclease (RGN); and
   (ii) at least one guide RNA compatible with the base editing system that directs the base editing system to a target sequence.

10. A method of deaminating a selected adenine in a nucleic acid, the method comprising contacting the nucleic acid with the ABE variant of claim 1, and at least one guide RNA compatible with the ABE variant that directs the ABE variant to a target sequence comprising the selected adenine.

11. The method of claim 10, wherein the nucleic acid is in a cell.

12. The method of claim 11, wherein the cell is in a living subject.

13. The method of claim 12, wherein the living subject is a mammal.

14. A composition comprising the ABE variant of claim 1, and at least one guide RNA compatible with the ABE variant that directs the ABE variant to a target sequence.

15. The composition of claim 14, further comprising one or more ribonucleoprotein (RNP) complexes.

16. The ABE variant of claim 1, wherein the at least one of the one or more *E. coli* TadA monomers comprise mutations at amino acid residue positions that correspond to amino acid residues 11A, and/or 139A/140A of the amino acid sequence of SEQ ID NO: 1 or the amino acid sequence of SEQ ID NO: 34.

17. The ABE variant of claim 1, wherein the at least one of the one or more *E. coli* TadA monomers comprise mutations that correspond to 58G, 72A, 128A/129A, 139A/140A, 148A, and 150A of the amino acid sequence of SEQ ID NO: 1 or the amino acid sequence of SEQ ID NO: 34.

18. The ABE variant of claim 1, wherein each *E. coli* TadA monomer has at least 95% sequence identity to the amino acid sequence of SEQ ID NO: 1 or the amino acid sequence of SEQ ID NO: 34.

19. The ABE variant of claim 1, wherein each *E. coli* TadA monomer has at least 98% sequence identity to the amino acid sequence of SEQ ID NO: 1 or the amino acid sequence of SEQ ID NO: 34.

* * * * *

UNITED STATES PATENT AND TRADEMARK OFFICE
CERTIFICATE OF CORRECTION

PATENT NO. : 11,946,040 B2
APPLICATION NO. : 16/781979
DATED : April 2, 2024
INVENTOR(S) : J. Keith Joung, Julian Grunewald and Ronghao Zhou It is certified that error appears in the above-identified patent and that said Letters Patent is hereby corrected as shown below:

In the Claims

In Column 191, Line 51 (approx.), Claim 1, delete "13, 21," and insert -- 13, 20, 21, --

In Column 191, Line 58 (approx.), Claim 2, before "11A," insert -- 10A, --

In Column 192, Line 42 (approx.), Claim 3, before "21A," insert -- 20A --

In Column 192, Line 43 (approx.), Claim 3, above "26A;" insert -- 25A; --

Signed and Sealed this
Tenth Day of December, 2024

Katherine Kelly Vidal
*Director of the United States Patent and Trademark Office*